(12) United States Patent
Ramsden et al.

(10) Patent No.: US 9,242,987 B2
(45) Date of Patent: *Jan. 26, 2016

(54) HETEROCYCLYL PYRAZOLOPYRIMIDINE ANALOGUES AS JAK INHIBITORS

(75) Inventors: Nigel Ramsden, Herts (GB); Richard John Harrison, Cambridge (GB); Sally Oxenford, Herts (GB); Kathryn Bell, London (GB); Nelly Piton, Newmarket (GB); Claudio Dagostin, Cambridge (GB); Cyrille Broussard, Saffron Walden (GB); Andrew Ratcliffe, Brentwood (GB)

(73) Assignee: Cellzome Limited, Brentford, Middlesex (GB)

(*) Notice: Subject to any disclaimer, the term of this patent is extended or adjusted under 35 U.S.C. 154(b) by 505 days.

This patent is subject to a terminal disclaimer.

(21) Appl. No.: 13/503,083

(22) PCT Filed: Oct. 19, 2010

(86) PCT No.: PCT/EP2010/065700
§ 371 (c)(1),
(2), (4) Date: Apr. 23, 2012

(87) PCT Pub. No.: WO2011/048082
PCT Pub. Date: Apr. 28, 2011

(65) Prior Publication Data
US 2012/0252779 A1    Oct. 4, 2012

Related U.S. Application Data

(60) Provisional application No. 61/375,358, filed on Aug. 20, 2010.

(30) Foreign Application Priority Data

Oct. 20, 2009  (EP) .................................... 09173535

(51) Int. Cl.
| | | |
|---|---|---|
| *C07D 487/04* | (2006.01) |
| *A61K 31/519* | (2006.01) |
| *A61P 29/00* | (2006.01) |
| *A61P 37/00* | (2006.01) |
| *A61P 37/08* | (2006.01) |
| *A61P 41/00* | (2006.01) |
| *A61K 31/541* | (2006.01) |
| *A61K 31/5386* | (2006.01) |
| *A61K 31/5377* | (2006.01) |
| *A61K 31/496* | (2006.01) |

(52) U.S. Cl.
CPC ..................... *C07D 487/04* (2013.01)

(58) Field of Classification Search
CPC ....................... A61K 31/519; C07D 487/04
USPC ........................ 544/262; 514/262.1
See application file for complete search history.

(56) References Cited

U.S. PATENT DOCUMENTS

2009/0203688 A1    8/2009  Gaul et al.
2012/0015963 A1*   1/2012  Woller et al. ............... 514/262.1

FOREIGN PATENT DOCUMENTS

| WO | 9835985 | 8/1998 |
| WO | 9902166 | 1/1999 |
| WO | 0047212 | 8/2000 |
| WO | 0132651 | 5/2001 |
| WO | 0142246 | 6/2001 |
| WO | 0160814 | 8/2001 |
| WO | 2006/074985 | 7/2006 |
| WO | 2006074985 | 7/2006 |
| WO | 2006134056 | 12/2006 |
| WO | 2007107318 | 9/2007 |
| WO | 2007137867 | 12/2007 |
| WO | 2008/009458 | 1/2008 |
| WO | 2008060301 | 5/2008 |

(Continued)

OTHER PUBLICATIONS

Marcelo Zaldini Hernandes et al., ("Halogen Atoms in the Modern Medicinal Chemistry: Hints for the Drug Design" Current Drug Targets, 2010, 11 pp. 01-12).*
Purser et al. (Chem. Soc. Rev., 2008, 37, pp. 320-330).*
Stella, Valentino J, Expert Opinion of Therapeutic Patents, Prodrugs as therapeutics, 2004 14(3), pp. 277-280.*
Wolff et al. (Burger's Medicinal Chemistry, 5th Ed., vol. 1, pp. 975-977, 1994).*

(Continued)

*Primary Examiner* — Susanna Moore
(74) *Attorney, Agent, or Firm* — Robert Steve Thomas

(57) ABSTRACT

The invention relates to compounds of formula (I)

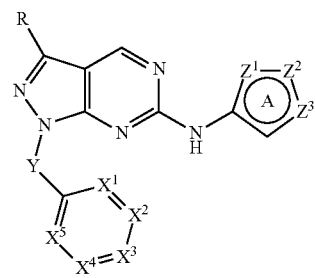

wherein $X^1$ to $X^5$, Y, $Z^1$ to $Z^3$, and R have the meaning as cited in the description and the claims. Said compounds are useful as JAK inhibitors for the treatment or prophylaxis of immunological, inflammatory, autoimmune, allergic disorders, and immunologically-mediated diseases. The invention also relates to pharmaceutical compositions including said compounds, the preparation of such compounds as well as the use as medicaments.

19 Claims, No Drawings

(56) References Cited

FOREIGN PATENT DOCUMENTS

| WO | 2008/094602 | 8/2008 |
|---|---|---|
| WO | 2008094602 | 8/2008 |
| WO | 2008118822 | 10/2008 |
| WO | 2008118823 | 10/2008 |
| WO | 2009008992 | 1/2009 |
| WO | 2010039939 | 4/2010 |
| WO | 2010118986 | 10/2010 |
| WO | 2011156698 | 12/2011 |

OTHER PUBLICATIONS

Testa, B., Biochemical Pharmacology, Prodrug Research: futile or fertile?, 2004, 68, pp. 2097-2106.*

Ettmayer, P., Medicinal Chemistry, Lessons Learned from Marketed and Investigational Prodrugs, 2004, 47(10), pp. 2394-2404.*

Yamaoka, et al., "The Janus kinases (Jaks)", Genome Biology, 2004 5(12): 253.

Musso, et al., "Regulation of JAK3 Expression in Human Monocytes: Phosphorylation in Response to Interleukins 2, 4, and 7", J. Exp Med., 1995, 181(4): 1425-31.

Rodig, et al., "Disruption of the JAK1 Gene Eemonstrates Obligatory and Nonredundant Roles of the Jaks in Cytokine-Induced Biologic Responses", Cell, 1998, 93(3): 373-83.

Neubauer, et al., "Jak2 Deficiency Defines an Essential Developmental Checkpoint in Definitive Hennatopoiesis", Cell, 1998, 93(3): 397-409.

Macchi, et al., "Mutations of Jak-3 gene in patients with autosomal severe combined immune deficiency (SCID)", Nature, 1995, 377(6544): 65-68.

Papageorgiou, et al., "Is JAK3 a new drug target for immunomodulation-based therapies?", Trends in Pharmacological Sciences, 2004, 25(11):558-62.

Walters, et al., "Activating alleles of JAK3 in acute megakaryoblastic leukemia", Cancer Cell, 2006, 10(1): 65-75.

O'Shea, et al., "A New Modality for Immunosuppression: Targeting the JAK/STAT Pathway", Nat. Rev. Drug Discov., 2004, 3(7): 555-64.

Changelian, et al., "Prevention of Organ Allograft Rejection by Specific Janus Kinase 3 Inhibitor", Science, 2003, 302 (5646): 875-888.

Pesu, et al., "Therapeutic targeting of Janus kinases", Immunol. Rev., 2008, 223: 132-142.

Jiang, et al., "Examining the Chirality, Conformation and Selective Kinase Inhibition of 3-((3R,4R)-4-methyl-3-(methyl(7H-pyrrolo[2,3-d] pyrimidin-4-yl)amino)piperidin-1-yl)-3-oxopropanenitrile (CP-690,550)", J. Med. Chem., 2008, 51(24): 8012-8018.

Ghoreschi, et al., "Selectivity and therapeutic inhibition of kinases: to be or not to be?", Nature Immunol, 2009, 4:356-360.

Schindler, et al., "JAK-STAT Signaling: From Interferons to Cytokines", J. Biol. Chem., 2007, 282(28): 20059-63.

Yang, et al., "Simplified staurosporine analogs as potent JAK inhibitors", Bioorg. Med Chem Letters, 2007, 17(2): 326-331.

Chen, et al., "Development of pyrimidine-based inhibitors of Janus tyrosine kinase 3", Bioorg. Med. Chem. Letters, 2006, 16(21): 5633-5638.

Firestein, "Evolving concepts of rheumatoid arthritis", Nature, 2003, 423: 356-361.

Asakura, et al., "Recent advances in basic and clinical aspects of inflammatory bowel disease: Which steps in the mucosal inflammation should we block for the treatment of inflammatory bowel disease", World J. Gastroenterol., 2007, 13(15): 2145-9.

Schon, et al., "Psoriasis", New Engl J Med, 2005, 352:1899-1912.

D'Cruz, et al., "Systemic lupus erythematosus", Lancet, 2007, 369(9561): 587-596.

Hemmer, et al., "New Concepts in the Immunopathogenesis of Multiple Sclerosis", Nat. Rev. Neuroscience, 2002, 3: 291-301.

Jackson, "Management of dysfunctional tear syndrome: a Canadian consensus", Canadian Journal Ophthalmology, 2009, 44(4): 385-394.

Lemp, "The Definition and Classification of Dry Eye Disease: Report of the Definition and Classification Subcommittee of the International Dry Eye Workshop (2007)", The Ocular Surface, 2007, 5(2): 75-92.

Srivastava, et al., "Uveitis: Mechanisms and recent advances in therapy", Clinica Chimica Acta, doi:10.1016/j.cca.2010.04.017 (2010).

Hanahan, et al., "The Hallmarks of Cancer", Cell, 2000, 100: 57-70.

Jeong, et al., "Somatic Mutations of JAK1 and JAK3 in Acute Leukemias and Solid Cancers", Clin. Cancer Res., 2008, 14:12 3716-3721.

Schutz-Geshwendener, et al., "Quantitative, Two-Color Western Blot Detection With Infrared Fluorescence." Published May 2004 by LI-COR Biosciences, www.licor.com.

Cetkovic-Cvrlje, et al., "Dual targeting of Bruton's tyrosine kinase and Janus Kinase 3 with rationally designed inhibitors prevents graft-versus-host disease (GVHD) in a murine allogeneic bone marrow transplantation model", British Journal of Haematology, 2004, 126: 821-827.

US Office Action Response dated Sep. 22, 2014 for case: U.S. Appl. No. 13/816,555.

* cited by examiner

HETEROCYCLYL PYRAZOLOPYRIMIDINE ANALOGUES AS JAK INHIBITORS

CROSS REFERENCE TO RELATED APPLICATIONS

The present application is a National Stage Application claiming the priority of co-pending PCT Application No. PCT/EP2010/065700 filed Oct. 19, 2010, which in turn, claims priority from European Patent Application No. 09173535.7 filed Oct. 20, 2009, and U.S. Provisional Application Serial No. 61/375,358 filed Aug. 20, 2010. Applicants claim the benefits of 35 U.S.C. §120 as to the PCT application and priority under 35 U.S.C. §119 as to the said European Patent application and the said U.S. Provisional application, and the entire disclosures of all applications are incorporated herein by reference in their entireties.

The present invention relates to a novel class of kinase inhibitors, including pharmaceutically acceptable salts, prodrugs and metabolites thereof, which are useful for modulating protein kinase activity for modulating cellular activities such as signal transduction, proliferation, and cytokine secretion. More specifically the invention provides compounds which inhibit, regulate and/or modulate kinase activity, in particular JAK3 activity, and signal transduction pathways relating to cellular activities as mentioned above. Furthermore, the present invention relates to pharmaceutical compositions comprising said compounds, for example for the treatment or prevention of an immunological, inflammatory, autoimmune, or allergic disorder or disease or a transplant rejection or a Graft-versus host disease and processes for preparing said compounds.

Kinases catalyze the phosphorylation of proteins, lipids, sugars, nucleosides and other cellular metabolites and play key roles in all aspects of eukaryotic cell physiology. Especially, protein kinases and lipid kinases participate in the signaling events which control the activation, growth, differentiation and survival of cells in response to extracellular mediators or stimuli such as growth factors, cytokines or chemokines. In general, protein kinases are classified in two groups, those that preferentially phosphorylate tyrosine residues and those that preferentially phosphorylate serine and/or threonine residues. The tyrosine kinases include membrane-spanning growth factor receptors such as the epidermal growth factor receptor (EGFR) and cytosolic non-receptor kinases such as Janus kinases (JAK).

Inappropriately high protein kinase activity is involved in many diseases including cancer, metabolic diseases, autoimmune or inflammatory disorders. This effect can be caused either directly or indirectly by the failure of control mechanisms due to mutation, overexpression or inappropriate activation of the enzyme. In all of these instances, selective inhibition of the kinase is expected to have a beneficial effect.

One group of kinases that has become a recent focus of drug discovery is the Janus kinase (JAK) family of non-receptor tyrosine kinases. In mammals, the family has four members, JAK1, JAK2, JAK3 and Tyrosine kinase 2 (TYK2). Each protein has a kinase domain and a catalytically inactive pseudo-kinase domain. The JAK proteins bind to cytokine receptors through their amino-terminal FERM (Band-4.1, ezrin, radixin, moesin) domains. After the binding of cytokines to their receptors, JAKs are activated and phosphorylate the receptors, thereby creating docking sites for signalling molecules, especially for members of the signal transducer and activator of transcription (Stat) family (Yamaoka et al., 2004. The Janus kinases (Jaks). Genome Biology 5(12): 253).

In mammals, JAK1, JAK2 and TYK2 are ubiquitously expressed. By contrast, the expression of JAK3 is predominantly in hematopoietic cells and it is highly regulated with cell development and activation (Musso et al., 1995. 181(4): 1425-31).

The study of JAK-deficient cell lines and gene-targeted mice has revealed the essential, nonredundant functions of JAKs in cytokine signalling. JAK1 knockout mice display a perinatal lethal phenotype, probably related to the neurological effects that prevent them from sucking (Rodig et al., 1998. Cell 93(3):373-83). Deletion of the JAK2 gene results in embryonic lethality at embryonic day 12.5 as a result of a defect in erythropoiesis (Neubauer et al., 1998. Cell 93(3): 397-409). Interestingly, JAK3 deficiency was first identified in humans with autosomal recessive severe combined immunodeficiency (SCID) (Macchi et al., 1995. Nature 377(6544): 65-68). JAK3 knockout mice too exhibit SCID but do not display non-immune defects, suggesting that an inhibitor of JAK3 as an immunosuppressant would have restricted effects in vivo and therefore presents a promising drug for immunosuppression (Papageorgiou and Wikman 2004, Trends in Pharmacological Sciences 25(11):558-62).

Activating mutations for JAK3 have been observed in acute megakaryoblastic leukemia (AMKL) patients (Walters et al., 2006. Cancer Cell 10(1):65-75). These mutated forms of JAK3 can transform Ba/F3 cells to factor-independent growth and induce features of megakaryoblastic leukemia in a mouse model.

Diseases and disorders associated with JAK3 inhibition are further described, for example in WO 01/42246 and WO 2008/060301.

Several JAK3 inhibitors have been reported in the literature which may be useful in the medical field (O'Shea et al., 2004. Nat. Rev. Drug Discov. 3(7):555-64). A potent JAK3 inhibitor (CP-690,550) was reported to show efficacy in an animal model of organ transplantation (Changelian et al., 2003, Science 302(5646):875-888) and clinical trials (reviewed in: Pesu et al., 2008. Immunol. Rev. 223, 132-142). The CP-690, 550 inhibitor is not selective for the JAK3 kinase and inhibits JAK2 kinase with almost equipotency (Jiang et al., 2008, J. Med. Chem. 51(24):8012-8018). It is expected that a selective JAK3 inhibitor that inhibits JAK3 with greater potency than JAK2 may have advantageous therapeutic properties, because inhibition of JAK2 can cause anemia (Ghoreschi et al., 2009. Nature Immunol. 4, 356-360).

Pyrimidine derivatives exhibiting JAK3 and JAK2 kinase inhibiting activities are described in WO-A 2008/009458. Pyrimidine compounds in the treatment of conditions in which modulation of the JAK pathway or inhibition of JAK kinases, particularly JAK3 are described in WO-A 2008/118822 and WO-A 2008/118823.

Fluoro substituted pyrimidine compounds as JAK3 inhibitors are described in International patent application with application N° PCT/EP2010/054685.

Even though JAK inhibitors are known in the art there is a need for providing additional JAK inhibitors having at least partially more effective pharmaceutically relevant properties, like activity, selectivity especially over JAK2 kinase, and ADME properties.

Thus, an object of the present invention is to provide a new class of compounds as JAK inhibitors which preferably show selectivity over JAK2 and may be effective in the treatment or prophylaxis of disorders associated with JAK.

Accordingly, the present invention provides compounds of formula (I)

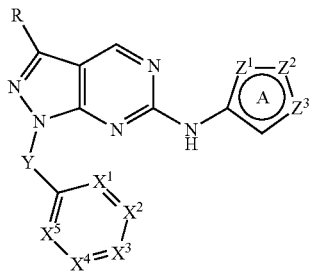

or a pharmaceutically acceptable salt, prodrug or metabolite thereof, wherein

R is H or F;

Ring A is a 5 membered aromatic heterocycle in which $Z^1$, $Z^2$ and $Z^3$ are independently selected from the group consisting of $C(R^1)$, N, $N(R^1)$, O and S, provided that at least one of $Z^1$, $Z^2$, $Z^3$ is N;

Each $R^1$ is independently H, halogen; CN; $C(O)OR^2$; $OR^2$; $C(O)R^2$; $C(O)N(R^2R^{2a})$; $S(O)_2N(R^2R^{2a})$; $S(O)N(R^2R^{2a})$; $S(O)_2R^2$; $S(O)R^2$; $N(R^2)S(O)_2N(R^{2a}R^{2b})$; $N(R^2)S(O)N(R^{2a}R^{2b})$; $SR^2$; $N(R^2R^{2a})$; $NO_2$; $OC(O)R^2$; $N(R^2)C(O)R^{2a}$; $N(R^2)S(O)_2R^{2a}$; $N(R^2)S(O)R^{2a}$; $N(R^2)C(O)N(R^{2a}R^{2b})$; $N(R^2)C(O)OR^{2a}$; $OC(O)N(R^2R^{2a})$; $T^1$; $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more $R^3$, which are the same or different;

$R^2$, $R^{2a}$, $R^{2b}$ are independently selected from the group consisting of H; $T^1$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^3$, which are the same or different;

$R^3$ is halogen; CN; $C(O)OR^4$; $OR^4$; $C(O)R^4$; $C(O)N(R^4R^{4a})$; $S(O)_2N(R^4R^{4a})$; $S(O)N(R^4R^{4a})$; $S(O)_2R^4$; $S(O)R^4$; $N(R^4)S(O)_2N(R^{4a}R^{4b})$; $N(R^4)S(O)N(R^{4a}R^{4b})$; $SR^4$; $N(R^4R^{4a})$; $NO_2$; $OC(O)R^4$; $N(R^4)C(O)R^{4a}$; $N(R^4)S(O)_2R^{4a}$; $N(R^4)S(O)R^{4a}$; $N(R^4)C(O)N(R^{4a}R^{4b})$; $N(R^4)C(O)OR^{4a}$; $OC(O)N(R^4R^{4a})$; or $T^1$;

$R^4$, $R^{4a}$, $R^{4b}$ independently selected from the group consisting of H; $T^1$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;

$T^1$ is $C_{3-7}$ cycloalkyl; or saturated 4 to 7 membered heterocyclyl, wherein $T^1$ is optionally substituted with one or more $R^{10}$, which are the same or different;

Y is $(C(R^5R^{5a}))_n$;

n is 0, 1, 2, 3 or 4;

$R^5$, $R^{5a}$ are independently selected from the group consisting of H; and unsubstituted $C_{1-6}$ alkyl; or jointly form oxo (=O);

Optionally, $R^5$, $R^{5a}$ are joined to form an unsubstituted $C_{3-7}$ cycloalkyl;

$X^1$ is $C(R^6)$ or N; $X^2$ is $C(R^{6a})$ or N; $X^3$ is $C(R^{6b})$ or N; $X^4$ is $C(R^{6c})$ or N; $X^5$ is $C(R^{6d})$ or N, provided that at most two of $X^1$, $X^2$, $X^3$, $X^4$, $X^5$ are N;

$R^6$, $R^{6a}$, $R^{6b}$, $R^{6c}$, $R^{6d}$ are independently selected from the group consisting of H; halogen; CN; $C(O)OR^7$; $OR^7$; $C(O)R^7$; $C(O)N(R^7R^{7a})$; $S(O)_2N(R^7R^{7a})$; $S(O)N(R^7R^{7a})$; $S(O)_2R^7$; $S(O)R^7$; $N(R^7)S(O)_2N(R^{7a}R^{7b})$; $N(R^7)S(O)N(R^{7a}R^{7b})$; $SR^7$; $N(R^7R^{7a})$; $NO_2$; $OC(O)R^7$; $N(R^7)C(O)R^{7a}$; $N(R^7)S(O)_2R^{7a}$; $N(R^7)S(O)R^{7a}$; $N(R^7)C(O)N(R^{7a}R^{7b})$; $N(R^7)C(O)OR^{7a}$; $OC(O)N(R^7R^{7a})$; $T^2$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{11}$, which are the same or different;

Optionally one of the pairs $R^6/R^{6a}$, $R^{6a}/R^{6b}$ is joined to form a ring $T^3$;

$R^7$, $R^{7a}$, $R^{7b}$ are independently selected from the group consisting of H; $T^2$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^8$, which are the same or different;

$R^8$ is halogen; CN; $C(O)OR^9$; $OR^9$; $C(O)R^9$; $C(O)N(R^9R^{9a})$; $S(O)_2N(R^9R^{9a})$; $S(O)N(R^9R^{9a})$; $S(O)_2R^9$; $S(O)R^9$; $N(R^9)S(O)_2N(R^{9a}R^{9b})$; $N(R^9)S(O)N(R^{9a}R^{9b})$; $SR^9$; $N(R^9R^{9a})$; $NO_2$; $OC(O)R^9$; $N(R^9)C(O)R^{9a}$; $N(R^9)S(O)_2R^{9a}$; $N(R^9)S(O)R^{9a}$; $N(R^9)C(O)N(R^{9a}R^{9b})$; $N(R^9)C(O)OR^{9a}$; $OC(O)N(R^9R^{9a})$; or $T^2$;

$R^9$, $R^{9a}$, $R^{9b}$ are independently selected from the group consisting of H; $T^2$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{12}$, which are the same or different;

$R^{10}$ is halogen; CN; $C(O)OR^{13}$; $OR^{13}$; oxo (=O), where the ring is at least partially saturated; $C(O)R^{13}$; $C(O)N(R^{13}R^{13a})$; $S(O)_2N(R^{13}R^{13a})$; $S(O)N(R^{13}R^{13a})$; $S(O)_2R^{13}$; $S(O)R^{13}$; $N(R^{13})S(O)_2N(R^{13a}R^{13b})$; $N(R^{13})S(O)N(R^{13a}R^{13b})$; $SR^{13}$; $N(R^{13}R^{13a})$; $NO_2$; $OC(O)R^{13}$; $N(R^{13})C(O)R^{13a}$; $N(R^{13})S(O)_2R^{13a}$; $N(R^{13})S(O)R^{13a}$; $N(R^{13})C(O)N(R^{13a}R^{13b})$; $N(R^{13})C(O)OR^{13a}$; $OC(O)N(R^{13}R^{13a})$; $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more $R^{14}$, which are the same or different;

$R^{13}$, $R^{13a}$, $R^{13b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{14}$, which are the same or different;

$R^{11}$, $R^{12}$ are independently selected from the group consisting of halogen; CN; $C(O)OR^{15}$; $OR^{15}$; $C(O)R^{15}$; $C(O)N(R^{15}R^{15a})$; $S(O)_2N(R^{15}R^{15a})$; $S(O)N(R^{15}R^{15a})$; $S(O)_2R^{15}$; $S(O)R^{15}$; $N(R^{15})S(O)_2N(R^{15a}R^{15b}))$; $N(R^{15})S(O)N(R^{15a}R^{15b}))$; $SR^{15}$; $N(R^{15}R^{15a})$; $NO_2$; $OC(O)R^{15}$; $N(R^{15})C(O)R^{15a}$; $N(R^{15})S(O)_2R^{15a}$; $N(R^{15})S(O)R^{15a}$; $N(R^{15})C(O)N(R^{15a}R^{15b})$; $N(R^{15})C(O)OR^{15a}$; $OC(O)N(R^{15}R^{15a})$; or $T^2$;

$R^{15}$, $R^{15a}$, $R^{15b}$ are independently selected from the group consisting of H; $T^2$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;

$R^{14}$ is halogen; CN; $C(O)OR^{16}$; $OR^{16}$; $C(O)R^{16}$; $C(O)N(R^{16}R^{16a})$; $S(O)_2N(R^{16}R^{16a})$; $S(O)N(R^{16}R^{16a})$; $S(O)_2R^{16}$; $S(O)R^{16}$; $N(R^{16})S(O)_2N(R^{16a}R^{16b})$; $N(R^{16})S(O)N(R^{16a}R^{16b})$; $SR^{16}$; $N(R^{16}R^{16a})$; $NO_2$; $OC(O)R^{16}$; $N(R^{16})C(O)R^{16a}$; $N(R^{16})S(O)_2R^{16a}$; $N(R^{16})S(O)R^{16a}$;

$R^{16}$, $R^{16a}$, $R^{16b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;

$T^2$ is phenyl; naphthyl; indenyl; indanyl; $C_{3-7}$ cycloalkyl; 4 to 7 membered heterocyclyl; or 7 to 11 membered heterobicyclyl, wherein $T^2$ is optionally substituted with one or more $R^{17}$, which are the same or different;

$T^3$ is phenyl; $C_{3-7}$ cycloalkyl; or 4 to 7 membered heterocyclyl, wherein $T^3$ is optionally substituted with one or more $R^{18}$, which are the same or different;

$R^{17}$, $R^{18}$ are independently selected from the group consisting of halogen; CN; $C(O)OR^{19}$; $OR^{19}$; oxo (=O), where the ring is at least partially saturated; $C(O)R^{19}$; $C(O)N(R^{19}R^{19a})$; $S(O)_2N(R^{19}R^{19a})$; $S(O)N(R^{19}R^{19a})$; $S(O)_2R^{19}$; $S(O)R^{19}$; $N(R^{19})S(O)_2N(R^{19a}R^{19})$; $N(R^{19})S(O)N(R^{19a}R^{19b})$; $SR^{19}$; $N(R^{19}R^{19a})$; $NO_2$; $OC(O)R^{19}$; $N(R^{19})C(O)R^{19a}$; $N(R^{19})S(O)_2R^{19a}$; $N(R^{19})S(O)R^{19a}$; $N(R^{19})C(O)N(R^{19a}R^{19b})$; $N(R^{19})C(O)OR^{19a}$; $OC(O)N(R^{19}R^{19a})$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{20}$, which are the same or different;

$R^{19}$, $R^{19a}$, $R^{19b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{20}$, which are the same or different;

$R^{20}$ is halogen; CN; $C(O)OR^{21}$; $OR^{21}$; $C(O)R^{21}$; $C(O)N(R^{21}R^{21a})$; $S(O)_2N(R^{21}R^{21a})$; $S(O)N(R^{21}R^{21a})$; $S(O)_2R^{21}$; $S(O)R^{21}$; $N(R^{21})S(O)_2N(R^{21a}R^{21b})$; $N(R^{21})S(O)N(R^{21a}R^{21b})$; $SR^{21}$; $N(R^{21}R^{21a})$; $NO_2$; $OC(O)R^{21}$; $N(R^{21})C(O)R^{21a}$; $N(R^{21})S(O)_2R^{21a}$; $N(R^{21})S(O)R^{21a}$; $N(R^{21})C(O)N(R^{21a}R^{21b})$; $N(R^{21})C(O)OR^{21a}$; or $OC(O)N(R^{21}R^{21a})$;

$R^{21}$, $R^{21a}$, $R^{21b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different.

In case a variable or substituent can be selected from a group of different variants and such variable or substituent occurs more than once the respective variants can be the same or different.

Within the meaning of the present invention the terms are used as follows:

"Alkyl" means a straight-chain or branched hydrocarbon chain. Each hydrogen of an alkyl carbon may be replaced by a substituent as further specified.

"Alkenyl" means a straight-chain or branched hydrocarbon chain that contains at least one carbon-carbon double bond. Each hydrogen of an alkenyl carbon may be replaced by a substituent as further specified.

"Alkynyl" means a straight-chain or branched hydrocarbon chain that contains at least one carbon-carbon triple bond. Each hydrogen of an alkynyl carbon may be replaced by a substituent as further specified.

"$C_{1-4}$ alkyl" means an alkyl chain having 1-4 carbon atoms, e.g. if present at the end of a molecule: methyl, ethyl, n-propyl, isopropyl, n-butyl, isobutyl, sec-butyl, tert-butyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-4}$ alkyl carbon may be replaced by a substituent as further specified.

"$C_{1-6}$ alkyl" means an alkyl chain having 1-6 carbon atoms, e.g. if present at the end of a molecule: $C_{1-4}$ alkyl, methyl, ethyl, n-propyl, isopropyl, n-butyl, isobutyl, sec-butyl; tert-butyl, n-pentyl, n-hexyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-6}$ alkyl carbon may be replaced by a substituent as further specified.

"$C_{2-6}$ alkenyl" means an alkenyl chain having 2 to 6 carbon atoms, e.g. if present at the end of a molecule: —$CH$=$CH_2$, —$CH$=$CH$—$CH_3$, —$CH_2$—$CH$=$CH_2$, —$CH$=$CH$—$CH_2$—$CH_3$, —$CH$=$CH$—$CH$=$CH_2$, or e.g. —$CH$=$CH$—, when two moieties of a molecule are linked by the alkenyl group. Each hydrogen of a $C_{2-6}$ alkenyl carbon may be replaced by a substituent as further specified.

"$C_{2-6}$ alkynyl" means an alkynyl chain having 2 to 6 carbon atoms, e.g. if present at the end of a molecule: —$C$≡$CH$, —$CH_2$—$C$≡$CH$, $CH_2$—$CH_2$—$C$≡$CH$, $CH_2$—$C$≡$C$—$CH_3$, or e.g. —$C$≡$C$— when two moieties of a molecule are linked by the alkynyl group. Each hydrogen of a $C_{2-6}$ alkynyl carbon may be replaced by a substituent as further specified.

"$C_{3-7}$ cycloalkyl" or "$C_{3-7}$ cycloalkyl ring" means a cyclic alkyl chain having 3-7 carbon atoms, e.g. cyclopropyl, cyclobutyl, cyclopentyl, cyclohexyl, cyclohexenyl, cycloheptyl. Preferably, cyloalkyl refers to cyclopropyl, cyclobutyl, cyclopentyl, cyclohexyl, or cycloheptyl. Each hydrogen of a cycloalkyl carbon may be replaced by a substituent as further specified. The term "$C_{3-5}$ cycloalkyl" or "$C_{3-5}$ cycloalkyl ring" is defined accordingly.

"Halogen" means fluoro, chloro, bromo or iodo. It is generally preferred that halogen is fluoro or chloro.

"4 to 7 membered heterocyclyl" or "4 to 7 membered heterocycle" means a ring with 4, 5, 6 or 7 ring atoms that may contain up to the maximum number of double bonds (aromatic or non-aromatic ring which is fully, partially or unsaturated) wherein at least one ring atom up to 4 ring atoms are replaced by a heteroatom selected from the group consisting of sulfur (including —$S(O)$—, —$S(O)_2$—), oxygen and nitrogen (including =$N(O)$—) and wherein the ring is linked to the rest of the molecule via a carbon or nitrogen atom. Examples for a 4 to 7 membered heterocycles are azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine. The term "5 to 6 membered heterocyclyl" or "5 to 6 membered heterocycle" is defined accordingly.

"Saturated 4 to 7 membered heterocyclyl" or "saturated 4 to 7 membered heterocycle" means fully saturated "4 to 7 membered heterocyclyl" or "4 to 7 membered heterocycle".

"5 membered aromatic heterocyclyl" or "5 membered aromatic heterocycle" means a heterocycle derived from cyclopentadienyl, where at least one carbon atom is replaced by a heteoatom selected from the group consisting of sulfur (including —$S(O)$—, —$S(O)_2$—), oxygen and nitrogen (including =$N(O)$—). Examples for such heterocycles are furan, thiophene, pyrrole, imidazole, pyrazole, oxazole, isoxazole, thiazole, isothiazole, thiadiazole, triazole, tetrazole.

"7 to 11 membered heterobicyclyl" or "7 to 11 membered heterobicycle" means a heterocyclic system of two rings with 7 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —$S(O)$—, —$S(O)_2$—), oxygen and nitrogen (including =$N(O)$—) and wherein the ring is linked to the rest of the molecule via a carbon or nitrogen atom. Examples for a 7 to 11 membered heterobicycle are indole, indoline, benzofuran, benzothiophene, benzoxazole, benzisoxazole, benzothiazole, benzisothiazole, benzimidazole, benzimidazo line, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 9 to 11 membered heterobicycle also includes spiro structures of two rings like 1,4-dioxa-8-azaspiro[4.5]decane or bridged heterocycles like 8-aza-bicyclo[3.2.1]octane.

Preferred compounds of formula (I) are those compounds in which one or more of the residues contained therein have the meanings given below, with all combinations of preferred substituent definitions being a subject of the present invention. With respect to all preferred compounds of the formula (I) the present invention also includes all tautomeric and stereoisomeric forms and mixtures thereof in all ratios, and their pharmaceutically acceptable salts.

In preferred embodiments of the present invention, the substituents mentioned below independently have the following meaning. Hence, one or more of these substituents can have the preferred or more preferred meanings given below.

Preferably, R is H.

Preferably, ring A is a pyrazole, a pyrrole or an imidazole ring. Also preferably, ring A is a pyrazole, an oxazole, or an isoxazole ring. More preferably ring A is a 4-pyrazole.

Preferably, 0, 1, or 2 $R^1$, which are the same or different, are other than H.

Preferably, $R^1$ is $OR^2$ or $C_{1-4}$ alkyl, which is optionally substituted with 1 or 2 $R^3$, which are the same or different.

Even more preferably, $R^1$ is $C_{1-4}$ alkyl.

Preferably, $R^3$ is halogen; CN; $OR^4$; $C(O)N(R^4R^{4a})$; or $C(O)T^1$, wherein $T^1$ is an unsubstituted 4 to 7 membered heterocycle (more preferably morpholine) containing at least one ring nitrogen atom which is attached to C(O). Preferably, $R^3$ is halogen; $OR^4$; $C(O)N(R^4R^{4a})$; $N(R^4R^{4a})$; or $T^1$.

Preferably, $T^1$ is unsubstituted or substituted with one or more unsubstituted $C_{1-6}$ alkyl, which are the same or different.

Preferably, n is 0, 1 or 2. More preferably, 0 or 1.

Preferably, $R^5$, $R^{5a}$ are H.

Preferably, none or one of $X^1$, $X^2$, $X^3$, $X^4$, $X^5$ is N.

In one preferred embodiment $R^6$, $R^{6a}$, $R^{6b}$, $R^{6c}$, $R^{6d}$ are H.

In an alternative preferred embodiment at least one of $R^6$, $R^{6a}$, $R^{6b}$, $R^{6c}$, $R^{6d}$ is other than H. More preferably, 1, 2 or 3 of $R^6$, $R^{6a}$, $R^{6b}$, $R^{6c}$, $R^{6d}$ are other than H. Even more preferably, $R^6$, $R^{6a}$, $R^{6b}$, $R^{6c}$, $R^{6d}$ are independently selected from the group consisting of H; halogen; CN; $C(O)OR^7$; $C(O)N(R^7R^{7a})$; $S(O)_2NR^7R^{7a}$; and $N(R^7)S(O)_2R^{7a}$, provided that 1 or 2 of $R^6$, $R^{6a}$, $R^{6b}$, $R^{6c}$, $R^{6d}$ are other than H. Even more preferably, $R^6$, $R^{6a}$, $R^{6b}$, $R^{6c}$, $R^{6d}$ are independently selected from the group consisting of H; halogen; CN; $C(O)N(R^7R^{7a})$; and $T^1$, provided that 1 or 2 of $R^6$, $R^{6a}$, $R^{6b}$, $R^{6c}$, $R^{6d}$ are other than H.

In one preferred embodiment one of the pairs $R^6/R^{6a}$, $R^{6a}/R^{6b}$ is joined to form a ring $T^3$. In another preferred embodiment none of the pairs $R^6/R^{6a}$, $R^{6a}/R^{6b}$ is joined to form a ring $T^3$.

Preferably, $R^7$, $R^{7a}$, $R^{7b}$ are independently selected from the group consisting of H; and unsubstituted $C_{1-4}$ alkyl.

Preferably, in case at least one of $R^6$, $R^{6a}$, $R^{6b}$, $R^{6c}$, $R^{6d}$ is other than H, in formula (I) Y, $X^1$, $X^2$, $X^3$, $X^4$, $X^5$ are selected to give formula (Ia)

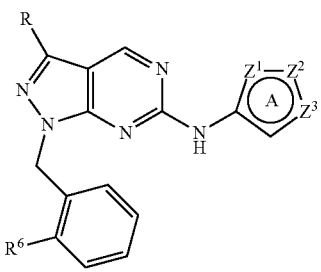

(Ia)

provided that $R^6$ is other than H.

Preferably, in case at least one of $R^6$, $R^{6a}$, $R^{6b}$, $R^{6c}$, $R^{6d}$ is other than H, in formula (I) Y, $X^1$, $X^2$, $X^3$, $X^4$, $X^5$ are selected to give formula (Ib)

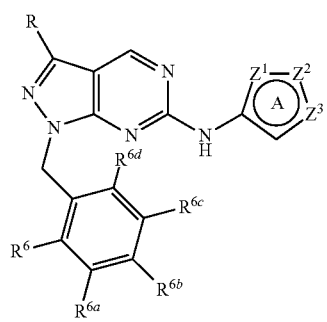

(Ib)

provided that $R^6$ and one of $R^{6a}$, $R^{6b}$, $R^{6c}$, $R^{6d}$ are other than H. Even more preferably, $R^{6b}$ is H.

Preferably, in case at least one of $R^6$, $R^{6a}$, $R^{6b}$, $R^{6c}$, $R^{6d}$ is other than H, in formula (I) Y, $X^1$, $X^2$, $X^3$, $X^4$, $X^5$ are selected to give formula (Ic)

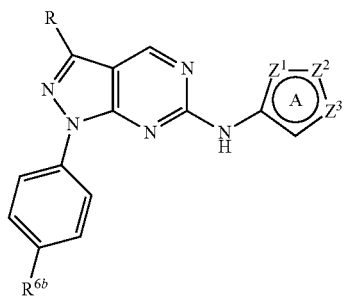

(Ic)

provided that $R^{6b}$ is other than H.

Preferably, $R^{11}$ is halogen.

Preferably, $R^{12}$ is halogen.

Preferably, $T^2$ is $C_{3-7}$ cycloalkyl; or saturated 4 to 7 membered heterocyclyl, wherein $T^2$ is optionally substituted with one or more unsubstituted $C_{1-6}$ alkyl, which are the same or different.

Compounds of formula (I) in which some or all of the above-mentioned groups have the preferred meanings are also an object of the present invention.

Further preferred compounds of the present invention are selected from the group consisting of 2-((6-(1-Methyl-1H-pyrazol-4-ylamino)-1H-pyrazolo[3,4-d]pyrimidin-1-yl)methyl)benzonitrile;

1-(2-Fluorobenzyl)-N-(1-methyl-1H-pyrazol-4-yl)-1H-pyrazolo[3,4-d]pyrimidin-6-amine;

2-((6-(1-Methyl-1H-pyrazol-3-ylamino)-1H-pyrazolo[3,4-d]pyrimidin-1-yl)methyl)benzonitrile;

2-((6-(1H-pyrazol-4-ylamino)-1H-pyrazolo[3,4-d]pyrimidin-1-yl)methyl)benzonitrile;

2-((6-(Isoxazol-4-ylamino)-1H-pyrazolo[3,4-d]pyrimidin-1-yl)methyl)benzonitrile;

2-((6-(1,3-Dimethyl-1H-pyrazol-4-ylamino)-1H-pyrazolo[3,4-d]pyrimidin-1-yl)methyl)benzonitrile;

2-((6-(1-Ethyl-3-methyl-1H-pyrazol-4-ylamino)-1H-pyrazolo[3,4-d]pyrimidin-1-yl)methyl)benzonitrile;

2-((6-(Isoxazol-3-ylamino)-1H-pyrazolo[3,4-d]pyrimidin-1-yl)methyl)benzonitrile;

2-((6-(1,5-Dimethyl-1H-pyrazol-3-ylamino)-1H-pyrazolo [3,4-d]pyrimidin-1-yl)methyl)benzonitrile;
2-((6-(1-(2-Methoxyethyl)-1H-pyrazol-4-ylamino)-1H-pyrazolo[3,4-d]pyrimidi-1-yl)methyl)benzonitrile;
2-((6-(1-Ethyl-1H-pyrazol-4-ylamino)-1H-pyrazolo[3,4-d] pyrimidin-1-yl)methyl)benzonitrile;
2-((6-(1-Isopropyl-1H-pyrazol-4-ylamino)-1H-pyrazolo[3, 4-d]pyrimidin-1-yl)methyl)benzonitrile;
2-(4-(1-(2-Cyanobenzyl)-1H-pyrazolo[3,4-d]pyrimidin-6-ylamino)-1H-pyrazol-1-yl)-N-methylacetamide;
2-((6-(1-(2-Morpholino-2-oxoethyl)-1H-pyrazol-4-ylamino)-1H-pyrazolo[3,4-d]pyrimidin-1-yl)methyl)benzonitrile;
2-((6-(1-(2-Cyanoethyl)-1H-pyrazol-4-ylamino)-1H-pyrazolo[3,4-d]pyrimidin-1-yl)methyl)benzonitrile;
2-((6-(1-Methyl-1H-pyrazol-4-ylamino)-1H-pyrazolo[3,4-d]pyrimidin-1-yl)methyl)benzamide;
N-Methyl-N-(4-(6-(1-methyl-1H-pyrazol-4-ylamino)-1H-pyrazolo[3,4-d]pyrimidin-1-yl)phenyl)methanesulfonamide;
N-(4-(6-(1-Methyl-1H-pyrazol-4-ylamino)-1H-pyrazolo[3, 4-d]pyrimidin-1-yl)phenyl)methanesulfonamide;
2-((6-(1-Isopropyl-1H-pyrazol-3-ylamino)-1H-pyrazolo[3, 4-d]pyrimidin-1-yl)methyl)benzonitrile;
2-((6-(1-(3-Cyanopropyl)-1H-pyrazol-4-ylamino)-1H-pyrazolo[3,4-d]pyrimidin-1-yl)methyl)benzonitrile;
2-((6-(3-Methyl-1-propyl-1H-pyrazol-4-ylamino)-1H-pyrazolo[3,4-d]pyrimidin yl)methyl)benzonitrile;
2-((6-(1-(2,2-Difluoroethyl)-3-methyl-1H-pyrazol-4-ylamino)-1H-pyrazolo[3,4-d]pyrimidin-1-yl)methyl)benzonitrile;
2-((6-(1-(2-methoxyethyl)-3-methyl-1H-pyrazol-4-ylamino)-1H-pyrazolo[3,4-d]pyrimidin-1-yl)methyl)benzonitrile;
2-((6-(1-(2,2-Difluoroethyl)-3-methoxy-1H-pyrazol-4-ylamino)-1H-pyrazolo[3,4-d]pyrimidin-1-yl)methyl)benzonitrile;
2-((6-(1-(2-Hydroxyethyl)-1H-pyrazol-4-ylamino)-1H-pyrazolo[3,4-d]pyrimidin-1-yl)methyl)benzonitrile;
1-(1-(2-Fluorophenyl)ethyl)-N-(1-methyl-1H-pyrazol-4-yl)-1H-pyrazolo[3,4-d]pyrimidin-6-amine;
1-(2-Chlorobenzyl)-N-(1-methyl-1H-pyrazol-4-yl)-1H-pyrazolo[3,4-d]pyrimidin-6-amine;
1-(2-fluorobenzyl)-N-(1-(2-methoxyethyl)-1H-pyrazol-4-yl)-1H-pyrazolo[3,4-d]pyrimidin-6-amine;
1-(2,6-Difluorobenzyl)-N-(1-methyl-1H-pyrazol-4-yl)-1H-pyrazolo[3,4-d]pyrimidin-6-amine;
1-(2,5-Difluorobenzyl)-N-(1-methyl-1H-pyrazol-4-yl)-1H-pyrazolo[3,4-d]pyrimidin-6-amine;
1-(2,3-Difluorobenzyl)-N-(1-methyl-1H-pyrazol-4-yl)-1H-pyrazolo[3,4-d]pyrimidin-6-amine;
2-(4-(1-(2,5-Difluorobenzyl)-1H-pyrazolo[3,4-d]pyrimidin-6-ylamino)-1H-pyrazol-1-yl)ethanol;
2-(4-(1-(2,3-Difluorobenzyl)-1H-pyrazolo[3,4-d]pyrimidin-6-ylamino)-1H-pyrazol-1-yl)ethanol;
2-(4-(1-(2-Fluorobenzyl)-1H-pyrazolo[3,4-d]pyrimidin-6-ylamino)-1H-pyrazol-1-yl)ethanol;
4-(6-(1-Methyl-1H-pyrazol-4-ylamino)-1H-pyrazolo[3,4-d] pyrimidin-1-yl)benzenesulfonamide;
2-((6-(1-(2,2-difluoro ethyl)-3-methoxy-1H-pyrazol-4-ylamino)-1H-pyrazolo[3,4-d]pyrimidin-1-yl)methyl)benzamide;
2-((6-(1,5-Dimethyl-1H-pyrazol-4-ylamino)-1H-pyrazolo [3,4-d]pyrimidin-1-yl)methyl)benzonitrile;
2-((6-(3-methoxy-1-(2,2,2-trifluoro ethyl)-1H-pyrazol-4-ylamino)-1H-pyrazolo[3,4-d]pyrimidin-1-yl)methyl)benzonitrile;
2-((6-(1-(2,2-Difluoroethyl)-1H-pyrazol-4-ylamino)-1H-pyrazolo[3,4-d]pyrimidin-1-yl)methyl)benzonitrile;
N-methyl-4-(6-(1-methyl-1H-pyrazol-4-ylamino)-1H-pyrazolo[3,4-d]pyrimidin-1-yl)benzenesulfonamide;
2-((6-(1-Methyl-1H-pyrazol-4-ylamino)-1H-pyrazolo[3,4-d]pyrimidin-1-yl)methyl)benzoic acid;
2-((6-(1-(2,2-Difluoroethyl)-1H-pyrazol-4-ylamino)-1H-pyrazolo[3,4-d]pyrimidin-1-yl)methyl)benzamide;
2-((6-(1-(2,2-Difluoroethyl)-3-methyl-1H-pyrazol-4-ylamino)-1H-pyrazolo[3,4-d]pyrimidin-1-yl)methyl)benzamide;
2-((6-(1-(2-Hydroxyethyl)-3-methoxy-1H-pyrazol-4-ylamino)-1H-pyrazolo[3,4-d]pyrimidin-1-yl)methyl)benzonitrile;
1-((2-Fluoropyridin-3-yl)methyl)-N-(1-methyl-1H-pyrazol-4-yl)-1H-pyrazolo[3,4-d]pyrimidin-6-amine;
1-((3-Fluoropyridin-4-yl)methyl)-N-(1-methyl-1H-pyrazol-4-yl)-1H-pyrazolo[3,4-d]pyrimidin-6-amine;
1-(2,4-Difluorobenzyl)-N-(1-methyl-1H-pyrazol-4-yl)-1H-pyrazolo[3,4-d]pyrimidin-6-amine;
N-(1-Methyl-1H-pyrazol-4-yl)-1-phenethyl-1H-pyrazolo[3, 4-d]pyrimidin-6-amine;
2-(4-(1-(2-Fluorobenzyl)-1H-pyrazolo[3,4-d]pyrimidin-6-ylamino)-3-methoxy-1H-pyrazol-1-yl)ethanol;
2-(4-(1-(2,3-Difluorobenzyl)-1H-pyrazolo[3,4-d]pyrimidin-6-ylamino)-3-methoxy-1H-pyrazol-1-yl)ethanol;
2-(4-(1-(2,5-Difluorobenzyl)-1H-pyrazolo[3,4-d]pyrimidin-6-ylamino)-3-methoxy-1H-pyrazol-1-yl)ethanol;
4-Fluoro-2-((6-(1-methyl-1H-pyrazol-4-ylamino)-1H-pyrazolo[3,4-d]pyrimidin-1-yl)methyl)benzonitrile;
4-fluoro-2-((6-(1-methyl-1H-pyrazol-4-ylamino)-1H-pyrazolo[3,4-d]pyrimidin-1-yl)methyl)benzamide;
N-(6-(6-(1-methyl-1H-pyrazol-4-ylamino)-1H-pyrazolo[3, 4-d]pyrimidin-1-yl)pyridin-3-yl)methanesulfonamide;
N-(2-methyl-6-(6-(1-methyl-1H-pyrazol-4-ylamino)-1H-pyrazolo[3,4-d]pyrimidin-1-yl)pyridin-3-yl)methanesulfonamide;
1-(4-fluorophenyl)-N-(1-methyl-1H-pyrazol-4-yl)-1H-pyrazolo[3,4-d]pyrimidin-6-amine;
1-(4-chlorophenyl)-N-(1-methyl-1H-pyrazol-4-yl)-1H-pyrazolo[3,4-d]pyrimidin-6-amine
1-(4-fluoro-3-methoxyphenyl)-N-(1-methyl-1H-pyrazol-4-yl)-1H-pyrazolo[3,4-d]pyrimidin-6-amine;
(R)—N-(1-methyl-1H-pyrazol-4-yl)-1-((6-(3-methylmorpholino)pyridin-2-yl)methyl)-1H-pyrazolo[3,4-d]pyrimidin-6-amine;
1-(4-fluoro-3-methylphenyl)-N-(1-methyl-1H-pyrazol-4-yl)-1H-pyrazolo[3,4-d]pyrimidin-6-amine;
N-(1-methyl-1H-pyrazol-4-yl)-1-(4-(methylsulfonyl)phenyl)-1H-pyrazolo[3,4-d]pyrimidin-6-amine;
1-(2-chloro-5-fluorobenzyl)-N-(1-methyl-1H-pyrazol-4-yl)-1H-pyrazolo[3,4-d]pyrimidin-6-amine;
1-(2-chloro-6-fluorobenzyl)-N-(1-methyl-1H-pyrazol-4-yl)-1H-pyrazolo[3,4-d]pyrimidin-6-amine;
1-(5-chloro-2-fluorobenzyl)-N-(1-methyl-1H-pyrazol-4-yl)-1H-pyrazolo[3,4-d]pyrimidin-6-amine;
N-(1-methyl-1H-pyrazol-4-yl)-1-(2-(trifluoromethyl)benzyl)-1H-pyrazolo[3,4-d]pyrimidin-6-amine;
N-(1-methyl-1H-pyrazol-4-yl)-1-(3-(trifluoromethyl)benzyl)-1H-pyrazolo[3,4-d]pyrimidin-6-amine;
1-(3-fluorobenzyl)-N-(1-methyl-1H-pyrazol-4-yl)-1H-pyrazolo[3,4-d]pyrimidin-6-amine;
3-((6-((1-methyl-1H-pyrazol-4-yl)amino)-1H-pyrazolo[3,4-d]pyrimidin-1-yl)methyl)benzonitrile;
1-(3-methoxybenzyl)-N-(1-methyl-1H-pyrazol-4-yl)-1H-pyrazolo[3,4-d]pyrimidin-6-amine;

1-(3-chlorobenzyl)-N-(1-methyl-1H-pyrazol-4-yl)-1H-pyrazolo[3,4-d]pyrimidin-6-amine;
4-(6-((1-(2,2-difluoroethyl)-3-methoxy-1H-pyrazol-4-yl)amino)-1H-pyrazolo[3,4-d]pyrimidin-1-yl)benzenesulfonamide;
1-(3-chloro-2-fluorobenzyl)-N-(1-methyl-1H-pyrazol-4-yl)-1H-pyrazolo[3,4-d]pyrimidin-6-amine;
2-(4-((1-(2,6-difluorobenzyl)-1H-pyrazolo[3,4-d]pyrimidin-6-yl)amino)-1H-pyrazol-1-yl)ethanol;
N-(1-methyl-1H-pyrazol-4-yl)-1-phenyl-1H-pyrazolo[3,4-d]pyrimidin-6-amine;
N-(2-((6-((1-methyl-1H-pyrazol-4-yl)amino)-1H-pyrazolo[3,4-d]pyrimidin-1-yl)methyl)phenyl)methanesulfonamide;
1-benzyl-N-(1-methyl-1H-pyrazol-4-yl)-1H-pyrazolo[3,4-d]pyrimidin-6-amine;
1-(2-fluorophenethyl)-N-(1-methyl-1H-pyrazol-4-yl)-1H-pyrazolo[3,4-d]pyrimidin-6-amine;
1-(3,4-difluorobenzyl)-N-(1-methyl-1H-pyrazol-4-yl)-1H-pyrazolo[3,4-d]pyrimidin-6-amine;
1-(3,5-difluorobenzyl)-N-(1-methyl-1H-pyrazol-4-yl)-1H-pyrazolo[3,4-d]pyrimidin-6-amine;
3-((6-((1-methyl-1H-pyrazol-4-yl)amino)-1H-pyrazolo[3,4-d]pyrimidin-1-yl)methyl)benzamide;
1-(3-fluorophenethyl)-N-(1-methyl-1H-pyrazol-4-yl)-1H-pyrazolo[3,4-d]pyrimidin-6-amine;
1-(4-fluorophenethyl)-N-(1-methyl-1H-pyrazol-4-yl)-1H-pyrazolo[3,4-d]pyrimidin-6-amine;
N-(1-methyl-1H-pyrazol-4-yl)-1-(3-methylbenzyl)-1H-pyrazolo[3,4-d]pyrimidin-6-amine;
N-(1-methyl-1H-pyrazol-4-yl)-1-(2-methylbenzyl)-1H-pyrazolo[3,4-d]pyrimidin-6-amine;
N-(1-methyl-1H-pyrazol-4-yl)-1-(2-(trifluoromethoxy)benzyl)-1H-pyrazolo[3,4-d]pyrimidin-6-amine;
N-(1-methyl-1H-pyrazol-4-yl)-1-(3-(trifluoromethoxy)benzyl)-1H-pyrazolo[3,4-d]pyrimidin-6-amine;
1-(2-methoxybenzyl)-N-(1-methyl-1H-pyrazol-4-yl)-1H-pyrazolo[3,4-d]pyrimidin-6-amine;
1-(2-fluorobenzyl)-N-(1H-pyrazol-4-yl)-1H-pyrazolo[3,4-d]pyrimidin-6-amine;
1-(4-((1-(2-fluorobenzyl)-1H-pyrazolo[3,4-d]pyrimidin-6-yl)amino)-1H-pyrazol-1-yl)propan-2-ol;
1-(2-fluoro-6-methoxybenzyl)-N-(1-methyl-1H-pyrazol-4-yl)-1H-pyrazolo[3,4-d]pyrimidin-6-amine;
1-(5-fluoro-2-methoxybenzyl)-N-(1-methyl-1H-pyrazol-4-yl)-1H-pyrazolo[3,4-d]pyrimidin-6-amine; (2-((6-((1-methyl-1H-pyrazol-4-yl)amino)-1H-pyrazolo[3,4-d]pyrimidin-1-yl)methyl)phenyl)methanol;
1-(2-fluoro-3-methoxybenzyl)-N-(1-methyl-1H-pyrazol-4-yl)-1H-pyrazolo[3,4-d]pyrimidin-6-amine;
1-(2-fluoro-5-methoxybenzyl)-N-(1-methyl-1H-pyrazol-4-yl)-1H-pyrazolo[3,4-d]pyrimidin-6-amine;
1-(4-((1-(2-fluorobenzyl)-1H-pyrazolo[3,4-d]pyrimidin-6-yl)amino)-1H-pyrazol-1-yl)ethanone;
1-(2-fluorobenzyl)-N-(1-(methylsulfonyl)-1H-pyrazol-4-yl)-1H-pyrazolo[3,4-d]pyrimidin-6-amine;
N-(3-chloro-1H-pyrazol-4-yl)-1-(2-fluorobenzyl)-1H-pyrazolo[3,4-d]pyrimidin-6-amine;
N-(1-methyl-1H-pyrazol-4-yl)-1-(2,3,6-trifluorobenzyl)-1H-pyrazolo[3,4-d]pyrimidin-6-amine;
1-(4-fluorobenzyl)-N-(1-methyl-1H-pyrazol-4-yl)-1H-pyrazolo[3,4-d]pyrimidin-6-amine;
1-(3-isopropylbenzyl)-N-(1-methyl-1H-pyrazol-4-yl)-1H-pyrazolo[3,4-d]pyrimidin-6-amine;
1-(2-isopropylbenzyl)-N-(1-methyl-1H-pyrazol-4-yl)-1H-pyrazolo[3,4-d]pyrimidin-6-amine;
1-(2-(2-methoxyethoxy)benzyl)-N-(1-methyl-1H-pyrazol-4-yl)-1H-pyrazolo[3,4-d]pyrimidin-6-amine;
4-((1-(2-fluorobenzyl)-1H-pyrazolo[3,4-d]pyrimidin-6-yl)amino)-1H-pyrazole-1-carboxamide;
1-(3-fluoro-5-methoxybenzyl)-N-(1-methyl-1H-pyrazol-4-yl)-1H-pyrazolo[3,4-d]pyrimidin-6-amine;
1-benzyl-N-(3-methoxy-1-methyl-1H-pyrazol-4-yl)-1H-pyrazolo[3,4-d]pyrimidin-6-amine;
2-(4-((1-benzyl-1H-pyrazolo[3,4-d]pyrimidin-6-yl)amino)-3-methoxy-1H-pyrazol-1-yl)ethanol;
2-fluoro-3-((6-((1-methyl-1H-pyrazol-4-yl)amino)-1H-pyrazolo[3,4-d]pyrimidin-1-yl)methyl)benzonitrile;
2-fluoro-6-((6-((1-methyl-1H-pyrazol-4-yl)amino)-1H-pyrazolo[3,4-d]pyrimidin-1-yl)methyl)benzonitrile;
1-benzyl-N-(1,5-dimethyl-1H-pyrazol-4-yl)-1H-pyrazolo[3,4-d]pyrimidin-6-amine;
1-benzyl-N-(1,3-dimethyl-1H-pyrazol-4-yl)-1H-pyrazolo[3,4-d]pyrimidin-6-amine;
1-(2-cyclopropylbenzyl)-N-(1-methyl-1H-pyrazol-4-yl)-1H-pyrazolo[3,4-d]pyrimidin-6-amine;
1-(4-((1-(2-fluorobenzyl)-1H-pyrazolo[3,4-d]pyrimidin-6-yl)amino)-1H-pyrazol-1-yl)-2-methylpropan-2-ol;
2-(4-((1-benzyl-1H-pyrazolo[3,4-d]pyrimidin-6-yl)amino)-3-methyl-1H-pyrazol-1-yl)ethanol;
1-(2-(benzyloxy)benzyl)-N-(1-methyl-1H-pyrazol-4-yl)-1H-pyrazolo[3,4-d]pyrimidin-6-amine;
1-(3-fluoro-2-methylbenzyl)-N-(1-methyl-1H-pyrazol-4-yl)-1H-pyrazolo[3,4-d]pyrimidin-6-amine;
1-(5-fluoro-2-methylbenzyl)-N-(1-methyl-1H-pyrazol-4-yl)-1H-pyrazolo[3,4-d]pyrimidin-6-amine;
1-(2-fluoro-6-methylbenzyl)-N-(1-methyl-1H-pyrazol-4-yl)-1H-pyrazolo[3,4-d]pyrimidin-6-amine;
1-benzyl-N-(1-(2,2-difluoroethyl)-1H-pyrazol-4-yl)-1H-pyrazolo[3,4-d]pyrimidin-6-amine;
1-benzyl-N-(1-(2,2-difluoroethyl)-3-methoxy-1H-pyrazol-4-yl)-1H-pyrazolo[3,4-d]pyrimidin-6-amine;
1-benzyl-N-(1-(2,2-difluoroethyl)-3-methyl-1H-pyrazol-4-yl)-1H-pyrazolo[3,4-d]pyrimidin-6-amine;
4-(6-((1-(2-hydroxyethyl)-1H-pyrazol-4-yl)amino)-1H-pyrazolo[3,4-d]pyrimidin-1-yl)benzenesulfonamide;
3-(6-((1-methyl-1H-pyrazol-4-yl)amino)-1H-pyrazolo[3,4-d]pyrimidin-1-yl)benzenesulfonamide;
N-(1-(2-(diethylamino)ethyl)-1H-pyrazol-4-yl)-1-(2-fluorobenzyl)-1H-pyrazolo[3,4-d]pyrimidin-6-amine;
1-(2-fluorobenzyl)-N-(1-(2-morpholinoethyl)-1H-pyrazol-4-yl)-1H-pyrazolo[3,4-d]pyrimidin-6-amine;
N-(1-(3-(dimethylamino)propyl)-1H-pyrazol-4-yl)-1-(2-fluorobenzyl)-1H-pyrazolo[3,4-d]pyrimidin-6-amine;
N-(2-((6-((1-methyl-1H-pyrazol-4-yl)amino)-1H-pyrazolo[3,4-d]pyrimidin-1-yl)methyl)phenyl)propane-2-sulfonamide;
4-(6-((1-(2,2-difluoroethyl)-1H-pyrazol-4-yl)amino)-1H-pyrazolo[3,4-d]pyrimidin-1-yl)benzenesulfonamide;
N-(1-(2,2-difluoroethyl)-1H-pyrazol-4-yl)-1-(2-fluorobenzyl)-1H-pyrazolo[3,4-d]pyrimidin-6-amine;
1-(2,5-difluorobenzyl)-N-(1-(2,2-difluoroethyl)-1H-pyrazol-4-yl)-1H-pyrazolo[3,4-d]pyrimidin-6-amine;
2-((6-((1-(2,2-difluoroethyl)-1H-pyrazol-4-yl)amino)-1H-pyrazolo[3,4-d]pyrimidin-1-yl)methyl)-4-fluorobenzonitrile;
N-(2-((6-((1-(2,2-difluoroethyl)-1H-pyrazol-4-yl)amino)-1H-pyrazolo[3,4-d]pyrimidin-1-yl)methyl)phenyl)methanesulfonamide hydrochloride;
1-(3-(2-methoxyethoxy)benzyl)-N-(1-methyl-1H-pyrazol-4-yl)-1H-pyrazolo[3,4-d]pyrimidin-6-amine;
2-(4-((1-benzyl-1H-pyrazolo[3,4-d]pyrimidin-6-yl)amino)-1H-pyrazol-1-yl)-N-methylacetamide;

2,2,2-trifluoro-N-(2-((6-((1-methyl-1H-pyrazol-4-yl)amino)-1H-pyrazolo[3,4-d]pyrimidin-1-yl)methyl)phenyl)ethanesulfonamide;
4-(6-((1-methyl-1H-pyrazol-4-yl)amino)-1H-pyrazolo[3,4-d]pyrimidin-1-yl)benzamide;
N-methyl-4-(6-((1-methyl-1H-pyrazol-4-yl)amino)-1H-pyrazolo[3,4-d]pyrimidin-1-yl)benzamide;
(4-(6-((1-methyl-1H-pyrazol-4-yl)amino)-1H-pyrazolo[3,4-d]pyrimidin-1-yl)phenyl)(morpholino)methanone;
2-fluoro-4-(6-((1-methyl-1H-pyrazol-4-yl)amino)-1H-pyrazolo[3,4-d]pyrimidin-1-yl)benzenesulfonamide;
N-(2-hydroxyethyl)-4-(6-((1-methyl-1H-pyrazol-4-yl)amino)-1H-pyrazolo[3,4-d]pyrimidin-1-yl)benzenesulfonamide;
N-(3-((6-((1-methyl-1H-pyrazol-4-yl)amino)-1H-pyrazolo[3,4-d]pyrimidin-1-yl)methyl)phenyl)methanesulfonamide;
N-(3-((6-((1-methyl-1H-pyrazol-4-yl)amino)-1H-pyrazolo[3,4-d]pyrimidin-1-yl)methyl)phenyl)propane-2-sulfonamide;
N-(3-fluoro-2-((6-((1-methyl-1H-pyrazol-4-yl)amino)-1H-pyrazolo[3,4-d]pyrimidin-1-yl)methyl)phenyl)methanesulfonamide;
1-(2-fluorobenzyl)-N-(1-(2-(piperidin-1-yl)ethyl)-1H-pyrazol-4-yl)-1H-pyrazolo[3,4-d]pyrimidin-6-amine;
1-(2-fluorobenzyl)-N-(1-(3-(piperidin-1-yl)propyl)-1H-pyrazol-4-yl)-1H-pyrazolo[3,4-d]pyrimidin-6-amine;
1-(2-fluorobenzyl)-N-(1-(3-morpholinopropyl)-1H-pyrazol-4-yl)-1H-pyrazolo[3,4-d]pyrimidin-6-amine;
(3-(6-((1-methyl-1H-pyrazol-4-yl)amino)-1H-pyrazolo[3,4-d]pyrimidin-1-yl)phenyl)(morpholino)methanone;
N-(2-hydroxyethyl)-3-(6-((1-methyl-1H-pyrazol-4-yl)amino)-1H-pyrazolo[3,4-d]pyrimidin-1-yl)benzamide;
N-(2-hydroxyethyl)-4-(6-((1-methyl-1H-pyrazol-4-yl)amino)-1H-pyrazolo[3,4-d]pyrimidin-1-yl)benzamide;
(4-(6-((1-methyl-1H-pyrazol-4-yl)amino)-1H-pyrazolo[3,4-d]pyrimidin-1-yl)phenyl)(4-methylpiperazin-1-yl)methanone;
1-(2,5-difluorobenzyl)-N-(1-(2,2-difluoro ethyl)-3-methyl-1H-pyrazol-4-yl)-1H-pyrazolo[3,4-d]pyrimidin-6-amine;
2-((6-((1-(2,2-difluoro ethyl)-3-methyl-1H-pyrazol-4-yl)amino)-1H-pyrazolo[3,4-d]pyrimidin-1-yl)methyl)-4-fluorobenzonitrile;
1-(2,5-difluorobenzyl)-N-(1-(2,2-difluoro ethyl)-3-methoxy-1H-pyrazol-4-yl)-1H-pyrazolo[3,4-d]pyrimidin-6-amine;
2-((6-((1-(2,2-difluoro ethyl)-3-methoxy-1H-pyrazol-4-yl)amino)-1H-pyrazolo[3,4-d]pyrimidin-1-yl)methyl)-4-fluorobenzonitrile;
N-(1-(2,2-difluoro ethyl)-1H-pyrazol-4-yl)-1-(3-fluoro-2-methylbenzyl)-1H-pyrazolo[3,4-d]pyrimidin-6-amine;
1-(2,3-difluorobenzyl)-N-(1-(2,2-difluoro ethyl)-1H-pyrazol-4-yl)-1H-pyrazolo[3,4-d]pyrimidin-6-amine;
1-(3-chloro-2-fluorobenzyl)-N-(1-(2,2-difluoroethyl)-1H-pyrazol-4-yl)-1H-pyrazolo[3,4-d]pyrimidin-6-amine;
N-(1-(2,2-difluoro ethyl)-1H-pyrazol-4-yl)-1-(2,3,6-trifluorobenzyl)-1H-pyrazolo[3,4-d]pyrimidin-6-amine;
N-(1-methyl-1H-pyrazol-4-yl)-1-(2,3,5-trifluorobenzyl)-1H-pyrazolo[3,4-d]pyrimidin-6-amine;
1-(2,6-difluoro-3-methoxybenzyl)-N-(1-methyl-1H-pyrazol-4-yl)-1H-pyrazolo[3,4-d]pyrimidin-6-amine;
1-(2,6-difluorobenzyl)-N-(1-(2,2-difluoro ethyl)-1H-pyrazol-4-yl)-1H-pyrazolo[3,4-d]pyrimidin-6-amine;
1-(2-cyclopropylbenzyl)-N-(1-(2,2-difluoro ethyl)-1H-pyrazol-4-yl)-1H-pyrazolo[3,4-d]pyrimidin-6-amine;
N-(1-methyl-1H-pyrazol-4-yl)-1-(3-morpholinobenzyl)-1H-pyrazolo[3,4-d]pyrimidin-6-amine;
N-(1-methyl-1H-pyrazol-4-yl)-1-(2,3,5,6-tetrafluorobenzyl)-1H-pyrazolo[3,4-d]pyrimidin-6-amine;
1-(2-fluoro-6-(trifluoromethyl)benzyl)-N-(1-methyl-1H-pyrazol-4-yl)-1H-pyrazolo[3,4-d]pyrimidin-6-amine;
1-(2-fluorobenzyl)-N-(1-(2-(tetrahydro-2H-pyran-4-yl)ethyl)-1H-pyrazol-4-yl)-1H-pyrazolo[3,4-d]pyrimidin-6-amine;
2-(3-((6-((1-methyl-1H-pyrazol-4-yl)amino)-1H-pyrazolo[3,4-d]pyrimidin-1-yl)methyl)phenoxy)ethanol;
N-(1-methyl-1H-pyrazol-4-yl)-1-(3-(2-(piperidin-1-yl)ethoxy)benzyl)-1H-pyrazolo[3,4-d]pyrimidin-6-amine;
2-(2-((6-((1-methyl-1H-pyrazol-4-yl)amino)-1H-pyrazolo[3,4-d]pyrimidin-1-yl)methyl)phenoxy)ethanol;
1-(3-(3-methoxypropoxy)benzyl)-N-(1-methyl-1H-pyrazol-4-yl)-1H-pyrazolo[3,4-d]pyrimidin-6-amine;
1-((6-fluoropyridin-2-yl)methyl)-N-(1-methyl-1H-pyrazol-4-yl)-1H-pyrazolo[3,4-d]pyrimidin-6-amine;
(S)-1-(3-(2-methoxypropoxy)benzyl)-N-(1-methyl-1H-pyrazol-4-yl)-1H-pyrazolo[3,4-d]pyrimidin-6-amine;
1-(3-(cyclopropylmethoxy)benzyl)-N-(1-methyl-1H-pyrazol-4-yl)-1H-pyrazolo[3,4-d]pyrimidin-6-amine;
1-(2-(cyclopropylmethoxy)benzyl)-N-(1-methyl-1H-pyrazol-4-yl)-1H-pyrazolo[3,4-d]pyrimidin-6-amine;
N-(1-methyl-1H-pyrazol-4-yl)-1-((6-morpholinopyridin-2-yl)methyl)-1H-pyrazolo[3,4-d]pyrimidin-6-amine;
1-(3-((2S,6R)-2,6-dimethylmorpholino)benzyl)-N-(1-methyl-1H-pyrazol-4-yl)-1H-pyrazolo[3,4-d]pyrimidin-6-amine;
N-(1-(2,2-difluoroethyl)-1H-pyrazol-4-yl)-1-(3-(2-methoxyethoxy)benzyl)-1H-pyrazolo[3,4-d]pyrimidin-6-amine;
N-(1-(3-(azetidin-1-yl)propyl)-1H-pyrazol-4-yl)-1-(2-fluorobenzyl)-1H-pyrazolo[3,4-d]pyrimidin-6-amine;
1-(2,3-dichlorobenzyl)-N-(1-methyl-1H-pyrazol-4-yl)-1H-pyrazolo[3,4-d]pyrimidin-6-amine;
2-methyl-3-((6-((1-methyl-1H-pyrazol-4-yl)amino)-1H-pyrazolo[3,4-d]pyrimidin-1-yl)methyl)phenol;
N-(1-methyl-1H-pyrazol-4-yl)-1-(2-morpholino benzyl)-1H-pyrazolo[3,4-d]pyrimidin-6-amine;
N-(1-methyl-1H-pyrazol-4-yl)-1-(3-((tetrahydrofuran-3-yl)oxy)benzyl)-1H-pyrazolo[3,4-d]pyrimidin-6-amine;
1-(2-fluorobenzyl)-N-(1-(2-(piperazin-1-yl)ethyl)-1H-pyrazol-4-yl)-1H-pyrazolo[3,4-d]pyrimidin-6-amine;
1-((6-(dimethylamino)pyridin-2-yl)methyl)-N-(1-methyl-1H-pyrazol-4-yl)-1H-pyrazolo[3,4-d]pyrimidin-6-amine;
N-(1-(3-(dimethylamino)propyl)-1H-pyrazol-4-yl)-1-(3-(2-methoxyethoxy)benzyl)-1H-pyrazolo[3,4-d]pyrimidin-6-amine;
1-(3-(2-methoxyethoxy)-2-methylbenzyl)-N-(1-methyl-1H-pyrazol-4-yl)-1H-pyrazolo[3,4-d]pyrimidin-6-amine;
N-(1-(3-(dimethylamino)propyl)-1H-pyrazol-4-yl)-1-(3-morpholinobenzyl)-1H-pyrazolo[3,4-d]pyrimidin-6-amine;
(R)—N-(1-methyl-1H-pyrazol-4-yl)-1-((6-((tetrahydrofuran-3-yl)amino)pyridin-2-yl)methyl)-1H-pyrazolo[3,4-d]pyrimidin-6-amine;
N-(1-methyl-1H-pyrazol-4-yl)-1-((6-(pyrrolidin-1-yl)pyridin-2-yl)methyl)-1H-pyrazolo[3,4-d]pyrimidin-6-amine;
4-methyl-3-((6-((1-methyl-1H-pyrazol-4-yl)amino)-1H-pyrazolo[3,4-d]pyrimidin-1-yl)methyl)phenol;
2-(4-((1-(3-morpholinobenzyl)-1H-pyrazolo[3,4-d]pyrimidin-6-yl)amino)-1H-pyrazol-1-yl)ethano 1;
(3-((6-((1-methyl-1H-pyrazol-4-yl)amino)-1H-pyrazolo[3,4-d]pyrimidin-1-yl)methyl)phenyl)(morpholino)methanone;
1-(2-fluorobenzyl)-N-(1-((1-methylpiperidin-3-yl)methyl)-1H-pyrazol-4-yl)-1H-pyrazolo[3,4-d]pyrimidin-6-amine;

(R)—N-(1-methyl-1H-pyrazol-4-yl)-1-((6-((tetrahydrofuran-2-yl)methoxy)pyridin-2-yl)methyl)-1H-pyrazolo[3,4-d]pyrimidin-6-amine;

1-(2-fluorobenzyl)-N-(1-(3-(4-methylpiperazin-1-yl)propyl)-1H-pyrazol-4-yl)-1H-pyrazolo[3,4-d]pyrimidin-6-amine;

N-(1-methyl-1H-pyrazol-4-yl)-1-(3-(morpholinomethyl)benzyl)-1H-pyrazolo[3,4-d]pyrimidin-6-amine;

2-(4-((1-(2,3,5,6-tetrafluorobenzyl)-1H-pyrazolo[3,4-d]pyrimidin-6-yl)amino)-1H-pyrazol-1-yl)ethano 1;

N-(1-methyl-1H-pyrazol-4-yl)-1-(3-(piperidin-1-yl)benzyl)-1H-pyrazolo[3,4-d]pyrimidin-6-amine;

N-(1-methyl-1H-pyrazol-4-yl)-1-(3-(tetrahydro-2H-pyran-4-yl)benzyl)-1H-pyrazolo[3,4-d]pyrimidin-6-amine;

N-(1-methyl-1H-pyrazol-4-yl)-1-(3-(4-methylpiperazin-1-yl)benzyl)-1H-pyrazolo[3,4-d]pyrimidin-6-amine;

N-(2-methoxyethyl)-3-((6-((1-methyl-1H-pyrazol-4-yl)amino)-1H-pyrazolo[3,4-d]pyrimidin-1-yl)methyl)benzamide;

N-(1-methyl-1H-pyrazol-4-yl)-1-(2-methyl-3-morpholino benzyl)-1H-pyrazolo[3,4-d]pyrimidin-6-amine;

N-methyl-2-(4-((1-(3-morpholino benzyl)-1H-pyrazolo[3,4-d]pyrimidin-6-yl)amino)-1H-pyrazol-1-yl)acetamide;

ethyl 1-(3-((6-((1-methyl-1H-pyrazol-4-yl)amino)-1H-pyrazolo[3,4-d]pyrimidin-1-yl)methyl)phenyl)piperidine-3-carboxylate;

3-(4-((1-(3-morpholinobenzyl)-1H-pyrazolo[3,4-d]pyrimidin-6-yl)amino)-1H-pyrazol-1-yl)propanamide;

1-(2-fluoro-5-morpholino benzyl)-N-(1-methyl-1H-pyrazol-4-yl)-1H-pyrazolo[3,4-d]pyrimidin-6-amine;

1-(3-(2-aminopyridin-4-yl)benzyl)-N-(1-methyl-1H-pyrazol-4-yl)-1H-pyrazolo[3,4-d]pyrimidin-6-amine;

N,N-dimethyl-3-(4-((1-(3-morpholinobenzyl)-1H-pyrazolo[3,4-d]pyrimidin-6-yl)amino)-1H-pyrazol-1-yl)propanamide;

(R)-1-(6-((6-((1-methyl-1H-pyrazol-4-yl)amino)-1H-pyrazolo[3,4-d]pyrimidin-1-yl)methyl)pyridin-2-yl)pyrrolidin-3-ol;

2-(3-((6-((1-methyl-1H-pyrazol-4-yl)amino)-1H-pyrazolo[3,4-d]pyrimidin-1-yl)methyl)phenoxy)acetamide;

N-(1-methyl-1H-pyrazol-4-yl)-1-(2,3,6-trifluoro-5-morpholinobenzyl)-1H-pyrazolo[3,4-d]pyrimidin-6-amine;

3-(4-((1-(3-morpholinobenzyl)-1H-pyrazolo[3,4-d]pyrimidin-6-yl)amino)-1H-pyrazol-1-yl)propan-1-ol;

1-(3-(4,4-difluoropiperidin-1-yl)benzyl)-N-(1-methyl-1H-pyrazol-4-yl)-1H-pyrazolo[3,4-d]pyrimidin-6-amine;

3-(4-((1-(3-morpholinobenzyl)-1H-pyrazolo[3,4-d]pyrimidin-6-yl)amino)-1H-pyrazol-1-yl)-1-(piperidin-1-yl)propan-1-one;

1-(2-fluoro-3-morpholino benzyl)-N-(1-methyl-1H-pyrazol-4-yl)-1H-pyrazolo[3,4-d]pyrimidin-6-amine;

N-(1-methyl-1H-pyrazol-4-yl)-1-(3-(piperazin-1-yl)benzyl)-1H-pyrazolo[3,4-d]pyrimidin-6-amine;

N-(1-(2,2-difluoro ethyl)-1H-pyrazol-4-yl)-1-(3-morpholinobenzyl)-1H-pyrazolo[3,4-d]pyrimidin-6-amine;

N-methyl-3-(4-((1-(3-morpholino benzyl)-1H-pyrazolo[3,4-d]pyrimidin-6-yl)amino)-1H-pyrazol-1-yl)propanamide;

1-(3-(3,6-dihydro-2H-pyran-4-yl)benzyl)-N-(1-methyl-1H-pyrazol-4-yl)-1H-pyrazolo[3,4-d]pyrimidin-6-amine;

6-(6-((1-methyl-1H-pyrazol-4-yl)amino)-1H-pyrazolo[3,4-d]pyrimidin-1-yl)-2H-benzo[b][1,4]oxazin-3(4H)-one;

N-(1-methyl-1H-pyrazol-4-yl)-1-(naphthalen-1-ylmethyl)-1H-pyrazolo[3,4-d]pyrimidin-6-amine;

1-(2-(2-(benzyloxy)ethoxy)benzyl)-N-(1-methyl-1H-pyrazol-4-yl)-1H-pyrazolo[3,4-d]pyrimidin-6-amine;

1-(3-(2-(benzyloxy)ethoxy)benzyl)-N-(1-methyl-1H-pyrazol-4-yl)-1H-pyrazolo[3,4-d]pyrimidin-6-amine;

4-(3-((6-((1-methyl-1H-pyrazol-4-yl)amino)-1H-pyrazolo[3,4-d]pyrimidin-1-yl)methyl)phenyl)thiomorpholine 1,1-dioxide;

N-(1-methyl-1H-pyrazol-4-yl)-1-(2-phenoxybenzyl)-1H-pyrazolo[3,4-d]pyrimidin-6-amine;

1-(2-(3-((6-((1-methyl-1H-pyrazol-4-yl)amino)-1H-pyrazolo[3,4-d]pyrimidin-1-yl)methyl)phenoxy)ethyl)pyrrolidin-2-one;

1-(3-(2-oxa-5-azabicyclo[2.2.2]octan-5-yl)benzyl)-N-(1-methyl-1H-pyrazol-4-yl)-1H-pyrazolo[3,4-d]pyrimidin-6-amine;

4-(3-((6-((1-methyl-1H-pyrazol-4-yl)amino)-1H-pyrazolo[3,4-d]pyrimidin-1-yl)methyl)phenyl)morpholin-3-one;

1-(benzo[d][1,3]dioxol-4-ylmethyl)-N-(1-methyl-1H-pyrazol-4-yl)-1H-pyrazolo[3,4-d]pyrimidin-6-amine;

1-((2,3-dihydrobenzo[b][1,4]dioxin-5-yl)methyl)-N-(1-methyl-1H-pyrazol-4-yl)-1H-pyrazolo[3,4-d]pyrimidin-6-amine;

N-(1-methyl-1H-pyrazol-4-yl)-1-(3-(pyridin-4-yl)benzyl)-1H-pyrazolo[3,4-d]pyrimidin-6-amine;

4-(3-((6-((1-(3-(dimethylamino)propyl)-1H-pyrazol-4-yl)amino)-1H-pyrazolo[3,4-d]pyrimidin-1-yl)methyl)phenyl)morpholin-3-one;

4-(3-((6-((1-(2-hydroxyethyl)-1H-pyrazol-4-yl)amino)-1H-pyrazolo[3,4-d]pyrimidin-1-yl)methyl)phenyl)morpholin-3-one;

1-(3-(4-((1-(3-morpholino benzyl)-1H-pyrazolo[3,4-d]pyrimidin-6-yl)amino)-1H-pyrazol-1-yl)propyl)pyrrolidin-2-one;

N-(1-((3-((dimethylamino)methyl)oxetan-3-yl)methyl)-1H-pyrazol-4-yl)-1-(3-morpholinobenzyl)-1H-pyrazolo[3,4-d]pyrimidin-6-amine;

4-(3-((6-((1-methyl-1H-pyrazol-4-yl)amino)-1H-pyrazolo[3,4-d]pyrimidin-1-yl)methyl)phenyl)morpholin-3-ol;

3-((1-(2-fluorobenzyl)-1H-pyrazolo[3,4-d]pyrimidin-6-yl)amino)-1-methyl-1H-pyrazole-5-carboxylic acid;

1-(2-fluorobenzyl)-N-(1-methyl-1H-imidazol-4-yl)-1H-pyrazolo[3,4-d]pyrimidin-6-amine;

2-(3-((1-(2-fluorobenzyl)-1H-pyrazolo[3,4-d]pyrimidin-6-yl)amino)-1H-pyrazol-1-yl)ethanol;

4-((1-(2-fluorobenzyl)-1H-pyrazolo[3,4-d]pyrimidin-6-yl)amino)-N-methyl-1H-pyrrole-2-carboxamide;

2-(4-((1-(2-fluorobenzyl)-1H-pyrazolo[3,4-d]pyrimidin-6-yl)amino)-1H-imidazol-1-yl)ethanol;

1-(2-fluorobenzyl)-N-(1H-pyrrol-3-yl)-1H-pyrazolo[3,4-d]pyrimidin-6-amine;

4-((1-(2-fluorobenzyl)-1H-pyrazolo[3,4-d]pyrimidin-6-yl)amino)-N,1-dimethyl-1H-pyrrole-2-carboxamide;

4-((1-(2-fluorobenzyl)-1H-pyrazolo[3,4-d]pyrimidin-6-yl)amino)-1-methyl-N-(2-morpholino ethyl)-1H-pyrrole-2-carboxamide;

(4-((1-(2-fluorobenzyl)-1H-pyrazolo[3,4-d]pyrimidin-6-yl)amino)-1-methyl-1H-pyrrol-2-yl)(morpholino)methanone;

N-(cyanomethyl)-4-((1-(2-fluorobenzyl)-1H-pyrazolo[3,4-d]pyrimidin-6-yl)amino)-1-methyl-1H-pyrrole-2-carboxamide;

4-((1-(2-fluorobenzyl)-1H-pyrazolo[3,4-d]pyrimidin-6-yl)amino)-N,N,1-trimethyl-1H-pyrrole-2-carboxamide;

2-(3-((1-(2-fluorobenzyl)-1H-pyrazolo[3,4-d]pyrimidin-6-yl)amino)-1H-pyrrol-1-yl)ethanol;

(1-methyl-4-((1-(3-morpholinobenzyl)-1H-pyrazolo[3,4-d]pyrimidin-6-yl)amino)-1H-pyrrol-2-yl)(morpholino) methanone;

N-(1-(3-(dimethylamino)-2-methylpropyl)-1H-pyrazol-4-yl)-1-(3-morpholinobenzyl)-1H-pyrazolo[3,4-d]pyrimidin-6-amine;

1-(dimethylamino)-3-(4-((1-(3-morpholinobenzyl)-1H-pyrazolo[3,4-d]pyrimidin-6-yl)amino)-1H-pyrazol-1-yl)propan-2-ol;

N-(1-(3-aminopropyl)-1H-pyrazol-4-yl)-1-(3-morpholinobenzyl)-1H-pyrazolo[3,4-d]pyrimidin-6-amine;

N-cyclopropyl-3-(4(1-(3-morpholinobenzyl)-1H-pyrazolo[3,4-d]pyrimidin-6-yl)amino)-1H-pyrazol-1-yl)propanamide;

1-(3-((6-((1-methyl-1H-pyrazol-4-yl)amino)-1H-pyrazolo[3,4-d]pyrimidin-1-yl)methyl)phenyl)piperazin-2-one;

2-(4-((1-(2,3,6-trifluorobenzyl)-1H-pyrazolo[3,4-d]pyrimidin-6-yl)amino)-1H-pyrazol-1-yl)ethanol;

1-(2,3-difluoro-5-morpholinobenzyl)-N-(1-methyl-1H-pyrazol-4-yl)-1H-pyrazolo[3,4-d]pyrimidin-6-amine;

1-(2,6-difluoro-3-morpholinobenzyl)-N-(1-methyl-1H-pyrazol-4-yl)-1H-pyrazolo[3,4-d]pyrimidin-6-amine;

2-(4-((1-(2-fluoro-3-morpholinobenzyl)-1H-pyrazolo[3,4-d]pyrimidin-6-yl)amino)-1H-pyrazol-1-yl)ethanol;

4-(2-fluoro-3-((6-((1-methyl-1H-pyrazol-4-yl)amino)-1H-pyrazolo[3,4-d]pyrimidin-1-yl)methyl)phenyl)morpholin-3-one;

N-(1-43-((methylamino)methyl)oxetan-3-yl)methyl)-1H-pyrazol-4-yl)-1-(3-morpholinobenzyl)-1H-pyrazolo[3,4-d]pyrimidin-6-amine;

2-(4-((1-(2-cyclopropylbenzyl)-1H-pyrazolo[3,4-d]pyrimidin-6-yl)amino)-1H-pyrazol-1-yl)ethanol;

2-(4-((1-(2-fluoro-6-(trifluoromethyl)benzyl)-1H-pyrazolo[3,4-d]pyrimidin-6-yl)amino)-1H-pyrazol-1-yl)ethanol;

N-(1-(3-(dimethylamino)propyl)-1H-pyrazol-4-yl)-1-(2,3,6-trifluoro-5-morpholino benzyl)-1H-pyrazolo[3,4-d]pyrimidin-6-amine;

N-(1-(3-(dimethylamino)propyl)-1H-pyrazol-4-yl)-1-(2-fluoro-3-morpholinobenzyl)-1H-pyrazolo[3,4-d]pyrimidin-6-amine;

2-(4-((1-(2-fluoro-5-morpholinobenzyl)-1H-pyrazolo[3,4-d]pyrimidin-6-yl)amino)-1H-pyrazol-1-yl)ethanol;

2-(4-((1-(2,3,6-trifluoro-5-morpholinobenzyl)-1H-pyrazolo[3,4-d]pyrimidin-6-yl)amino)-1H-pyrazol-1-yl)ethanol;

4-(2-fluoro-3-((6-((1-(2-hydroxyethyl)-1H-pyrazol-4-yl)amino)-1H-pyrazolo[3,4-d]pyrimidin-1-yl)methyl)phenyl)morpholin-3-one;

2-(4-((1-(3-(piperazin-1-yl)benzyl)-1H-pyrazolo[3,4-d]pyrimidin-6-yl)amino)-1H-pyrazol-1-yl)ethanol;

1-(3-morpholino benzyl)-N-(1-(piperidin-3-ylmethyl)-1H-pyrazol-4-yl)-1H-pyrazolo[3,4-d]pyrimidin-6-amine;

1-(3-fluoro-5-morpholino benzyl)-N-(1-methyl-1H-pyrazol-4-yl)-1H-pyrazolo[3,4-d]pyrimidin-6-amine;

4-(3-((6-((1-(3-(dimethylamino)propyl)-1H-pyrazol-4-yl)amino)-1H-pyrazolo[3,4-d]pyrimidin-1-yl)methyl)-2-fluorophenyl)morpholin-3-one;

2-(4-((1-(3-fluoro-5-morpholinobenzyl)-1H-pyrazolo[3,4-d]pyrimidin-6-yl)amino)-1H-pyrazol-1-yl)ethano 1;

4-(3-fluoro-5-((6-((1-methyl-1H-pyrazol-4-yl)amino)-1H-pyrazolo[3,4-d]pyrimidin-1-yl)methyl)phenyl)morpholin-3-one;

4-(3,4-difluoro-5-((6-((1-methyl-1H-pyrazol-4-yl)amino)-1H-pyrazolo[3,4-d]pyrimidin-1-yl)methyl)phenyl)morpholin-3-one;

1-(2-fluoro-3-((6-((1-methyl-1H-pyrazol-4-yl)amino)-1H-pyrazolo[3,4-d]pyrimidin-1-yl)methyl)phenyl)piperazin-2-one;

1-(2-fluoro-3-((6-((1-(2-hydroxyethyl)-1H-pyrazol-4-yl)amino)-1H-pyrazolo[3,4-d]pyrimidin-1-yl)methyl)phenyl)piperazin-2-one;

2-(4-((1-(2,3-difluoro-5-morpholinobenzyl)-1H-pyrazolo[3,4-d]pyrimidin-6-yl)amino)-1H-pyrazol-1-yl)ethano 1;

1-(3-((6-((1-(2-hydroxyethyl)-1H-pyrazol-4-yl)amino)-1H-pyrazolo[3,4-d]pyrimidin-1-yl)methyl)phenyl)piperazin-2-one;

4-(3-fluoro-5-((6-((1-(2-hydroxyethyl)-1H-pyrazol-4-yl)amino)-1H-pyrazolo[3,4-d]pyrimidin-1-yl)methyl)phenyl)morpholin-3-one;

4-(3,4-difluoro-5-((6-((1-(2-hydroxyethyl)-1H-pyrazol-4-yl)amino)-1H-pyrazolo[3,4-d]pyrimidin-1-yl)methyl)phenyl)morpholin-3-one;

1-(3-morpholino benzyl)-N-(1-(pyrrolidin-3-ylmethyl)-1H-pyrazol-4-yl)-1H-pyrazolo[3,4-d]pyrimidin-6-amine;

4-(2,4,5-trifluoro-3-((6-((1-methyl-1H-pyrazol-4-yl)amino)-1H-pyrazolo[3,4-d]pyrimidin-1-yl)methyl)phenyl)morpholin-3-one;

4-(2,4,5-trifluoro-3-((6-((1-(2-hydroxyethyl)-1H-pyrazol-4-yl)amino)-1H-pyrazolo[3,4-d]pyrimidin-1-yl)methyl)phenyl)morpholin-3-one;

2-(4-((1-(2,3,6-trifluoro-5-(piperazin-1-yl)benzyl)-1H-pyrazolo[3,4-d]pyrimidin-6-yl)amino)-1H-pyrazol-1-yl)ethanol;

1-(3-fluoro-5-((6-((1-(2-hydroxyethyl)-1H-pyrazol-4-yl)amino)-1H-pyrazolo[3,4-d]pyrimidin-1-yl)methyl)phenyl)piperazin-2-one;

1-(3-fluoro-5-((6-((1-methyl-1H-pyrazol-4-yl)amino)-1H-pyrazolo[3,4-d]pyrimidin-1-yl)methyl)phenyl)piperazin-2-one;

1-(3-(3-methoxyazetidin-1-yl)benzyl)-N-(1-methyl-1H-pyrazol-4-yl)-1H-pyrazolo[3,4-d]pyrimidin-6-amine;

N-(1-methyl-1H-pyrazol-4-yl)-1-(2,3,6-trifluoro-5-(piperazin-1-yl)benzyl)-1H-pyrazolo[3,4-d]pyrimidin-6-amine;

1-(2-fluoro-3-(piperazin-1-yl)benzyl)-N-(1-methyl-1H-pyrazol-4-yl)-1H-pyrazolo[3,4-d]pyrimidin-6-amine;

2-(4-((1-(3-fluoro-5-(3-oxomorpholino)benzyl)-1H-pyrazolo[3,4-d]pyrimidin-6-yl)amino)-1H-pyrazol-1-yl)-N-methylacetamide;

2-(4-((1-(2-fluorobenzyl)-1H-pyrazolo[3,4-d]pyrimidin-6-yl)amino)-1H-pyrazol-1-yl)-N-methylacetamide;

2-(4-((1-((6-fluoropyridin-2-yl)methyl)-1H-pyrazolo[3,4-d]pyrimidin-6-yl)amino)-1H-pyrazol-1-yl)-N-methylacetamide;

4-(2,4-difluoro-3-((6-((1-methyl-1H-pyrazol-4-yl)amino)-1H-pyrazolo[3,4-d]pyrimidin-1-yl)methyl)phenyl)morpholin-3-one;

4-(2,4-difluoro-3-((6-((1-(2-hydroxyethyl)-1H-pyrazol-4-yl)amino)-1H-pyrazolo[3,4-d]pyrimidin-1-yl)methyl)phenyl)morpholin-3-one;

4-(3-((6-((1-(3-(dimethylamino)propyl)-1H-pyrazol-4-yl)amino)-1H-pyrazolo[3,4-d]pyrimidin-1-yl)methyl)-2,4,5-trifluorophenyl)morpholin-3-one;

1-(3,4-difluoro-5-((6-((1-methyl-1H-pyrazol-4-yl)amino)-1H-pyrazolo[3,4-d]pyrimidin-1-yl)methyl)phenyl)piperazin-2-one;

1-(3,4-difluoro-5-((6-((1-(2-hydroxyethyl)-1H-pyrazol-4-yl)amino)-1H-pyrazolo[3,4-d]pyrimidin-1-yl)methyl)phenyl)piperazin-2-one;

4-(2,5-difluoro-3-((6-((1-methyl-1H-pyrazol-4-yl)amino)-1H-pyrazolo[3,4-d]pyrimidin-1-yl)methyl)phenyl)morpholin-3-one;

4-(2,5-difluoro-3-((6-((1-(2-hydroxyethyl)-1H-pyrazol-4-yl)amino)-1H-pyrazolo[3,4-d]pyrimidin-1-yl)methyl)phenyl)morpholin-3-one;

4-(3-((6-((1-(3-(dimethylamino)propyl)-1H-pyrazol-4-yl)amino)-1H-pyrazolo[3,4-d]pyrimidin-1-yl)methyl)-2,4-difluorophenyl)morpholin-3-one;

1-(2,4-difluoro-3-((6-((1-methyl-1H-pyrazol-4-yl)amino)-1H-pyrazolo[3,4-d]pyrimidin-1-yl)methyl)phenyl)piperazin-2-one;

1-(2,6-difluoro-3-(piperazin-1-yl)benzyl)-N-(1-methyl-1H-pyrazol-4-yl)-1H-pyrazolo[3,4-d]pyrimidin-6-amine;
1-(2,4-difluoro-3-((6-((1-(2-hydroxyethyl)-1H-pyrazol-4-yl)amino)-1H-pyrazolo[3,4-d]pyrimidin-1-yl)methyl)phenyl)piperazin-2-one;
1-(3-(4-methoxypiperidin-1-yl)benzyl)-N-(1-methyl-1H-pyrazol-4-yl)-1H-pyrazolo[3,4-d]pyrimidin-6-amine;
2-(4-((1-(2,6-difluoro-3-(piperazin-1-yl)benzyl)-1H-pyrazolo[3,4-d]pyrimidin-6-yl)amino)-1H-pyrazol-1-yl)ethanol;
2-(4-((1-(2,3-difluoro-5-(piperazin-1-yl)benzyl)-1H-pyrazolo[3,4-d]pyrimidin-6-yl)amino)-1H-pyrazol-1-yl)ethanol;
1-(2-fluorobenzyl)-N-(1-(pyrrolidin-3-ylmethyl)-1H-pyrazol-4-yl)-1H-pyrazolo[3,4-d]pyrimidin-6-amine;
(3-fluoro-5-((6-((1-methyl-1H-pyrazol-4-yl)amino)-1H-pyrazolo[3,4-d]pyrimidin-1-yl)methyl)phenyl)(morpholino)methanone;
(3-fluoro-5-((6-((1-methyl-1H-pyrazol-4-yl)amino)-1H-pyrazolo[3,4-d]pyrimidin-1-yl)methyl)phenyl)(piperazin-1-yl)methanone;
N-(1H-pyrazol-4-yl)-1-(2,3,6-trifluoro-5-morpholinobenzyl)-1H-pyrazolo[3,4-d]pyrimidin-6-amine;
2-(4-((1-(2,6-difluoro-3-morpholinobenzyl)-1H-pyrazolo[3,4-d]pyrimidin-6-yl)amino)-1H-pyrazol-1-yl)ethanol;
2-(4-((1-(2-fluoro-3-(piperazin-1-yl)benzyl)-1H-pyrazolo[3,4-d]pyrimidin-6-yl)amino)-1H-pyrazol-1-yl)ethanol;
4-(3-((6-((1H-pyrazol-4-yl)amino)-1H-pyrazolo[3,4-d]pyrimidin-1-yl)methyl)-5-fluorophenyl)morpholin-3-one;
(2-fluoro-3-((6-((1-methyl-1H-pyrazol-4-yl)amino)-1H-pyrazolo[3,4-d]pyrimidin-1-yl)methyl)phenyl)(morpholino)methanone;
2-(4-((1-((6-fluoropyridin-2-yl)methyl)-1H-pyrazolo[3,4-d]pyrimidin-6-yl)amino)-1H-pyrazol-1-yl)ethanol;
1-(2,3-difluoro-5-(piperazin-1-yl)benzyl)-N-(1-methyl-1H-pyrazol-4-yl)-1H-pyrazolo[3,4-d]pyrimidin-6-amine; and
(2-fluoro-3-((6-((1-methyl-1H-pyrazol-4-yl)amino)-1H-pyrazolo[3,4-d]pyrimidin-1-yl)methyl)phenyl)(morpholino)methanone.

One preferred group of compounds according to the present invention refers to compounds of examples 1 to 58. A further group is formed by examples 59 to 283.

Prodrugs of the compounds of the present invention are also within the scope of the present invention.

"Prodrug" means a derivative that is converted into a compound according to the present invention by a reaction with an enzyme, gastric acid or the like under a physiological condition in the living body, e.g. by oxidation, reduction, hydrolysis or the like, each of which is carried out enzymatically. Examples of a prodrug are compounds, wherein the amino group in a compound of the present invention is acylated, alkylated or phosphorylated to form, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated. These compounds can be produced from compounds of the present invention according to well-known methods.

Metabolites of compounds of formula (I) are also within the scope of the present invention.

The term "metabolites" refers to all molecules derived from any of the compounds according to the present invention in a cell or organism, preferably mammal.

Preferably the term relates to molecules which differ from any molecule which is present in any such cell or organism under physiological conditions.

The structure of the metabolites of the compounds according to the present invention will be obvious to any person skilled in the art, using the various appropriate methods.

Where tautomerism, e.g. keto-enol tautomerism, of compounds of general formula (I) may occur, the individual forms, e.g. the keto and enol form, are comprised separately and together as mixtures in any ratio. The same applies for stereoisomers, e.g. enantiomers, cis/trans isomers, conformers and the like.

If desired, isomers can be separated by methods well known in the art, e.g. by liquid chromatography. The same applies for enantiomers by using e.g. chiral stationary phases. Additionally, enantiomers may be isolated by converting them into diastereomers, i.e. coupling with an enantiomerically pure auxiliary compound, subsequent separation of the resulting diastereomers and cleavage of the auxiliary residue. Alternatively, any enantiomer of a compound of formula (I) may be obtained from stereoselective synthesis using optically pure starting materials.

The compounds of formula (I) may exist in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (ssNMR).

In case the compounds according to formula (I) contain one or more acidic or basic groups, the invention also comprises their corresponding pharmaceutically or toxicologically acceptable salts, in particular their pharmaceutically utilizable salts. Thus, the compounds of the formula (I) which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the formula (I) which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the formula (I) simultaneously contain acidic and basic groups in the molecule, the invention also includes, in addition to the salt forms mentioned, inner salts or betaines (zwitterions). The respective salts according to the formula (I) can be obtained by customary methods which are known to the person skilled in the art like, for example by contacting these with an organic or inorganic acid or base in a solvent or dispersant, or by anion exchange or cation exchange with other salts. The present invention also includes all salts of the compounds of the formula (I) which, owing to low physiological compatibility, are not directly suitable for use in pharmaceuticals but which can be used, for example, as intermediates for chemical reactions or for the preparation of pharmaceutically acceptable salts.

Throughout the invention, the term "pharmaceutically acceptable" means that the corresponding compound, carrier or molecule is suitable for administration to humans. Preferably, this term means approved by a regulatory agency such as the EMEA (Europe) and/or the FDA (US) and/or any other national regulatory agency for use in animals, preferably in humans.

The present invention furthermore includes all solvates of the compounds according to the invention.

According to the present invention "JAK" comprises all members of the JAK family (e.g. JAK1, JAK2, JAK3, and TYK2).

According to the present invention, the expression "JAK1" or "JAK1 kinase" means "Janus kinase 1". The human gene encoding JAK1 is located on chromosome 1p31.3.

According to the present invention, the expression "JAK2" or "JAK2 kinase" means "Janus kinase 2". The human gene encoding JAK2 is located on chromosome 9p24.

According to the present invention, the expression "JAK3" or "JAK3 kinase" means "Janus kinase 3". The gene encoding JAK3 is located on human chromosome 19p13.1 and it is predominantly in hematopoietic cells. JAK3 is a cytoplasmic protein tyrosine kinase that associates with the gamma-chain of the interleukin 2 (IL-2) receptor. This chain also serves as a component for the receptors of several lymphotropic cytokines, including interleukins IL-4, IL-7, IL-9, IL-15 and IL-21 (Schindler et al., 2007. J. Biol. Chem. 282(28):20059-63). JAK3 plays a key role in the response of immune cells to cytokines, especially in mast cells, lymphocytes and macrophages Inhibition of JAK3 has shown beneficial effects in the prevention of transplant rejection (Changelian et al., 2003, Science 302(5646):875-888).

Moreover, according to the present invention, the expression "JAK3" or "JAK3 kinase" includes mutant forms of JAK3, preferably JAK3 mutants found in acute megakaryoblastic leukemia (AMKL) patients. More preferred, these mutants are single amino acid mutations. Activating JAK3 mutations were observed in acute megakaryoblastic leukemia (AMKL) patients (Walters et al., 2006. Cancer Cell 10(1):65-75). Therefore, in a preferred embodiment, the expression "JAK" also includes a JAK3 protein having a V722I or P132T mutation.

According to the present invention, the expression "TYK2" or "TYK2 kinase" means "Protein-Tyrosine kinase 2". The JAK3 and TYK2 genes are clustered on chromosome 19p13.1 and 19p13.2, respectively.

As shown in the examples, compounds of the invention were tested for their selectivity for JAK3 over JAK2 kinases. As shown, all tested compounds bind JAK3 more selectively than, JAK2 (see table 5 below).

Consequently, the compounds of the present invention are considered to be useful for the prevention or treatment of diseases and disorders associated with JAK, for example immunological, inflammatory, autoimmune, or allergic disorders, transplant rejection, Graft-versus-Host-Disease or proliferative diseases such as cancer.

In a preferred embodiment, the compounds of the present invention are selective JAK3 inhibitors.

Equally preferred are dual JAK1/JAK3 inhibitors.

The compounds of the present invention may be further characterized by determining whether they have an effect on JAK3, for example on its kinase activity (Changelian et al., 2003, Science 302(5646):875-888 and online supplement; Yang et al., 2007. Bioorg. Med. Chem. Letters 17(2): 326-331).

Briefly, JAK3 kinase activity can be measured using a recombinant GST-JAK3 fusion protein comprising the catalytic domain (JH1 catalytic domain). JAK3 kinase activity is measured by ELISA as follows: Plates are coated overnight with a random L-glutamic acid and tyrosine co-polymer (4:1; 100 µg/ml) as a substrate. The plates are washed and recombinant JAK3 JH1:GST protein (100 ng/well) with or without inhibitors is incubated at room temperature for 30 minutes. The a HPR-conjugated PY20 anti-phosphotyrosine antibody (ICN) is added and developed by TMB (3,3',5,5'-tetramethylbenzidine) (Changelian et al., 2003, Science 302(5646): 875-888 and online supplement).

A cell-based assays (TF-1 cell proliferation) was described to assess the inhibitory activity of small molecule drugs toward JAK2 or JAK3-dependent signal transduction (Chen et al., 2006. Bioorg. Med. Chem. Letters 16(21): 5633-5638).

The present invention provides pharmaceutical compositions comprising a compound of formula (I) or a pharmaceutically acceptable salt thereof as active ingredient together with a pharmaceutically acceptable carrier, optionally in combination with one or more other pharmaceutical compositions.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E.W. Martin. Such compositions will contain a therapeutically effective amount of the therapeutic, preferably in purified form, together with a suitable amount of carrier so as to provide the form for proper administration to the patient. The formulation should suit the mode of administration.

A pharmaceutical composition of the present invention may comprise one or more additional compounds as active ingredients like one or more compounds of formula (I) not being the first compound in the composition or other JAK inhibitors. Further bioactive compounds may be steroids, leukotriene antagonists, cyclosporine or rapamycin.

The compounds of the present invention or pharmaceutically acceptable salt(s) thereof and the other pharmaceutically active agent(s) may be administered together or separately and, when administered separately, this may occur separately or sequentially in any order. When combined in the same formulation it will be appreciated that the two compounds must be stable and compatible with each other and the other components of the formulation. When formulated separately they may be provided in any convenient formulation, conveniently in such manner as are known for such compounds in the art.

It is further included within the present invention that the compound of formula (I), or a pharmaceutically acceptable salt thereof, or a pharmaceutical composition comprising a compound of formula (I) is administered in combination with another drug or pharmaceutically active agent and/or that the pharmaceutical composition of the invention further comprises such a drug or pharmaceutically active agent.

In this context, the term "drug or pharmaceutically active agent" includes a drug or pharmaceutical agent that will elicit the biological or medical response of a tissue, system, animal or human that is being sought, for instance, by a researcher or clinician.

"Combined" or "in combination" or "combination" should be understood as a functional coadministration, wherein some or all compounds may be administered separately, in different formulations, different modes of administration (for example subcutaneous, intravenous or oral) and different times of administration. The individual compounds of such combinations may be administered either sequentially in separate pharmaceutical compositions as well as simultaneously in combined pharmaceutical compositions.

For example, in rheumatoid arthritis therapy, combination with other chemotherapeutic or antibody agents is envisaged. Suitable examples of pharmaceutically active agents which may be employed in combination with the compounds of the present invention and their salts for rheumatoid arthritis therapy include: immunosuppresants such as amtolmetin guacil, mizoribine and rimexolone; anti-TNFα agents such as etanercept, infliximab, Adalimumab, Anakinra, Abatacept, Rituximab; tyrosine kinase inhibitors such as leflunomide; kallikrein antagonists such as subreum; interleukin 11 agonists such as oprelvekin; interferon beta 1 agonists; hyaluronic acid agonists such as NRD-101 (Aventis); interleukin 1 receptor antagonists such as anakinra; CD8 antagonists such as amiprilose hydrochloride; beta amyloid precursor protein antagonists such as reumacon; matrix metalloprotease inhibitors such as cipemastat and other disease modifying antirheumatic drugs (DMARDs) such as methotrexate, sulphasalazine, cyclosporin A, hydroxychoroquine, auranofin, aurothioglucose, gold sodium thiomalate and penicillamine.

In particular, the treatment defined herein may be applied as a sole therapy or may involve, in addition to the compounds of the invention, conventional surgery or radiotherapy or chemotherapy. Accordingly, the compounds of the invention can also be used in combination with existing therapeutic agents for the treatment proliferative diseases such as cancer. Suitable agents to be used in combination include:

(i) antiproliferative/antineoplastic drugs and combinations thereof, as used in medical oncology such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like paclitaxel and taxotere); and topoisomerase inhibitors (for example epipodophyllotoxins like etoposide and teniposide, amsacrine, topotecan and camptothecins);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxy-quinazo line (AZD0530) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825), and metalloproteinase inhibitors like marimastat and inhibitors of urokinase plasminogen activator receptor function);

(iv) inhibitors of growth factor function: for example such inhibitors include growth factor antibodies and growth factor receptor antibodies (for example the anti-erbB2 antibody trastuzumab [Herceptin™] and the anti-erbB1 antibody cetuximab [C225]); such inhibitors also include, for example, tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy) quinazolin-4-amine (gefitinib, ZD 1839), Λ/-(3-ethynylphenyl)-6,7-bis(2-methoxyethoxy)quinazolin-4-amine (erlotinib, OSI-774) and 6-acrylamido-Λ/-(3-chloro-4-fluorophenyl)-7-(3-morpholinopropoxy)-quinazolin-4-amine (CI 1033) and erbB2 tyrosine kinase inhibitors such as lapatinib), inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)) and inhibitors of cell signalling through MEK and/or Akt kinases;

(v) antiangiogenic agents such as those which inhibit the effects of vascular endothelial growth factor, for example the anti-vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-yl-propoxy)quinazoline (AZD2171; Example 240 within WO 00/47212), vatalanib (PTK787; WO 98/35985) and SUI 1248 (sunitinib; WO 01/60814), and compounds that work by other mechanisms (for example linomide, inhibitors of integrin αvβ3 function and angiostatin);
(vi) vascular damaging agents such as combretastatin A4 and compounds disclosed in International Patent Application WO 99/02166;
(vii) antisense therapies, for example those which are directed to the targets listed above, such as ISIS 2503, an anti-ras antisense agent;
(viii) gene therapy approaches, including approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapeutic approaches, including ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Further combination treatments are described in WO-A 2009/008992 and WO-A 2007/107318), incorporated herein by reference.

Accordingly, the individual compounds of such combinations may be administered either sequentially in separate pharmaceutical compositions as well as simultaneously in combined pharmaceutical compositions.

The pharmaceutical compositions of the present invention include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of formula (I) can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally, for example, as liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula (I) may also be administered parenterally. Solutions or suspensions of these active compounds can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of formula (I) are administered orally.

The effective dosage of active ingredient employed may vary depending on the particular compound employed, the mode of administration, the condition being treated and the severity of the condition being treated. Such dosage may be ascertained readily by a person skilled in the art.

A therapeutically effective amount of a compound of the present invention will normally depend upon a number of factors including, for example, the age and weight of the animal, the precise condition requiring treatment and its severity, the nature of the formulation, and the route of administration. However, an effective amount of a compound of formula (I) for the treatment of an inflammatory disease, for example rheumatoid arthritis (RA), will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a pharmaceutically acceptable salt, prodrug or metabolite thereof, may be determined as a proportion of the effective amount of the compound of formula (I) per se. It is envisaged that similar dosages would be appropriate for treatment of the other conditions referred to above.

As used herein, the term "effective amount" means that amount of a drug or pharmaceutical agent that will elicit the biological or medical response of a tissue, system, animal or human that is being sought, for instance, by a researcher or clinician.

Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Another aspect of the present invention is a compound of the present invention or a pharmaceutically acceptable salt thereof for use as a medicament.

Another aspect of the present invention is a compound of the present invention or a pharmaceutically acceptable salt thereof for use in a method of treating or preventing a disease or disorder associated with JAK.

In the context of the present invention, a disease or disorder associated with JAK is defined as a disease or disorder where JAK is involved.

In a preferred embodiment, wherein the diseases or disorder is associated with JAK is an immunological, inflammatory, autoimmune, or allergic disorder or disease of a transplant rejection or a Graft-versus host disease.

Consequently, another aspect of the present invention is a compound or a pharmaceutically acceptable salt thereof of the present invention for use in a method of treating or preventing an immunological, inflammatory, autoimmune, or allergic disorder or disease of a transplant rejection or a Graft-versus host disease.

Inflammation of tissues and organs occurs in a wide range of disorders and diseases and in certain variations, results from activation of the cytokine family of receptors. Exemplary inflammatory disorders associated with activation of JAK include, in a non-limiting manner, skin inflammation due radiation exposure, asthma, allergic inflammation and chronic inflammation.

According to the present invention, an autoimmune disease is a disease which is at least partially provoked by an immune reaction of the body against own components, for example proteins, lipids or DNA. Examples of organ-specific autoimmune disorders are insulin-dependent diabetes (Type 1) which affects the pancreas, Hashimoto's thyroiditis and Graves' disease which affect the thyroid gland, pernicious anemia which affects the stomach, Cushing's disease and Addison's disease which affect the adrenal glands, chronic active hepatitis which affects the liver; polycystic ovary syndrome (PCOS), celiac disease, psoriasis, inflammatory bowel disease (IBD) and ankylosing spondylitis. Examples of non-organ-specific autoimmune disorders are rheumatoid arthritis, multiple sclerosis, systemic lupus and myasthenia gravis.

Type 1 diabetes ensues from the selective aggression of autoreactive T-cells against insulin secreting beta-cells of the islets of Langerhans. Targeting JAK3 in this disease is based on the observation that multiple cytokines that signal through the JAK pathway are known to participate in the T-cell mediated autoimmune destruction of beta-cells. Indeed, a JAK3 inhibitor, JANEX-1 was shown to prevent spontaneous autoimmune diabetes development in the NOD mouse model of type I diabetes.

In a preferred embodiment, the autoimmune disease is selected from the group consisting of rheumatoid arthritis (RA), inflammatory bowel disease (IBD; Crohn's disease and ulcerative colitis), psoriasis, systemic lupus erythematosus (SLE), and multiple sclerosis (MS).

Rheumatoid arthritis (RA) is a chronic progressive, debilitating inflammatory disease that affects approximately 1% of the world's population. RA is a symmetric polyarticular arthritis that primarily affects the small joints of the hands and feet. In addition to inflammation in the synovium, the joint lining, the aggressive front of tissue called pannus invades and destroys local articular structures (Firestein 2003, Nature 423:356-361).

Inflammatory bowel disease (IBD) is characterized by a chronic relapsing intestinal inflammation. IBD is subdivided into Crohn's disease and ulcerative colitis phenotypes. Crohn disease involves most frequently the terminal ileum and colon, is transmural and discontinuous. In contrast, in ulcerative colitis, the inflammation is continuous and limited to rectal and colonic mucosal layers. In approximately 10% of cases confined to the rectum and colon, definitive classification of Crohn's disease or ulcerative colitis cannot be made and are designated 'indeterminate colitis.' Both diseases include extraintestinal inflammation of the skin, eyes, or joints. Neutrophil-induced injuries may be prevented by the use of neutrophils migration inhibitors (Asakura et al., 2007, World J Gastroenterol. 13(15):2145-9).

Psoriasis is a chronic inflammatory dermatosis that affects approximately 2% of the population. It is characterized by red, scaly skin patches that are usually found on the scalp, elbows, and knees, and may be associated with severe arthritis. The lesions are caused by abnormal keratinocyte proliferation and infiltration of inflammatory cells into the dermis and epidermis (Schön et al., 2005, New Engl. J. Med. 352: 1899-1912).

Systemic lupus erythematosus (SLE) is a chronic inflammatory disease generated by T cell-mediated B-cell activation, which results in glomerulonephritis and renal failure. Human SLE is characterized at early stages by the expansion of long-lasting autoreactive CD4+ memory cells (D'Cruz et al., 2007, Lancet 369(9561):587-596).

Multiple sclerosis (MS) is an inflammatory and demyelating neurological disease. It has bee considered as an autoimmune disorder mediated by CD4+ type 1 T helper cells, but recent studies indicated a role of other immune cells (Hemmer et al., 2002, Nat. Rev. Neuroscience 3, 291-301).

Mast cells express JAK3 and JAK3 is a key regulator of the IgE mediated mast cell responses including the release of inflammatory mediators. JAK3 was shown to be a valid target in the treatment of mast cell mediated allergic reaction. Allergic disorders associated with mast cell activation include Type I immediate hypersensitivity reactions such as allergic rhinitis (hay fever), allergic urticaria (hives), angioedema, allergic asthma and anaphylaxis, for example anaphylatic shock. These disorders may be treated or prevented by inhibition of JAK3 activity, for example, by administration of a JAK3 inhibitor according to the present invention.

Transplant rejection (allograft transplant rejection) includes, without limitation, acute and chronic allograft rejection following for example transplantation of kidney, heart, liver, lung, bone marrow, skin and cornea. It is known that T cells play a central role in the specific immune response of allograft rejection. Hyperacute, acute and chronic organ transplant rejection may be treated. Hyperacute rejection occurs within minutes of transplantation. Acute rejection generally occurs within six to twelve months of the transplant. Hyperacute and acute rejections are typically reversible where treated with immunosuppressant agents. Chronic rejection, characterized by gradual loss of organ function, is an ongoing concern for transplant recipients because it can occur anytime after transplantation.

Graft-versus-host disease (GVDH) is a major complication in allogeneic bone marrow transplantation (BMT). GVDH is caused by donor T cells that recognize and react to recipient differences in the histocompatibility complex system, resulting in significant morbidity and mortality. JAK3 plays a key role in the induction of GVHD and treatment with a JAK3 inhibitor, JANEX-1, was shown to attenuate the severity of GVHD (reviewed in Cetkovic-Cvrlje and Ucken, 2004).

In a preferred embodiment, the inflammatory disease is an eye disease.

Dry eye syndrome (DES, also known as keratoconjunctivitis sicca) is one of the most common problems treated by eye physicians. Sometimes DES is referred to as dysfunctional tear syndrome (Jackson, 2009. Canadian Journal Ophthalmology 44(4), 385-394). DES affects up to 10% of the population between the ages of 20 to 45 years, with this percentage increasing with age. Although a wide variety of artificial tear products are available, these products provide only transitory relief of symptoms. As such, there is a need for agents, compositions and therapeutic methods to treat dry eye.

As used herein, "dry eye disorder" is intended to encompass the disease states summarized in a recent official report of the Dry Eye Workshop (DEWS), which defined dry eye as "a multifactorial disease of the tears and ocular surface that results in symptoms of discomfort, visual disturbance, and tear film instability with potential damage to the ocular surface. It is accompanied by increased osmolality of the tear film and inflammation of the ocular surface."(Lemp, 2007. "The Definition and Classification of Dry Eye Disease: Report of the Definition and Classification Subcommittee of the International Dry Eye Workshop", The Ocular Surface, 5(2), 75-92). Dry eye is also sometimes referred to as keratoconjunctivitis sicca. In some embodiments, the treatment of the dry eye disorder involves ameliorating a particular symptom of dry eye disorder, such as eye discomfort, visual disturbance, tear film instability, tear hyperosmolarity, and inflammation of the ocular surface.

Uveitis is the most common form of intraocular inflammation and remains a significant cause of visual loss. Current treatments for uveitis employs systemic medications that have severe side effects and are globally immunosuppressive. Clinically, chronic progressive or relapsing forms of non-infectious uveitis are treated with topical and/or systemic corticosteroids. In addition, macrolides such as cyclosporine and rapamycin are used, and in some cases cytotoxic agents such as cyclophosphamide and chlorambucil, and antimetabolites such as azathioprine, methotrexate, and leflunomide (Srivastava et al., 2010. Uveitis: Mechanisms and recent advances in therapy. Clinica Chimica Acta, doi:10.1016/j.cca.2010.04.017).

Further eye diseases, combination treatments and route of administration are described for example in WO-A 2010/039939, which is hereby incorporated herein by reference.

In a further preferred embodiment, the disease or disorder associated with JAK is a proliferative disease, especially cancer.

Diseases and disorders associated especially with JAK are proliferative disorders or diseases, especially cancer.

Therefore, another aspect of the present invention is a compound or a pharmaceutically acceptable salt thereof of the present invention for use in a method of treating or preventing a proliferative disease, especially cancer.

Cancer comprises a group of diseases characterized by uncontrolled growth and spread of abnormal cells. All types of cancers generally involve some abnormality in the control of cell growth, division and survival, resulting in the malignant growth of cells. Key factors contributing to said malignant growth of cells are independence from growth signals, insensitivity to anti-growth signals, evasion of apoptosis, limitless replicative potential, sustained angiogenesis, tissue invasion and metastasis, and genome instability (Hanahan and Weinberg, 2000. The Hallmarks of Cancer. Cell 100, 57-70).

Typically, cancers are classified as hematological cancers (for example leukemias and lymphomas) and solid cancers such as sarcomas and carcinomas (for example cancers of the brain, breast, lung, colon, stomach, liver, pancreas, prostate, ovary).

The JAK inhibitors of the present invention may also useful in treating certain malignancies, including skin cancer and hematological malignancy such as lymphomas and leukemias.

Especially cancers in which the JAK-STAT signal transduction pathway is activated, for example due to activation of JAK3 are expected to respond to treatment with JAK3 inhibitors. Examples of cancers harboring JAK3 mutations are acute megakaryoblastic leukemia (AMKL) (Walters et al., 2006. Cancer Cell 10(1):65-75) and breast cancer (Jeong et al., 2008. Clin. Cancer Res. 14, 3716-3721).

Proliferative diseases or disorders comprise a group of diseases characterized by increased cell multiplication as observed in myeloprolifetative disorders (MPD) such as polycythemia vera (PV).

Yet another aspect of the present invention is the use of a compound of the present invention or a pharmaceutically acceptable salt thereof for the manufacture of a medicament for the treatment or prophylaxis of diseases and disorders associated with JAK.

Yet another aspect of the present invention is the use of a compound of the present invention or a pharmaceutically acceptable salt thereof for the manufacture of a medicament for treating or preventing an immunological, inflammatory, autoimmune, or allergic disorder or disease or a transplant rejection or a Graft-versus host disease.

Yet another aspect of the present invention is the use of a compound of the present invention or a pharmaceutically acceptable salt thereof for the manufacture of a medicament for treating or preventing a proliferative disease, especially cancer.

In the context of these uses of the invention, diseases and disorders associated with JAK are as defined above.

Yet another aspect of the present invention is a method for treating, controlling, delaying or preventing in a mammalian patient in need thereof one or more conditions selected from the group consisting of diseases and disorders associated with JAK, wherein the method comprises the administration to said patient a therapeutically effective amount of a compound according to present invention or a pharmaceutically acceptable salt thereof.

Yet another aspect of the present invention is a method for treating, controlling, delaying or preventing in a mammalian patient in need thereof one or more conditions selected from the group consisting of an immunological, inflammatory, autoimmune, or allergic disorder or disease or a transplant rejection or a Graft-versus host disease, wherein the method comprises the administration to said patient a therapeutically effective amount of a compound according to present invention or a pharmaceutically acceptable salt thereof.

Yet another aspect of the present invention is a method for treating, controlling, delaying or preventing in a mammalian patient in need thereof a proliferative disease, especially cancer, wherein the method comprises the administration to said patient a therapeutically effective amount of a compound according to present invention or a pharmaceutically acceptable salt thereof.

In the context of these methods of the invention, diseases and disorders associated with JAK are as defined above.

As used herein, the term "treating" or "treatment" is intended to refer to all processes, wherein there may be a slowing, interrupting, arresting, or stopping of the progression of a disease, but does not necessarily indicate a total elimination of all symptoms.

All embodiments discussed above with respect to the pharmaceutical composition of the invention also apply to the above mentioned first or second medical uses or methods of the invention.

In general, compounds of the present invention may be prepared according to a method comprising the steps of
(a) reacting a compound of formula (II)

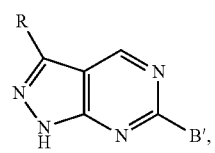
(II)

wherein B' is a suitable leaving group, like chloro, and R has the meaning as indicated above with a compound of formula

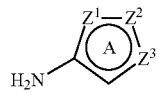

to yield a compound of formula (III)

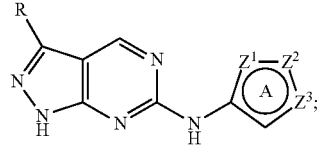
(III)

and
(b) reacting compound of formula (III) with a compound of formula (IV)

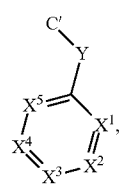
(IV)

wherein $X^1$ to $X^5$, Y have the meaning as indicated above and C' is a suitable reactive group, like bromo, to yield a compound of formula (I).

Exemplary routes for the preparation of compounds of the present invention are described below. It is clear to a practitioner in the art to combine or adjust such routes especially in combination with the introduction of activating or protective chemical groups.

Exemplary general routes for the preparation of compounds according to the present invention are outlined in Schemes 1 and 2, wherein by way of example R is H, Y is a chemical bond (n=0) or methylene (n=1 and $R^5$, $R^{5a}$ are H) and $X^1$ to $X^5$ are CH (resulting in a phenyl group Ph).

Scheme 1

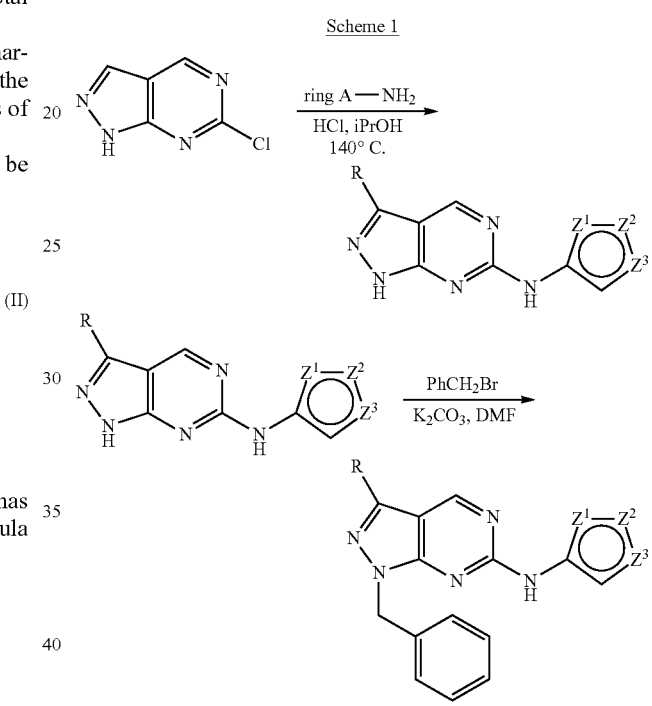

Scheme 2

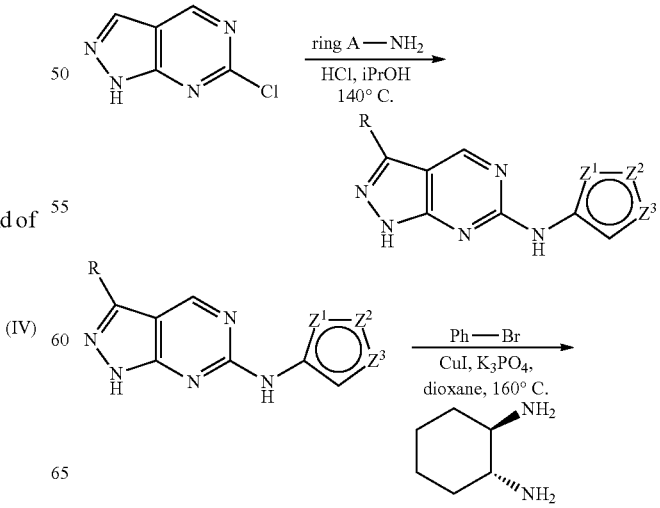

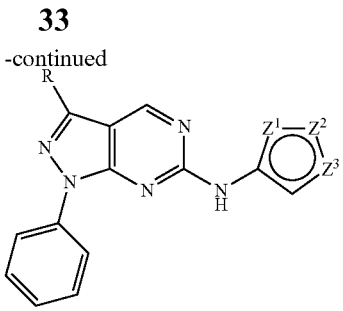

EXAMPLES

Analytical Methods

NMR spectra were obtained on a Brucker dpx400. LCMS was carried out on an Agilent 1100 using a Gemini C18, 3×30 mm, 3 micron. Column flow was 1.2 mL/min and solvents used were water and acetonitrile (0.1% formic acid-high pH, 0.1% ammonia-low pH) with an injection volume of 3 μL. Wavelengths were 254 and 210 nm.

Method A

Column: Phenomenex Gemini-C18, 3×30 mm, 3 microns. Flow rate: 1.2 mL/min

TABLE 1

| Time (min) | Water (%) | ACN (%) |
| --- | --- | --- |
| 0 | 95 | 5 |
| 3 | 5 | 95 |
| 4.5 | 5 | 95 |
| 4.6 | 95 | 5 |
| 5 | STOP | |

Method B

Column: Phenomenex Gemini-C18, 4.6×150 mm, 5 microns. Flow rate: 1.0 mL/min

TABLE 2

| Time (min) | Water (%) | ACN (%) |
| --- | --- | --- |
| 0.00 | 95.0 | 5.0 |
| 11.00 | 5.0 | 95.0 |
| 13.00 | 5.0 | 95.0 |
| 13.01 | 95.0 | 5.0 |
| 14.00 | STOP | |

TABLE 3

| Abbreviations | |
| --- | --- |
| ACN | Acetonitrile |
| Ar | Aryl |
| aq | Aqueous |
| br | Broad |
| Boc | Tert-Butoxycarbonyl |
| BuLi | Butyllithium |
| d | Doublet |
| DCM | Dichloromethane |
| dd | Double doublet |
| ddd | Double doublet of doublets |
| DEAD | Diethyl azodicarboxylate |
| DIAD | Diisopropyl azodicarboxylate |
| DIPEA | Diisopropylethylamine |
| DME | 1,2-Dimethoxyethane |
| DMF | N,N'-Dimethylformamide |
| DMF-DMA | N,N-dimethylformamide dimethylacetal |
| DMSO | N,N'-dimethylsulfoxide |
| DP | Drug pulldown |
| dt | Doublet of triplets |
| DTT | Dithiothreitol |
| EDC | 1-Ethyl-3-(3-dimethylaminopropyl)carbodiimide |
| EDTA | Ethylenediaminetetraacetic acid |
| EtOAc | Ethyl acetate |
| EtOH | Ethanol |
| eq | Equivalents |
| g | Grams |
| h | Hours |
| HCl | Hydrochloric acid |
| $H_2O$ | Water |
| $H_2S$ | Hydrogen sulfide |
| HOBt | 1-Hydroxybenzotriazole |
| HPLC | High performance liquid chromatography |
| $IC_{50}$ | 50% inhibition concentration |
| iPr | Isopropyl |
| L | Litres |
| LC-MS | Liquid chromatography mass spectroscopy |
| m | Multiplet |
| M | Molar |
| MeOH | Methanol |
| Mesyl | Methanesulfonyl chloride |
| mg | Milligrams |
| $MgSO_4$ | Magnesium Sulphate |
| min | Minutes |
| mL | Millilitres |
| mm | Millimetres |
| mmol | Millimoles |
| mol % | Molar percent |
| μL | Microlitres |
| nm | Nanometres |
| NMR | Nuclear magnetic resonance |
| PBS | Phosphate buffered saline |
| q | Quartet |
| rpm | Revolutions per minute |
| rt | Room temperature |
| RT | Retention time |
| s | Singlet |
| sat. | Saturated |
| t | Triplet |
| td | Triplet of doublets |
| tdd | Triple doublet of doublets |
| THF | Tetrahydrofuran |
| tt | Triplet of triplets |
| tert | Tertiary |

Experimental
Procedure A:
General Procedure for the Synthesis of 4-Amino-1-N-alkylated-pyrazoles A solution of 4-nitropyrazole (300 mg, 2.65 mmol), potassium carbonate (2 eq) and the alkylating reagent (1.1 eq) in acetonitrile (10 mL) was heated at 60° C. for 18 h. After cooling to rt the mixture was diluted with EtOAc and washed with water. The organic phase was collected, dried ($MgSO_4$) and concentrated in vacuo. The crude residue was dissolved in methanol (10 mL), palladium on carbon (50 mg) was added and the reaction was stirred under a balloon of hydrogen for 18 h. The resulting mixture was filtered through Celite and the filtrate concentrated in vacuo to give the desired product.

Procedure B:
General Procedure for the Synthesis of 4-Amino-3-methyl-1-N-alkylated pyrazoles A solution of 3-methylpyrazole (1.96 mL, 24.0 mmol) in sulfuric acid (15 mL) was cooled to −5° C. and potassium nitrate (1.1 eq) was added portion-wise. The reaction was warmed to rt and stirred for 16 h. The mixture was cooled to 0° C. and neutralized with ammonium hydroxide solution. The resulting solid was filtered and air-dried to give 3-methyl-4-nitro-1H-pyrazole. To a solution of 3-methyl-4-nitropyrazole (300 mg, 2.6 mmol), potassium carbonate (2 eq) and the alkylating reagent (1.1 eq) in acetonitrile (10 mL) was heated at 60° C. for 18 h. After cooling to rt the mixture was diluted with EtOAc and washed with water. The organic phase was collected, dried (MgSO$_4$) and concentrated in vacuo. The crude residue was dissolved in methanol (10 mL), palladium on carbon (50 mg) was added and the reaction was stirred under a balloon of hydrogen for 18 h. The resulting mixture was filtered through Celite and the filtrate concentrated in vacuo to give the desired product.

Procedure C:

General Procedure for the Synthesis of 3-Methoxy, N-Substituted Pyrazoles

A solution of 3-methoxy-4-nitro-1H-pyrazole (200 mg, 1.4 mmol), potassium carbonate (2 eq) and the alkylating reagent (1.1 eq) in acetonitrile (10 mL) was heated at 60° C. for 18 h. After cooling to rt the mixture was diluted with EtOAc and washed with water. The organic phase was collected, dried (MgSO$_4$) and concentrated in vacuo. The crude residue was dissolved in methanol (10 mL), palladium on carbon (50 mg) was added and the reaction was stirred under a balloon of hydrogen for 18 h. The resulting mixture was filtered through Celite and the filtrate concentrated in vacuo to give the desired product.

Example 1

2-((6-(1-Methyl-1H-pyrazol-4-ylamino)-1H-pyrazolo[3,4-d]pyrimidin-1-yl)methyl)benzonitrile

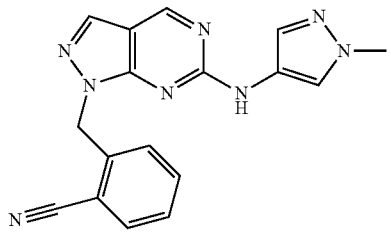 [SMILES: Cn1cc(Nc2ncc3cnn(Cc4ccccc4C#N)c3n2)cn1]

Step (i)

A suspension of 1-methyl-1H-pyrazol-4-amine (173 mg, 1.29 mmol), 6-chloro-1H-pyrazolo[3,4-d]pyrimidine (200 mg, 1.29 mmol) and HCl (25 μL, 4M in dioxane) in isopropanol (2 mL) was heated in the microwave at 140° C. for 1 h. After cooling to rt, the mixture was filtered and the resulting solid washed with cold isopropanol and diethyl ether to give N-(1-methyl-1H-pyrazol-4-yl)-1H-pyrazolo[3,4-d]pyrimidin-6-amine.

Step (ii)

A solution of N-(1-methyl-1H-pyrazol-4-yl)-1H-pyrazolo[3,4-d]pyrimidin-6-amine (100 mg, 0.46 mmol), 2-(bromomethyl)benzonitrile (1.1 eq) and potassium carbonate (2 eq) in DMF (2 mL) was stirred at rt for 18 h. The resultant mixture was diluted with EtOAc and washed with H$_2$O, then brine. The organic phase was collected, dried (MgSO$_4$) and concentrated in vacuo. The resultant residue was purified by column chromatography (petroleum ether: EtOAc) to give the title product. $^1$H NMR (d$_6$-DMSO) δ 9.94 (s, 1H), 8.93 (s, 1H), 8.09 (s, 2H), 7.91 (dd, 1H), 7.67 (td, 1H), 7.51-7.54 (m, 2H), 7.36-7.38 (m, 1H), 5.76 (s, 2H), 3.82 (s, 3H); LC-MS method B, (ES+) 331.0, RT=8.04 min.

Example 2

1-(2-Fluorobenzyl)-N-(1-methyl-1H-pyrazol-4-yl)-1H-pyrazolo[3,4-d]pyrimidin-6-amine The following compound was made according to the procedure in Example 1, using 1-(bromomethyl)-2-fluorobenzene:

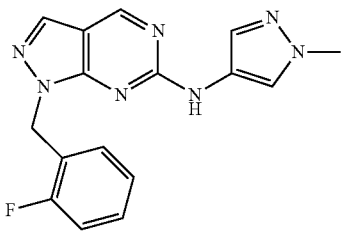 [SMILES: Cn1cc(Nc2ncc3cnn(Cc4ccccc4F)c3n2)cn1]

$^1$H NMR (d$_6$-DMSO) δ 9.91 (s, 1H), 8.91 (s, 1H), 8.05-8.07 (m, 1H), 7.56 (s, 1H), 7.33-7.38 (m, 1H), 7.21-7.26 (m, 2H), 7.14-7.17 (m, 1H), 5.61 (s, 2H), 3.83 (s, 3H); LC-MS method B, (ES+) 324.1, RT=8.46 min.

Example 3

2-((6-(1-Methyl-1H-pyrazol-3-ylamino)-1H-pyrazolo[3,4-d]pyrimidin-1-yl)methyl)benzonitrile The following compound was made according to the procedure in Example 1 using 1-methyl-1H-pyrazol-3-amine:

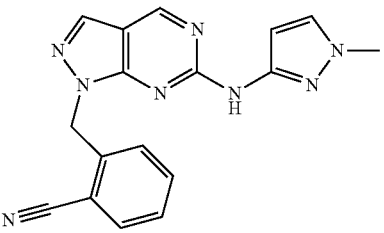 [SMILES: Cn1ccc(Nc2ncc3cnn(Cc4ccccc4C#N)c3n2)n1]

$^1$H NMR (CDCl$_3$) δ 8.89 (s, 1H), 8.01 (s, 1H), 7.98 (s, 1H), 7.70 (dd, 1H), 7.48-7.50 (m, 1H), 7.37-7.39 (m, 1H), 7.29 (d, 1H), 7.19 (d, 1H), 6.86 (d, 1H), 5.78 (s, 2H), 3.84 (s, 3H); LC-MS method B, (ES+) 331.1, RT=8.28 min.

Example 4

2-((6-(1H-Pyrazol-4-ylamino)-1H-pyrazolo[3,4-d]pyrimidin-1-yl)methyl)benzonitrile The following compound was made according to the procedure in Example 1, using 1H-pyrazol-4-amine:

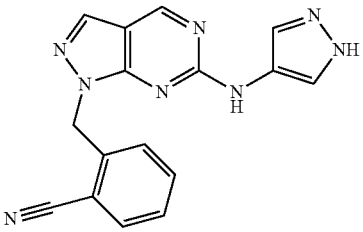 [SMILES: N#Cc1ccccc1Cn1ncc2cnc(Nc3cn[nH]c3)nc21]

$^1$H NMR (d$_6$-DMSO) δ 12.60 (s, 1H), 9.98 (s, 1H), 8.99 (s, 1H), 8.15 (s, 2H), 7.96 (dd, 1H), 7.70-7.74 (m, 2H), 7.57 (td, 1H), 7.37-7.39 (m, 1H), 5.79 (s, 2H); LC-MS method B, (ES+) 317.1, RT=7.35 min.

Example 5

2-46-(Isoxazol-4-ylamino)-1H-pyrazolo[3,4-d]pyrimidin-1-yl)methyl)benzonitrile

The following compound was made according to the procedure in Example 1, using isoxazol-4-amine:

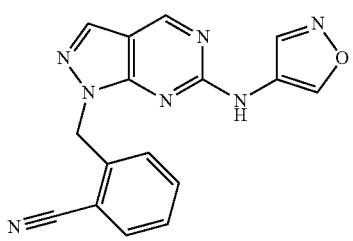 [SMILES: N#Cc1ccccc1Cn1ncc2cnc(Nc3cnoc3)nc21]

¹H NMR (d₆-DMSO) δ 9.18 (s, 1H), 8.95 (s, 1H), 8.55 (s, 1H), 8.09 (s, 1H), 7.84 (s, 1H), 7.79 (dd, 1H), 7.62 (td, 1H), 7.49 (td, 1H), 7.36 (d, 1H), 5.82 (s, 2H); LC-MS method B, (ES+) 318.0, RT=8.85 min.

Example 6

2-((6-(1,3-Dimethyl-1H-pyrazol-4-ylamino)-1H-pyrazolo[3,4-d]pyrimidin-1-yl)methyl)benzonitrile The following compound was made according to the procedure in Example 1, using 1,3-dimethyl-1H-pyrazol-4-amine:

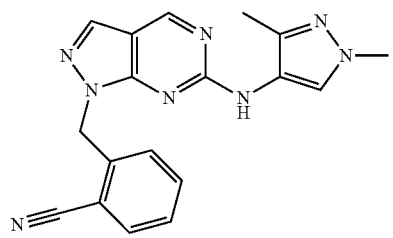 [SMILES: Cc1nn(C)cc1Nc1ncc2cnn(Cc3ccccc3C#N)c2n1]

¹H NMR (d₆-DMSO) δ 8.87 (s, 1H), 8.05 (s, 1H), 8.01 (s, 1H), 7.80 (dd, 1H), 7.60 (td, 1H), 7.48 (td, 1H), 7.33 (d, 1H), 5.75 (s, 2H), 3.85 (s, 3H), 2.20 (s, 3H); LC-MS method B, (ES+) 345.1, RT=8.18 min.

Example 7

2-((6-(1-Ethyl-3-methyl-1H-pyrazol-4-ylamino)-1H-pyrazolo[3,4-d]pyrimidin-1-yl)methyl)benzonitrile The following compound was made according to the procedure in Example 1, using 1-ethyl-3-methyl-1H-pyrazol-4-amine:

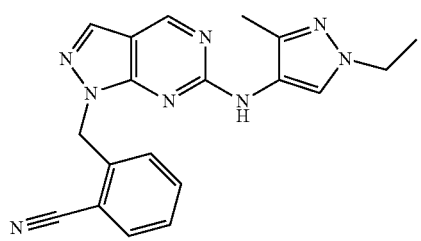 [SMILES: CCn1cc(Nc2ncc3cnn(Cc4ccccc4C#N)c3n2)c(C)n1]

¹H NMR (d₆-DMSO) δ 9.31 (br s, 1H), 8.94 (s, 1H), 8.09 (s, 1H), 8.05 (br s, 1H), 7.90 (dd, 1H), 7.66 (td, 1H), 7.51 (td, 1H), 7.31 (br s, 1H), 5.70 (s, 2H), 4.03 (q, 2H), 2.14 (s, 3H), 1.33 (t, 1H); LC-MS method B, (ES+) 359.1, RT=8.70 min.

Example 8

2-46-(Isoxazol-3-ylamino)-1H-pyrazolo[3,4-d]pyrimidin-1-yl)methyl)benzonitrile

The following compound was made according to the procedure in Example 1, using isoxazol-3-amine:

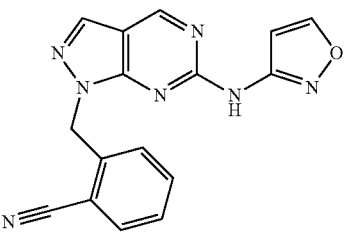 [SMILES: N#Cc1ccccc1Cn1ncc2cnc(Nc3ccon3)nc21]

¹H NMR (d₆-DMSO) δ 10.86 (s, 1H), 9.09 (s, 1H), 8.78 (d, 1H), 8.21 (s, 1H), 7.90 (dd, 1H), 7.67 (td, 1H), 7.52 (td, 1H), 7.35 (d, 1H), 7.24 (d, 1H), 5.74 (s, 2H); LC-MS method B, (ES+) 318.0, RT=8.66 min.

Example 9

2-((6-(1,5-Dimethyl-1H-pyrazol-3-ylamino)-1H-pyrazolo[3,4-d]pyrimidin-1-yl)methyl)benzonitrile The following compound was made according to the procedure in Example 1, using 1,5-dimethyl-1H-pyrazol-3-amine:

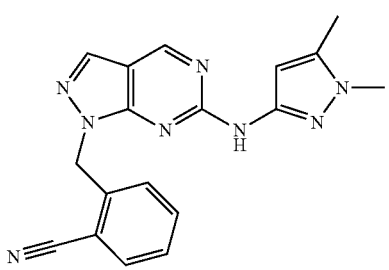 [SMILES: Cc1cc(Nc2ncc3cnn(Cc4ccccc4C#N)c3n2)nn1C]

¹H NMR (d₆-DMSO) δ 10.01 (s, 1H), 8.94 (s, 1H), 8.11 (s, 1H), 7.90 (d, 1H), 7.65 (t, 1H), 7.51 (t, 1H), 7.31 (d, 1H), 6.55 (s, 1H), 5.70 (s, 2H), 3.61 (s, 3H), 2.24 (s, 3H); LC-MS method B, (ES+) 345.1, RT=8.58 min.

Example 10

2-((6-(1-(2-Methoxyethyl)-1H-pyrazol-4-ylamino)-1H-pyrazolo[3,4-d]pyrimidi-1-yl)methyl)benzonitrile The following compound was made according to the procedure in Example 1, using 1-(2-methoxyethyl)-1H-pyrazol-4-amine:

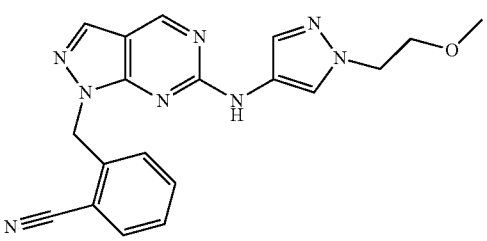 [SMILES: COCCn1cc(Nc2ncc3cnn(Cc4ccccc4C#N)c3n2)cn1]

¹H NMR (d₆-DMSO) δ 9.94 (s, 1H), 8.93 (s, 1H), 8.09-8.11 (m, 2H), 7.89 (dd, 1H), 7.65 (td, 1H), 7.55 (s, 1H), 7.51 (td, 1H), 7.32-7.34 (m, 1H), 5.74 (s, 2H), 4.21-4.24 (m, 2H), 3.64-3.67 (m, 4H), 3.19 (s, 3H); LC-MS method B, (ES+) 375.1, RT=8.22 min.

Example 11

2-((6-(1-Ethyl-1H-pyrazol-4-ylamino)-1H-pyrazolo[3,4-d]pyrimidin-1-yl)methyl)benzonitrile The following compound was made according to the procedure in Example 1, using 1-ethyl-1H-pyrazol-4-amine. 1-ethyl-1H-pyrazol-4-amine was prepared by Procedure A using ethyl iodide as alkylating agent:

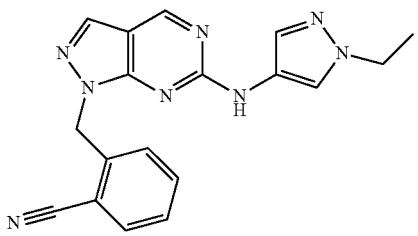 [SMILES: CCn1cc(Nc2ncc3cnn(Cc4ccccc4C#N)c3n2)cn1]

¹H NMR (d₆-DMSO) δ 9.94 (s, 1H), 8.94 (s, 1H), 8.10 (s, 2H), 7.91 (dd, 1H), 7.66 (td, 1H), 7.49-7.53 (m, 2H), 7.35-7.37 (m, 1H), 5.76 (s, 2H), 4.11 (q, 2H), 1.35 (t, 3H); LC-MS method B, (ES+) 345.1, RT=8.58 min.

Example 12

2-((6-(1-Isopropyl-1H-pyrazol-4-ylamino)-1H-pyrazolo[3,4-d]pyrimidin-1-yl)methyl)benzonitrile The following compound was made according to the procedure in Example 1, using 1-isopropyl-1H-pyrazol-4-amine. 1-isopropyl-1H-pyrazol-4-amine was prepared by Procedure A using isopropyl iodide as alkylating agent:

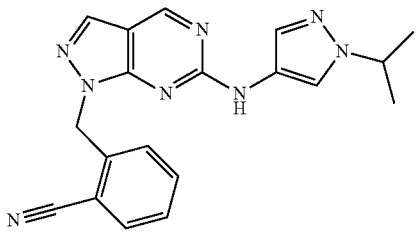 [SMILES: CC(C)n1cc(Nc2ncc3cnn(Cc4ccccc4C#N)c3n2)cn1]

¹H NMR (d₆-DMSO) δ 9.93 (s, 1H), 8.94 (s, 1H), 8.10 (s, 1H), 8.06 (s, 1H), 7.91 (dd, 1H), 7.66 (td, 1H), 7.49-7.55 (m, 2H), 7.31-7.33 (m, 1H), 5.75 (s, 2H), 4.48 (sept, 1H), 1.39 (d, 6H); LC-MS method B, (ES+) 359.1, RT=9.07 min.

Example 13

2-(4-(1-(2-Cyanobenzyl)-1H-pyrazolo[3,4-d]pyrimidin-6-ylamino)-1H-pyrazol-1-yl)-N-methylacetamide The following compound was made according to the procedure in Example 1, using 2-(4-amino-1H-pyrazol-1-yl)-N-methylacetamide. 2-(4-amino-1H-pyrazol-1-yl)-N-methylacetamide was prepared by Procedure A using 2-bromo-N-methylacetamide as alkylating agent:

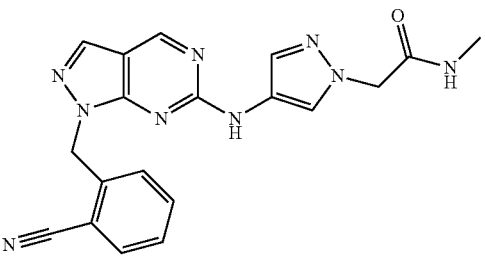 [SMILES: CNC(=O)Cn1cc(Nc2ncc3cnn(Cc4ccccc4C#N)c3n2)cn1]

¹H NMR (d₆-DMSO) δ 10.00 (s, 1H), 8.94 (s, 1H), 8.17 (s, 1H), 8.09 (s, 1H), 7.88-7.90 (m, 2H), 7.66 (td, 1H), 7.60 (s, 1H), 7.51 (td, 1H), 7.37-7.39 (m, 1H), 5.75 (s, 2H), 4.74 (s, 2H), 2.61 (d, 3H); LC-MS method B, (ES+) 388.1, RT=7.11 min.

Example 14

2-((6-(1-(2-Morpholino-2-oxoethyl)-1H-pyrazol-4-ylamino)-1H-pyrazolo[3,4-d]pyrimidin-1-yl)methyl)benzonitrile The following compound was made according to the procedure in Example 1, using 2-(4-amino-1H-pyrazol-1-yl)-1-morpholinoethanone. 2-(4-amino-1H-pyrazol-1-yl)-1-morpholinoethanone was prepared by Procedure A using 2-chloro-1-morpholinoethanone as alkylating agent:

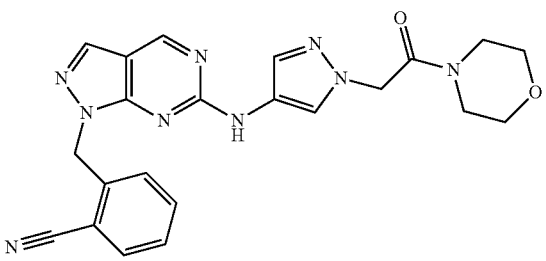 [SMILES: N#Cc1ccccc1Cn1ncc2cnc(Nc3cnn(CC(=O)N4CCOCC4)c3)nc21]

¹H NMR (d₆-DMSO) δ 9.98 (s, 1H), 8.94 (s, 1H), 8.10 (s, 2H), 7.87 (d, 1H), 7.65 (td, 1H), 7.57 (s, 1H), 7.51 (t, 1H), 7.35-7.37 (m, 1H), 5.75 (s, 2H), 5.10 (s, 2H), 3.57-3.62 (m, 4H), 3.45-3.52 (m, 4H); LC-MS method B, (ES+) 444.1, RT=7.43 min.

Example 15

2-((6-(1-(2-Cyanoethyl)-1H-pyrazol-4-ylamino)-1H-pyrazolo[3,4-d]pyrimidin-1-yl)methyl)benzonitrile The following compound was made according to the procedure in Example 1, using 3-(4-amino-1H-pyrazol-1-yl)propanenitrile. 3-(4-amino-1H-pyrazol-1-yl)propanenitrile was prepared by Procedure A using 3-bromopropanenitrile as alkylating agent:

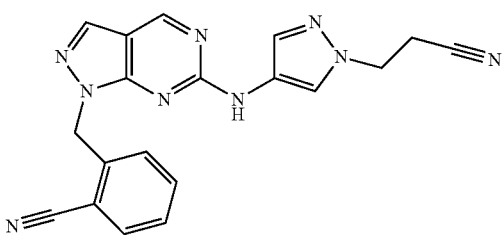 [SMILES: N#CCCn1cc(Nc2ncc3cnn(Cc4ccccc4C#N)c3n2)cn1]

¹H NMR (d₆-DMSO) δ 10.01 (s, 1H), 8.95 (s, 1H), 8.29 (s, 1H), 8.10 (s, 1H), 7.90 (dd, 1H), 7.66 (td, 1H), 7.63 (s, 1H), 7.51 (td, 1H), 7.40-7.42 (m, 1H), 5.77 (s, 2H), 4.38 (t, 2H), 3.05 (t, 2H); LC-MS method B, (ES+) 370.1, RT=7.61 min.

Example 16

2-((6-(1-Methyl-1H-pyrazol-4-ylamino)-1H-pyrazolo[3,4-d]pyrimidin-1-yl)methyl)benzamide

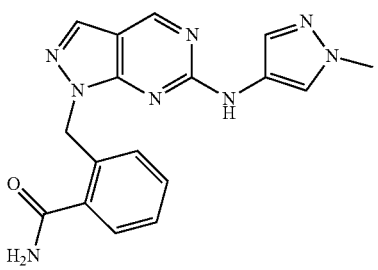 [SMILES: Cn1cc(Nc2ncc3cnn(Cc4ccccc4C(N)=O)c3n2)cn1]

A suspension of 2-((6-(1-methyl-1H-pyrazol-4-ylamino)-1H-pyrazolo[3,4-d]pyrimidin-1-yl)methyl)benzonitrile (see Example 1) (40 mg, 0.24 mmol), sodium hydroxide (0.5 mL, 1M in H₂O) and hydrogen peroxide (0.2 mL of a 33% solution in water) in ethanol (5 mL) was heated at 60° C. for 3 h. After cooling to rt the mixture was diluted with EtOAc and washed with water. The organic phase was collected, dried (MgSO₄) and concentrated in vacuo to give the title product. ¹H NMR (d₆-DMSO) δ 9.95 (s, 1H), 8.99 (s, 1H), 8.10-8.16 (m, 3H), 7.66 (s, 1H), 7.60 (dd, 1H), 7.54 (s, 1H), 7.37-7.40 (m, 2H), 6.95 (br s, 1H), 5.85 (s, 2H), 3.88 (s, 3H); LC-MS method B, (ES+) 349.1, RT=6.46 min.

Example 17

N-Methyl-N-(4-(6-(1-methyl-1H-pyrazol-4-ylamino)-1H-pyrazolo[3,4-d]pyrimidin-1-yl)phenyl)methanesulfonamide

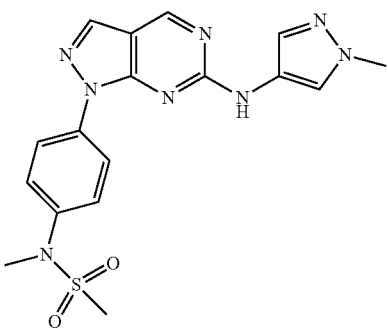

Step (i)

A solution of 4-bromoaniline (1.00 g, 5.81 mmol) and methanesulfonyl chloride (1 eq) in dichloromethane (10 mL) and pyridine (5 mL) was stirred at rt for 18 h. The resultant mixture was then diluted with dichloromethane and washed with water and then brine. The organic phase was collected, dried (MgSO₄) and concentrated in vacuo to give N-(4-bromophenyl)methanesulfonamide.

Step (ii)

A solution of N-(4-bromophenyl)methanesulfonamide (200 mg, 0.80 mmol), potassium carbonate (2 eq) and methyl iodide (2 eq) in DMF (2 mL) was heated at 60° C. for 18 h. After cooling to rt the mixture was diluted with EtOAc and washed with water. The organic phase was collected, dried (MgSO₄) and concentrated in vacuo to give N-(4-bromophenyl)-N-methylmethanesulfonamide.

Step (iii)

A suspension of N-(1-methyl-1H-pyrazol-4-yl)-1H-pyrazolo[3,4-d]pyrimidin-6-amine (see Example 1, step (i)) (60 mg, 0.28 mmol), N-(4-bromophenyl)-N-methylmethanesulfonamide (1.1 eq), copper iodide (0.1 eq), potassium phosphate (2 eq) and trans-1,2-diaminocyclohexane (0.1 eq) in dioxane (2 mL) was heated in the microwave at 160° C. for 2 h. After cooling to rt the mixture was diluted with EtOAc and washed with water. The organic phase was collected, dried (MgSO₄) and concentrated in vacuo. The resultant residue was purified by column chromatography (petroleum ether: EtOAc) to give the title product. ¹H NMR (d₆-DMSO) δ 10.07 (s, 1H), 9.03 (s, 1H), 8.33 (s, 1H), 8.19 (d, 2H), 7.97 (s, 1H), 7.66 (d, 2H), 7.60 (s, 1H), 3.84 (s, 3H), 3.01 (s, 3H); LC-MS method B, (ES+) 399.1, RT=8.18 min.

Example 18

N-(4-(6-(1-Methyl-1H-pyrazol-4-ylamino)-1H-pyrazolo[3,4-d]pyrimidin-1-yl)phenyl)methanesulfonamide The following compound was made according to the procedure in Example 17 (Steps and iii):

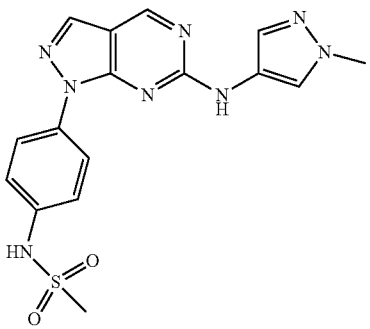 [SMILES: Cn1cc(Nc2ncc3cnn(-c4ccc(NS(C)(=O)=O)cc4)c3n2)cn1]

¹H NMR (d₆-DMSO) δ 10.02 (s, 1H), 9.93 (s, 1H), 9.01 (s, 1H), 8.28 (s, 1H), 8.09 (d, 2H), 7.94 (s, 1H), 7.61 (s, 1H), 7.42 (d, 2H), 3.83 (s, 3H), 3.05 (s, 3H); LC-MS method B, (ES+) 385.1, RT=7.55 min.

Example 19

2-((6-(1-Isopropyl-1H-pyrazol-3-ylamino)-1H-pyrazolo[3,4-d]pyrimidin-1-yl)methyl)benzonitrile The following compound was made according to the procedure in Example 1, using 1-isopropyl-1H-pyrazol-3-amine:

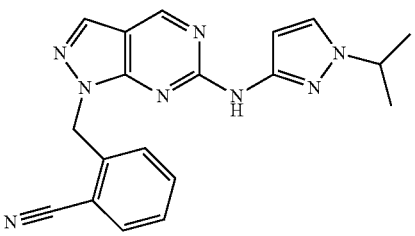 [SMILES: CC(C)n1ccc(Nc2ncc3cnn(Cc4ccccc4C#N)c3n2)n1]

¹H NMR (d₆-DMSO) δ 10.15 (s, 1H), 8.95 (s, 1H), 8.11 (s, 1H), 7.89 (d, 1H), 7.61-7.67 (m, 2H), 7.51 (t, 1H), 6.73 (d, 1H), 5.69 (s, 2H), 4.38 (septet, 1H), 1.39 (d, 3H); LC-MS method B, (ES+) 359.1, RT=9.03 min.

Example 20

2-((6-(1-(3-Cyanopropyl)-1H-pyrazol-4-ylamino)-1H-pyrazolo[3,4-d]pyrimidin-1-yl)methyl)benzonitrile The following compound was made according to the procedure in Example 1, using 4-(4-amino-1H-pyrazol-1-yl)butanenitrile. 4-(4-amino-1H-pyrazol-1-yl)butanenitrile was prepared by Procedure A using 4-bromobutanenitrile as alkylating agent:

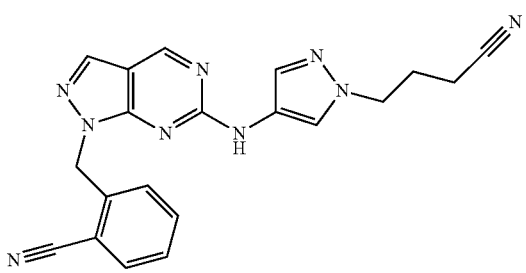 [SMILES: N#CCCCn1cc(Nc2ncc3cnn(Cc4ccccc4C#N)c3n2)cn1]

¹H NMR (d₆-DMSO) δ 9.97 (s, 1H), 8.93 (s, 1H), 8.14 (s, 1H), 8.09 (s, 1H), 7.90 (d, 1H), 7.66 (t, 1H), 7.57 (s, 1H), 7.51 (t, 1H), 7.38-7.40 (m, 1H), 5.75 (s, 2H), 4.16 (t, 2H), 2.44 (t, 2H), 2.06 (quintet, 1H); LC-MS method B, (ES+) 384.2, RT=7.85 min.

Example 21

2-((6-(3-Methyl-1-propyl-1H-pyrazol-4-ylamino)-1H-pyrazolo[3,4-d]pyrimidin-1-yl)methyl)benzonitrile The following compound was made according to the procedure in Example 1, using 3-methyl-1-propyl-1H-pyrazol-4-amine:

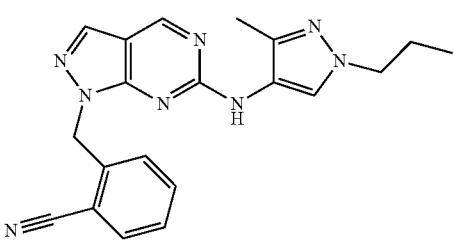 [SMILES: CCCn1cc(Nc2ncc3cnn(Cc4ccccc4C#N)c3n2)c(C)n1]

¹H NMR (d₆-DMSO) δ 9.07-9.19 (m, 1H), 8.90 (s, 1H), 8.06 (s, 1H), 7.87 (d, 1H), 7.63 (t, 2H), 7.50 (t, 1H), 7.18 (d, 1H), 5.58 (s, 2H), 3.94 (t, 1H), 2.15 (s, 3H), 1.68-1.73 (m, 2H), 0.83 (t, 3H); LC-MS method B, (ES+) 373.2, RT=8.51 min.

Example 22

2-((6-(1-(2,2-Difluoroethyl)-3-methyl-1H-pyrazol-4-ylamino)-1H-pyrazolo[3,4-d]pyrimidin-1-yl)methyl)benzonitrile The following compound was made according to the procedure in Example 1, using 1-(2,2-difluoroethyl)-3-methyl-1H-pyrazol-4-amine:

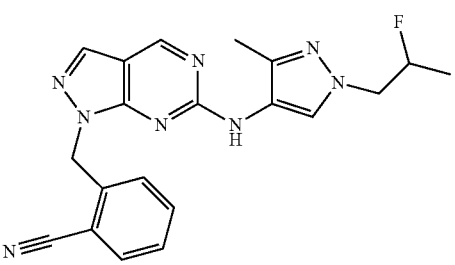 [SMILES: Cc1nn(CC(C)F)cc1Nc1ncc2cnn(Cc3ccccc3C#N)c2n1]

¹H NMR (d₆-DMSO) δ 9.40 (br s, 1H), 8.96 (s, 1H), 8.25 (br s, 1H), 8.10 (s, 1H), 7.88 (dd, 1H), 7.65 (td, 1H), 7.51 (td, 1H), 7.35 (br s, 1H), 6.31 (tt, 1H), 5.70 (s, 2H), 4.52 (td, 2H), 2.18 (s, 3H); LC-MS method B, (ES+) 395.1, RT=8.56 min.

Example 23

2-((6-(1-(2-methoxyethyl)-3-methyl-1H-pyrazol-4-ylamino)-1H-pyrazolo[3,4-d]pyrimidin-1-yl)methyl)benzonitrile The following compound was made according to the procedure in Example 1, using 1-(2-methoxyethyl)-3-methyl-1H-pyrazol-4-amine. 1-(2-methoxyethyl)-3-methyl-1H-pyrazol-4-amine was prepared by Procedure B using 1-bromo-2-methoxyethane as alkylating agent:

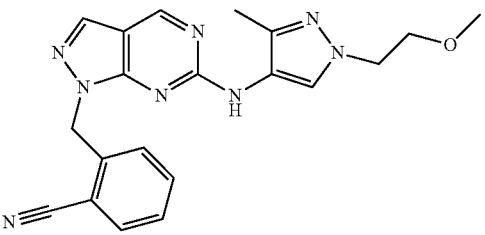 [SMILES: COCCn1cc(Nc2ncc3cnn(Cc4ccccc4C#N)c3n2)c(C)n1]

¹H NMR (d₆-DMSO) δ 9.29-9.36 (m, 1H), 8.94 (s, 1H), 8.09 (s, 1H), 7.89 (d, 1H), 7.65 (td, 1H), 7.51 (t, 1H), 7.28-7.30 (m, 1H), 5.68 (s, 2H), 4.15 (t, 2H), 3.63 (t, 2H), 3.18 (s, 3H), 2.14 (s, 3H); LC-MS method B, (ES+) 389.1, RT=7.86 min.

Example 24

2-((6-(1-(2,2-Difluoroethyl)-3-methoxy-1H-pyrazol-4-ylamino)-1H-pyrazolo[3,4-d]pyrimidin-1-yl)methyl)benzonitrile The following compound was made according to the procedure in Example 1, using 1-(2,2-difluoroethyl)-3-methoxy-1H-pyrazol-4-amine as alkylating agent:

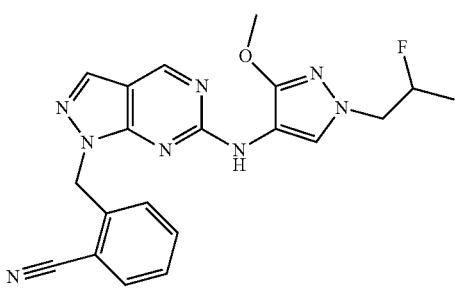 [SMILES: COc1nn(CC(C)F)cc1Nc1ncc2cnn(Cc3ccccc3C#N)c2n1]

¹H NMR (d₆-DMSO) δ 9.06 (br s, 1H), 8.93 (s, 1H), 8.09-8.14 (m, 2H), 7.89 (d, 1H), 7.65 (t, 1H), 7.51 (t, 1H), 7.34 (br s, 1H), 6.29 (tt, 1H), 5.67 (s, 2H), 4.44 (td, 2H), 3.82 (s, 3H); LC-MS method B, (ES+) 411.1, RT=9.14 min.

Example 25

2-((6-(1-(2-Hydroxyethyl)-1H-pyrazol-4-ylamino)-1H-pyrazolo[3,4-d]pyrimidin-1-yl)methyl)benzonitrile The following compound was made according to the procedure in Example 1, using 2-(4-amino-1H-pyrazol-1-yl)ethanol. 2-(4-amino-1H-pyrazol-1-yl)ethanol was prepared by Procedure A using 2-bromoethanol as alkylating agent:

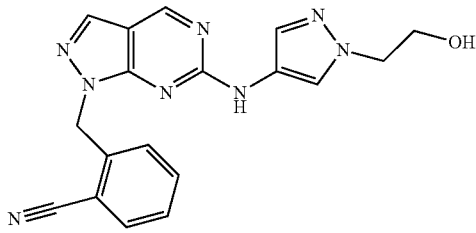 [SMILES: N#Cc1ccccc1Cn1ncc2cnc(Nc3cnn(CCO)c3)nc21]

¹H NMR (d₆-DMSO) δ 9.93 (s, 1H), 8.92 (s, 1H), 8.08 (s, 2H), 7.89 (dd, 1H), 7.65 (td, 1H), 7.57 (s, 1H), 7.50 (td, 1H), 7.36-7.38 (m, 1H), 5.73 (s, 2H), 4.86 (t, 1H), 4.11 (t, 1H), 3.68-3.72 (m, 2H); LC-MS method B, (ES+) 361.1, RT=6.74 min.

Example 26

1-(1-(2-Fluorophenyl)ethyl)-N-(1-methyl-1H-pyrazol-4-yl)-1H-pyrazolo[3,4-d]pyrimidin-6-amine The following compound was made according to the procedure in Example 1, using 141-bromoethyl)-2-fluorobenzene as alkylating agent:

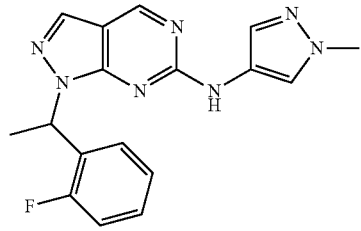 [SMILES: CC(c1ccccc1F)n1ncc2cnc(Nc3cnn(C)c3)nc21]

¹H NMR (d₄-methanol) δ 8.83 (s, 1H), 8.07 (s, 1H), 8.03 (s, 1H), 7.60 (s, 1H), 7.37 (td, 1H), 7.27-7.32 (m, 1H), 7.11-7.17 (m, 2H), 6.44 (q, 1H), 3.91 (s, 3H), 1.97 (d, 3H); LC-MS method B, (ES+) 338.1, RT=8.69 min.

Example 27

1-(2-Chlorobenzyl)-N-(1-methyl-1H-pyrazol-4-yl)-1H-pyrazolo[3,4-d]pyrimidin-6-amine The following compound was made according to the procedure in Example 1, using 1-(bromomethyl)-2-chlorobenzene as alkylating agent:

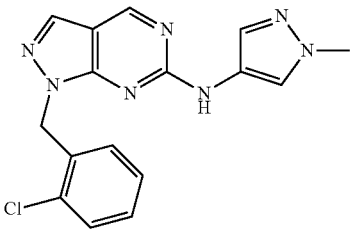 [SMILES: Cn1cc(Nc2ncc3cnn(Cc4ccccc4Cl)c3n2)cn1]

¹H NMR (d₆-DMSO) δ 9.09 (s, 1H), 8.93 (s, 1H), 8.08 (s, 1H), 8.01 (s, 1H), 7.50-7.54 (m, 2H), 7.27-7.36 (m, 2H), 7.14 (br s, 1H), 3.81 (s, 3H); LC-MS method B, (ES+) 340.0, RT=8.56 min.

Example 28

1-(2-Fluorobenzyl)-N-(1-(2-methoxyethyl)-1H-pyrazol-4-yl)-1H-pyrazolo[3,4-d]pyrimidin-6-amine The following compound was made according to the procedure in Example 1, using 1-(2-methoxyethyl)-1H-pyrazol-4-amine then 1-(bromomethyl)-2-fluorobenzene as alkylating

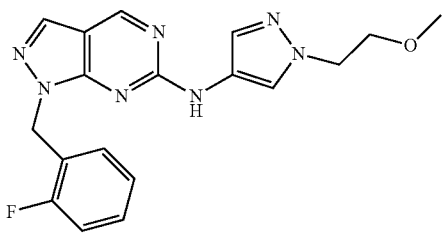 [SMILES: COCCn1cc(Nc2ncc3cnn(Cc4ccccc4F)c3n2)cn1]

¹H NMR (d₆-DMSO) δ 9.91 (s, 1H), 8.92 (s, 1H), 8.13 (s, 1H), 8.06 (s, 1H), 7.60 (s, 1H), 7.33-7.37 (m, 1H), 7.20-7.25 (m, 2H), 7.15 (t, 1H), 5.60 (s, 2H), 4.24 (t, 2H), 3.67 (t, 2H), 3.21 (s, 3H); LC-MS method B, (ES+) 368.1, RT=8.19 min.

Example 29

1-(2,6-Difluorobenzyl)-N-(1-methyl-1H-pyrazol-4-yl)-1H-pyrazolo[3,4-d]pyrimidin-6-amine

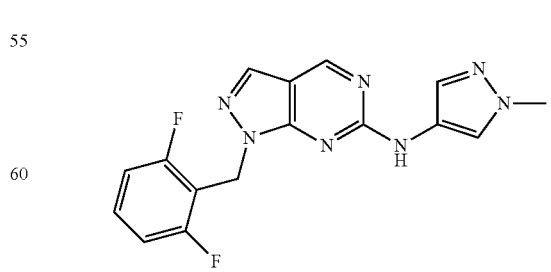

The following compound was made according to the procedure in Example 1, using 2-(bromomethyl)-1,3-difluorobenzene as alkylating agent:

$^1$H NMR (d$_6$-DMSO) δ 9.89 (s, 1H), 8.88 (s, 1H), 8.13 (s, 1H), 7.99 (s, 1H), 7.57 (s, 1H), 7.40-7.48 (m, 1H), 7.10-7.15 (m, 2H), 5.59 (s, 2H), 3.84 (s, 3H); LC-MS method B, (ES+) 342.0, RT=7.99 min.

Example 30

1-(2,5-Difluorobenzyl)-N-(1-methyl-1H-pyrazol-4-yl)-1H-pyrazolo[3,4-d]pyrimidin-6-amine The following compound was made according to the procedure in Example 1, using 2-(bromomethyl)-1,4-difluorobenzene as alkylating agent:

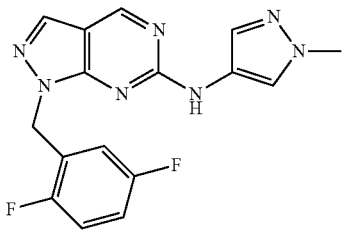 [SMILES: Cn1cc(Nc2ncc3cnn(Cc4cc(F)ccc4F)c3n2)cn1]

$^1$H NMR (d$_6$-DMSO) δ 9.91 (s, 1H), 8.90 (s, 1H), 8.05-8.07 (m, 2H), 7.55 (s, 1H), 7.27-7.32 (m, 1H), 7.17-7.23 (m, 1H), 7.09-7.13 (m, 1H), 5.59 (s, 2H), 3.82 (s, 3H); LC-MS method B, (ES+) 342.0, RT=8.27 min.

Example 31

1-(2,3-Difluorobenzyl)-N-(1-methyl-1H-pyrazol-4-yl)-1H-pyrazolo[3,4-d]pyrimidin-6-amine The following compound was made according to the procedure in Example 1, using 1-(bromomethyl)-2,3-difluorobenzene as alkylating agent:

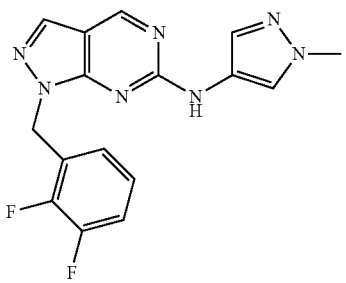 [SMILES: Cn1cc(Nc2ncc3cnn(Cc4cccc(F)c4F)c3n2)cn1]

$^1$H NMR (d$_6$-DMSO) δ 9.93 (s, 1H), 8.92 (s, 1H), 8.06-8.09 (m, 2H), 7.56 (s, 1H), 7.38-7.41 (m, 1H), 7.15-7.20 (m, 1H), 7.07-7.12 (m, 1H), 5.66 (s, 2H), 3.83 (s, 3H); LC-MS method B, (ES+) 342.0, RT=8.31 min.

Example 32

2-(4-(1-(2,5-Difluorobenzyl)-1H-pyrazolo[3,4-d]pyrimidin-6-ylamino)-1H-pyrazol-1-yl)ethanol The following compound was made according to the procedure in Example 1, using 2-(4-amino-1H-pyrazol-1yl)ethanol and 2-(bromomethyl)-1,4-difluorobenzene as alkylating agent. 2-(4-amino-1H-pyrazol-1yl)ethanol was prepared by Procedure A using 2-bromoethanol as alkylating agent:

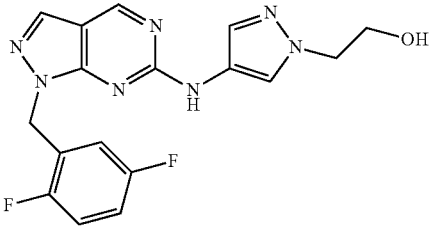 [SMILES: OCCn1cc(Nc2ncc3cnn(Cc4cc(F)ccc4F)c3n2)cn1]

$^1$H NMR (d$_6$-DMSO) δ 9.93 (s, 1H), 8.92 (s, 1H), 8.11 (s, 1H), 8.07 (s, 1H), 7.62 (s, 1H), 7.28-7.33 (m, 1H), 7.19-7.25 (m, 1H), 7.11 (br s, 1H), 5.59 (s, 2H), 4.90 (br s, 1H), 4.11-4.14 (m, 2H), 3.72-3.74 (m, 2H); LC-MS method B, (ES+) 372.1, RT=7.34 min.

Example 33

2-(4-(1-(2,3-Difluorobenzyl)-1H-pyrazolo[3,4-d]pyrimidin-6-ylamino)-1H-pyrazol-1-yl)ethanol The following compound was made according to the procedure in Example 1, using 2-(4-amino-1H-pyrazol-1yl)ethanol and 1-(bromomethyl)-2,3-difluorobenzene as alkylating agent. 2-(4-amino-1H-pyrazol-1yl)ethanol was prepared by Procedure A using 2-bromoethanol as alkylating agent:

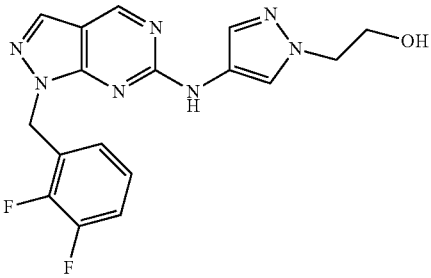 [SMILES: OCCn1cc(Nc2ncc3cnn(Cc4cccc(F)c4F)c3n2)cn1]

$^1$H NMR (d$_6$-DMSO) δ 9.93 (s, 1H), 8.92 (s, 1H), 8.13 (s, 1H), 8.06 (s, 1H), 7.62 (s, 1H), 7.35-7.42 (m, 1H), 7.12-7.20 (m, 2H), 5.65 (s, 2H), 4.90 (t, 1H), 4.13 (t, 2H), 3.73 (q, 2H); LC-MS method B, (ES+) 372.1, RT=7.39 min.

Example 34

2-(4-(1-(2-Fluorobenzyl)-1H-pyrazolo[3,4-d]pyrimidin-6-ylamino)-1H-pyrazol-1-yl)ethanol The following compound was made according to the procedure in Example 1, using 2-(4-amino-1H-pyrazol-1yl)ethanol and 1-(bromomethyl)-2-fluorobenzene as alkylating agent. 2-(4-amino-1H-pyrazol-1yl)ethanol was prepared by Procedure A using 2-bromo ethanol as alkylating agent:

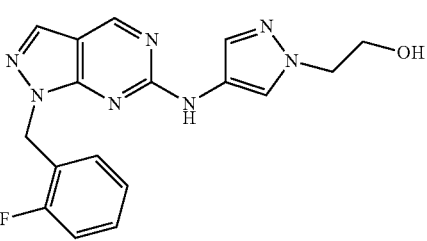 [SMILES: OCCn1cc(Nc2ncc3cnn(Cc4ccccc4F)c3n2)cn1]

$^1$H NMR (d$_6$-DMSO) δ 9.90 (s, 1H), 8.91 (s, 1H), 8.11 (s, 1H), 8.05 (s, 1H), 7.61 (s, 1H), 7.33-7.38 (m, 1H), 7.29 (br s,

1H), 7.21-7.26 (m, 1H), 7.14-7.18 (m, 1H), 5.95 (s, 2H), 4.91 (t, 1H), 4.13 (t, 2H), 3.73 (q, 2H); LC-MS method B, (ES+) 354.0, RT=7.13 min.

Example 35

4-(6-(1-Methyl-1H-pyrazol-4-ylamino)-1H-pyrazolo[3,4-d]pyrimidin-1-yl)benzenesulfonamide The following compound was made according to the procedure in Example 17, Step (iii), using 4-(bromomethyl)benzenesulphonamide as alkylating agent:

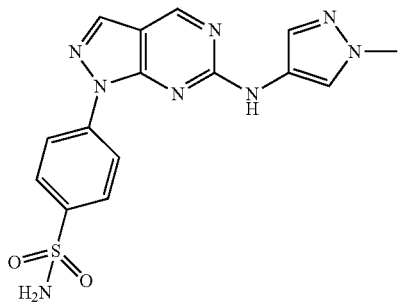 [SMILES: Cn1cc(Nc2ncc3cnn(-c4ccc(S(N)(=O)=O)cc4)c3n2)cn1]

$^1$H NMR (d$_6$-DMSO) δ 10.12 (s, 1H), 9.04 (s, 1H), 8.37-8.41 (m, 3H), 8.05 (d, 2H), 7.95 (s, 1H), 7.66 (s, 1H), 7.48 (s, 2H), 3.87 (s, 3H); LC-MS method B, (ES+) 371.0, RT=6.68 min.

Example 36

2-((6-(1-(2,2-Difluoroethyl)-3-methoxy-1H-pyrazol-4-ylamino)-1H-pyrazolo[3,4-d]pyrimidin-1-yl)methyl)benzamide The following compound was made according to the procedure in Example 16, using 2-((6-(1-(2,2-Difluoroethyl)-3-methoxy-1H-pyrazol-4-ylamino)-1H-pyrazolo[3,4-d]pyrimidin-1-yl)methyl)benzonitrile (Example 24):

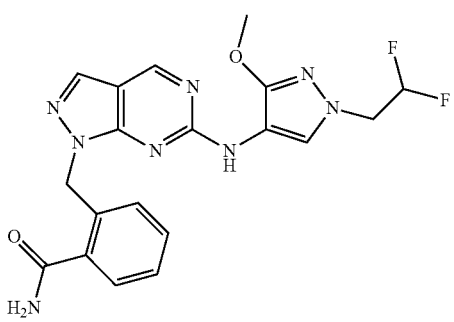 [SMILES: COc1nn(CC(F)F)cc1Nc1ncc2cnn(Cc3ccccc3C(N)=O)c2n1]

$^1$H NMR (d$_6$-DMSO) δ 8.97 (s, 1H), 8.92 (s, 1H), 8.09 (s, 2H), 8.01 (s, 1H), 7.57 (s, 1H), 7.52 (s, 1H), 7.29-7.32 (m, 2H), 6.87 (s, 1H), 6.14-6.41 (m, 1H), 5.71 (s, 2H), 4.39-4.48 (m, 2H), 3.79 (s, 3H); LC-MS method B, (ES+) 429.0, RT=7.38 min.

Example 37

2-((6-(1,5-Dimethyl-1H-pyrazol-4-ylamino)-1H-pyrazolo[3,4-d]pyrimidin-1-yl)methyl)benzonitrile The following compound was made according to the procedure in Example 1, using 1,5-dimethyl-1H-pyrazol-4-amine.hydrochloride:

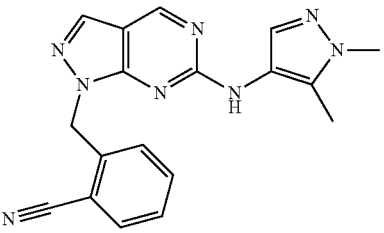 [SMILES: Cc1c(Nc2ncc3cnn(Cc4ccccc4C#N)c3n2)cnn1C]

$^1$H NMR (d$_6$-DMSO) δ 9.18 (br s, 1H), 8.91 (s, 1H), 8.07 (s, 1H), 7.88 (d, 1H), 7.62-7.67 (m, 2H), 7.50 (t, 1H), 7.21-7.23 (m, 1H), 5.60 (s, 2H), 3.72 (s, 3H), 2.16 (s, 3H); LC-MS method B, (ES+) 345.0, RT=7.38 min.

Example 38

2-46-(3-Methoxy-1-(2,2,2-trifluoroethyl)-1H-pyrazol-4-ylamino)-1H-pyrazolo[3,4-d]pyrimidin-1-yl)methyl)benzonitrile The following compound was made according to the procedure in Example 1, using 3-methoxy-1-(2,2,2-trifluoroethyl)-1H-pyrazol-4-amine:

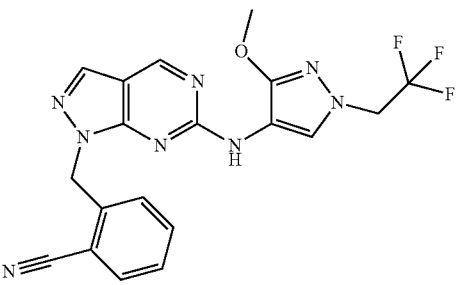 [SMILES: COc1nn(CC(F)(F)F)cc1Nc1ncc2cnn(Cc3ccccc3C#N)c2n1]

$^1$H NMR (d$_6$-DMSO) δ 9.14 (br s, 1H), 8.94 (s, 1H), 8.22 (br s, 1H), 8.10 (s, 1H), 7.88 (d, 1H), 7.65 (t, 1H), 7.51 (t, 1H), 7.34 (br s, 1H), 5.68 (s, 2H), 4.93 (q, 1H), 3.84 (s, 3H); LC-MS method B, (ES+) 429.0, RT=9.77 min.

Example 39

2-((6-(1-(2,2-Difluoroethyl)-1H-pyrazol-4-ylamino)-1H-pyrazolo[3,4-d]pyrimidin-1-yl)methyl)benzonitrile The following compound was made according to the procedure in Example 1, using 1-(2,2-difluoroethyl)-1H-pyrazol-4-amine. 1-(2,2-difluoroethyl)-1H-pyrazol-4-amine was prepared by Procedure A using 2,2-difluoromethane sulfonate as alkylating agent:

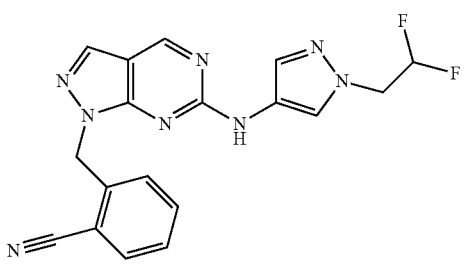 [SMILES: N#Cc1ccccc1Cn1ncc2cnc(Nc3cnn(CC(F)F)c3)nc21]

2,2-difluoromethane sulfonate was prepared by stirring a solution of 2,2-difluoroethanol (0.38 mL, 6.1 mmol), methanesulfonyl chloride (0.94 mL, 12.2 mmol) and pyridine (5 mL) in dichloromethane (10 mL) at rt for 16 h. The mixture was then diluted with dichloromethane and washed with H$_2$O and then brine. The organic phase was collected, dried (MgSO$_4$) and concentrated in vacuo to give 2,2-difluoromethane sulfonate. $^1$H NMR (d$_6$-DMSO) δ 10.03 (s, 1H), 8.96 (s, 1H), 8.27 (s, 1H), 8.11 (s, 1H), 7.90 (d, 1H), 7.64-7.68 (m, 2H), 7.52 (t, 1H), 7.37-7.40 (m, 1H), 6.21-6.49 (m, 1H), 5.77 (s, 2H), 4.56-4.65 (m, 2H); LC-MS method B, (ES+) 381.0, RT=8.43 min.

Example 40

N-Methyl-4-(6-(1-methyl-1H-pyrazol-4-ylamino)-1H-pyrazolo[3,4-d]pyrimidin-1-yl)benzenesulfonamide The following compound was made according to the procedure in Example 17 (step iii), using 4-bromo-N-methylbenzenesulfonamide as alkylating agent:

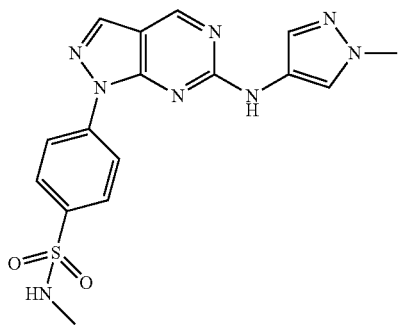 [SMILES: CNS(=O)(=O)c1ccc(-n2ncc3cnc(Nc4cnn(C)c4)nc32)cc1]

4-bromo-N-methylbenzenesulfonamide was prepared by stirring a solution of 4-bromobenzenesulfonyl chloride (400 mg, 1.57 mmol), methylamine (0.78 mL, 2M solution in THF) and pyridine (1 mL) in dichloromethane (5 mL) was at rt for 16 h. The mixture was then diluted with dichloromethane and washed with H$_2$O and then brine. The organic phase was collected, dried (MgSO$_4$) and concentrated in vacuo to give 4-bromo-N-methylbenzenesulfonamide. $^1$H NMR (d$_6$-DMSO) δ 10.12 (s, 1H0, 9.04 (s, 1H), 8.45 (d, 2H), 8.38 (s, 1H), 8.00 (d, 2H), 7.96 (s, 1H), 7.64 (s, 1H), 7.57 (s, 1H), 3.87 (s, 3H), 2.47 (s, 3H); LC-MS method B, (ES+) 385.0, RT=7.45 min.

Example 41

2-((6-(1-Methyl-1H-pyrazol-4-ylamino)-1H-pyrazolo[3,4-d]pyrimidin-1-yl)methyl)benzoic acid

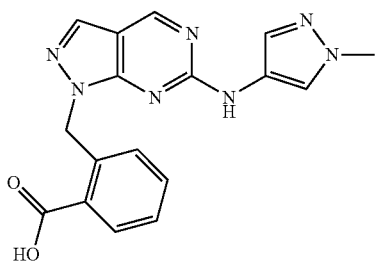 [SMILES: Cn1cc(Nc2ncc3cnn(Cc4ccccc4C(=O)O)c3n2)cn1]

Step (i)

A solution of methyl-o-toluate (0.93 mL, 6.6 mmol), N-bromosuccinimide (1.25 g, 7.0 mmol) and azaisobutryonitrile (11 mg, 0.07 mmol) in chloroform (10 mL) was heated at 65° for 16 h. After cooling to rt, the mixture was diluted with dichloromethane and washed with H$_2$O and then brine. The organic phase was collected, dried (MgSO$_4$) and concentrated in vacuo to give methyl 2-(bromomethyl)benzoate.

Step (ii)

Methyl 2-((6-(1-methyl-1H-pyrazol-4-ylamino)-1H-pyrazolo[3,4-d]pyrimidin-1-yl)methyl)benzoate was prepared according to the procedure in Example 1 using methyl 2-(bromomethyl)benzoate.

Step (iii)

A solution of methyl 2-((6-(1-methyl-1H-pyrazol-4-ylamino)-1H-pyrazolo[3,4-d]pyrimidin-1-yl)methyl)benzoate (15 mg, 0.04 mmol) and sodium hydroxide (1 mL, 4M aqueous solution) in THF (3 mL) was stirred at rt for 2 h. The mixture was then acidified with HCl (2M) and extracted into EtOAc. The organic phase was collected, dried (MgSO$_4$) and concentrated in vacuo to give the title product. $^1$H NMR (d$_6$-DMSO) δ 9.86 (s, 1H), 8.94 (s, 1H), 8.11 (s, 1H), 7.93 (d, 1H), 7.89 (s, 1H), 7.47 (s, 1H), 7.36-7.41 (m, 2H), 6.79 (s, 1H), 5.95 (s, 2H), 3.78 (s, 3H); LC-MS method B, (ES+) 350.0, RT=6.91 min.

Example 42

2-((6-(1-(2,2-Difluoroethyl)-1H-pyrazol-4-ylamino)-1H-pyrazolo[3,4-d]pyrimidin-1-yl)methyl)benzamide The following compound was made according to the procedure in Example 16 using 24(641-(2,2-difluoroethyl)-1H-pyrazol-4-ylamino)-1H-pyrazolo[3,4-d]pyrimidin-1-yl)methyl)benzonitrile (see Example 39):

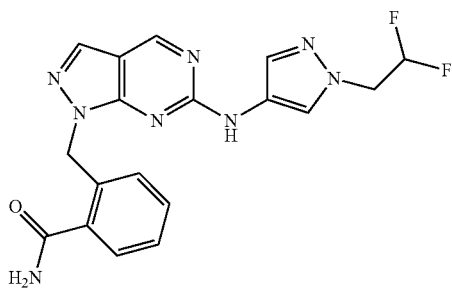 [SMILES: NC(=O)c1ccccc1Cn1ncc2cnc(Nc3cnn(CC(F)F)c3)nc21]

$^1$H NMR (d$_6$-DMSO) δ 9.96 (s, 1H), 8.94 (s, 1H), 8.24 (s, 1H), 8.10 (s, 1H), 8.03 (s, 1H), 7.59-7.62 (m, 2H), 7.53 (s, 1H), 7.30-7.33 (m, 2H), 6.92 (s, 1H), 6.19-6.46 (m, 1H), 5.79 (s, 2H), 4.56-4.64 (m, 2H); LC-MS method B, (ES+) 399.0, RT=6.80 min.

Example 43

2-((6-(1-(2,2-Difluoroethyl)-3-methyl-1H-pyrazol-4-ylamino)-1H-pyrazolo[3,4-d]pyrimidin-1-yl)methyl)benzamide The following compound was made according to the procedure in Example 16 using 24(641-(2,2-difluoro ethyl)-3-methyl-1H-pyrazol-4-ylamino)-1H-pyrazolo[3,4-d]pyrimidin-1-yl)methyl)benzonitrile (see Example 22):

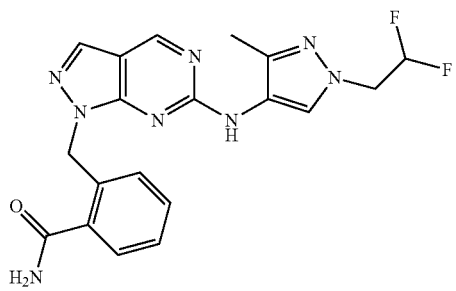 [SMILES: Cc1nn(CC(F)F)cc1Nc1ncc2cnn(Cc3ccccc3C(N)=O)c2n1]

$^1$H NMR (d$_6$-DMSO) δ 9.35 (s, 1H), 8.96 (s, 1H), 8.22 (s, 1H), 8.10 (s, 1H), 8.01 (s, 1H), 7.57 (s, 1H), 7.53 (s, 1H), 7.30-7.33 (m, 2H), 6.87 (s, 1H), 6.17-6.45 (m, 1H), 5.75 (s, 2H), 4.47-4.55 (m, 2H), 2.16 (s, 3H); LC-MS method B, (ES+) 413.0, RT=6.85 min.

Example 44

2-((6-(1-(2-Hydroxyethyl)-3-methoxy-1H-pyrazol-4-ylamino)-1H-pyrazolo[3,4-d]pyrimidin-1-yl)methyl)benzonitrile The following compound was made according to the procedure in Example 1 using 2-(4-amino-3-methoxy-1H-pyrazol-1-yl)ethanol. 2-(4-amino-3-methoxy-1H-pyrazol-1-yl)ethanol was prepared by Procedure C using 2-bromoethanol as alkylating reagent:

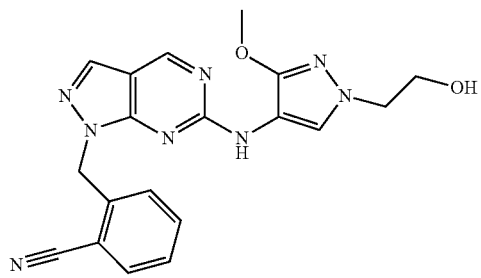 [SMILES: COc1nn(CCO)cc1Nc1ncc2cnn(Cc3ccccc3C#N)c2n1]

$^1$H NMR (d$_6$-DMSO) δ 8.90 (s, 1H), 8.07 (s, 1H), 7.96 (s, 1H), 7.89 (d, 1H), 7.63-7.68 (m, 1H), 7.49-7.53 (m, 1H), 7.34 (s, 1H), 5.65 (s, 2H), 4.85 (t, 1H), 3.96-3.99 (m, 2H), 3.79 (s, 3H), 3.66-3.71 (m, 2H); LC-MS method B, (ES+) 391.0, RT=7.12 min.

Example 45

1-((2-Fluoropyridin-3-yl)methyl)-N-(1-methyl-1H-pyrazol-4-yl)-1H-pyrazolo[3,4-d]pyrimidin-6-amine

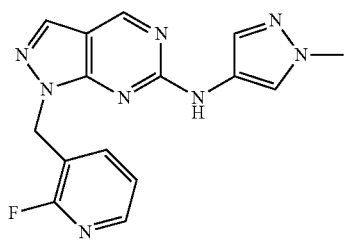 [SMILES: Cn1cc(Nc2ncc3cnn(Cc4cccnc4F)c3n2)cn1]

Step (i)

A solution of 2-fluoropyridine-3-carboxaldehyde (400 mg, 3.2 mmol) and sodium borohydride (121 mg, 3.2 mmol) in methanol (8 mL) was stirred at rt for 16 h. The mixture was then diluted with EtOAc and washed with H$_2$O, then brine. The organic phase was collected, dried (MgSO$_4$) and concentrated in vacuo to give (2-fluoropyridin-3-yl)methanol.

Step (ii)

A solution of (2-fluoropyridin-3-yl)methanol (400 mg, 3.1 mmol), methanesulfonyl chloride (0.37 mL, 4.7 mmol) and triethylamine (0.88 mL, 6.30 mmol) in dichloromethane (10 mL) was stirred at rt for 16 h. The mixture was then diluted with dichloromethane and washed with H$_2$O, then brine. The organic phase was collected, dried (MgSO$_4$) and concentrated in vacuo to give (2-fluoropyridin-3-yl)methyl methanesulfonate.

Step (iii)

The title compound was made according to the procedure in Example 1 using (2-fluoropyridin-3-yl)methyl methanesulfonate. $^1$H NMR (d$_6$-DMSO) δ 9.92 (s, 1H), 8.92 (s, 1H), 8.19 (d, 1H), 8.07 (s, 2H), 7.81 (br s, 1H), 7.55 (s, 1H), 7.33-7.35 (m, 1H), 5.62 (s, 2H), 3.83 (s, 3H); LC-MS method B, (ES+) 325.0, RT=6.71 min.

Example 46

1-((3-Fluoropyridin-4-yl)methyl)-N-(1-methyl-1H-pyrazol-4-yl)-1H-pyrazolo[3,4-d]pyrimidin-6-amine The following compound was made according to the procedure in Example 45 using 3-fluoropyridine-4-carboxaldehyde:

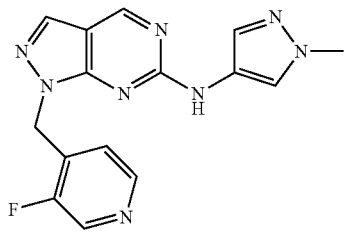

¹H NMR (d₆-DMSO) δ 9.95 (s, 1H), 8.94 (s, 1H), 8.61 (s, 1H), 8.37 (d, 1H), 8.10 (s, 1H), 8.04 (s, 1H), 7.54 (s, 1H), 7.19 (br s, 1H), 5.70 (s, 2H), 3.82 (s, 3H); LC-MS method B, (ES+) 325.0, RT=6.31 min.

Example 47

1-(2,4-Difluorobenzyl)-N-(1-methyl-1H-pyrazol-4-yl)-1H-pyrazolo[3,4-d]pyrimidin-6-amine The following compound was made according to the procedure in Example 1 using 1-(bromomethyl)-2,4-difluorobenzene:

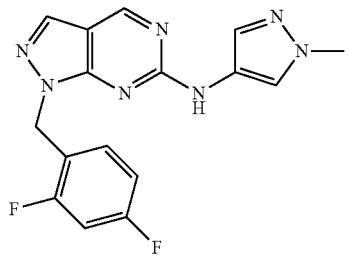 [SMILES: Cn1cc(Nc2ncc3cnn(Cc4ccc(F)cc4F)c3n2)cn1]

¹H NMR (d₆-DMSO) δ 9.91 (s, 1H), 8.91 (s, 1H), 8.09 (s, 1H), 8.04 (s, 1H), 7.57 (s, 1H), 7.36-7.38 (m, 1H), 7.29 (td, 1H), 7.07 (td, 1H), 5.58 (s, 2H), 3.84 (s, 3H); LC-MS method B, (ES+) 342.0, RT=8.34 min.

Example 48

N-(1-Methyl-1H-pyrazol-4-yl)-1-phenethyl-1H-pyrazolo[3,4-d]pyrimidin-6-amine

The following compound was made according to the procedure in Example 1, using 2-(bromoethyl)benzene as alkylating agent:

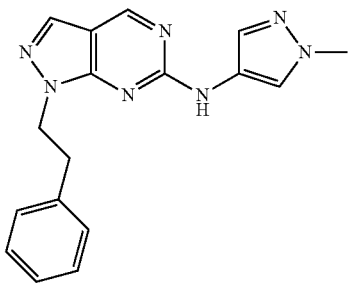 [SMILES: Cn1cc(Nc2ncc3cnn(CCc4ccccc4)c3n2)cn1]

¹H NMR (d₆-DMSO) δ 9.74 (s, 1H), 8.85 (s, 1H), 8.02 (s, 1H), 7.96 (s, 1H), 7.54 (s, 1H), 7.12-7.22 (m, 5H), 4.55 (s, 2H), 3.85 (s, 3H), 3.17 (t, 2H); LC-MS method B, (ES+) 320.0, RT=8.46 min.

Example 49

2-(4-(1-(2-Fluorobenzyl)-1H-pyrazolo[3,4-d]pyrimidin-6-ylamino)-3-methoxy-1H-pyrazol-1-yl)ethanol The following compound was prepared according to Example 1 using 2-(4-amino-3-methoxy-1H-pyrazol-1-yl)ethanol and 2-fluorobenzylbromide as alkylating reagent. 2-(4-amino-3-methoxy-1H-pyrazol-1-yl)ethanol was prepared by Procedure C using 2-bromoethanol as alkylating reagent:

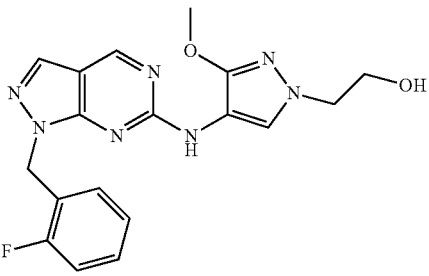 [SMILES: COc1nn(CCO)cc1Nc1ncc2cnn(Cc3ccccc3F)c2n1]

¹H NMR (d₆-DMSO) δ 8.88 (s, 1H), 8.04 (s, 1H), 7.97 (s, 1H), 7.33-7.36 (m, 1H), 7.13-7.27 (m, 3H), 5.51 (s, 2H), 4.87 (t, 1H), 3.95-3.98 (m, 2H), 3.80 (s, 3H0, 3.68-3.71 (m, 2H); LC-MS method B, (ES+) 384.0, RT=7.51 min.

Example 50

2-(4-(1-(2,3-Difluorobenzyl)-1H-pyrazolo[3,4-d]pyrimidin-6-ylamino)-3-methoxy-1H-pyrazol-1-yl)ethanol The following compound was prepared according to Example 1 using 2-(4-amino-3-methoxy-1H-pyrazol-1-yl)ethanol and 2,3-difluorobenzylbromide as alkylating reagent. 2-(4-amino-3-methoxy-1H-pyrazol-1-yl)ethanol was prepared by Procedure C using 2-bromoethanol as alkylating reagent:

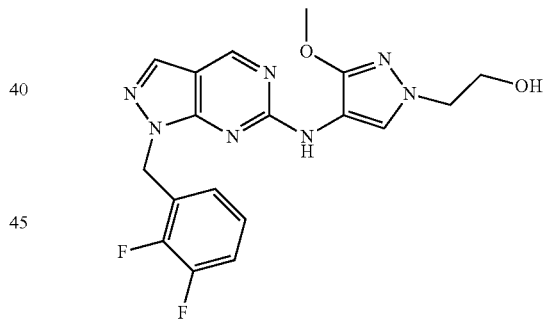

¹H NMR (d₄-methanol) δ 8.85 (s, 1H), 8.02 (s, 1H), 7.16-7.25 (m, 2H), 7.04-7.11 (m, 3H), 5.65 (s, 2H), 4.07-4.10 (m, 2H), 3.96 (s, 3H), 3.87-3.90 (m, 2H); LC-MS method B, (ES+) 402.0, RT=7.78 min.

Example 51

2-(4-(1-(2,5-Difluorobenzyl)-1H-pyrazolo[3,4-d]pyrimidin-6-ylamino)-3-methoxy-1H-pyrazol-1-yl)ethanol The following compound was prepared according to Example 1 using 2-(4-amino-3-methoxy-1H-pyrazol-1-yl)ethanol and 2,5-difluorobenzylbromide as alkylating reagent. 2-(4-amino-3-methoxy-1H-pyrazol-1-yl)ethanol was prepared by Procedure C using 2-bromoethanol as alkylating reagent:

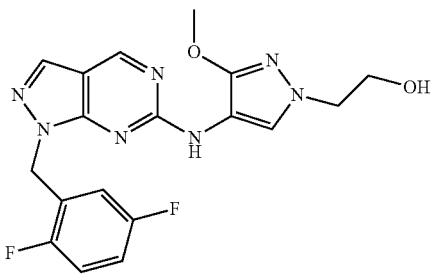 [SMILES: COc1nn(CCO)cc1Nc1ncc2cnn(Cc3cc(F)ccc3F)c2n1]

¹H NMR (d₆-DMSO) δ 8.89 (s, 1H), 8.05 (s, 1H), 7.19-7.32 (m, 3H), 7.02-7.08 (m, 1H), 5.50 (s, 2H), 4.87 (t, 1H), 3.95-3.99 (m, 2H), 3.80 (s, 3H), 3.68-3.72 (m, 2H); LC-MS method B, (ES+) 402.0, RT=7.74 min.

Example 52

4-Fluoro-2-((6-(1-methyl-1H-pyrazol-4-ylamino)-1H-pyrazolo[3,4-d]pyrimidin-1-yl)methyl)benzonitrile The following compound was prepared according to Example 1 using 3-(bromomethyl)-4-fluorobenzonitrile as alkylating reagent:

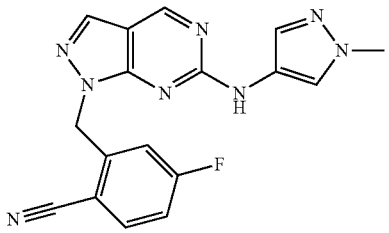

¹H NMR (d₆-DMSO) δ 9.95 (s, 1H), 8.94 (s, 1H), 8.11 (s, 2H), 8.04 (dd, 1H), 7.51 (s, 1H), 7.43 (td, 1H), 7.23-7.27 (m, 1H), 5.76 (s, 2H), 3.83 (s, 3H); LC-MS method B, (ES+) 349.0, RT=7.91 min.

Example 53

4-Fluoro-2-((6-(1-methyl-1H-pyrazol-4-ylamino)-1H-pyrazolo[3,4-d]pyrimidin-1-yl)methyl)benzamide The following compound was prepared according to Example 16 using 4-Fluoro-2-((6-(1-methyl-1H-pyrazol-4-ylamino)-1H-pyrazolo[3,4-d]pyrimidin-1-yl)methyl)benzonitrile (see Example 52):

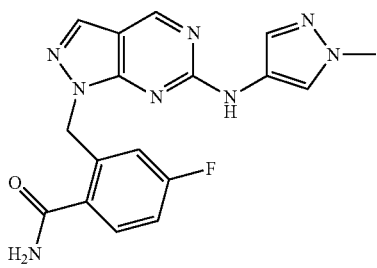 [SMILES: Cn1cc(Nc2ncc3cnn(Cc4cc(F)ccc4C(N)=O)c3n2)cn1]

¹H NMR (d₆-DMSO) δ 10.22 (s, 1H), 9.90 (s, 1H), 8.94 (s, 1H), 8.06-8.12 (m, 3H), 7.61-7.63 (m, 2H), 7.48 (s, 1H), 7.20 (td, 1H), 5.81 (s, 2H), 3.83 (s, 3H); LC-MS method B, (ES+) 367.0, RT=6.41 min.

Example 54

N-(6-(6-(1-Methyl-1H-pyrazol-4-ylamino)-1H-pyrazolo[3,4-d]pyrimidin-1-yl)pyridin-3-yl)methanesulfonamide The following compound was made according to the procedure in Example 17 (Steps and iii) using 6-bromopyridin-3-amine:

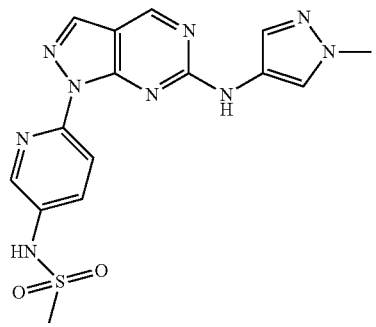 [SMILES: Cn1cc(Nc2ncc3cnn(-c4ccc(NS(C)(=O)=O)cn4)c3n2)cn1]

¹H NMR (d₆-DMSO) δ 10.10 (s, 1H), 9.02 (s, 1H), 8.51 (s, 1H), 8.22-8.41 (m, 2H), 7.98-8.00 (m, 1H), 7.90-7.92 (m, 1H), 7.39-7.68 (m, 2H), 3.86 (s, 3H), 3.14 (s, 3H); LC-MS method B, (ES+) 386, RT=6.16 min.

Example 55

N-(2-Methyl-6-(6-(1-methyl-1H-pyrazol-4-ylamino)-1H-pyrazolo[3,4-d]pyrimidin-1-yl)pyridin-3-yl)methanesulfonamide The following compound was made according to the procedure in Example 17 (Steps and iii) using 6-bromo-2-methylpyridin-3-amine:

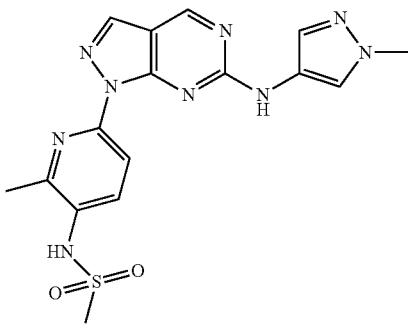

¹H NMR (d₆-DMSO) δ 10.09 (s, 1H), 9.53 (brs, 1H), 9.01 (s, 1H), 8.31 (s, 2H), 8.15 (s, 1H), 7.89-7.94 (m, 1H), 7.79-7.84 (m, 2H), 3.84 (s, 3H), 3.10 (s, 3H), 2.70 (s, 3H); LC-MS method B, (ES+) 400, RT=6.17 min.

Example 56

1-(4-Fluorophenyl)-N-(1-methyl-1H-pyrazol-4-yl)-1H-pyrazolo[3,4-d]pyrimidin-6-amine The following compound was made according to the procedure in Example 17 (Step iii) using 1-bromo-4-fluorobenzene:

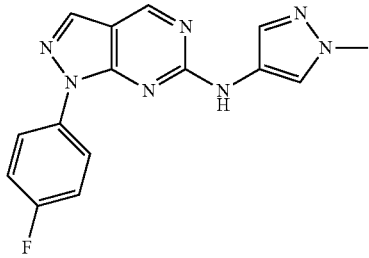 [SMILES: Cn1cc(Nc2ncc3cnn(-c4ccc(F)cc4)c3n2)cn1]

$^1$H NMR (d$_6$-DMSO) δ 10.04 brs, 1H), 9.01 (s, 1H), 8.29-8.30 (m, 1H), 8.15-8.17 (m, 2H), 7.94 (s, 1H), 7.56 (s, 1H), 7.47-7.48 (m, 2H), 3.84 (s, 3H); LC-MS method B, (ES+) 310, RT=8.64 min.

Example 57

1-(4-Chlorophenyl)-N-(1-methyl-1H-pyrazol-4-yl)-1H-pyrazolo[3,4-d]pyrimidin-6-amine The following compound was made according to the procedure in Example 17 (Step iii) using 1-bromo-4-chlorobenzene:

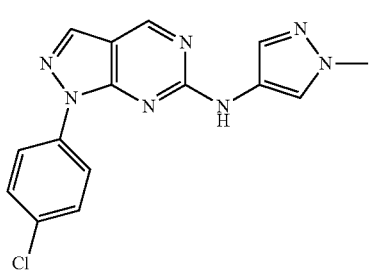 [SMILES: Cn1cc(Nc2ncc3cnn(-c4ccc(Cl)cc4)c3n2)cn1]

$^1$H NMR (d$_6$-DMSO) δ 10.04 (s, 1H), 8.98 (s, 1H), 8.28 (s, 1H), 8.16-8.19 (m, 2H), 7.91 (s, 1H), 7.64-7.66 (m, 2H), 7.54 (s, 1H), 3.82 (s, 3H); LC-MS method B, (ES+) 326, RT=9.86 min.

Example 58

1-(4-Fluoro-3-methoxyphenyl)-N-(1-methyl-1H-pyrazol-4-yl)-1H-pyrazolo[3,4-d]pyrimidin-6-amine The following compound was made according to the procedure in Example 17 (Step iii) using 4-bromo-1-fluoro-2-methoxybenzene:

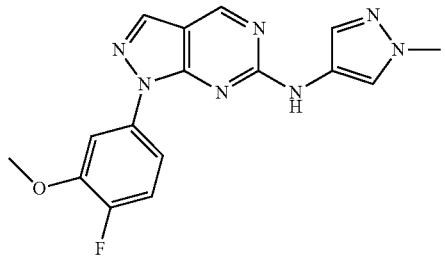

$^1$H NMR (d$_6$-DMSO) δ 10.01 (s, 1H), 9.02 (s, 1H), 8.30 (s, 1H), 7.91-7.92 (m, 2H), 7.66-7.71 (m, 2H), 7.45-7.50 (m, 1H), 3.92 (s, 3H), 3.83 (s, 3H); LC-MS method B, (ES+) 340, RT=8.97 min.

Example 59

(R)—N-(1-Methyl-1H-pyrazol-4-yl)-1-((6-(3-methylmorpholino)pyridin-2-yl)methyl)-1H-pyrazolo[3,4-d]pyrimidin-6-amine The title compound was made following the procedure in Example 188 using (R)-3-methylmorpholine:

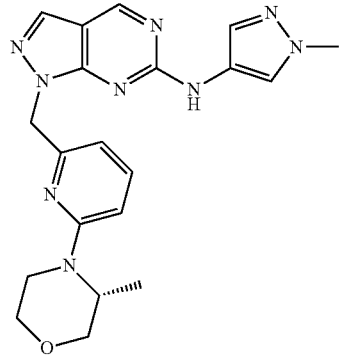 [SMILES: C[C@@H]1COCCN1c1cccc(Cn2ncc3cnc(Nc4cnn(C)c4)nc32)n1]

$^1$H NMR (d$_6$-Acetone) δ 8.86 (s, 1H), 8.04 (s, 1H), 7.97 (s, 1H), 7.61 (s, 1H), 7.44 (t, 1H), 6.58 (d, 1H), 6.36 (bs, 1H), 5.51 (s, 2H), 4.24 (d, 1H), 3.88-3.75 (m, 5H), 3.60 (dt, 2H), 3.45 (td, 1H), 3.03 (ddd, 1H), 1.04 (d, 3H); LC-MS method B, (ES+) 406, RT=7.28 min

Example 60

1-(4-fluoro-3-methylphenyl)-N-(1-methyl-1H-pyrazol-4-yl)-1H-pyrazolo[3,4-d]pyrimidin-6-amine The following compound was made according to the procedure in Example 74 using 4-fluoro-3-methyl-phenylboronic acid:

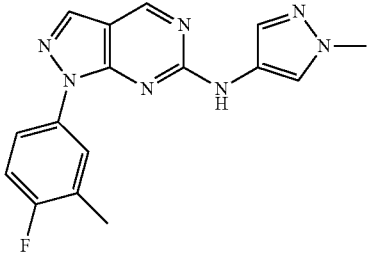 [SMILES: Cc1cc(-n2ncc3cnc(Nc4cnn(C)c4)nc32)ccc1F]

$^1$H NMR (d$_6$-DMSO) δ 10.04 (s, 1H), 9.02 (s, 1H), 8.29 (s, 1H), 8.17 (s, 1H), 7.99-7.88 (m, 2H), 7.61 (s, 1H), 7.40 (m, 1H), 3.85 (s, 3H), 2.40 (s, 3H); LC-MS method B, (ES+) 324.0, RT=9.30 min.

Example 61

N-(1-methyl-1H-pyrazol-4-yl)-1-(4-(methylsulfonyl)phenyl)-1H-pyrazolo[3,4-d]pyrimidin-6-amine The following compound was made according to the procedure in Example 74 using 4-methanesulfonylphenylboronic acid:

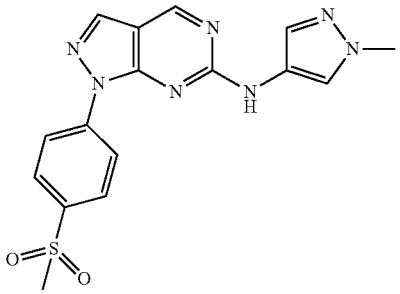 [SMILES: Cn1cc(Nc2ncc3cnn(-c4ccc(S(C)(=O)=O)cc4)c3n2)cn1]

$^1$H NMR (d$_6$-DMSO) δ 10.14 (s, 1H), 9.05 (s, 1H), 8.51 (d, J=7.5 Hz, 2H), 8.40 (s, 1H), 8.17 (d, J=7.5 Hz, 2H), 7.97 (s, 1H), 7.63 (s, 1H), 3.88 (s, 3H), 3.30 (s, 3H); LC-MS method B, (ES+) 370.0, RT=7.38 min.

Example 62

1-(2-Chloro-5-fluorobenzyl)-N-(1-methyl-1H-pyrazol-4-yl)-1H-pyrazolo[3,4-d]pyrimidin-6-amine The following compound was made according to the procedure in Example 1 (Step ii) using 2-(bromomethyl)-1-chloro-4-fluorobenzene:

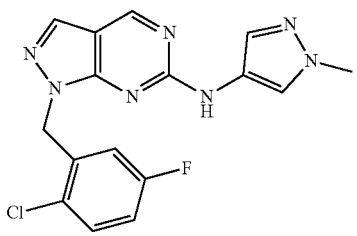 [SMILES: Cn1cc(Nc2ncc3cnn(Cc4cc(F)ccc4Cl)c3n2)cn1]

$^1$H NMR (d$_6$-DMSO) δ 9.91 (s, 1H), 8.93 (s, 1H), 8.09 (s, 1H), 8.02 (s, 1H), 7.54-7.59 (m, 2H), 7.24 (td, 1H), 7.00 (s, 1H), 5.65 (s, 2H), 3.81 (s, 3H); LC-MS method B, (ES+) 358.0, RT=8.83 min.

Example 63

1-(2-Chloro-6-fluorobenzyl)-N-(1-methyl-1H-pyrazol-4-yl)-1H-pyrazolo[3,4-d]pyrimidin-6-amine The following compound was made according to the procedure in Example 1 (Step ii) using 2-(bromomethyl)-1-chloro-3-fluorobenzene:

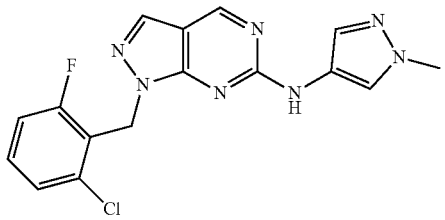 [SMILES: Cn1cc(Nc2ncc3cnn(Cc4c(F)cccc4Cl)c3n2)cn1]

$^1$H NMR (d$_6$-DMSO) δ 9.89 (s, 1H), 8.89 (s, 1H), 8.14 (s, 1H), 7.98 (s, 1H), 7.59 (s, 1H), 7.49-7.43 (m, 1H), 7.37-7.39 (m, 1H), 7.31-7.21 (m, 1H), 5.66 (s, 2H), 3.85 (s, 3H); LC-MS method B, (ES+) 358.0, RT=8.45 min.

Example 64

145-Chloro-2-fluorobenzyl)-N-(1-methyl-1H-pyrazol-4-yl)-1H-pyrazolo[3,4-d]pyrimidin-6-amine The following compound was made according to the procedure in Example 1 (Step ii) using 2-(bromomethyl)-4-chloro-1-fluorobenzene:

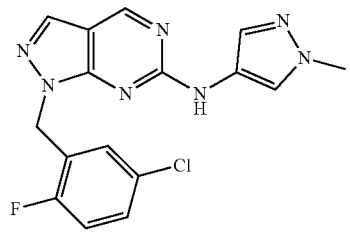 [SMILES: Cn1cc(Nc2ncc3cnn(Cc4cc(Cl)ccc4F)c3n2)cn1]

$^1$H NMR (d$_6$-DMSO) δ 9.92 (s, 1H), 8.92 (s, 1H), 8.10 (s, 1H), 8.07 (s, 1H), 7.57 (s, 1H), 7.42-7.46 (m, 1H), 7.38 (s, 1H), 7.29-7.33 (m, 1H), 5.61 (s, 2H), 3.84 (s, 3H); LC-MS method B, (ES+) 358.0, RT=8.81 min.

Example 65

N-(1-Methyl-1H-pyrazol-4-yl)-1-(2-(trifluoromethyl)benzyl)-1H-pyrazolo[3,4-d]pyrimidin-6-amine The following compound was made according to the procedure in Example 1 (Step ii) using 1-(bromomethyl)-2-trifluoromethylbenzene:

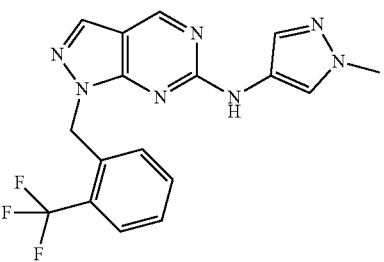 [SMILES: Cn1cc(Nc2ncc3cnn(Cc4ccccc4C(F)(F)F)c3n2)cn1]

$^1$H NMR (d$_6$-DMSO) δ 9.92 (s, 1H), 8.96 (s, 1H), 8.14 (s, 1H), 7.90 (s, 1H), 7.82 (d, 1H), 7.56-7.60 (m, 1H), 7.50-7.54

(m, 2H), 7.00 (s, 1H), 5.74 (s, 2H), 3.77 (s, 3H); LC-MS method B, (ES+) 374.0, RT=9.03 min.

Example 66

N-(1-Methyl-1H-pyrazol-4-yl)-1-(3-(trifluoromethyl)benzyl)-1H-pyrazolo[3,4-d]pyrimidin-6-amine The following compound was made according to the procedure in Example 1 (Step ii) using 1-(bromomethyl)-3-trifluoromethylbenzene:

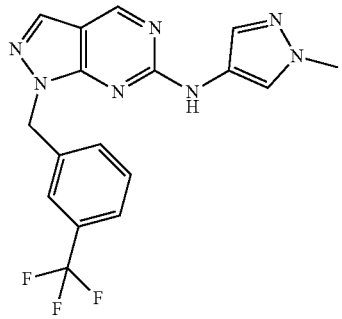 [SMILES: Cn1cc(Nc2ncc3cnn(Cc4cccc(C(F)(F)F)c4)c3n2)cn1]

$^1$H NMR (d$_6$-DMSO) δ 9.92 (s, 1H), 8.93 (s, 1H), 8.09 (s, 2H), 7.76 (s, 1H), 7.66 (d, 1H), 7.54-7.60 (m, 3H), 5.70 (s, 2H), 3.83 (s, 3H); LC-MS method B, (ES+) 374.0, RT=8.97 min.

Example 67

1-(3-Fluorobenzyl)-N-(1-methyl-1H-pyrazol-4-yl)-1H-pyrazolo[3,4-d]pyrimidin-6-amine The following compound was made according to the procedure in Example 1 (Step ii) using 1-(bromomethyl)-3-fluorobenzene:

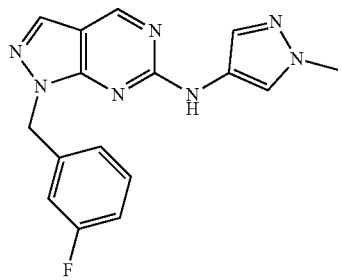 [SMILES: Cn1cc(Nc2ncc3cnn(Cc4cccc(F)c4)c3n2)cn1]

$^1$H NMR (d$_6$-DMSO) δ 9.90 (s, 1H), 8.93 (s, 1H), 8.08 (s, 1H), 8.04 (s, 1H), 7.54 (s, 1H), 7.36-7.41 (m, 1H), 7.09-7.14 (m, 3H), 5.60 (s, 2H), 3.83 (s, 3H); LC-MS method B, (ES+) 324.0, RT=8.05 min.

Example 68

3-((6-((1-Methyl-1H-pyrazol-4-yl)amino)-1H-pyrazolo[3,4-d]pyrimidin-1-yl)methyl)benzonitrile The following compound was made according to the procedure in Example 1 (Step ii) using 3-(bromomethyl)benzonitrile:

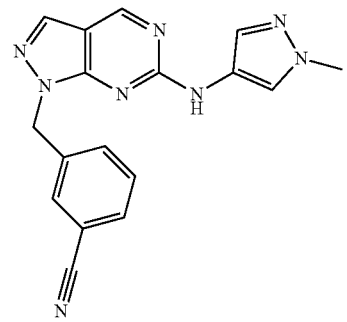 [SMILES: Cn1cc(Nc2ncc3cnn(Cc4cccc(C#N)c4)c3n2)cn1]

$^1$H NMR (d$_6$-DMSO) δ 9.91 (s, 1H), 8.93 (s, 1H), 8.09 (s, 1H), 8.06 (s, 1H), 7.76-7.80 (m, 2H), 7.53-7.57 (m, 3H), 5.60 (s, 2H), 3.84 (s, 3H); LC-MS method B, (ES+) 331.0, RT=7.49 min.

Example 69

1-(3-Methoxybenzyl)-N-(1-methyl-1H-pyrazol-4-yl)-1H-pyrazolo[3,4-d]pyrimidin-6-amine The following compound was made according to the procedure in Example 1 (Step ii) using 1-(bromomethyl)-3-methoxybenzene:

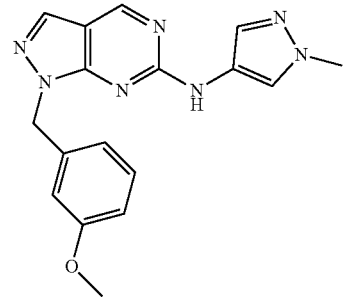 [SMILES: COc1cccc(Cn2ncc3cnc(Nc4cnn(C)c4)nc32)c1]

$^1$H NMR (d$_6$-DMSO) δ 9.87 (s, 1H), 8.91 (s, 1H), 8.06 (s, 2H), 7.57 (s, 1H), 7.24 (t, 1H), 6.91 (s, 1H), 6.82-6.86 (m, 2H), 5.53 (s, 2H), 3.83 (s, 3H), 3.69 (s, 3H); LC-MS method B, (ES+) 336.0, RT=7.89 min.

Example 70

1-(3-Chlorobenzyl)-N-(1-methyl-1H-pyrazol-4-yl)-1H-pyrazolo[3,4-d]pyrimidin-6-amine The following compound was made according to the procedure in Example 1 (Step ii) using 1-(bromomethyl)-3-chlorobenzene:

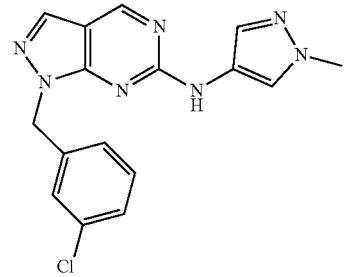

$^1$H NMR (d$_6$-DMSO) δ 9.90 (s, 1H), 8.93 (s, 1H), 8.08 (s, 2H), 7.57 (s, 1H), 7.35-7.39 (m, 3H), 7.22-7.24 (m, 1H), 5.59 (s, 2H), 3.84 (s, 3H); LC-MS method B, (ES+) 340.0, RT=8.62 min.

Example 71

4-(6-((1-(2,2-Difluoroethyl)-3-methoxy-1H-pyrazol-4-yl)amino)-1H-pyrazolo[3,4-d]pyrimidin-1-yl)benzenesulfonamide The following compound was made according to the procedures in Example 1 (Step i) using 1-(2,2-difluoroethyl)-3-methoxy-1H-pyrazol-4-amine to afford N-(1-(2,2-difluoroethyl)-3-methoxy-1H-pyrazol-4-yl)-1H-pyrazolo[3,4-d]pyrimidin-6-amine then Example 17 (Step iii) using 4-bromobenzenesulfonamide as alkylating agent:

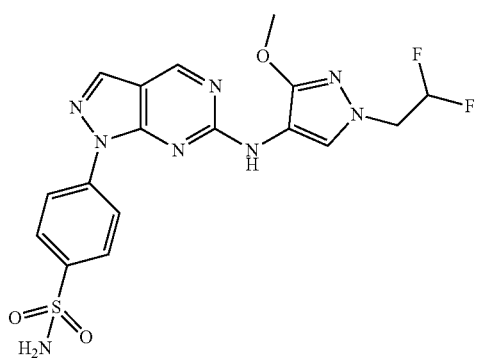 [SMILES: COc1nn(CC(F)F)cc1Nc1ncc2cnn(-c3ccc(S(N)(=O)=O)cc3)c2n1]

$^1$H NMR (d$_6$-DMSO) δ 8.89 (s, 1H), 8.41 (br s, 2H), 8.17 (s, 1H), 8.03-8.06 (m, 2H), 7.97 (s, 1H), 7.67 (s, 2H), 5.97-6.26 (m, 1H), 4.31-4.39 (m, 2H), 3.97 (s, 3H); LC-MS method B, (ES+) 451.0, RT=7.73 min.

Example 72

1-(3-Chloro-2-fluorobenzyl)-N-(1-methyl-1H-pyrazol-4-yl)-1H-pyrazolo[3,4-d]pyrimidin-6-amine The following compound was made according to the procedure in Example 1 (Step ii) using 1-(bromomethyl)-3-chloro-2-fluorobenzene:

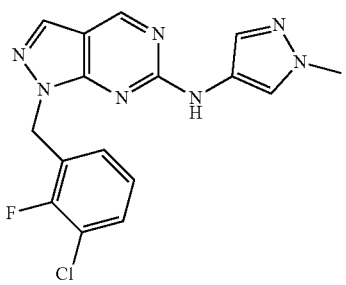 [SMILES: Cn1cc(Nc2ncc3cnn(Cc4cccc(Cl)c4F)c3n2)cn1]

$^1$H NMR (d$_6$-DMSO) δ 9.92 (s, 1H), 8.92 (s, 1H), 8.06-8.09 (m, 2H), 7.52-7.57 (m, 2H), 7.18-7.25 (m, 2H), 5.66 (s, 2H), 3.84 (s, 3H); LC-MS method B, (ES+) 357.9, RT=8.73 min.

Example 73

2-(4-((1-(2,6-Difluorobenzyl)-1H-pyrazolo[3,4-d]pyrimidin-6-yl)amino)-1H-pyrazol-1-yl)ethanol The following compound was made according to the procedure in Example 1 using 2-(bromomethyl)-1,3-difluorobenzene and 2-(4-amino-1H-pyrazol-1-yl)ethanol which was prepared following Procedure A using 2-bromoethanol as alkylating agent:

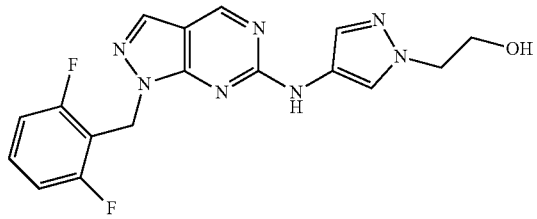 [SMILES: OCCn1cc(Nc2ncc3cnn(Cc4c(F)cccc4F)c3n2)cn1]

$^1$H NMR (d$_6$-DMSO) δ 9.88 (s, 1H), 8.89 (s, 1H), 8.16 (s, 1H), 7.99 (s, 1H), 7.66 (s, 1H), 7.42-7.49 (m, 1H), 7.11-7.16 (m, 2H), 5.59 (s, 2H), 4.90 (t, 1H), 4.13-4.16 (m, 2H), 3.74-3.76 (m, 2H); LC-MS method B, (ES+) 372.0, RT=6.99 min.

Example 74

N-(1-Methyl-1H-pyrazol-4-yl)-1-phenyl-1H-pyrazolo[3,4-d]pyrimidin-6-amine

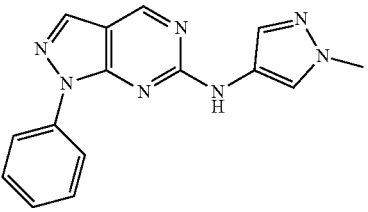 [SMILES: Cn1cc(Nc2ncc3cnn(-c4ccccc4)c3n2)cn1]

Step (i)

A suspension of 6-chloro-1H-pyrazolo[3,4-d]pyrimidine (100 mg, 0.65 mmol), benzene boronic acid (1.5 eq), copper acetate (2 eq) and pyridine (2 eq) in dichloromethane (2 mL) was heated in the microwave at 80° C. for 15 min. After cooling to rt, the mixture was filtered and the resulting filtrate concentrated to give 6-chloro-1-phenyl-1H-pyrazolo[3,4-d]pyrimidine as a green oil (138 mg, 92%) which was used without further purification in the next step.

Step (ii)

The title compound was made according to the procedure in Example 1 (Step i) using 6-chloro-1-phenyl-1H-pyrazolo[3,4-d]pyrimidine and 1-methyl-1H-pyrazol-4-amine. $^1$H NMR (CDCl$_3$) δ 8.87 (s, 1H), 8.18 (dt, 2H), 8.09 (s, 1H), 7.97 (s, 1H), 7.69 (s, 1H), 7.55 (dt, 2H), 7.34 (t, 1H), 3.92 (s, 3H); LC-MS method B, (ES+) 292, RT=8.31 min.

Example 75

N-(2-((6-((1-Methyl-1H-pyrazol-4-yl)amino)-1H-pyrazolo[3,4-d]pyrimidin-1-yl)methyl)phenyl)methanesulfonamide

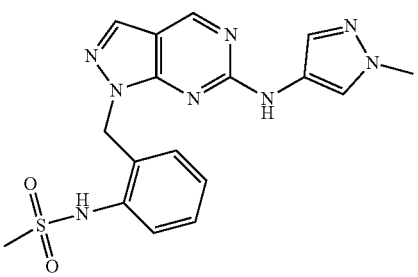

Step (i)

A solution of 6-chloro-1H-pyrazol[3,4-c]pyrimidine (305 mg, 1.97 mmol), 2-nitrobenzylbromide (1.97 mmol) and potassium carbonate (3.94 mmol) in DMF was stirred at rt for 2 h. The resultant mixture was washed with $H_2O$, extracted with DCM then dried using a hydrophobic frit. The organic phase was concentrated in vacuo to afford a brown oil. The resultant oil was purified using flash column chromatography (DCM:EtOAc) to afford 6-Chloro-1-(2-nitrobenzyl)-1H-pyrazolo[3,4-d]pyrimidine as a yellow solid.

Step (ii)

A suspension of 6-chloro-1-(2-nitrobenzyl)-1H-pyrazolo[3,4-d]pyrimidine (170 mg, 0.59 mmol) and tin chloride (2.95 mmol) in ethanol was stirred at rt for 16 h. The resultant mixture was washed with $H_2O$, extracted with DCM then dried using a hydrophobic frit. The organic phase was concentrated in vacuo to afford 2-((6-chloro-1H-pyrazolo[3,4-c]pyrimidin-1-yl)methyl)aniline.

Step (iii)

A suspension of 2-((6-chloro-1H-pyrazolo[3,4-c]pyrimidin-1-yl)methyl)aniline (260 mg, 1.00 mmol) and methanesulfonyl chloride (1.65 mmol) in DCM:pyridine (50:50) was stirred at rt for 17 h. The resultant mixture was washed with $H_2O$, extracted with DCM then dried using a hydrophobic frit. The organic phase was concentrated in vacuo to afford N-(2-((6-chloro-1H-pyrazolo[3,4-d]pyrimidin-1-yl)methyl)phenyl)methanesulfonamide as a yellow gum.

Step (iv)

A suspension of N-(2-((6-chloro-1H-pyrazolo[3,4-d]pyrimidin-1-yl)methyl)phenyl)methanesulfonamide (53 mg, 0.16 mmol), 1-methyl-1H-pyrazol-4-amine (0.24 mmol) and HCl (0.26 mmol, 4M in dioxane) in isopropanol was heated in the microwave at 140° C. for 1 h. After cooling to rt the mixture was washed with $H_2O$, extracted with DCM then dried using a hydrophobic frit. The organic phase was concentrated in vacuo. Purification was performed by prep. HPLC. The desired fractions were concentrated in vacuo to afford the title compound. $^1$H NMR ($d_6$-DMSO) δ 9.88 (s, 1H), 9.44 (s, 1H), 8.94 (s, 1H), 8.11 (s, 1H), 7.99 (s, 1H), 7.48 (s, 1H), 7.38 (d, 1H), 7.30 (t, 1H), 7.13 (t, 1H), 6.71 (s, 1H), 5.71 (s, 2H), 3.79 (s, 3H), 3.06 (s, 3H); LC-MS method B, (ES+) 399, RT=7.14 min Example 76

1-Benzyl-N-(1-methyl-1H-pyrazol-4-yl)-1H-pyrazolo[3,4-d]pyrimidin-6-amine

The following compound was made according to the procedure in Example 1 (Step ii) using (bromomethyl)benzene:

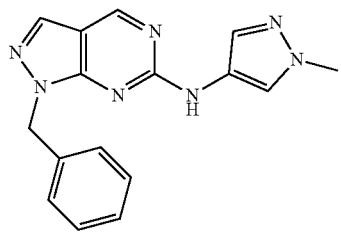 [SMILES: Cn1cc(Nc2ncc3cnn(Cc4ccccc4)c3n2)cn1]

$^1$H NMR ($d_6$-DMSO) δ 9.86 (s, 1H), 8.91 (s, 1H), 8.05 (s, 1H), 8.02 (s, 1H), 7.56 (s, 1H), 7.27-7.33 (m, 5H), 5.56 (s, 2H), 3.85 (s, 3H); LC-MS method B, (ES+) 306, RT=7.86 min.

Example 77

1-(2-Fluorophenethyl)-N-(1-methyl-1H-pyrazol-4-yl)-1H-pyrazolo[3,4-d]pyrimidin-6-amine The following compound was made according to the procedure in Example 1 (Step ii) using 1-(2-bromoethyl)-2-fluorobenzene:

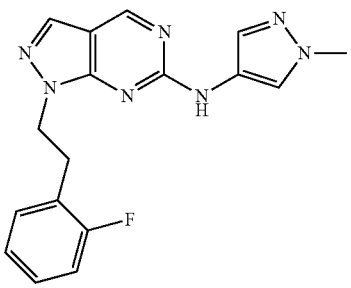 [SMILES: Cn1cc(Nc2ncc3cnn(CCc4ccccc4F)c3n2)cn1]

$^1$H NMR ($d_6$-DMSO) δ 9.74 (s, 1H), 8.85 (s, 1H), 8.01 (s, 1H), 7.99 (s, 1H), 7.54 (s, 1H), 7.12-7.18 (m, 2H), 7.09 (t, 1H), 7.01 (t, 1H), 4.56 (t, 2H), 3.86 (s, 3H), 3.19 (t, 2H); LC-MS method B, (ES+) 338, RT=8.29 min.

Example 78

1-(3,4-Difluorobenzyl)-N-(1-methyl-1H-pyrazol-4-yl)-1H-pyrazolo[3,4-d]pyrimidin-6-amine The following compound was made according to the procedure in Example 1 (Step ii) using 4-(bromomethyl)-1,2-difluorobenzene:

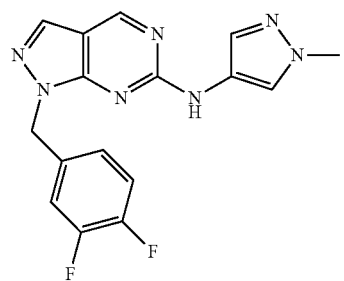 [SMILES: Cn1cc(Nc2ncc3cnn(Cc4ccc(F)c(F)c4)c3n2)cn1]

$^1$H NMR ($d_6$-DMSO) δ 9.90 (s, 1H), 8.92 (s, 1H), 8.07 (s, 2H), 7.55 (s, 1H), 7.37-7.44 (m, 2H), 7.12 (s, 1H), 5.57 (s, 2H), 3.84 (s, 3H); LC-MS method B, (ES+) 342.0, RT=8.31 min.

Example 79

1-(3,5-Difluorobenzyl)-N-(1-methyl-1H-pyrazol-4-yl)-1H-pyrazolo[3,4-d]pyrimidin-6-amine The following compound was made according to the procedure in Example 1 (Step ii) using 1-(bromomethyl)-3,5-difluorobenzene:

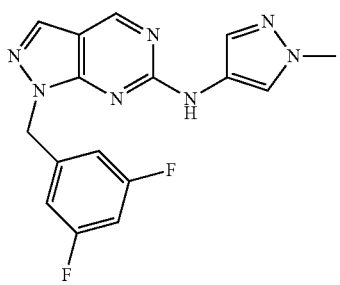

¹H NMR (d₆-DMSO) δ 9.91 (s, 1H), 8.93 (s, 1H), 8.09 (s, 1H), 8.05 (s, 1H), 7.54 (s, 1H), 7.15-7.20 (m, 1H), 6.98-7.00 (m, 2H), 5.62 (s, 2H), 3.83 (s, 3H); LC-MS method B, (ES+) 342.0, RT=8.37 min.

Example 80

3-((6-((1-Methyl-1H-pyrazol-4-yl)amino)-1H-pyrazolo[3,4-d]pyrimidin-1-yl)methyl)benzamide 3-((6-((1-Methyl-1H-pyrazol-4-yl)amino)-1H-pyrazolo[3,4-d]pyrimidin-1-yl)methyl)benzonitrile (Example 68) was hydrolysed according to the procedure in Example 16 to afford the title compound:

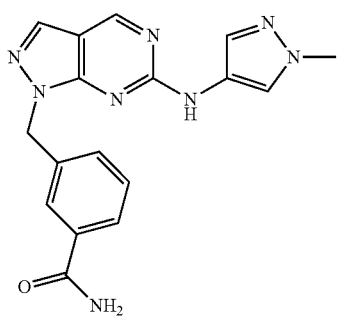 [SMILES: Cn1cc(Nc2ncc3cnn(Cc4cccc(C(N)=O)c4)c3n2)cn1]

¹H NMR (d₆-DMSO) δ 9.94 (s, 1H), 8.98 (s, 1H), 8.13 (s, 1H), 8.04-8.09 (m, 2H), 7.90 (s, 1H), 7.82-7.85 (m, 1H), 7.59 (s, 1H), 7.44-7.48 (m, 3H), 5.66 (s, 2H), 3.89 (s, 3H); LC-MS method B, (ES+) 349.0, RT=5.93 min.

Example 81

1-(3-Fluorophenethyl)-N-(1-methyl-1H-pyrazol-4-yl)-1H-pyrazolo[3,4-d]pyrimidin-6-amine The following compound was made according to the procedure in Example 1 (Step ii) using 1-fluoro-3-(2-bromoethyl)benzene:

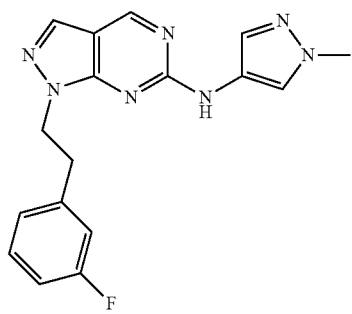 [SMILES: Cn1cc(Nc2ncc3cnn(CCc4cccc(F)c4)c3n2)cn1]

¹H NMR (d₆-DMSO) δ 9.71 (s, 1H), 8.84 (s, 1H), 8.02 (s, 1H), 7.96 (s, 1H), 7.53 (s, 1H), 7.17 (q, 1H), 7.01 (d, 1H), 6.90-6.93 (m, 2H), 4.57 (t, 2H), 3.85 (s, 3H), 3.19 (t, 2H); LC-MS method B, (ES+) 338, RT=8.26 min.

Example 82

1-(4-Fluorophenethyl)-N-(1-methyl-1H-pyrazol-4-yl)-1H-pyrazolo[3,4-d]pyrimidin-6-amine The following compound was made according to the procedure in Example 1 (Step ii) using 1-(2-bromoethyl)-4-fluorobenzene:

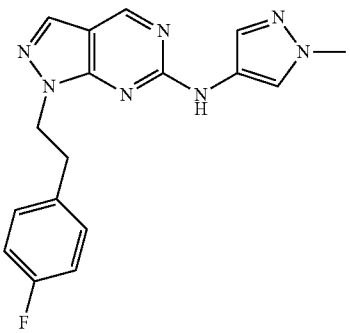 [SMILES: Cn1cc(Nc2ncc3cnn(CCc4ccc(F)cc4)c3n2)cn1]

¹H NMR (d₆-DMSO) δ 9.71 (s, 1H), 8.84 (s, 1H), 8.01 (s, 1H), 7.94 (s, 1H), 7.54 (s, 1H), 7.15 (dd, 2H), 6.98 (t, 2H), 4.54 (t, 2H), 3.85 (s, 3H), 3.16 (t, 2H); LC-MS method B, (ES+) 338, RT=8.26 min.

Example 83

N-(1-Methyl-1H-pyrazol-4-yl)-1-(3-methylbenzyl)-1H-pyrazolo[3,4-d]pyrimidin-6-amine The following compound was made according to the procedure in Example 1 (Step ii) using 1-(bromomethyl)-3-methylbenzene:

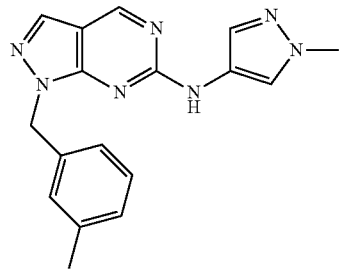 [SMILES: Cc1cccc(Cn2ncc3cnc(Nc4cnn(C)c4)nc32)c1]

¹H NMR (d₆-DMSO) δ 9.87 (s, 1H), 8.91 (s, 1H), 8.05 (s, 2H), 7.56 (s, 1H), 7.21 (t, 1H), 7.14 (s, 1H), 7.08 (d, 2H), 5.51 (s, 2H), 3.84 (s, 3H), 2.25 (s, 3H); LC-MS method B, (ES+) 320.0, RT=8.41 min.

Example 84

N-(1-Methyl-1H-pyrazol-4-yl)-1-(2-methylbenzyl)-1H-pyrazolo[3,4-d]pyrimidin-6-amine

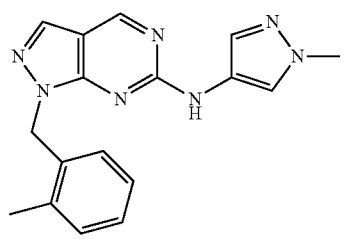

The following compound was made according to the procedure in Example 1 (Step ii) using 1-(bromomethyl)-2-methylbenzene:

$^1$H NMR (d$_6$-DMSO) δ 9.86 (s, 1H), 8.92 (s, 1H), 8.05 (s, 2H), 7.54 (s, 1H), 7.23-7.03 (m, 4H), 5.54 (s, 2H), 3.83 (s, 3H), 2.36 (s, 3H); LC-MS method B, (ES+) 320.0, RT=8.36 min.

Example 85

N-(1-Methyl-1H-pyrazol-4-yl)-1-(2-(trifluoromethoxy)benzyl)-1H-pyrazolo[3,4-d]pyrimidin-6-amine The following compound was made according to the procedure in Example 1 (Step ii) using 1-(bromomethyl)-2-(trifluoromethoxy)benzene:

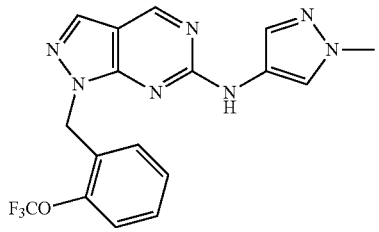 [SMILES: Cn1cc(Nc2ncc3cnn(Cc4ccccc4OC(F)(F)F)c3n2)cn1]

$^1$H NMR (d$_6$-DMSO) δ 9.89 (s, 1H), 8.93 (s, 1H), 8.07 (s, 1H), 7.99 (s, 1H), 7.54 (s, 1H), 7.49-7.39 (m, 2H), 7.38-7.33 (m, 1H), 7.27 (s, 1H), 5.63 (s, 2H), 3.81 (s, 3H); LC-MS method B, (ES+) 390.0, RT=9.08 min.

Example 86

N-(1-Methyl-1H-pyrazol-4-yl)-1-(3-(trifluoromethoxy)benzyl)-1H-pyrazolo[3,4-d]pyrimidin-6-amine The following compound was made according to the procedure in Example 1 (Step ii) using 1-(bromomethyl)-3-(trifluoromethoxy)benzene:

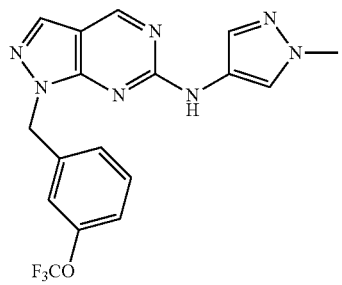 [SMILES: Cn1cc(Nc2ncc3cnn(Cc4cccc(OC(F)(F)F)c4)c3n2)cn1]

$^1$H NMR (d$_6$-DMSO) δ 9.91 (s, 1H), 8.93 (s, 1H), 8.08 (s, 2H), 7.54 (s, 1H), 7.51-7.43 (m, 1H), 7.40-7.20 (m, 3H), 5.65 (s, 2H), 3.83 (s, 3H); LC-MS method B, (ES+) 390.0, RT=9.21 min.

Example 87

1-(2-Methoxybenzyl)-N-(1-methyl-1H-pyrazol-4-yl)-1H-pyrazolo[3,4-d]pyrimidin-6-amine The following compound was made according to the procedure in Example 1 (Step ii) using 1-(chloromethyl)-2-(methoxy)benzene:

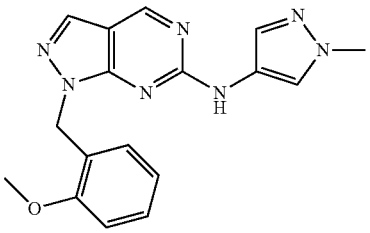

$^1$H NMR (d$_6$-DMSO) δ 9.83 (s, 1H), 8.91 (s, 1H), 8.05 (s, 1H), 7.94 (s, 1H), 7.59-7.62 (m, 1H), 7.22-7.25 (m, 1H), 7.04 (d, 1H), 6.83-6.91 (m, 2H), 5.51 (s, 2H), 3.82 (s, 3H), 3.80 (s, 3H); LC-MS method B, (ES+) 336.0, RT=8.01 min.

Example 88

1-(2-Fluorobenzyl)-N-(1H-pyrazol-4-yl)-1H-pyrazolo[3,4-d]pyrimidin-6-amine

The following compound was made according to the procedures in Example 1 (Step ii) using 1-(bromomethyl)-2-fluorobenzene and 6-chloro-1H-pyrazolo[3,4-d]pyrimidine followed by Example 1 (Step i) using 6-chloro-1-(2-fluorobenzyl)-1H-pyrazolo[3,4-d]pyrimidine and 1-methyl-1H-pyrazol-4-amine:

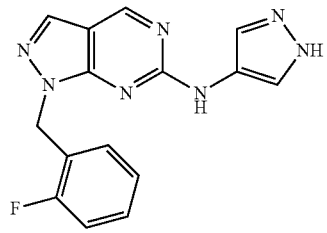 [SMILES: Fc1ccccc1Cn1ncc2cnc(Nc3cn[nH]c3)nc21]

$^1$H NMR (d$_6$-DMSO) δ 12.5 (s, 1H), 9.88 (s, 1H), 8.92 (s, 1H), 8.09-8.05 (m, 2H), 7.66 (s, 1H), 7.38-7.13 (m, 3H), 5.58 (s, 2H); LC-MS method B, (ES+) 310.0, RT=7.23 min.

Example 89

1-(4-((1-(2-Fluorobenzyl)-1H-pyrazolo[3,4-d]pyrimidin-6-yl)amino)-1H-pyrazol-1-yl)propan-2-ol The following compound was made according to the procedure in Example 1 (Step ii) using 1-(bromomethyl)-2-fluorobenzene and 6-chloro-1H-pyrazolo[3,4-d]pyrimidine followed by Example 1 (Step i) using 6-chloro-1-(2-fluorobenzyl)-1H-pyrazolo[3,4-d]pyrimidine and 1-(4-amino-1H-pyrazol-1-yl)propan-2-ol. 1-(4-amino-1H-pyrazol-1-yl)propan-2-ol was prepared following Procedure A using 1-bromopropan-2-ol as alkylating agent:

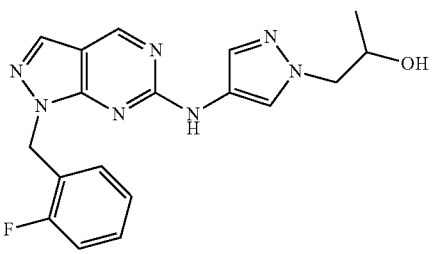 [SMILES: CC(O)Cn1cc(Nc2ncc3cnn(Cc4ccccc4F)c3n2)cn1]

$^1$H NMR (d$_6$-DMSO) δ 9.88 (s, 1H), 8.90 (s, 1H), 8.09 (s, 1H), 8.04 (s, 1H), 7.60 (s, 1H), 7.34-7.36 (m, 1H), 7.12-7.30

(m, 3H), 5.58 (s, 2H), 4.90 (d, 1H), 3.95-3.99 (m, 2H), 3.55-3.60 (m, 1H), 1.01 (d, 3H); LC-MS method B, (ES+) 368.0, RT=7.45 min.

Example 90

1-(2-Fluoro-6-methoxybenzyl)-N-(1-methyl-1H-pyrazol-4-yl)-1H-pyrazolo[3,4-d]pyrimidin-6-amine The following compound was made according to the procedure in Example 1 (Step ii) using 2-(bromomethyl)-1-fluoro-3-methoxybenzene:

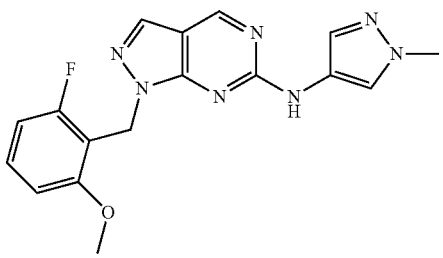 [SMILES: COc1cccc(F)c1Cn1ncc2cnc(Nc3cnn(C)c3)nc21]

¹H NMR (d₆-DMSO) δ 9.83 (s, 1H), 8.87 (s, 1H), 8.12 (s, 1H), 7.94 (s, 1H), 7.64 (s, 1H), 7.37 (q, 1H), 6.76-6.83 (m, 2H), 5.51 (s, 2H), 3.85 (s, 3H), 3.73 (s, 3H); LC-MS method B, (ES+) 354.0, RT=8.01 min.

Example 91

1-(5-Fluoro-2-methoxybenzyl)-N-(1-methyl-1H-pyrazol-4-yl)-1H-pyrazolo[3,4-d]pyrimidin-6-amine The following compound was made according to the procedure in Example 1 (Step ii) using 2-(bromomethyl)-4-fluoro-1-methoxybenzene:

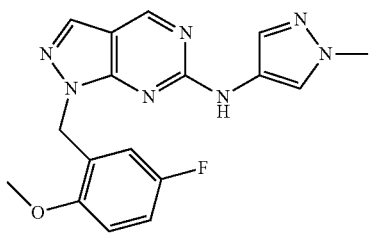

¹H NMR (d₆-DMSO) δ 9.86 (s, 1H), 8.93 (s, 1H), 8.07 (s, 1H), 7.97 (s, 1H), 7.60 (br s, 1H), 7.05-7.14 (m, 2H), 6.76 (s, 1H), 5.51 (s, 2H), 3.82 (s, 3H); LC-MS method B, (ES+) 354.0, RT=8.27 min.

Example 92

(2-((6-((1-Methyl-1H-pyrazol-4-yl)amino)-1H-pyrazolo[3,4-d]pyrimidin-1-yl)methyl)phenyl)methanol The following compound was made according to the procedure in Example 1 (Step ii) using (2-(bromomethyl)phenyl)methanol:

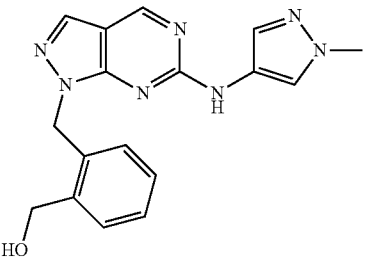 [SMILES: Cn1cc(Nc2ncc3cnn(Cc4ccccc4CO)c3n2)cn1]

¹H NMR (d₆-DMSO) δ 9.88 (s, 1H), 8.93 (s, 1H), 8.16-8.01 (m, 2H), 7.52 (s, 1H), 7.47-7.39 (m, 1H), 7.31-7.23 (m, 1H), 7.23-7.15 (m, 1H), 7.03 (s, 1H), 5.63 (s, 2H), 5.29 (t, J=5.5 Hz, 1H), 4.69 (d, J=5.5 Hz, 2H), 3.82 (s, 3H); LC-MS method B, (ES+) 336.0, RT=6.72 min.

Example 93

1-(2-Fluoro-3-methoxybenzyl)-N-(1-methyl-1H-pyrazol-4-yl)-1H-pyrazolo[3,4-d]pyrimidin-6-amine The following compound was made according to the procedures in Example 45 (Step ii) using (2-fluoro-3-methoxyphenyl)methanol then Example 1 (Step ii):

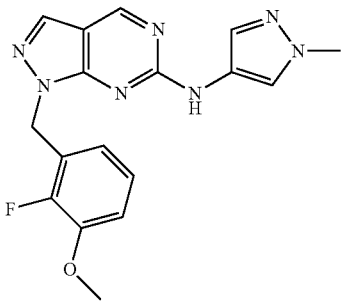 [SMILES: COc1cccc(Cn2ncc3cnc(Nc4cnn(C)c4)nc32)c1F]

¹H NMR (d₆-DMSO) δ 9.89 (s, 1H), 8.91 (s, 1H), 8.05 (s, 2H), 7.56 (s, 1H), 7.02-7.09 (m, 2H), 6.77 (s, 1H), 5.59 (s, 2H), 3.83 (s, 3H), 3.82 (s, 3H); LC-MS method B, (ES+) 354.0, RT=7.97 min.

Example 94

1-(2-Fluoro-5-methoxybenzyl)-N-(1-methyl-1H-pyrazol-4-yl)-1H-pyrazolo[3,4-d]pyrimidin-6-amine The following compound was made according to the procedures in Example 45 (Step ii) using (2-fluoro-5-methoxyphenyl)methanol then Example 1 (Step ii):

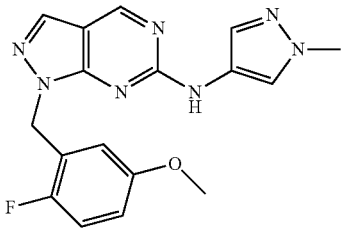 [SMILES: COc1ccc(F)c(Cn2ncc3cnc(Nc4cnn(C)c4)nc32)c1]

¹H NMR (d₆-DMSO) δ 9.90 (s, 1H), 8.91 (s, 1H), 8.09 (s, 1H), 8.05 (s, 1H), 7.57 (s, 1H), 7.16 (t, 1H), 6.86-6.91 (m,

1H), 6.82 (s, 1H), 5.57 (s, 2H), 3.84 (s, 3H), 3.64 (s, 3H); LC-MS method B, (ES+) 354.0, RT=8.07 min.

Example 95

1-(4-((1-(2-Fluorobenzyl)-1H-pyrazolo[3,4-d]pyrimidin-6-yl)amino)-1H-pyrazol-1-yl)ethanone

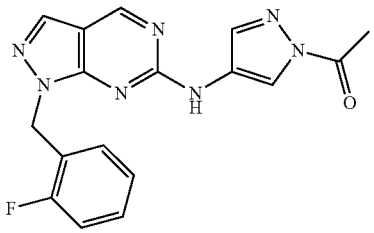 [SMILES: CC(=O)n1cc(Nc2ncc3cnn(Cc4ccccc4F)c3n2)cn1]

To a solution of 1-(2-fluorobenzyl)-N-(1H-pyrazol-4-yl)-1H-pyrazolo[3,4-d]pyrimidin-6-amine (56 mg, 0.18 mmol), (Example 88), in DCM (2 mL) were added triethylamine (384, 1.5 eq) and acetyl chloride (154, 1.2 eq). After stirring for 30 min at rt, the reaction mixture was quenched with water. The aqueous phase was extracted with DCM and the combined organic phases dried over sodium sulfate and concentrated in vacuo. The residue was purified with the preparative HPLC to give the title product. $^1$H NMR (d$_6$-DMSO) δ 10.25 (s, 1H), 9.03 (s, 1H), 8.67 (s, 1H), 8.15 (s, 1H), 8.04 (s, 1H), 7.41-7.31 (m, 2H), 7.26-7.12 (m, 2H), 5.60 (s, 2H), 2.63 (s, 3H); LC-MS method B, (ES+) 352.0, RT=9.09 min.

Example 96

1-(2-Fluorobenzyl)-N-(1-(methylsulfonyl)-1H-pyrazol-4-yl)-1H-pyrazolo[3,4-d]pyrimidin-6-amine

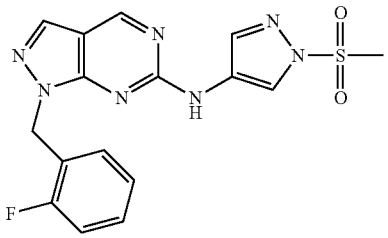 [SMILES: CS(=O)(=O)n1cc(Nc2ncc3cnn(Cc4ccccc4F)c3n2)cn1]

Step (i)

To a solution of 4-nitro-1H-pyrazole (250 mg, 2.2 mmol) in DCM (5 mL) were added triethylamine (0.46 mL, 1.5 eq) and methanesulfonyl chloride (0.20 mL, 1.2 eq). After stirring for 1 h at rt, water was added and the aqueous phase extracted with DCM. The combined organic phases were dried over sodium sulfate and concentrated in vacuo. The residue was dissolved in 5 mL methanol and palladium on carbon added under an inert atmosphere. The reaction mixture was stirred overnight at rt under an hydrogen atmosphere. The resulting mixture was filtered through Celite and the filtrate concentrated in vacuo to give 1-(methylsulfonyl)-1H-pyrazol-4-amine as a brown oil (0.34 g, 2.1 mmol, 96%).

Step (ii)

The title compound was made according to the procedure in Example 1 (Step ii) using 1-(bromomethyl)-2-fluorobenzene and 6-chloro-1H-pyrazolo[3,4-d]pyrimidine followed by Example 1 (Step i) using 6-chloro-1-(2-fluorobenzyl)-1H-pyrazolo[3,4-d]pyrimidine and 1-(methylsulfonyl)-1H-pyrazol-4-amine. $^1$H NMR (d$_6$-DMSO) δ 10.26 (s, 1H), 9.03 (s, 1H), 8.54 (s, 1H), 8.15 (s, 1H), 8.11 (s, 1H), 7.43-7.29 (m, 2H), 7.26-7.14 (m, 2H), 5.60 (s, 2H), 3.50 (s, 3H); LC-MS method B, (ES+) 387.9, RT=8.61 min.

Example 97

N-(3-Chloro-1H-pyrazol-4-yl)-1-(2-fluorobenzyl)-1H-pyrazolo[3,4-d]pyrimidin-6-amine

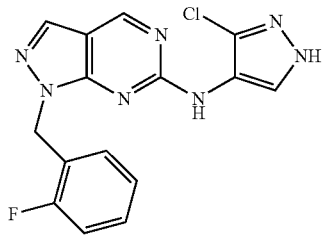 [SMILES: Fc1ccccc1Cn1ncc2cnc(Nc3c[nH]nc3Cl)nc21]

Step (i)

A solution of 4-nitropyrazole (500 mg, 4.4 mmol) and palladium on alumina (50 mg) in ethanol (10 mL) and hydrochloric acid (2 mL, 6M aqueous solution) was stirred at rt under a balloon of H$_2$ for 16 h. The mixture was then filtered through Celite and the filtrate concentrated in vacuo to give 3-chloro-1H-pyrazol-4-amine.

Step (ii)

The title compound was made according to the procedure in Example 1 (Step ii) using 1-(bromomethyl)-2-fluorobenzene and 6-chloro-1H-pyrazolo[3,4-d]pyrimidine followed by Example 1 (Step i) using 6-chloro-1-(2-fluorobenzyl)-1H-pyrazolo[3,4-d]pyrimidine and 3-chloro-1H-pyrazol-4-amine. $^1$H NMR (d$_6$-DMSO) δ 12.92 (s, 1H), 9.10 (s, 1H), 8.94 (s, 1H), 8.11 (s, 1H), 8.08 (s, 1H), 7.34-7.36 (m, 1H), 7.14-7.24 (m, 3H), 5.51 (s, 2H); LC-MS method B, (ES+) 343.9, RT=8.26 min.

Example 98

N-(1-Methyl-1H-pyrazol-4-yl)-1-(2,3,6-trifluorobenzyl)-1H-pyrazolo[3,4-d]pyrimidin-6-amine The following compound was made according to the procedure in Example 1 (Step ii) using 2-(bromomethyl)-1,3,4-trifluorobenzene:

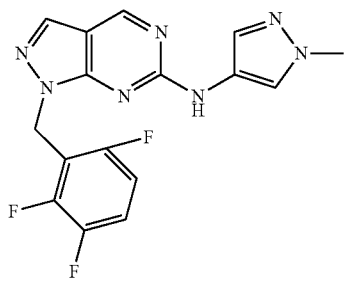 [SMILES: Cn1cc(Nc2ncc3cnn(Cc4c(F)ccc(F)c4F)c3n2)cn1]

$^1$H NMR (d$_6$-DMSO) δ 9.92 (s, 1H), 8.90 (s, 1H), 8.13 (s, 1H), 8.02 (s, 1H), 7.70-7.42 (m, 2H), 7.19 (tdd, 1H), 5.65 (s, 2H), 3.85 (s, 3H); LC-MS method B, (ES+) 360, RT=8.18 min.

Example 99

1-(4-Fluorobenzyl)-N-(1-methyl-1H-pyrazol-4-yl)-1H-pyrazolo[3,4-d]pyrimidin-6-amine The following compound was made according to the procedure in Example 1 (Step ii) using 1-(bromomethyl)-4-fluorobenzene:

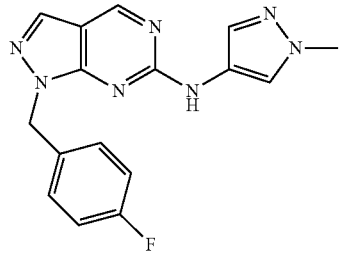 [SMILES: Cn1cc(Nc2ncc3cnn(Cc4ccc(F)cc4)c3n2)cn1]

¹H NMR (d₆-DMSO) δ 9.88 (s, 1H), 8.92 (s, 1H), 8.06 (s, 2H), 7.56 (s, 1H), 7.36 (s, 2H), 7.18 (ddd, 2H), 5.56 (s, 2H), 3.84 (s, 3H); LC-MS method B, (ES+) 324, RT=8.06 min.

Example 100

1-(3-Isopropylbenzyl)-N-(1-methyl-1H-pyrazol-4-yl)-1H-pyrazolo[3,4-d]pyrimidin-6-amine The following compound was made according to the procedure in Example 45 using 3-isopropylbenzaldehyde:

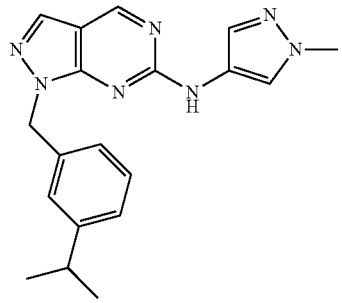 [SMILES: CC(C)c1cccc(Cn2ncc3cnc(Nc4cnn(C)c4)nc32)c1]

¹H NMR (d₆-DMSO) δ 9.72 (s, 1H), 8.78 (s, 1H), 7.95 (s, 1H), 7.91 (s, 1H), 7.44 (s, 1H), 7.15 (s, 1H), 7.09 (m, 1H), 7.03-6.99 (m, 1H), 6.96-6.89 (m, 1H), 5.40 (s, 2H), 3.70 (s, 3H), 2.74-2.64 (m, 1H), 1.01 (s, 3H), 1.00 (s, 3H); LC-MS method B, (ES+) 348.0, RT=9.48 min.

Example 101

1-(2-Isopropylbenzyl)-N-(1-methyl-1H-pyrazol-4-yl)-1H-pyrazolo[3,4-d]pyrimidin-6-amine The following compound was made according to the procedure in Example 45 using 2-isopropylbenzaldehyde:

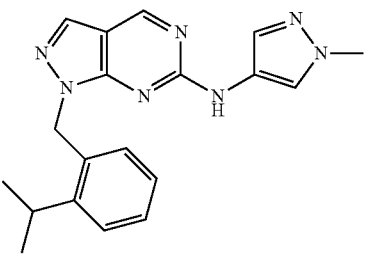 [SMILES: CC(C)c1ccccc1Cn1ncc2cnc(Nc3cnn(C)c3)nc21]

¹H NMR (d₆-DMSO) δ 9.85 (s, 1H), 8.91 (s, 1H), 8.04 (s, 2H), 7.56 (s, 1H), 7.36-7.31 (m, 1H), 7.31-7.24 (m, 1H), 7.17-7.08 (m, 2H), 5.61 (s, 2H), 3.82 (s, 3H), 3.59-3.47 (m, 1H), 1.09 (s, 3H), 1.08 (s, 3H),); LC-MS method B, (ES+) 348.0, RT=9.34 min.

Example 102

1-(2-(2-Methoxyethoxy)benzyl)-N-(1-methyl-1H-pyrazol-4-yl)-1H-pyrazolo[3,4-d]pyrimidin-6-amine The following compound was made according to the procedure in Example 45 using 2-(2-methoxyethoxy)benzaldehyde which was synthesized as follows:

A mixture of salicylaldehyde (0.50 mL, 4.7 mmol), (2-bromomethyl)methylether (0.54 mL, 1.2 eq) and potassium carbonate (0.66 g, 1 eq) in methanol (1.5 mL) was heated by microwave to 100° C. for 2 h. After evaporation, the residue was triturated with petrol ether and the triturate concentrated in vacuo to yield 2-(2-methoxyethoxy)benzaldehyde as a yellow oil (0.64 g, 3.6 mmol, 75%).

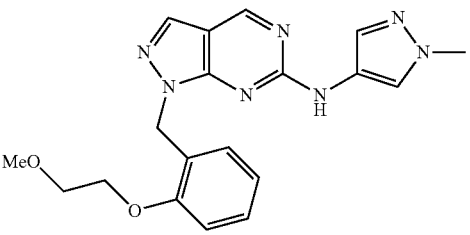 [SMILES: COCCOc1ccccc1Cn1ncc2cnc(Nc3cnn(C)c3)nc21]

¹H NMR (d₆-DMSO) δ 9.82 (s, 1H), 8.92 (s, 1H), 8.03 (s, 1H), 7.95 (s, 1H), 7.57 (s, 1H), 7.28-7.23 (m, 1H), 7.06-7.01 (m, 1H), 6.99-6.82 (m, 2H), 5.52 (s, 2H), 4.13-4.08 (m, 2H), 3.81 (s, 3H), 3.59-3.53 (m, 2H), 3.21 (s, 3H); LC-MS method B, (ES+) 380.0, RT=7.83 min.

Example 103

4-((1-(2-Fluorobenzyl)-1H-pyrazolo[3,4-d]pyrimidin-6-yl)amino)-1H-pyrazole-1-carboxamide

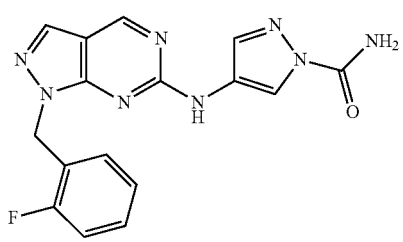 [SMILES: NC(=O)n1cc(Nc2ncc3cnn(Cc4ccccc4F)c3n2)cn1]

To a solution of 1-(2-fluorobenzyl)-N-(1H-pyrazol-4-yl)-1H-pyrazolo[3,4-d]pyrimidin-6-amine (Example 88), (111 mg, 0.36 mmol) in ACN/H$_2$O (9:1, 4 mL) was added potassium cyanate (35 mg, 1.2 eq). After 30 min at rt, the reaction mixture was neutralized with saturated sodium carbonate and the aqueous phase extracted with DCM. The combined organic phases were dried over sodium sulfate and concentrated in vacuo. The residue was purified by preparative HPLC to give the title product. $^1$H NMR (d$_6$-DMSO) δ 10.12 (s, 1H), 9.00 (s, 1H), 8.57 (s, 1H), 8.12 (s, 1H), 7.94 (s, 1H), 7.80 (s, 1H), 7.71 (s, 1H), 7.41-7.28 (m, 2H), 7.26-7.14 (m, 2H), 5.58 (s, 2H); LC-MS method B, (ES+) 353.0, RT=7.75 min.

Example 104

1-(3-Fluoro-5-methoxybenzyl)-N-(1-methyl-1H-pyrazol-4-yl)-1H-pyrazolo[3,4-d]pyrimidin-6-amine The following compound was made according to the procedure in Example 1 (Step ii) using 1-(bromomethyl)-3-fluoro-5-methoxybenzene:

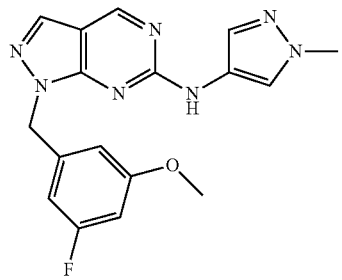 [SMILES: COc1cc(F)cc(Cn2ncc3cnc(Nc4cnn(C)c4)nc32)c1]

$^1$H NMR (d$_6$-DMSO) δ 9.88 (s, 1H), 8.91 (s, 1H), 8.06 (s, 1H), 8.03 (s, 1H), 7.54 (s, 1H), 6.72-6.75 (m, 2H), 6.63 (d, 1H), 5.53 (s, 2H), 3.82 (s, 3H), 3.69 (s, 3H); LC-MS method B, (ES+) 354, RT=8.31 min Example 105

1-Benzyl-N-(3-methoxy-1-methyl-1H-pyrazol-4-yl)-1H-pyrazolo[3,4-d]pyrimidin-6-amine The following compound was made according to the procedure in Example 1, using 3-methoxy-1-methyl-1H-pyrazol-4-amine and (bromomethyl)benzene. 3-methoxy-1-methyl-1H-pyrazol-4-amine was prepared by Procedure C using methyl iodide as alkylating agent:

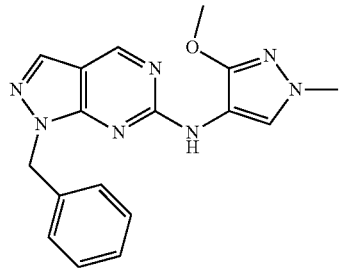 [SMILES: COc1nn(C)cc1Nc1ncc2cnn(Cc3ccccc3)c2n1]

$^1$H NMR (d$_6$-Acetone) δ 8.85 (s, 1H), 8.01 (br s, 1H), 7.96 (s, 1H), 7.70 (br s, 1H), 7.42-7.21 (m, 5H), 5.54 (s, 2H), 3.88 (s, 3H), 3.72 (s, 3H); LC-MS method B, (ES+) 336.0, RT=8.41 min.

Example 106

2-(4-((1-Benzyl-1H-pyrazolo[3,4-d]pyrimidin-6-yl)amino)-3-methoxy-1H-pyrazol-1-yl)ethanol The following compound was made according to the procedure in Example 1, using 2-(4-amino-3-methoxy-1H-pyrazol-1-yl)ethanol and (bromomethyl)benzene. 2-(4-amino-3-methoxy-1H-pyrazol-1-yl)ethanol was prepared by Procedure C using 2-bromoethanol as alkylating agent:

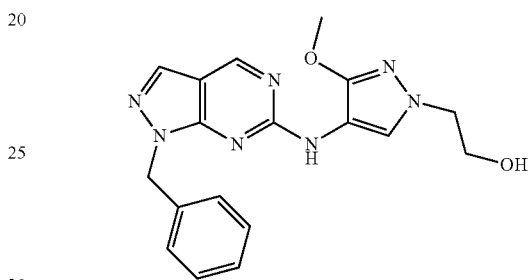

$^1$H NMR (d$_6$-DMSO): δ 8.98 (br s, 1H), 8.93 (s, 1H), 8.10 (s, 1H), 7.98 (br s, 1H), 7.42-7.13 (m, 6H), 5.47 (s, 2H), 4.00 (t, J=5.6 Hz, 2H), 3.81 (s, 3H), 3.71 (t, J=5.7 Hz, 2H); LC-MS method B, (ES+) 366.0, RT=7.31 min.

Example 107

2-Fluoro-3-((6-((1-methyl-1H-pyrazol-4-yl)amino)-1H-pyrazolo[3,4-d]pyrimidin-1-yl)methyl)benzonitrile The following compound was made according to the procedure in Example 41 (Steps i-ii), using 2-fluoro-3-methylbenzonitrile:

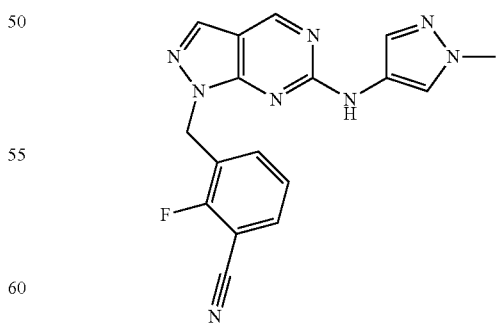

$^1$H NMR (d$_6$-DMSO) δ 9.94 (s, 1H), 8.92 (s, 1H), 8.07-8.10 (m, 2H), 7.88-7.92 (m, 1H), 7.65 (s, 1H), 7.56 (s, 1H), 7.40 (t, 1H), 5.69 (s, 2H), 3.85 (s, 3H); LC-MS method B, (ES+) 349.0, RT=7.73 min.

Example 108

2-Fluoro-6-((6-((1-methyl-1H-pyrazol-4-yl)amino)-1H-pyrazolo[3,4-d]pyrimidin-1-yl)methyl)benzonitrile The following compound was made according to the procedure in Example 41 (Steps i-ii), using 2-fluoro-6-methylbenzonitrile:

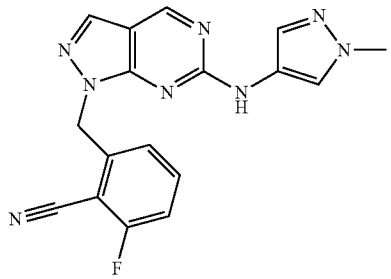 [SMILES: Cn1cc(Nc2ncc3cnn(Cc4cccc(F)c4C#N)c3n2)cn1]

¹H NMR (d₆-DMSO) δ 9.98 (s, 1H), 8.98 (s, 1H), 8.15 (s, 1H), 8.11 (s, 1H), 7.76-7.82 (m, 1H), 7.52-7.56 (m, 2H), 7.26-7.28 (m, 1H), 5.81 (s, 2H), 3.86 (s, 3H); LC-MS method B, (ES+) 349.0, RT=7.83 min.

Example 109

1-Benzyl-N-(1,5-dimethyl-1H-pyrazol-4-yl)-1H-pyrazolo[3,4-d]pyrimidin-6-amine

The following compound was made according to the procedure in Example 1, using 1,5-dimethyl-1H-pyrazol-4-amine and (bromomethyl)benzene. 1,5-dimethyl-1H-pyrazol-4-amine was prepared by Procedure B using methyl iodide as alkylating agent:

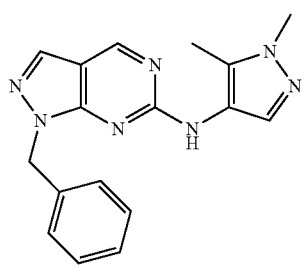 [SMILES: Cc1c(Nc2ncc3cnn(Cc4ccccc4)c3n2)cnn1C]

¹H NMR (d₆-Acetone): δ 8.82 (s, 1H), 8.07 (br s, 1H), 7.94 (s, 1H), 7.69 (br s, 1H), 7.38-7.19 (m, 5H), 5.46 (s, 2H), 3.76 (s, 3H), 2.24 (s, 3H); LC-MS method B, (ES+) 320.0, RT=7.71 min.

Example 110

1-Benzyl-N-(1,3-dimethyl-1H-pyrazol-4-yl)-1H-pyrazolo[3,4-d]pyrimidin-6-amine

The following compound was made according to the procedure in Example 1, using 1,3-dimethyl-1H-pyrazol-4-amine and (bromomethyl)benzene. 1,3-dimethyl-1H-pyrazol-4-amine was prepared by Procedure B using methyl iodide as alkylating agent:

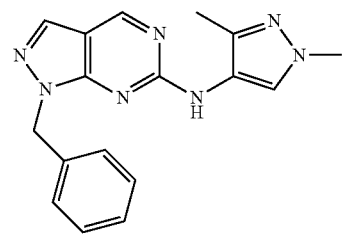 [SMILES: Cc1nn(C)cc1Nc1ncc2cnn(Cc3ccccc3)c2n1]

¹H NMR (d₆-Acetone): δ 8.85 (s, 1H), 8.12 (br s, 1H), 8.03 (br s, 1H), 7.95 (s, 1H), 7.46-7.18 (m, 5H), 5.53 (s, 2H), 3.79 (s, 3H), 2.24 (s, 3H); LC-MS method B, (ES+) 320.0, RT=7.97 min.

Example 111

1-(2-Cyclopropylbenzyl)-N-(1-methyl-1H-pyrazol-4-yl)-1H-pyrazolo[3,4-d]pyrimidin-6-amine The following compound was made according to the procedure in Example 45, using 2-cyclopropylbenzaldehyde:

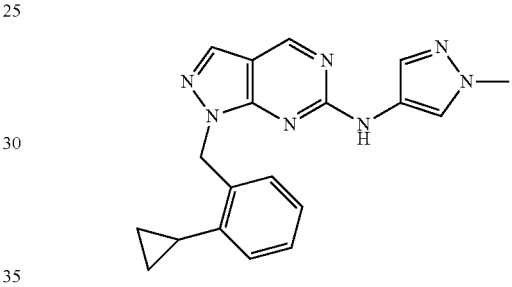

¹H NMR (d₆-DMSO) δ 9.87 (s, 1H), 8.97 (s, 1H), 8.11 (s, 1H), 8.00 (s, 1H), 7.58 (s, 1H), 7.27-7.20 (m, 1H), 7.18-7.11 (m, 1H), 7.10-6.98 (m, 2H), 5.77 (s, 2H), 3.85 (s, 3H), 2.23 (s, 1H), 0.96-0.83 (m, 2H), 0.73-0.63 (m, 2H); LC-MS method B, (ES+) 346.0, RT=9.01 min.

Example 112

1-(4-((1-(2-Fluorobenzyl)-1H-pyrazolo[3,4-d]pyrimidin-6-yl)amino)-1H-pyrazol-1-yl)-2-methylpropan-2-ol The following compound was made according to the procedure in Example 1, using 1-(4-amino-1H-pyrazol-1-yl)-2-methylpropan-2-ol and 1-(bromomethyl)-2-fluorobenzene. 1-(4-amino-1H-pyrazol-1-yl)-2-methylpropan-2-ol was prepared by Procedure A using 1-chloro-2-methylpropan-2-ol as alkylating agent:

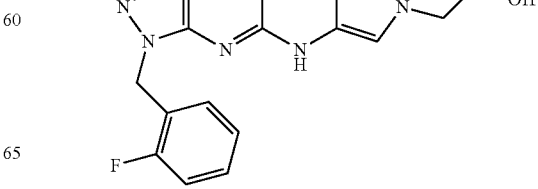

¹H NMR (d₆-DMSO) δ 9.90 (s, 1H), 8.92 (s, 1H), 8.12 (s, 1H), 8.05 (s, 1H), 7.63 (s, 1H), 7.39-7.32 (m, 1H), 7.32-7.19 (m, 2H), 7.17-7.12 (m, 1H), 5.58 (s, 2H), 4.69 (s, 1H), 3.99 (s, 2H), 1.06 (s, 6H); LC-MS method B, (ES+) 382.0, RT=7.87 min.

Example 113

2-(4-((1-Benzyl-1H-pyrazolo[3,4-d]pyrimidin-6-yl)amino)-3-methyl-1H-pyrazol-1-yl)ethanol The following compound was made according to the procedure in Example 1, using 2-(4-amino-3-methyl-1H-pyrazol-1-yl)ethanol and (bromomethyl)benzene. 2-(4-amino-3-methyl-1H-pyrazol-1-yl)ethanol was prepared by Procedure B using 2-bromoethanol as alkylating agent:

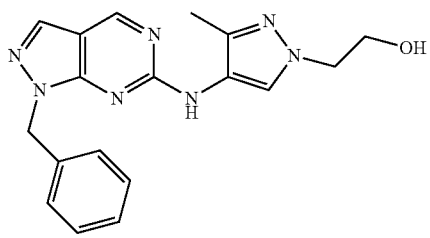 [SMILES: Cc1nn(CCO)cc1Nc1ncc2cnn(Cc3ccccc3)c2n1]

¹H NMR (d₆-Acetone): δ 8.85 (s, 1H), 8.21 (br s, 1H), 8.13 (br s, 1H), 7.95 (s, 1H), 7.45-7.16 (m, 5H), 5.52 (s, 2H), 4.16 (m, 2H), 4.08 (br s, 1H), 3.94-3.85 (m, 2H), 2.26 (s, 3H); LC-MS method B, (ES+) 350.0, RT=7.04 min Example 114

1-(2-(Benzyloxy)benzyl)-N-(1-methyl-1H-pyrazol-4-yl)-1H-pyrazolo[3,4-d]pyrimidin-6-amine The following compound was made according to the procedure in Example 45, using 2-(benzyloxy)benzaldehyde:

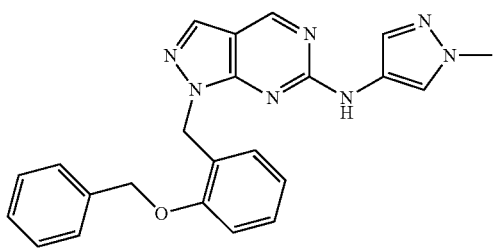 [SMILES: Cn1cc(Nc2ncc3cnn(Cc4ccccc4OCc4ccccc4)c3n2)cn1]

¹H NMR (d₆-DMSO) δ 9.81 (s, 1H), 8.91 (s, 1H), 8.04 (s, 1H), 7.96 (s, 1H), 7.57 (s, 1H), 7.43-7.34 (m, 2H), 7.33-7.21 (m, 4H), 7.14-7.06 (m, 1H), 6.99 (s, 1H), 6.88 (m, 1H), 5.58 (s, 2H), 5.16 (s, 2H), 3.76 (s, 3H); LC-MS method B, (ES+) 412.0, RT=9.47 min.

Example 115

1-(3-Fluoro-2-methylbenzyl)-N-(1-methyl-1H-pyrazol-4-yl)-1H-pyrazolo[3,4-d]pyrimidin-6-amine The following compound was made according to the procedure in Example 1 (Step ii), using 1-(bromomethyl)-3-fluoro-2-methylbenzene:

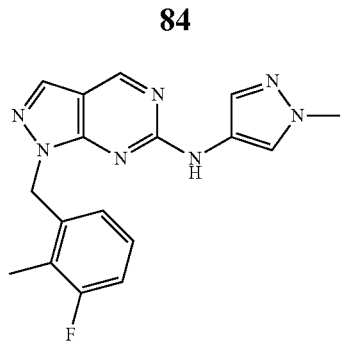

¹H NMR (d₆-DMSO) δ 9.88 (s, 1H), 8.92 (s, 1H), 8.06 (s, 2H), 7.54 (s, 1H), 7.25-7.04 (m, 2H), 6.95 (s, 1H), 5.59 (s, 2H), 3.83 (s, 3H), 2.26 (s, 3H); LC-MS method B, (ES+) 338.0, RT=8.61 min.

Example 116

145-Fluoro-2-methylbenzyl)-N-(1-methyl-1H-pyrazol-4-yl)-1H-pyrazolo[3,4-d]pyrimidin-6-amine The following compound was made according to the procedure in Example 1 (Step ii), using 2-(bromomethyl)-4-fluoro-1-methylbenzene:

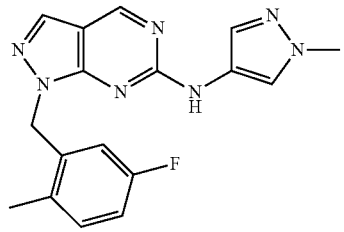

¹H NMR (d₆-DMSO) δ 9.83 (s, 1H), 8.88 (s, 1H), 8.02 (s, 2H), 7.49 (s, 1H), 7.19 (m, 1H), 6.98 (m, 1H), 6.82 (s, 1H), 5.50 (s, 2H), 3.77 (s, 3H), 2.26 (s, 3H); LC-MS method B, (ES+) 338.0, RT=8.58 min.

Example 117

1-(2-Fluoro-6-methylbenzyl)-N-(1-methyl-1H-pyrazol-4-yl)-1H-pyrazolo[3,4-d]pyrimidin-6-amine The following compound was made according to the procedure in Example 45, using 2-fluoro-6-methylbenzaldehyde:

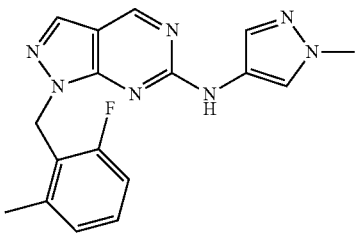

¹H NMR (d₆-DMSO) δ 9.88 (s, 1H), 8.89 (s, 1H), 8.17 (s, 1H), 7.98 (s, 1H), 7.57 (s, 1H), 7.34-7.23 (m, 1H), 7.13-7.01 (m, 2H), 5.57 (s, 2H), 3.86 (s, 3H), 2.33 (s, 3H); LC-MS method B, (ES+) 338.0, RT=8.51 min.

Example 118

1-Benzyl-N-(1-(2,2-difluoroethyl)-1H-pyrazol-4-yl)-1H-pyrazolo[3,4-d]pyrimidin-6-amine The following compound was made according to the procedure in Example 1, using 1-(2,2-difluoroethyl)-1H-pyrazol-4-amine and (bromomethyl)benzene. 1-(2,2-difluoroethyl)-1H-pyrazol-4-amine was prepared by Procedure B using 2,2-difluoromethane sulfonate as alkylating agent (see Example 39):

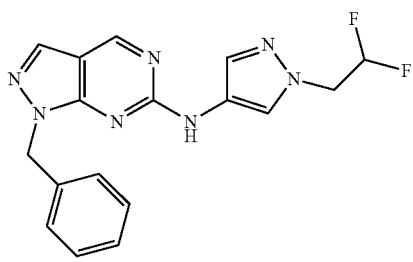 [SMILES: FC(F)Cn1cc(Nc2ncc3cnn(Cc4ccccc4)c3n2)cn1]

$^1$H NMR (d$_6$-DMSO): δ 9.99 (s, 1H), 8.95 (s, 1H), 8.24 (s, 1H), 8.08 (s, 1H), 7.67 (s, 1H), 7.45-7.22 (m, 5H), 6.35 (tt, 1H), 5.57 (s, 2H), 4.64 (td, 2H); LC-MS method B, (ES+) 356.0, RT=8.62 min.

Example 119

1-Benzyl-N-(1-(2,2-difluoroethyl)-3-methoxy-1H-pyrazol-4-yl)-1H-pyrazolo[3,4-d]pyrimidin-6-amine The following compound was made according to the procedure in Example 1, using 1-(2,2-difluoroethyl)-3-methoxy-1H-pyrazol-4-amine and (bromomethyl)benzene:

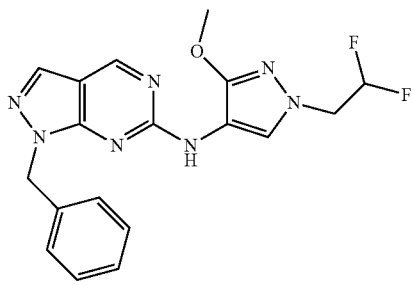 [SMILES: COc1nn(CC(F)F)cc1Nc1ncc2cnn(Cc3ccccc3)c2n1]

$^1$H NMR (d$_6$-DMSO): δ 9.08 (br s, 1H), 8.96 (s, 1H), 8.10 (br s and s, 2H), 7.45-7.11 (m, 5H), 6.31 (tt, 1H), 5.50 (s, 2H), 4.48 (td, 2H), 3.84 (s, 3H); LC-MS method B, (ES+) 386.0, RT=9.32 min.

Example 120

1-Benzyl-N-(1-(2,2-difluoroethyl)-3-methyl-1H-pyrazol-4-yl)-1H-pyrazolo[3,4-d]pyrimidin-6-amine The following compound was made according to the procedure in Example 1, using 1-(2,2-difluoroethyl)-3-methyl-1H-pyrazol-4-amine and (bromomethyl)benzene:

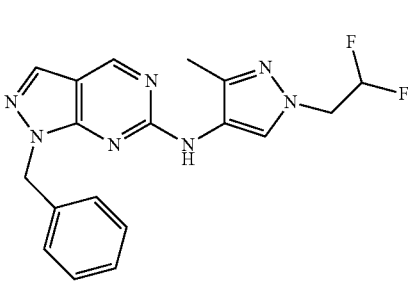 [SMILES: Cc1nn(CC(F)F)cc1Nc1ncc2cnn(Cc3ccccc3)c2n1]

$^1$H NMR (d$_6$-DMSO): δ 9.40 (br s, 1H), 8.96 (s, 1H), 8.25 (br s, 1H), 8.08 (s, 1H), 7.42-7.15 (m, 5H), 6.33 (tt, 1H), 5.52 (s, 2H), 4.59-4.47 (m, 2H), 2.19 (s, 3H); LC-MS method B, (ES+) 370.0, RT=8.81 min.

Example 121

4-(6-((1-(2-Hydroxyethyl)-1H-pyrazol-4-yl)amino)-1H-pyrazolo[3,4-d]pyrimidin-1-yl)benzenesulfonamide The following compound was made according to the procedures in Example 1 (Step i), using 2-(4-amino-1H-pyrazol-1-yl)ethanol then Example 17 (Step iii) using 4-bromobenzenesulfonamide:

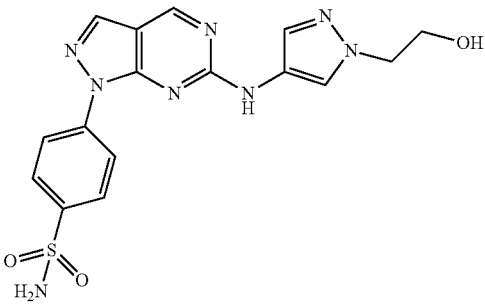 [SMILES: NS(=O)(=O)c1ccc(-n2ncc3cnc(Nc4cnn(CCO)c4)nc32)cc1]

$^1$H NMR (d$_6$-DMSO) δ 10.14 (s, 1H), 9.04 (s, 1H), 8.42 (d, 2H), 8.38 (s, 1H), 8.07 (d, 2H), 8.02 (s, 1H), 7.69 (s, 1H), 7.47 (s, 2H), 4.99 (s, 1H), 4.15-4.17 (m, 2H), 3.75-3.77 (m, 2H); LC-MS method B, (ES+) 401.0, RT=6.17 min.

Example 122

3-(6-((1-Methyl-1H-pyrazol-4-yl)amino)-1H-pyrazolo[3,4-d]pyrimidin-1-yl)benzenesulfonamide The following compound was made according to the procedures in Example 17 (Step iii), using 3-bromobenzenesulfonamide:

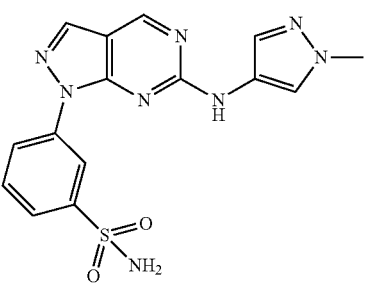 [SMILES: Cn1cc(Nc2ncc3cnn(-c4cccc(S(N)(=O)=O)c4)c3n2)cn1]

¹H NMR (d₆-DMSO) δ 10.14 (s, 1H), 9.05 (s, 1H), 8.76 (s, 1H), 8.37 (s, 1H), 8.32 (m, 2H), 8.10 (s, 1H), 7.84 (s, 1H), 7.56 (s, 2H), 7.50 (s, 1H), 3.87 (s, 3H); LC-MS method B, (ES+) 371.0, RT=6.83 min.

Example 123

N-(1-(2-(Diethylamino)ethyl)-1H-pyrazol-4-yl)-1-(2-fluorobenzyl)-1H-pyrazolo[3,4-d]pyrimidin-6-amine The following compound was made according to the procedure in Example 1, using 1-(2-(diethylamino)ethyl)-1H-pyrazol-4-amine and 1-(bromomethyl)-2-fluorobenzene. 1-(2-(diethylamino)ethyl)-1H-pyrazol-4-amine was prepared by Procedure A using 2-chloro-N,N-diethylethanamine.hydrochloride as alkylating agent:

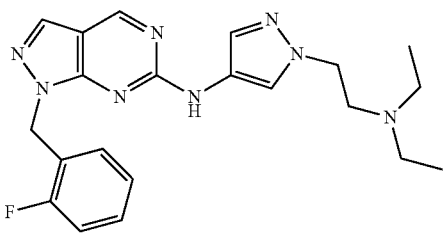 [SMILES: CCN(CC)CCn1cc(Nc2ncc3cnn(Cc4ccccc4F)c3n2)cn1]

¹H NMR (d₆-DMSO) δ 9.88 (s, 1H), 8.91 (s, 1H), 8.29-7.98 (m, 2H), 7.56 (s, 1H), 7.35 (ddd, J=14.5, 5.5, 1.9 Hz, 1H), 7.29-7.09 (m, 3H), 5.60 (s, 2H), 4.12 (t, J=6.6 Hz, 2H), 2.77 (t, J=6.6 Hz, 2H), 2.49 (q J=7.1 Hz, 4H), 0.89 (t, J=7.1 Hz, 6H); LC-MS method B, (ES+) 409, RT=5.61 min.

Example 124

1-(2-Fluorobenzyl)-N-(1-(2-morpholinoethyl)-1H-pyrazol-4-yl)-1H-pyrazolo[3,4-d]pyrimidin-6-amine The following compound was made according to the procedure in Example 1, using 1-(2-morpholino ethyl)-1H-pyrazol-4-amine and 1-(bromomethyl)-2-fluorobenzene. 1-(2-morpholinoethyl)-1H-pyrazol-4-amine was prepared by Procedure A using 4-(2-chloroethyl)morpholine.hydrochloride as alkylating agent:

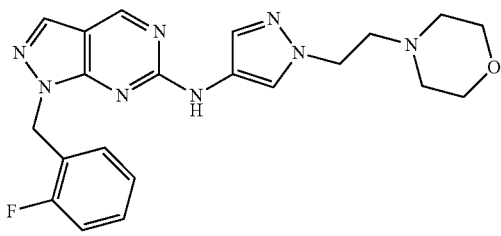 [SMILES: Fc1ccccc1Cn1ncc2cnc(Nc3cnn(CCN4CCOCC4)c3)nc21]

¹H NMR (d₆-DMSO) δ 9.89 (s, 1H), 8.91 (s, 1H), 8.12 (s, 1H), 8.05 (s, 1H), 7.58 (s, 1H), 7.42-7.30 (m, 1H), 7.31-7.08 (m, 3H), 5.60 (s, 2H), 4.21 (t, J=6.6 Hz, 2H), 3.61-3.45 (m, 4H), 2.69 (t, J=6.6 Hz, 2H), 2.40 (m, 4H); LC-MS method B, (ES+) 423.1, RT=5.49 min.

Example 125

N-(1-(3-(Dimethylamino)propyl)-1H-pyrazol-4-yl)-1-(2-fluorobenzyl)-1H-pyrazolo[3,4-d]pyrimidin-6-amine The following compound was made according to the procedure in Example 1, using 1-(3-(dimethylamino)propyl)-1H-pyrazol-4-amine and 1-(bromomethyl)-2-fluorobenzene. 1-(3-(dimethylamino)propyl)-1H-pyrazol-4-amine was prepared by Procedure A using 3-chloro-N,N-dimethylpropan-1-amine.hydrochloride as alkylating agent:

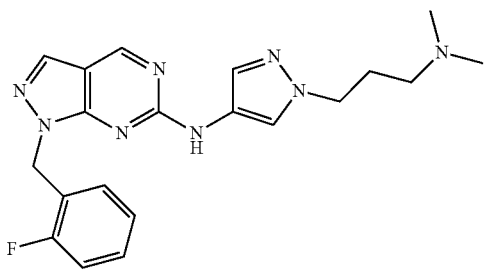 [SMILES: CN(C)CCCn1cc(Nc2ncc3cnn(Cc4ccccc4F)c3n2)cn1]

¹H NMR (d₆-DMSO) δ 9.89 (s, 1H), 8.91 (s, 1H), 8.07 (s, 1H), 8.05 (s, 1H), 7.58 (s, 1H), 7.39-7.30 (m, 1H), 7.30-7.11 (m, 3H), 5.60 (s, 2H), 4.09 (t, J=7.0 Hz, 2H), 2.17 (t, J=7.0 Hz, 2H), 2.11 (s, 6H), 1.88 (p, J=7.0 Hz, 2H); LC-MS method B, (ES+) 395, RT=5.36 min.

Example 126

N-(2-((6-((1-Methyl-1H-pyrazol-4-yl)amino)-1H-pyrazolo[3,4-d]pyrimidin-1-yl)methyl)phenyl)propane-2-sulfonamide The following compound was made according to the procedure in Example 75, using propane-2-sulfonyl chloride:

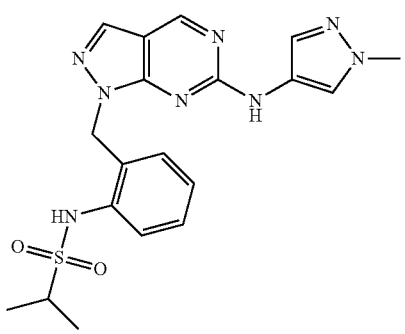 [SMILES: CC(C)S(=O)(=O)Nc1ccccc1Cn1ncc2cnc(Nc3cnn(C)c3)nc21]

¹H NMR (d₆-DMSO) δ 9.90 (s, 1H), 9.38 (s, 1H), 8.95 (s, 1H), 8.13 (s, 1H), 8.01 (s, 1H), 7.50 (s, 1H), 7.37 (dd, 1H), 7.29 (td, 1H), 7.13 (t, 1H), 6.68 (s, 1H), 5.73 (s, 2H), 3.79 (s, 3H), 3.42-3.36 (m, 1H), 1.34 (d, 6H); LC-MS method B, (ES+) 427, RT=8.15 min Example 127

4-(6-((1-(2,2-Difluoroethyl)-1H-pyrazol-4-yl)amino)-1H-pyrazolo[3,4-d]pyrimidin-1-yl)benzenesulfonamide The following compound was made according to the procedures in Example 1 (Step i), using 1-(2,2-difluoroethyl)-

1H-pyrazol-4-amine (see Example 118) then Example 17 (Step iii) using 4-bromobenzenesulphonamide:

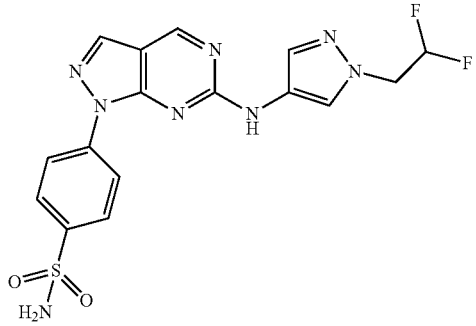 [SMILES: NS(=O)(=O)c1ccc(-n2ncc3cnc(Nc4cnn(CC(F)F)c4)nc32)cc1]

¹H NMR (d₆-DMSO) δ 10.17 (s, 1H), 9.06 (s, 1H), 8.39-8.43 (m, 3H), 8.07 (s, 1H), 8.03 (d, 2H), 7.78 (s, 1H), 7.46 (s, 2H), 6.25-6.39 (m, 1H), 4.65 (t, 2H); LC-MS method B, (ES+) 421.0, RT=7.25 min.

Example 128

N-(1-(2,2-Difluoroethyl)-1H-pyrazol-4-yl)-1-(2-fluorobenzyl)-1H-pyrazolo[3,4-d]pyrimidin-6-amine The following compound was made according to the procedure in Example 1, using 1-(2,2-difluoroethyl)-1H-pyrazol-4-amine and 1-(bromomethyl)-2-fluorobenzene. 1-(2,2-difluoroethyl)-1H-pyrazol-4-amine was prepared by Procedure A using 2,2-difluoromethane sulfonate as alkylating agent (see Example 39):

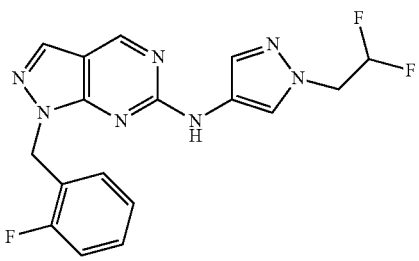 [SMILES: Fc1ccccc1Cn1ncc2cnc(Nc3cnn(CC(F)F)c3)nc21]

¹H NMR (d₆-DMSO) δ 9.96 (s, 1H), 8.93 (s, 1H), 8.23 (s, 1H), 8.06 (s, 1H), 7.68 (s, 1H), 7.34-7.39 (m, 1H), 7.19-7.26 (m, 2H), 7.14 (td, 1H), 6.34 (tt, 1H), 5.61 (s, 2H), 4.61 (td, 2H); LC-MS method B, (ES+) 374, RT=8.72 min.

Example 129

1-(2,5-Difluorobenzyl)-N-(1-(2,2-difluoroethyl)-1H-pyrazol-4-yl)-1H-pyrazolo[3,4-d]pyrimidin-6-amine The following compound was made according to the procedure in Example 1, using 1-(2,2-difluoroethyl)-1H-pyrazol-4-amine and 2-(bromomethyl)-1,4-difluorobenzene. 1-(2,2-difluoroethyl)-1H-pyrazol-4-amine was prepared by Procedure A using 2,2-difluoromethane sulfonate as alkylating agent (see Example 39):

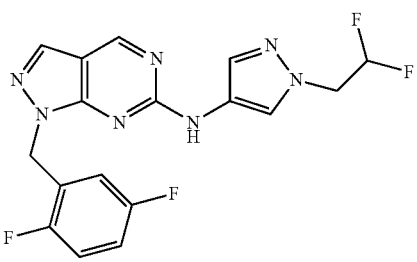 [SMILES: Fc1ccc(F)c(Cn2ncc3cnc(Nc4cnn(CC(F)F)c4)nc32)c1]

¹H NMR (d₆-DMSO) δ 9.98 (s, 1H), 8.93 (s, 1H), 8.22 (s, 1H), 8.07 (s, 1H), 7.68 (s, 1H), 7.26-7.32 (m, 1H), 7.20-7.24 (m, 1H), 7.10 (s, 1H), 6.34 (tt, 1H), 5.60 (s, 2H), 4.61 (td, 2H); LC-MS method B, (ES+) 392, RT=8.91 min.

Example 130

2-((6-((1-(2,2-Difluoroethyl)-1H-pyrazol-4-yl)amino)-1H-pyrazolo[3,4-d]pyrimidin-1-yl)methyl)-4-fluorobenzonitrile The following compound was made according to the procedure in Example 1, using 1-(2,2-difluoroethyl)-1H-pyrazol-4-amine and 2-(bromomethyl)-4-fluorobenzonitrile. 1-(2,2-difluoroethyl)-1H-pyrazol-4-amine was prepared by Procedure A using 2,2-difluoromethane sulfonate as alkylating agent (see Example 39):

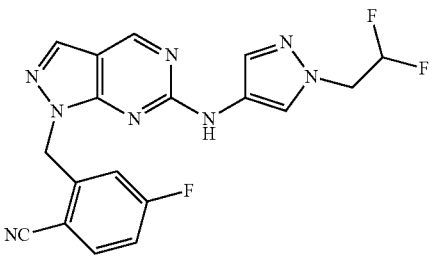 [SMILES: N#Cc1ccc(F)cc1Cn1ncc2cnc(Nc3cnn(CC(F)F)c3)nc21]

¹H NMR (d₆-DMSO) δ 10.02 (s, 1H), 8.96 (s, 1H), 8.24 (s, 1H), 8.12 (s, 1H), 8.02 (dd, 1H), 7.65 (s, 1H), 7.43 (td, 1H), 7.25 (s, 1H), 6.34 (tt, 1H), 5.76 (s, 2H), 4.60 (td, 2H); LC-MS method B, (ES+) 399, RT=8.60 min.

Example 131

N-(2-((6-((1-(2,2-Difluoroethyl)-1H-pyrazol-4-yl)amino)-1H-pyrazolo[3,4-d]pyrimidin-1-yl)methyl)phenyl)methanesulfonamide hydrochloride The following compound was made according to the procedure in Example 75 using 1-(2,2-difluoroethyl)-1H-pyrazol-4-amine in Step (iv). 1-(2,2-difluoroethyl)-1H-pyrazol-4-amine was prepared by Procedure A using 2,2-difluoromethane sulfonate as alkylating agent (see Example 39):

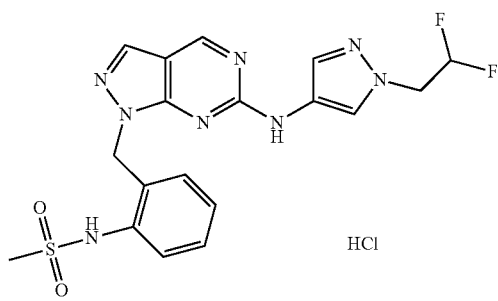 [SMILES: CS(=O)(=O)Nc1ccccc1Cn1ncc2cnc(Nc3cnn(CC(F)F)c3)nc21 ; Cl]

¹H NMR (d₆-DMSO) δ 9.99 (s, 1H), 9.43 (s, 1H), 8.97 (s, 1H), 8.16 (s, 1H), 8.14 (s, 1H), 7.64 (s, 1H), 7.40 (d, 1H), 7.32 (td, 1H), 7.16 (td, 1H), 6.80 (s, 1H), 6.30 (tt, 1H), 5.72 (s, 2H), 4.57 (td, 2H), 3.08 (s, 3H); LC-MS method B, (ES+) 449, RT=7.89 min.

Example 132

1-(3-(2-Methoxyethoxy)benzyl)-N-(1-methyl-1H-pyrazol-4-yl)-1H-pyrazolo[3,4-d]pyrimidin-6-amine The following compound was made according to the procedure in Example 102, using 3-hydroxybenzaldehyde:

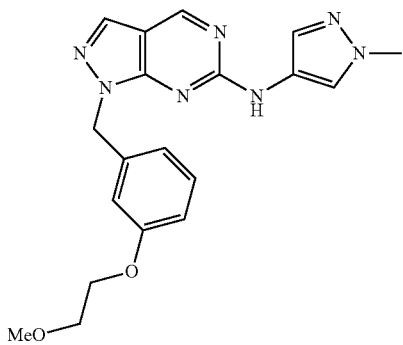 [SMILES: COCCOc1cccc(Cn2ncc3cnc(Nc4cnn(C)c4)nc32)c1]

¹H NMR (d₆-DMSO) δ 9.86 (s, 1H), 8.92 (s, 1H), 8.06 (m, 2H), 7.56 (s, 1H), 7.23 (t, J=7.9 Hz, 1H), 6.92-6.82 (m, 3H), 5.52 (s, 2H), 4.03-3.98 (m, 2H), 3.83 (s, 3H), 3.62-3.57 (m, 2H), 3.26 (s, 3H); LC-MS method B, (ES+) 380.0, RT=7.75 min.

Example 133

2-(4-((1-Benzyl-1H-pyrazolo[3,4-d]pyrimidin-6-yl)amino)-1H-pyrazol-1-yl)-N-methylacetamide The following compound was made according to the procedure in Example 1, using 2-(4-amino-1H-pyrazol-1-yl)-N-methylacetamide and (bromomethyl)benzene. 2-(4-amino-1H-pyrazol-1-yl)-N-methylacetamide was prepared by Procedure A using 2-bromo-N-methylacetamide as alkylating agent:

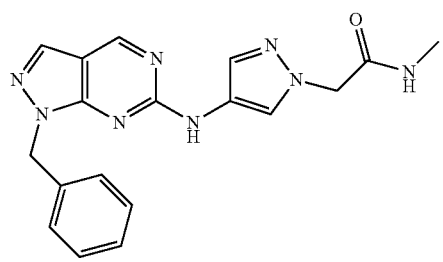 [SMILES: CNC(=O)Cn1cc(Nc2ncc3cnn(Cc4ccccc4)c3n2)cn1]

¹H NMR (d₆-Acetone): δ 8.98 (br s, 1H), 8.87 (s, 1H), 8.32 (s, 1H), 7.97 (s, 1H), 7.72 (s, 1H), 7.50-7.17 (m, 5H), 6.79 (br s, 1H), 5.58 (s, 2H), 4.78 (s, 2H), 2.72 (d, J=4.7 Hz, 3H); LC-MS method B, (ES+) 363.0, RT=6.88 min.

Example 134

2,2,2-Trifluoro-N-(2-((6-((1-methyl-1H-pyrazol-4-yl)amino)-1H-pyrazolo[3,4-d]pyrimidin-1-yl)methyl)ethanesulfonamide The following compound was made according to the procedure in Example 75, using 2,2,2-trifluoroethanesulfonyl chloride in Step (iii):

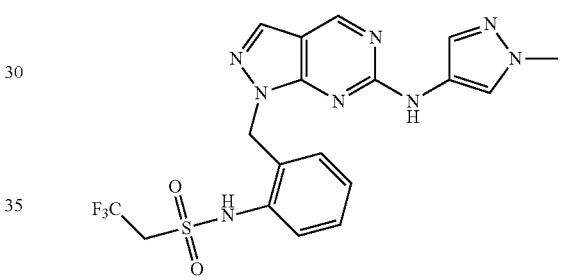

¹H NMR (d₆-DMSO) δ 10.12 (s, 1H), 9.88 (s, 1H), 8.95 (s, 1H), 8.12 (s, 1H), 7.98 (s, 1H), 7.48 (d, 1H), 7.44 (d, 1H), 7.33 (td, 1H), 7.20 (t, 1H), 6.69 (d, 1H), 5.70 (s, 2H), 4.64 (q, 2H), 3.77 (s, 3H); LC-MS method B, (ES+) 467, RT=8.47 min.

Example 135

4-(6-((1-Methyl-1H-pyrazol-4-yl)amino)-1H-pyrazolo[3,4-d]pyrimidin-1-yl)benzamide The following compound was made according to the procedure in Example 17 (Step iii), using 4-bromobenzamide:

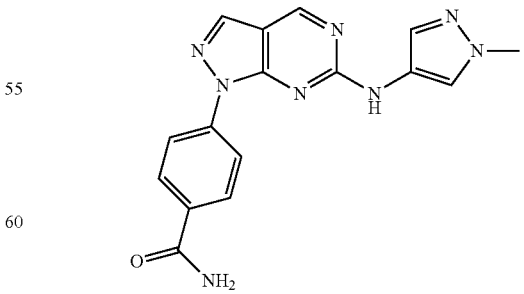

¹H NMR (d₆-DMSO) δ 10.07 (s, 1H), 9.05 (d, 1H), 8.35 (s, 1H), 8.33-8.28 (m, 2H), 8.12-8.17 (m, 3H), 7.96 (s, 1H), 7.65 (s, 1H), 7.44 (s, 1H), 3.88 (s, 3H); LC-MS method B, (ES+) 335.0, RT=6.28 min.

Example 136

N-methyl-4-(6-((1-methyl-1H-pyrazol-4-yl)amino)-1H-pyrazolo[3,4-d]pyrimidin-1-yl)benzamide The following compound was made according to the procedure in Example 17 (Step iii), using 4-bromo-N-methylbenzamide which was prepared as follows:

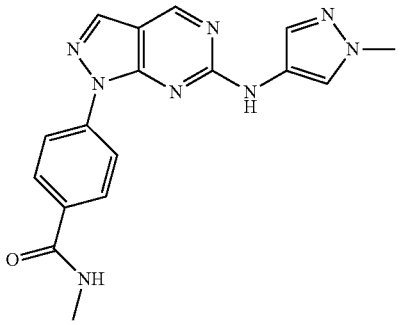 [SMILES: CNC(=O)c1ccc(-n2ncc3cnc(Nc4cnn(C)c4)nc32)cc1]

A solution of 4-bromobenzoic acid (300 mg, 1.49 mmol), hydroxybenzotriazole (1.1 eq), 1(3-dimethylaminoprpyl)-3-ethylcarbodiimide HCl (1.1 eq) and diisopropylethylamine (2 eq) in DMF (2 mL) was stirred at rt for 20 min. Methylamine (1 eq) was added and the reaction stirred at rt for 16 h then quenched with saturated aqueous sodium hydrogencarbonate solution and extracted into ethyl acetate. The organic layer was washed with brine, dried (MgSO$_4$) and concentrated in vacuo to give 4-bromo-N-methylbenzamide. $^1$H NMR (d$_6$-DMSO) δ 10.07 (s, 1H), 9.03 (s, 1H), 8.56 (s, 1H), 8.38 (s, 1H), 8.32-8.36 (m, 2H), 8.05-8.09 (m, 2H), 7.94 (s, 1H), 7.67 (s, 1H), 3.87 (s, 3H), 2.83 (d, 3H); LC-MS method B, (ES+) 349.0, RT=6.68 min.

Example 137

(4-(6-((1-Methyl-1H-pyrazol-4-yl)amino)-1H-pyrazolo[3,4-d]pyrimidin-1-yl)phenyl)(morpholino)methanone The following compound was made according to the procedure in Example 17 (Step iii), using (2-bromophenyl)(morpholino)methanone. (2-bromophenyl)(morpholino)methanone was prepared as in Example 136 using morpholine:

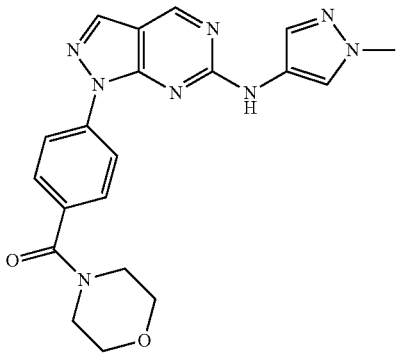 [SMILES: Cn1cc(Nc2ncc3cnn(-c4ccc(C(=O)N5CCOCC5)cc4)c3n2)cn1]

$^1$H NMR (d$_6$-DMSO) δ 10.07 (s, 1H), 9.04 (s, 1H), 8.35 (s, 1H), 8.28-8.32 (m, 2H), 7.99 (s, 1H), 7.67-7.69 (m, 2H), 7.59 (s, 1H), 3.86 (s, 3H), 3.46-3.64 (m, 8H); LC-MS method B, (ES+) 405.1, RT=6.89 min.

Example 138

2-Fluoro-4-(6-((1-methyl-1H-pyrazol-4-yl)amino)-1H-pyrazolo[3,4-d]pyrimidin-1-yl)benzenesulfonamide The following compound was made according to the procedure in Example 17 (Step iii), using 4-bromo-2-fluorobenzenesulfonamide:

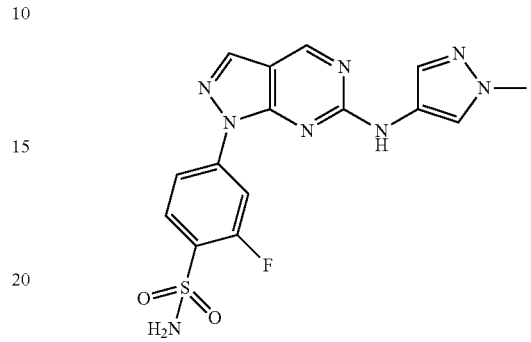

$^1$H NMR (d$_6$-DMSO) δ 10.15 (s, 1H), 9.05 (s, 1H), 8.40-8.44 (m, 2H), 8.22-8.24 (m, 1H), 7.99-8.02 (m, 1H), 7.98 (s, 1H), 7.76 (s, 2H), 7.65 (s, 1H), 3.87 (s, 3H); LC-MS method B, (ES+) 389.0, RT=7.01 min.

Example 139

N-(2-Hydroxyethyl)-4-(6-((1-methyl-1H-pyrazol-4-yl)amino)-1H-pyrazolo[3,4-d]pyrimidin-1-yl)benzenesulfonamide The following compound was made according to the procedure in Example 40, using 2-aminoethanol:

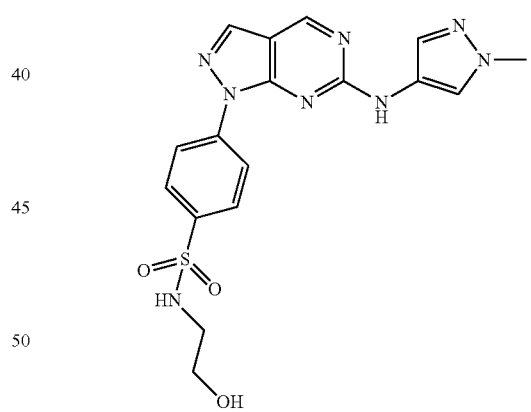

$^1$H NMR (d$_6$-DMSO) δ 10.10 (s, 1H), 9.04 (s, 1H), 8.38-8.44 (m, 2H), 7.96-8.01 (m, 2H), 7.83 (s, 1H), 7.63-7.70 (m, 2H), 4.70 (s, 1H), 3.86 (s, 3H), 3.35-3.40 (m, 2H), 2.82-2.87 (m, 2H); LC-MS method B, (ES+) 415.0, RT=6.66 min.

Example 140

N-(3-((6-((1-Methyl-1H-pyrazol-4-yl)amino)-1H-pyrazolo[3,4-d]pyrimidin-1-yl)methyl)phenyl)methanesulfonamide The following compound was made according to the procedure in Example 75 (Steps i, iii-iv), using 3-(bromomethyl)aniline in Step (i):

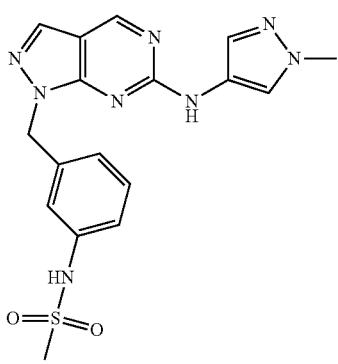 [SMILES: Cn1cc(Nc2ncc3cnn(Cc4cccc(NS(C)(=O)=O)c4)c3n2)cn1]

¹H NMR (d₆-DMSO) δ 9.84 (s, 1H), 9.74 (s, 1H), 8.92 (s, 1H), 8.06 (s, 1H), 8.01 (s, 1H), 7.53 (s, 1H), 7.28 (t, 1H), 7.09-7.11 (m, 2H), 7.01 (d, 1H), 5.52 (s, 2H), 3.82 (s, 3H), 2.91 (s, 3H); LC-MS method B, (ES+) 399, RT=6.78 min.

Example 141

N-(3-((6-((1-Methyl-1H-pyrazol-4-yl)amino)-1H-pyrazolo[3,4-d]pyrimidin-1-yl)methyl)phenyl)propane-2-sulfonamide The following compound was made according to the procedure in Example 75 (Steps i, iii-iv), using 3-(bromomethyl) aniline (Step i) and propane-2-sulfonyl chloride (Step iii):

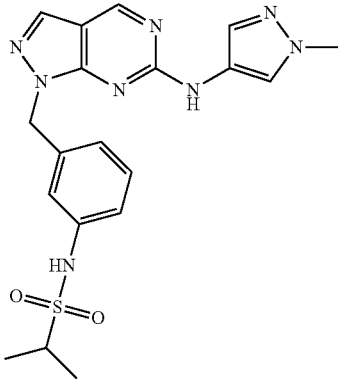 [SMILES: CC(C)S(=O)(=O)Nc1cccc(Cn2ncc3cnc(Nc4cnn(C)c4)nc32)c1]

¹H NMR (d₄-Methanol) δ 8.86 (s, 1H), 8.00 (s, 1H), 7.91 (s, 1H), 7.57 (s, 1H), 7.30 (t, 1H), 7.11-7.13 (m, 3H), 5.56 (s, 2H), 3.86 (s, 3H), 2.99-3.06 (m, 1H), 1.13 (d, 6H); LC-MS method B, (ES+) 427, RT=7.35 min.

Example 142

N-(3-Fluoro-2-46-((1-methyl-1H-pyrazol-4-yl) amino)-1H-pyrazolo[3,4-d]pyrimidin-1-yl)methyl) phenyl)methanesulfonamide The following compound was made according to the procedure in Example 75 using 2-(bromomethyl)-1-fluoro-3-nitrobenzene:

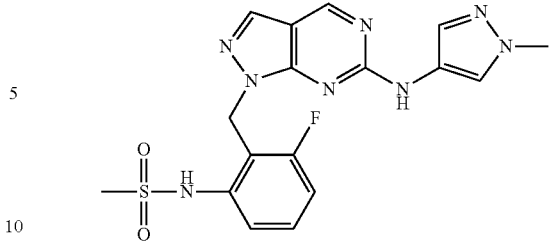

¹H NMR (d₆-DMSO) δ 9.87 (s, 1H), 9.62 (s, 1H), 8.90 (s, 1H), 8.13 (s, 1H), 8.01 (s, 1H), 7.58 (s, 1H), 7.43-7.37 (m, 1H), 7.08 (t, 1H), 7.30 (br d, 1H), 5.66 (s, 2H), 3.84 (s, 3H), 3.03 (s, 3H); LC-MS method B, (ES+) 417, RT=7.69 min.

Example 143

1-(2-Fluorobenzyl)-N-(1-(2-(piperidin-1-yl)ethyl)-1H-pyrazol-4-yl)-1H-pyrazolo[3,4-d]pyrimidin-6-amine The following compound was made according to the procedure in Example 1 (Step ii) using 6-chloro-1H-pyrazolo[3,4-d]pyrimidine and 1-(bromomethyl)-2-fluorobenzene followed by Example 1 (Step i) using 6-chloro-1-(2-fluorobenzyl)-1H-pyrazolo[3,4-d]pyrimidine and 1-(2-(piperidin-1-yl)ethyl)-1H-pyrazol-4-amine. 1-(2-(piperidin-1-yl)ethyl)-1H-pyrazol-4-amine was prepared by procedure A using 1-(2-chloroethyl)piperidine:

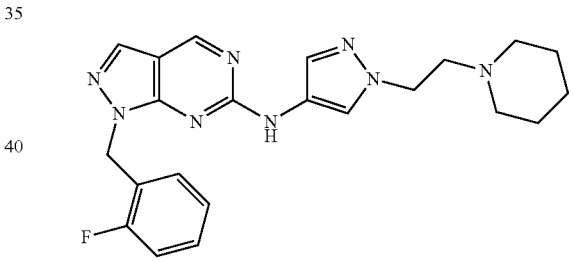

¹H NMR (d₆-DMSO) δ 9.98 (s, 1H), 8.94 (s, 1H), 8.21 (s, 1H), 8.07 (s, 1H), 7.73 (s, 1H), 7.41-7.33 (m, 1H), 7.32-7.11 (m, 3H), 5.63 (s, 2H), 4.63-4.51 (m, 2H), 3.58-3.36 (m, 4H), 3.00-2.80 (m, 2H), 1.85-1.57 (m, 5H), 1.45-1.28 (m, 1H); LC-MS method B, (ES+) 421.1, RT=5.64 min.

Example 144

1-(2-Fluorobenzyl)-N-(1-(3-(piperidin-1-yl)propyl)-1H-pyrazol-4-yl)-1H-pyrazolo[3,4-d]pyrimidin-6-amine The following compound was made according to the procedure in Example 1 (Step ii) using 6-chloro-1H-pyrazolo[3,4-d]pyrimidine and 1-(bromomethyl)-2-fluorobenzene followed by Example 1 (Step i) using 6-chloro-1-(2-fluorobenzyl)-1H-pyrazolo[3,4-d]pyrimidine and 1-(3-(piperidin-1-yl)propyl)-1H-pyrazol-4-amine. 1-(3-(piperidin-1-yl)propyl)-1H-pyrazol-4-amine was prepared by procedure A using 1-(3-chloropropyl)piperidine:

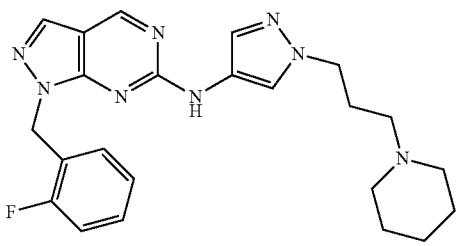 [SMILES: Fc1ccccc1Cn1ncc2cnc(Nc3cnn(CCCN4CCCCC4)c3)nc21]

¹H NMR (d₆-DMSO) δ 9.87 (s, 1H), 8.92 (s, 1H), 8.12-8.01 (m, J=5.6 Hz, 2H), 7.57 (s, 1H), 7.39-7.33 (m, 1H), 7.31-7.19 (m, 2H), 7.18-7.13 (m, 1H), 5.60 (s, 2H), 4.10 (t, J=7.0 Hz, 2H), 2.27 (m, 4H), 2.20 (t, J=7.0 Hz, 2H), 1.95-1.83 (m, 2H), 1.53-1.40 (m, 4H), 1.41-1.29 (m, 2H); LC-MS method B, (ES+) 435.1, RT=5.55 min.

Example 145

1-(2-Fluorobenzyl)-N-(1-(3-morpholinopropyl)-1H-pyrazol-4-yl)-1H-pyrazolo[3,4-d]pyrimidin-6-amine The following compound was made according to the procedure in Example 1 (Step ii) using 6-chloro-1H-pyrazolo[3,4-d]pyrimidine and 1-(bromomethyl)-2-fluorobenzene followed by Example 1 (Step i) using 6-chloro-1-(2-fluorobenzyl)-1H-pyrazolo[3,4-d]pyrimidine and 1-(3-morpholinopropyl)-1H-pyrazol-4-amine. 1-(3-morpholinopropyl)-1H-pyrazol-4-amine was prepared by procedure A using 4-(3-chloropropyl)morpholine

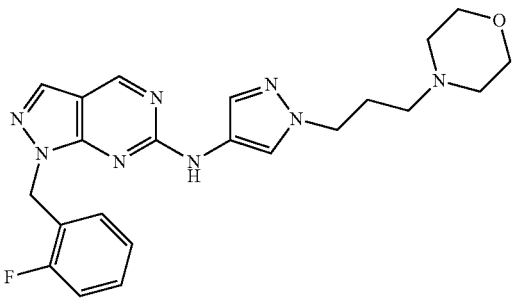 [SMILES: Fc1ccccc1Cn1ncc2cnc(Nc3cnn(CCCN4CCOCC4)c3)nc21]

¹H NMR (d₆-DMSO) δ 9.87 (s, 1H), 8.92 (s, 1H), 8.14-8.01 (m, 2H), 7.59 (s, 1H), 7.39-7.33 (m, 1H), 7.31-7.20 (m, 2H), 7.18-7.13 (m, 1H), 5.60 (s, 2H), 4.12 (t, J=7.0 Hz, 2H), 3.59-3.49 (m, 4H), 2.31 (m, 4H), 2.24 (t, J=7.0 Hz, 2H), 1.92 (m, 2H); LC-MS method B, (ES+) 437.1, RT=5.56 min.

Example 146

(3-(6-((1-Methyl-1H-pyrazol-4-yl)amino)-1H-pyrazolo[3,4-d]pyrimidin-1-yl)phenyl)(morpholino)methanone The following compound was made according to the procedure in Example 17 (Step iii), using (3-bromophenyl)(morpholino)methanone. (3-bromophenyl)(morpholino)methanone was prepared as in Example 136 using 3-bromobenzoic acid and morpholine:

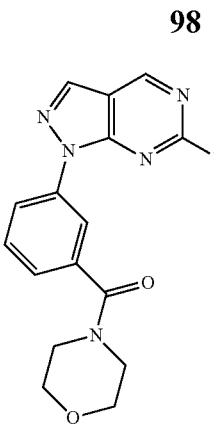

¹H NMR (d₆-DMSO) δ 10.07 (s, 1H), 9.03 (s, 1H), 8.40-8.45 (m, 1H), 8.33 (s, 1H), 8.16-8.18 (m, 1H), 8.00-8.03 (m, 1H), 7.63-7.66 (m, 1H), 7.55 (s, 1H), 7.39-7.41 (m, 1H), 3.89 (s, 3H), 3.44-3.70 (m, 8H); LC-MS method B, (ES+) 405.0, RT=7.06 min.

Example 147

N-(2-Hydroxyethyl)-3-(6-((1-methyl-1H-pyrazol-4-yl)amino)-1H-pyrazolo[3,4-d]pyrimidin-1-yl)benzamide The following compound was made according to the procedure in Example 17 (Step iii), using 3-bromo-N-(2-hydroxyethyl)benzamide. 3-bromo-N-(2-hydroxyethyl)benzamide was prepared as in Example 136 using 3-bromobenzoic acid and 2-aminoethanol:

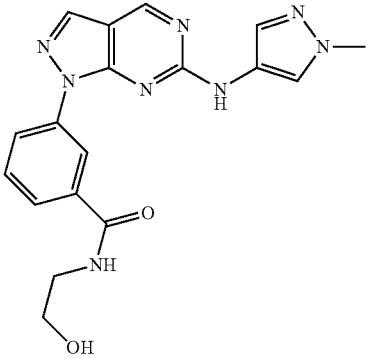 [SMILES: Cn1cc(Nc2ncc3cnn(-c4cccc(C(=O)NCCO)c4)c3n2)cn1]

¹H NMR (d₆-DMSO) δ 10.09 (s, 1H), 9.04 (s, 1H), 8.8 (s, 1H), 8.66 (s, 1H), 8.34 (s, 1H), 8.22 (s, 2H), 7.87 (d, 1H), 7.72-7.75 (m, 1H), 7.51 (s, 1H), 4.77 (s, 1H), 3.88 (s, 3H), 3.54-3.57 (m, 2H), 3.40-3.43 (m, 2H); LC-MS method B, (ES+) 379.0, RT=6.24 min.

Example 148

N-(2-Hydroxyethyl)-4-(6-((1-methyl-1H-pyrazol-4-yl)amino)-1H-pyrazolo[3,4-d]pyrimidin-1-yl)benzamide The following compound was made according to the procedure in Example 17 (Step iii), using 4-bromo-N-(2-hydroxyethyl)benzamide. 4-bromo-N-(2-hydroxyethyl)benzamide was prepared as in Example 136 using 2-aminoethanol:

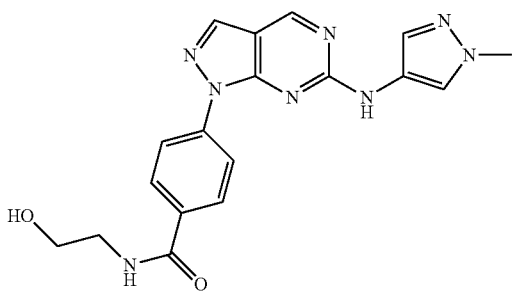 [SMILES: Cn1cc(Nc2ncc3cnn(-c4ccc(C(=O)NCCO)cc4)c3n2)cn1]

$^1$H NMR (d$_6$-DMSO) δ 10.04 (s, 1H), 9.04 (s, 1H), 8.55-8.58 (m, 1H), 8.29-8.33 (m, 2H), 8.06-8.10 (m, 2H), 7.93 (s, 1H), 7.66-7.69 (m, 1H), 4.78 (t, 1H), 3.87 (s, 3H), 3.53-3.56 (m, 2H), 3.34-3.37 (m, 2H); LC-MS method B, (ES+) 379.0, RT=6.14 min.

Example 149

(4-(6-((1-Methyl-1H-pyrazol-4-yl)amino)-1H-pyrazolo[3,4-d]pyrimidin-1-yl)phenyl)(4-methylpiperazin-1-yl)methanone The following compound was made according to the procedure in Example 17 (Step iii), using (4-bromophenyl)(4-methylpiperazin-1-yl)methanone. (4-bromophenyl)(4-methylpiperazin-1-yl)methanone was prepared as in Example 136 using 1-methylpiperazine:

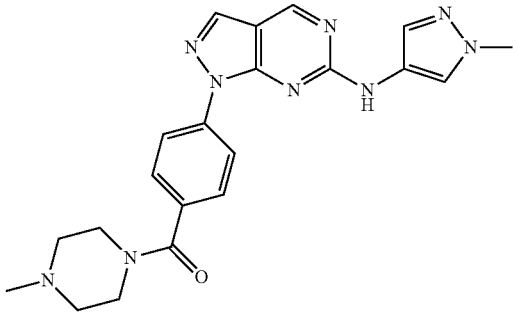

$^1$H NMR (d$_6$-DMSO) δ 10.06 (s, 1H), 9.04 (s, 1H), 8.34 (s, 1H), 8.27-8.29 (m, 2H), 7.99 (s, 1H), 7.64-7.65 (m, 2H), 7.59 (s, 1H), 3.86 (s, 3H), 3.32-3.71 (m, 4H), 2.29-2.42 (m, 4H), 2.22 (s, 3H); LC-MS method B, (ES+) 418.1, RT=4.73 min.

Example 150

1-(2,5-Difluorobenzyl)-N-(1-(2,2-difluoro ethyl)-3-methyl-1H-pyrazol-4-yl)-1H-pyrazolo[3,4-d]pyrimidin-6-amine The following compound was made according to the procedure in Example 1, using 1-(2,2-difluoroethyl)-3-methyl-1H-pyrazol-4-amine and 2-(bromomethyl)-1,4-difluorobenzene. 1-(2,2-difluoroethyl)-3-methyl-1H-pyrazol-4-amine was prepared by Procedure B using 2,2-difluoromethane sulfonate as alkylating agent (see Example 39):

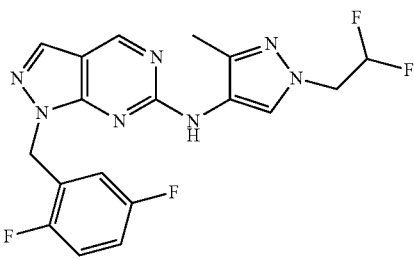 [SMILES: Cc1nn(CC(F)F)cc1Nc1ncc2cnn(Cc3cc(F)ccc3F)c2n1]

$^1$H NMR (d$_6$-DMSO) δ 9.35 (s, 1H), 8.95 (s, 1H), 8.22 (s, 1H), 8.07 (s, 1H), 7.21-7.29 (m, 2H), 7.03 (s, 1H), 6.18-6.48 (m, 1H), 5.56 (s, 2H), 4.53 (td, 2H), 2.19 (s, 3H); LC-MS method B, (ES+) 406.0, RT=9.06 min.

Example 151

2-((6-((1-(2,2-Difluoroethyl)-3-methyl-1H-pyrazol-4-yl)amino)-1H-pyrazolo[3,4-d]pyrimidin-1-yl)methyl)-4-fluorobenzonitrile The following compound was made according to the procedure in Example 1, using 1-(2,2-difluoroethyl)-3-methyl-1H-pyrazol-4-amine and 2-(bromomethyl)-4-fluorobenzonitrile. 1-(2,2-difluoroethyl)-3-methyl-1H-pyrazol-4-amine was prepared by Procedure B using 2,2-difluoromethane sulfonate as alkylating agent (see Example 39):

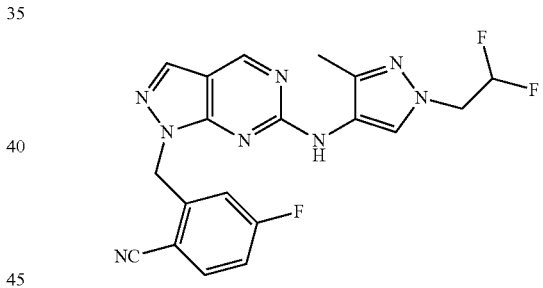

$^1$H NMR (d$_6$-DMSO) δ 9.39 (s, 1H), 8.97 (s, 1H), 8.23 (s, 1H), 8.12 (s, 1H), 8.00-8.03 (m, 1H), 7.41-7.44 (m, 1H), 7.22 (s, 1H), 6.16-6.47 (m, 1H), 5.71 (s, 2H), 4.51 (td, 2H), 2.19 (s, 3H); LC-MS method B, (ES+) 413.0, RT=8.73 min.

Example 152

1-(2,5-Difluorobenzyl)-N-(1-(2,2-difluoroethyl)-3-methoxy-1H-pyrazol-4-yl)-1H-pyrazolo[3,4-d]pyrimidin-6-amine The following compound was made according to the procedure in Example 1, using 1-(2,2-difluoroethyl)-3-methoxy-1H-pyrazol-4-amine and 2-(bromomethyl)-1,4-difluorobenzene. 1-(2,2-difluoroethyl)-3-methoxy-1H-pyrazol-4-amine was prepared by Procedure C using 2,2-difluoromethane sulfonate as alkylating agent (see Example 39):

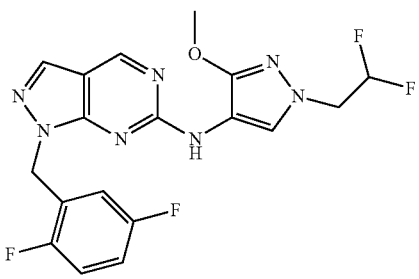 [SMILES: COc1nn(CC(F)F)cc1Nc1ncc2cnn(Cc3cc(F)ccc3F)c2n1]

¹H NMR (d₆-DMSO) δ 8.96 (br s, 1H), 8.91 (s, 1H), 8.09 (s, 1H), 8.06 (s, 1H), 7.35-7.27 (m, 2H), 7.04 (s, 1H), 6.44-6.15 (m, 1H), 5.53 (s, 2H), 4.52 (td, 2H), 3.83 (s, 3H); LC-MS method B, (ES+) 422.0, RT=9.53 min.

Example 153

2-((6-((1-(2,2-Difluoroethyl)-3-methoxy-1H-pyrazol-4-yl)amino)-1H-pyrazolo[3,4-d]pyrimidin-1-yl)methyl)-4-fluorobenzonitrile The following compound was made according to the procedure in Example 1, using 1-(2,2-difluoroethyl)-3-methoxy-1H-pyrazol-4-amine and 2-(bromomethyl)-4-fluorobenzonitrile. 1-(2,2-difluoroethyl)-3-methoxy-1H-pyrazol-4-amine was prepared by Procedure C using 2,2-difluoromethane sulfonate as alkylating agent (see Example 39):

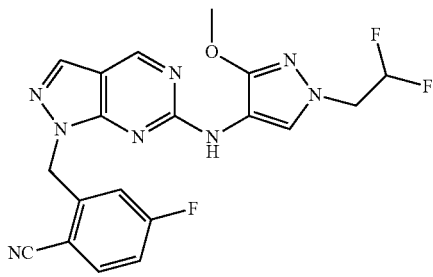 [SMILES: COc1nn(CC(F)F)cc1Nc1ncc2cnn(Cc3cc(F)ccc3C#N)c2n1]

¹H NMR (d₆-DMSO) δ 9.02 (s, 1H), 8.93 (s, 1H), 8.11 (s, 2H), 8.02 (td, 1H), 7.42 (td, 1H), 7.21 (s, 1H), 6.16-6.44 (m, 1H), 5.68 (s, 2H), 4.44 (td, 2H), 3.83 (s, 3H); LC-MS method B, (ES+) 429.0, RT=9.22 min.

Example 154

N-(1-(2,2-Difluoroethyl)-1H-pyrazol-4-yl)-1-(3-fluoro-2-methylbenzyl)-1H-pyrazolo[3,4-d]pyrimidin-6-amine The following compound was made according to the procedure in Example 1, using 1-(2,2-difluoroethyl)-1H-pyrazol-4-amine and 1-(bromomethyl)-3-fluoro-2-methylbenzene. 1-(2,2-difluoroethyl)-1H-pyrazol-4-amine was prepared by Procedure A using 2,2-difluoromethane sulfonate as alkylating agent (see Example 39):

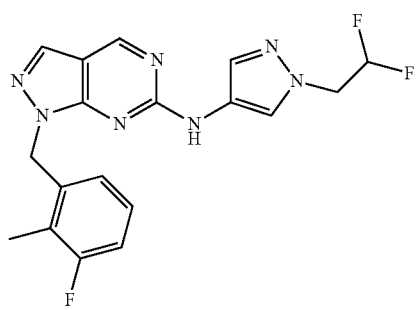 [SMILES: Cc1c(F)cccc1Cn1ncc2cnc(Nc3cnn(CC(F)F)c3)nc21]

¹H NMR (d₆-DMSO) δ 9.95 (s, 1H), 8.95 (s, 1H), 8.24 (s, 1H), 8.08 (s, 1H), 7.66 (s, 1H), 7.10-7.18 (m, 2H), 6.99 (s, 1H), 6.21-6.48 (m, 1H), 5.60 (s, 2H), 4.62 (td, 2H), 2.27 (s, 3H); LC-MS method B, (ES+) 388.1, RT=9.22 min.

Example 155

1-(2,3-Difluorobenzyl)-N-(1-(2,2-difluoroethyl)-1H-pyrazol-4-yl)-1H-pyrazolo[3,4-d]pyrimidin-6-amine The following compound was made according to the procedure in Example 1, using 1-(2,2-difluoroethyl)-1H-pyrazol-4-amine and 1-(bromomethyl)-2,3-difluorobenzene. 1-(2,2-difluoroethyl)-1H-pyrazol-4-amine was prepared by Procedure A using 2,2-difluoromethane sulfonate as alkylating agent (see Example 39):

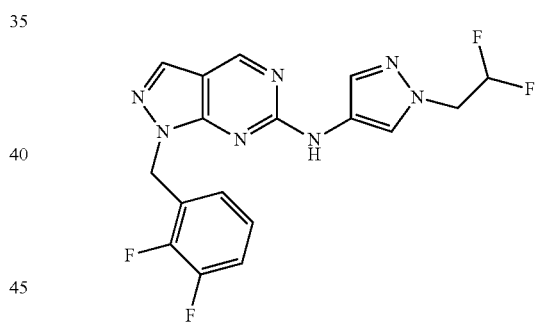

¹H NMR (d₆-DMSO) δ 9.97 (s, 1H), 8.94 (s, 1H), 8.23 (s, 1H), 8.08 (s, 1H), 7.69 (s, 1H), 7.36-7.41 (m, 1H), 7.10-7.22 (m, 2H), 6.21-6.50 (m, 1H), 5.67 (s, 2H), 4.61 (td, 2H); LC-MS method B, (ES+) 392.1, RT=8.86 min.

Example 156

1-(3-Chloro-2-fluorobenzyl)-N-(1-(2,2-difluoroethyl)-1H-pyrazol-4-yl)-1H-pyrazolo[3,4-d]pyrimidin-6-amine The following compound was made according to the procedure in Example 1, using 1-(2,2-difluoroethyl)-1H-pyrazol-4-amine and 1-(bromomethyl)-3-chloro-2-fluorobenzene. 1-(2,2-difluoroethyl)-1H-pyrazol-4-amine was prepared by Procedure A using 2,2-difluoromethane sulfonate as alkylating agent (see Example 39):

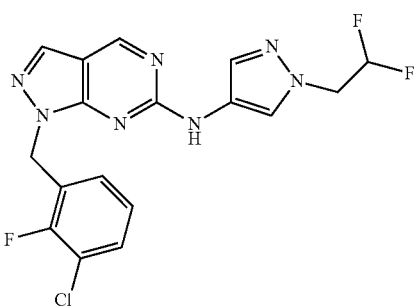 [SMILES: Fc1cccc(Cn2ncc3cnc(Nc4cnn(CC(F)F)c4)nc32)c1F]

¹H NMR (d₆-DMSO) δ 9.98 (s, 1H), 8.94 (s, 1H), 8.24 (s, 1H), 8.08 (s, 1H), 7.69 (s, 1H), 7.55 (t, 1H), 7.26 (s, 1H), 7.55 (t, 1H), 6.21-6.49 (m, 1H), 5.66 (s, 2H), 4.62 (td, 2H); LC-MS method B, (ES+) 408.0, RT=9.32 min.

Example 157

N-(1-(2,2-Difluoroethyl)-1H-pyrazol-4-yl)-1-(2,3,6-trifluorobenzyl)-1H-pyrazolo[3,4-d]pyrimidin-6-amine The following compound was made according to the procedure in Example 1, using 1-(2,2-difluoroethyl)-1H-pyrazol-4-amine and 2-(bromomethyl)-1,3,4-trifluorobenzene. 1-(2,2-difluoroethyl)-1H-pyrazol-4-amine was prepared by Procedure A using 2,2-difluoromethane sulfonate as alkylating agent (see Example 39):

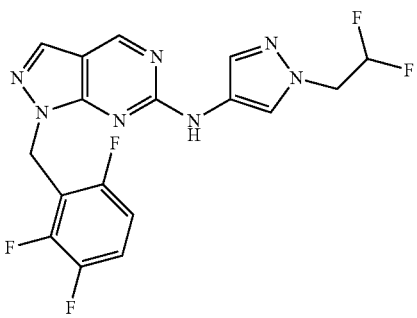 [SMILES: Fc1ccc(F)c(Cn2ncc3cnc(Nc4cnn(CC(F)F)c4)nc32)c1F]

¹H NMR (d₆-DMSO) δ 9.97 (s, 1H), 8.92 (s, 1H), 8.03 (s, 1H), 7.73 (s, 1H), 7.51-7.56 (m, 1H), 7.15-7.20 (m, 1H), 6.36 (m, 1H), 5.64 (s, 2H), 4.62 (td, 2H); LC-MS method B, (ES+) 410, RT=8.92 min Example 158

N-(1-Methyl-1H-pyrazol-4-yl)-1-(2,3,5-trifluorobenzyl)-1H-pyrazolo[3,4-d]pyrimidin-6-amine The following compound was made according to the procedure in Example 1 (Step ii), using 1-(bromomethyl)-2,3,5-trifluorobenzene:

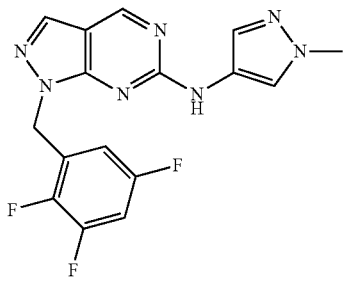 [SMILES: Cn1cc(Nc2ncc3cnn(Cc4cc(F)cc(F)c4F)c3n2)cn1]

¹H NMR (d₆-DMSO) δ 9.89 (s, 1H), 8.90 (s, 1H), 8.12 (s, 1H), 8.02 (s, 1H), 7.65-7.47 (m, 2H), 7.19 (m, 1H), 5.64 (s, 2H), 3.85 (s, 3H); LC-MS method B, (ES+) 360, RT=8.17 min.

Example 159

1-(2,6-Difluoro-3-methoxybenzyl)-N-(1-methyl-1H-pyrazol-4-yl)-1H-pyrazolo[3,4-d]pyrimidin-6-amine The following compound was made according to the procedure in Example 1 (Step ii), using 2-(bromomethyl)-1,3-difluoro-4-methoxybenzene:

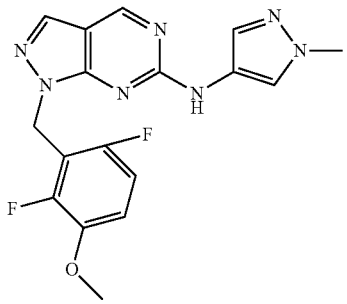

¹H NMR (d₆-DMSO) δ 9.86 (s, 1H), 8.89 (s, 1H), 8.12 (s, 1H), 7.99 (s, 1H), 7.58 (s, 1H), 7.19 (td, 1H), 7.06 (td, 1H), 5.59 (s, 2H), 3.86 (s, 3H), 3.82 (s, 3H); LC-MS method B, (ES+) 372, RT=7.89 min.

Example 160

1-(2,6-Difluorobenzyl)-N-(1-(2,2-difluoroethyl)-1H-pyrazol-4-yl)-1H-pyrazolo[3,4-d]pyrimidin-6-amine The following compound was made according to the procedure in Example 1, using 1-(2,2-difluoroethyl)-1H-pyrazol-4-amine and 2-(bromomethyl)-1,3-difluorobenzene. 1-(2,2-difluoroethyl)-1H-pyrazol-4-amine was prepared by Procedure A using 2,2-difluoromethane sulfonate as alkylating agent (see Example 39):

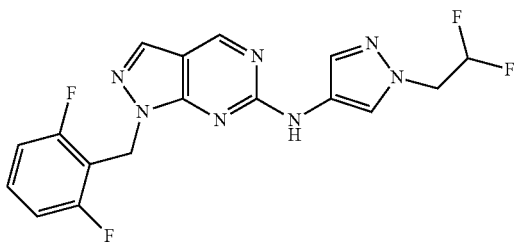 [SMILES: Fc1cccc(F)c1Cn1ncc2cnc(Nc3cnn(CC(F)F)c3)nc21]

¹H NMR (d₆-DMSO) δ 9.93 (s, 1H), 8.90 (s, 1H), 8.26 (s, 1H), 8.00 (s, 1H), 7.72 (s, 1H), 7.46-7.49 (m, 1H), 7.12-7.16

(m, 2H), 6.21-6.49 (m, 1H), 5.60 (s, 2H), 4.62 (td, 2H); LC-MS method B, (ES+) 392.0, RT=8.61 min.

Example 161

1-(2-Cyclopropylbenzyl)-N-(1-(2,2-difluoroethyl)-1H-pyrazol-4-yl)-1H-pyrazolo[3,4-d]pyrimidin-6-amine The following compound was made according to the procedure in Example 1, using 1-(2,2-difluoroethyl)-1H-pyrazol-4-amine and 1-cyclopropyl-2-((methylsulfonyl)methyl)benzene. 1-(2,2-difluoroethyl)-1H-pyrazol-4-amine was prepared by Procedure A using 2,2-difluoromethane sulfonate as alkylating agent (see Example 39). 1-cyclopropyl-2-((methylsulfonyl)methyl)benzene was prepared as in Example 45 (Step i and ii) using 2-cyclopropylbenzaldehyde:

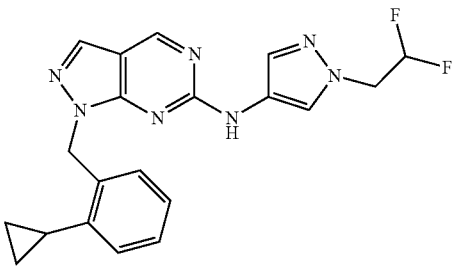 [SMILES: FC(F)Cn1cc(Nc2ncc3cnn(Cc4ccccc4C4CC4)c3n2)cn1]

$^1$H NMR (d$_6$-DMSO) δ 9.90 (s, 1H), 8.94 (s, 1H), 8.06-8.14 (m, 2H), 7.67 (s, 1H), 7.19-6.86 (m, 4H), 6.18-6.46 (m, 1H), 5.73 (s, 2H), 4.55-4.62 (m, 2H), 2.15-2.19 (m, 1H), 0.83 (s, 2H), 0.62 (s, 2H); LC-MS method B, (ES+) 396.1, RT=9.61 min.

Example 162

N-(1-Methyl-1H-pyrazol-4-yl)-1-(3-morpholinobenzyl)-1H-pyrazolo[3,4-d]pyrimidin-6-amine

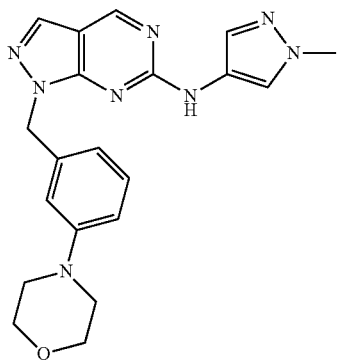

Step (i)
1-(3-iodobenzyl)-N-(1-methyl-1H-pyrazol-4-yl)-1H-pyrazolo[3,4-d]pyrimidin-6-amine was made according to the procedure in Example 1, using 1-(bromomethyl)-3-iodobenzene.
Step (ii)
1-(3-iodobenzyl)-N-(1-methyl-1H-pyrazol-4-yl)-1H-pyrazolo[3,4-d]pyrimidin-6-amine (80 mg, 0.185 mmol), was dissolved in dioxane (1.2 mL) and added to a microwave tube. A mixture of Cs$_2$CO$_3$ (150 mg, 0.462 mmol) and X-Phos ligand (dicyclohexyl(2',4',6'-triisopropyl-[1,1'-biphenyl]-2-yl)phosphine, 4.4 mg, 9.2 μmol) and morpholine (40 μL, 0.462 mmol) was then added to the stirred solution, followed by the catalyst Pd$_2$(dba)$_3$ (1.65 mg, 1.8 μmol). The solution was degassed for 5 minutes with nitrogen and the tube was sealed under Nitrogen. The tube was heated in the microwave oven for 1 h at 140° C. then the mixture was diluted with ethyl acetate and washed with water. The aqueous phase was extracted with ethyl acetate and the combined organics were washed with brine and dried over Na$_2$SO$_4$. The solution was then filtered and the solvent removed in vacuo to obtain a crude solid which was purified by flash chromatography (ethyl acetate 100% to ethyl acetate/MeOH=85:15) to give the title compound as a white solid (38 mg, 52% yield). $^1$H NMR (d$_6$-DMSO) δ 9.83 (br s, 1H), 8.91 (s, 1H), 8.08-7.98 (m, 2H), 7.59 (s, 1H), 7.15 (t, 1H), 7.03 (s, 1H), 6.84 (dd, J=8.2, 2.1 Hz, 1H), 6.69 (d, J=6.1 Hz, 1H), 5.49 (s, 2H), 3.84 (s, 3H), 3.72-3.63 (m, 4H), 3.07-2.95 (m, 4H); LC-MS method B, (ES+) 391.0, RT=7.44 min.

Example 163

N-(1-Methyl-1H-pyrazol-4-yl)-1-(2,3,5,6-tetrafluorobenzyl)-1H-pyrazolo[3,4-d]pyrimidin-6-amine The following compound was made according to the procedure in Example 1 (Step ii), using 3-(bromomethyl)-1,2,4,5-tetrafluorobenzene:

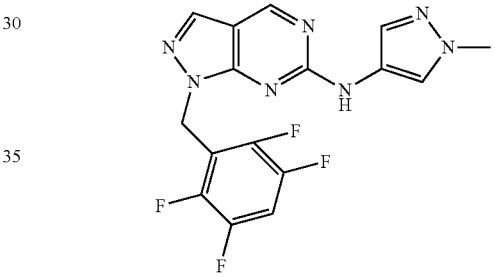

$^1$H NMR (d$_6$-DMSO) δ 9.92 (s, 1H), 8.91 (s, 1H), 8.11 (s, 1H), 8.04 (s, 1H), 7.93 (tt, 1H), 7.60 (s, 1H), 5.70 (s, 2H), 3.85 (s, 3H); LC-MS method B, (ES+) 377.9, RT=8.49 min.

Example 164

1-(2-Fluoro-6-(trifluoromethyl)benzyl)-N-(1-methyl-1H-pyrazol-4-yl)-1H-pyrazolo[3,4-d]pyrimidin-6-amine The following compound was made according to the procedure in Example 1 (Step ii), using 2-(bromomethyl)-1-fluoro-3-(trifluoromethyl)benzene:

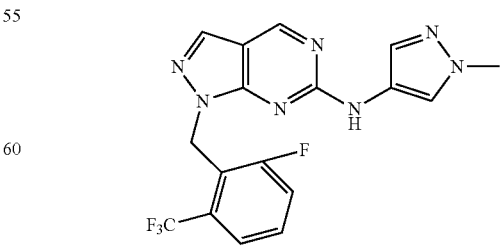

$^1$H NMR (d$_6$-DMSO) δ 9.87 (s, 1H), 8.90 (s, 1H), 8.11 (s, 1H), 7.96 (s, 1H), 7.59-7.70 (m, 3H), 5.68 (s, 2H), 3.84 (s, 3H); LC-MS method B, (ES+) 391.9, RT=8.74 min.

Example 165

1-(2-Fluorobenzyl)-N-(1-(2-(tetrahydro-2H-pyran-4-yl)ethyl)-1H-pyrazol-4-yl)-1H-pyrazolo[3,4-d]pyrimidin-6-amine The following compound was made according to the procedure in Example 1, using 1-(2-(tetrahydro-2H-pyran-4-yl)ethyl)-1H-pyrazol-4-amine and 1-(bromomethyl)-2-fluorobenzene:

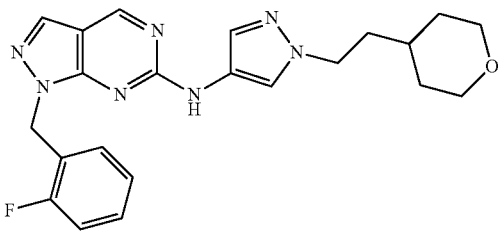 [SMILES: Fc1ccccc1Cn1ncc2cnc(Nc3cnn(CCC4CCOCC4)c3)nc21]

To prepare 1-(2-(tetrahydro-2H-pyran-4-yl)ethyl)-1H-pyrazol-4-amine, diethyl azodicarboxylate (500 mg, 451 µl, 2.86 mmol) was added dropwise to a solution of 2-(tetrahydro-2H-pyran-4-yl)ethanol (287 mg, 2.2 mmol), 4-nitropyrazole (250 mg, 2.2 mmol), and triphenylphosphine (696 mg, 2.64 mmol) in anhydrous THF (10 mL). The reaction mixture was stirred at rt for 2 h, diluted with DCM (100 mL) and washed with water (50 mL). The organics were collected, dried over MgSO4, filtered and reduced in vacuo. The crude product was purified by flash chromatography (Petroleum ether 100% to petroleum ether/ethyl acetate, 70:30) to give the desired intermediate. The residue was dissolved in methanol (10 mL), palladium on carbon (50 mg) was added and the reaction was stirred under a balloon of hydrogen for 18 h. The resulting mixture was filtered through Celite and the filtrate concentrated in vacuo to afford 1-(2-(tetrahydro-2H-pyran-4-yl)ethyl)-1H-pyrazol-4-amine which was used without further purification. $^1$H NMR (d$_6$-DMSO) δ 9.88 (s, 1H), 8.92 (s, 1H), 8.19-7.99 (m, 2H), 7.57 (s, 1H), 7.40-7.32 (m, 1H), 7.30-7.19 (m, 2H), 7.19-7.12 (m, 1H), 5.60 (s, 2H), 4.13 (t, J=7.0 Hz, 2H), 3.80 (dd, J=11.5, 2.6 Hz, 2H), 3.21 (td, J=11.5, 1.8 Hz, 2H), 1.72 (q, J=7.0 Hz, 2H), 1.58 (dd, J=12.8, 1.8 Hz, 2H), 1.50-1.33 (m, 1H), 1.26-1.10 (m, 2H); LC-MS method B, (ES+) 422.1, RT=8.81 min.

Example 166

2-(3-((6-((1-Methyl-1H-pyrazol-4-yl)amino)-1H-pyrazolo[3,4-d]pyrimidin-1-yl)methyl)phenoxy)ethanol

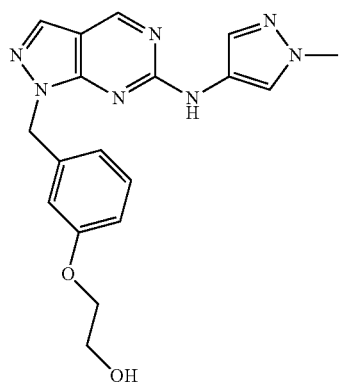 [SMILES: Cn1cc(Nc2ncc3cnn(Cc4cccc(OCCO)c4)c3n2)cn1]

Step (i)
3-(2-(benzyloxy)ethoxy)benzaldehyde was prepared as in Example 171 using 2-benzyloxyethanol.
Step (ii)
1-(3-(2-(benzyloxy)ethoxy)benzyl)-N-(1-methyl-1H-pyrazol-4-yl)-1H-pyrazolo[3,4-d]pyrimidin-6-amine was made according to the procedure in Example 45 (Steps i to iii) using 3-(2-(benzyloxy)ethoxy)benzaldehyde.
Step (iii)
1-(3-(2-(benzyloxy)ethoxy)benzyl)-N-(1-methyl-1H-pyrazol-4-yl)-1H-pyrazolo[3,4-d]pyrimidin-6-amine (39 mg, 86 µmol) was dissolved in 2 mL methanol then palladium on carbon added under an inert atmosphere and the reaction mixture stirred overnight at rt under an hydrogen atmosphere. The reaction mixture was filtered through Celite and evaporated to afford the title compound after purification by preparative HPLC. $^1$H NMR (d$_6$-DMSO) δ 9.85 (s, 1H), 8.92 (s, 1H), 8.11-7.97 (m, 2H), 7.56 (s, 1H), 7.23 (t, J=8.0 Hz, 1H), 6.95-6.74 (m, 3H), 5.52 (s, 2H), 4.81 (t, J=5.5 Hz, 1H), 3.90 (t, J=5.0 Hz, 2H), 3.83 (s, 3H), 3.65 (m, 2H); LC-MS method B, (ES+) 366.0, RT=6.64 min.

Example 167

N-(1-Methyl-1H-pyrazol-4-yl)-1-(3-(2-(piperidin-1-yl)ethoxy)benzyl)-1H-pyrazolo[3,4-d]pyrimidin-6-amine

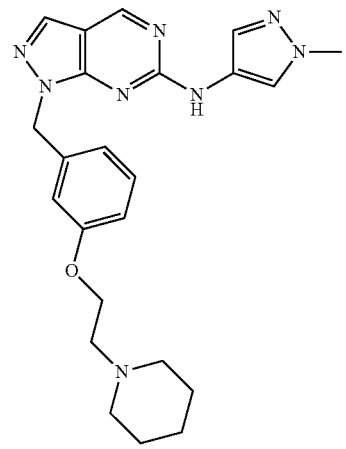 [SMILES: Cn1cc(Nc2ncc3cnn(Cc4cccc(OCCN5CCCCC5)c4)c3n2)cn1]

Step (i)
tert-butyldimethylsilyl chloride (3.7 g, 1.5 eq) was added portionwise to a solution of 3-hydroxybenzaldehyde (2.0 g, 16 mmol), triethylamine (3.4 mL, 1.5 eq) and dimethylaminopyridine (50 mg, 0.025 eq) in DCM (100 mL). After stirring for 2 h at rt, water was added. The aqueous phase was extracted with DCM, the combined organic phases dried over sodium sulfate and concentrated in vacuo to afford 3-((tert-butyldimethylsilyl)oxy)benzaldehyde (3.6 g, 16 mmol, 100%).
Step (ii)
3-((6-((1-methyl-1H-pyrazol-4-yl)amino)-1H-pyrazolo[3,4-d]pyrimidin-1-yl)methyl)phenol was made according to the procedure described in Example 45 (Steps i to iii) with simultaneous deprotection of the TBDMS group at the last step.
Step (iii)
To a solution of 3-((6-((1-methyl-1H-pyrazol-4-yl)amino)-1H-pyrazolo[3,4-d]pyrimidin-1-yl)methyl)phenol (15 mg, 47 µmol) in DMF (1 mL) were added 1-(2-chloroethyl)piperidine, HCl (24 mg, 1.5 eq) and potassium carbonate (30 mg, 2.5 eq). After 3 h at 60° C., the reaction mixture was partitioned between DCM and water. The aqueous phase was extracted with DCM and the combined organic phases dried over sodium sulfate and concentrated in vacuo. The residue was purified by preparative HPLC to afford the title compound (2.2 mg, 5 µmol, 11%). LC-MS method B, (ES+) 433.10, RT=5.18 min.

Example 168

2-(2-((6-((1-Methyl-1H-pyrazol-4-yl)amino)-1H-pyrazolo[3,4-d]pyrimidin-1-yl)methyl)phenoxy)ethanol The following compound was made according to the procedure in Example 166 (Steps i-iii), using 2-hydroxybenzaldehyde:

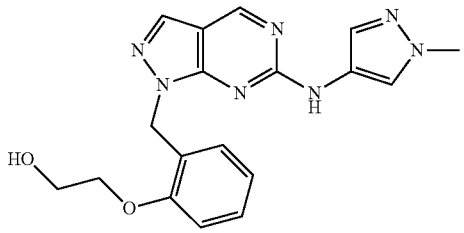 [SMILES: Cn1cc(Nc2ncc3cnn(Cc4ccccc4OCCO)c3n2)cn1]

LC-MS method B, (ES+) 366.0, RT=7.03 min.

Example 169

1-(3-(3-Methoxypropoxy)benzyl)-N-(1-methyl-1H-pyrazol-4-yl)-1H-pyrazolo[3,4-d]pyrimidin-6-amine The following compound was made according to the procedure in Example 45 using 3-(3-methoxypropoxy)benzaldehyde, which was prepared as in Example 171 using 3-methoxy-1-propanol:

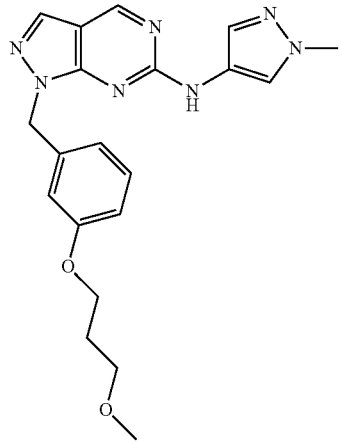 [SMILES: COCCCOc1cccc(Cn2ncc3cnc(Nc4cnn(C)c4)nc32)c1]

$^1$H NMR (d$_6$-DMSO) δ 9.85 (s, 1H), 8.92 (s, 1H), 8.13-7.98 (m, 2H), 7.56 (s, 1H), 7.23 (t, J=7.9 Hz, 1H), 6.90 (s, 1H), 6.86-6.77 (m, 2H), 5.52 (s, 2H), 3.93 (t, J=6.4 Hz, 2H), 3.83 (s, 3H), 3.41 (t, J=6.3 Hz, 2H), 3.21 (s, 3H), 1.88 (m, 2H); LC-MS method B, (ES+) 394.0, RT=8.30 min.

Example 170

1-((6-Fluoropyridin-2-yl)methyl)-N-(1-methyl-1H-pyrazol-4-yl)-1H-pyrazolo[3,4-d]pyrimidin-6-amine The following compound was made according to the procedure in Example 45 using 6-fluoropicolinaldehyde:

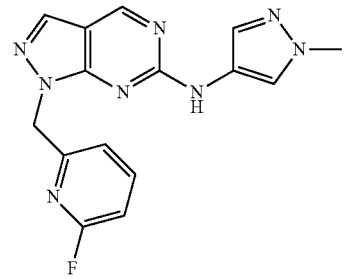 [SMILES: Cn1cc(Nc2ncc3cnn(Cc4cccc(F)n4)c3n2)cn1]

$^1$H NMR (d$_6$-Acetone) δ 8.92 (br s, 1H), 8.90 (s, 1H), 8.12 (s, 1H), 8.03 (s, 1H), 7.93 (dd, J=15.7, 8.1 Hz, 1H), 7.59 (s, 1H), 7.06 (d, J=6.6 Hz, 1H), 7.01 (dd, J=8.2, 2.2 Hz, 1H), 5.64 (m, 2H), 3.85 (s, 3H); LC-MS method B, (ES+) 324.9, RT=6.94 min.

Example 171

(S)-1-(3-(2-Methoxypropoxy)benzyl)-N-(1-methyl-1H-pyrazol-4-yl)-1H-pyrazolo[3,4-d]pyrimidin-6-amine The following compound was made according to the procedure in Example 45 using (S)-3-(2-methoxypropoxy)benzaldehyde:

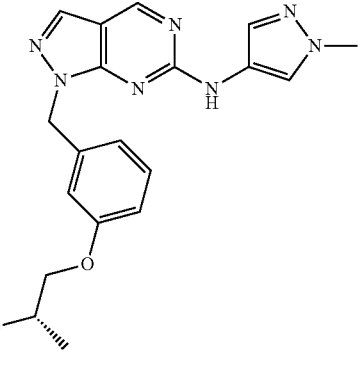

To prepare (S)-3-(2-methoxypropoxy)benzaldehyde, triphenylphosphine (0.96 g, 3.66 mmol) was dissolved in dry THF (4 mL) in a 2-neck flask under Nitrogen. The mixture was cooled to 0° C. in an ice bath and diethyl azodicarboxylate (0.638 g, 3.66 mmol) was added dropwise followed by (S)-2-methoxypropan-1-ol (0.33 g, 3.66 mmol). Finally a solution of 3-hydroxybenzaldehyde (0.343 g, 2.82 mmol) in dry THF (4 mL) was added and the reaction mixture stirred at rt for 24 h. The mixture was then diluted in diethyl ether (25 mL), washed with water (20 mL) and brine (20 mL). The organic phase was then dried over Na$_2$SO$_4$, filtered and the solvent evaporated under vacuum to give a crude product which was purified by Flash chromatography (hexane 100% to hexane:ethyl acetate, 1:1) to yield (S)-3-(2-methoxypropoxy)benzaldehyde as a transparent oil (64 mg, 12% yield). $^1$H NMR (d$_6$-Acetone) δ 8.89 (s, 1H), 8.87 (s, 1H), 8.15 (s, 1H), 7.98 (s, 1H), 7.64 (s, 1H), 7.25 (t, J=7.9 Hz, 1H), 7.01 (s, 1H), 6.95 (d, J=7.3 Hz, 1H), 6.86 (dd, 1H), 5.56 (s, 2H), 3.95-3.89 (m, 1H), 3.88 (s, 3H), 3.85 (m, 1H), 3.69-3.60 (m, 1H), 3.33 (s, 3H), 1.17 (d, J=6.3 Hz, 3H); LC-MS method B, (ES+) 394, RT=8.20 min.

Example 172

1-(3-(Cyclopropylmethoxy)benzyl)-N-(1-methyl-1H-pyrazol-4-yl)-1H-pyrazolo[3,4-d]pyrimidin-6-amine The following compound was made according to the procedure in Example 45 using 3-(cyclopropylmethoxy)benzaldehyde, which was synthesized as in Example 102, using 3-hydroxybenzaldehyde and (bromomethyl)cyclopropane as alkylating agent:

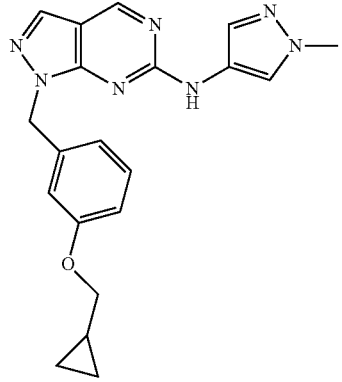 [SMILES: Cn1cc(Nc2ncc3cnn(Cc4cccc(OCC5CC5)c4)c3n2)cn1]

$^1$H NMR (d$_6$-DMSO) δ 9.84 (s, 1H), 8.91 (s, 1H), 8.13-7.93 (m, 2H), 7.56 (s, 1H), 7.21 (t, J=7.9 Hz, 1H), 6.96-6.73 (m, 3H), 5.51 (s, 2H), 3.83 (s, 3H), 3.72 (d, J=7.0 Hz, 2H), 1.23-1.06 (m, 1H), 0.58-0.43 (m, 2H), 0.32-0.18 (m, 2H); LC-MS method B, (ES+) 376.0, RT=9.05 min.

Example 173

1-(2-(Cyclopropylmethoxy)benzyl)-N-(1-methyl-1H-pyrazol-4-yl)-1H-pyrazolo[3,4-d]pyrimidin-6-amine The following compound was made according to the procedure in Example 45 using 2-(cyclopropylmethoxy)benzaldehyde. 2-(cyclopropylmethoxy)benzaldehyde was prepared as in Example 102 using 2-hydroxybenzaldehyde and (bromomethyl)cyclopropane as alkylating agent: $^1$H NMR (d$_6$-DMSO) δ 9.76 (s, 1H), 8.91 (s, 1H), 8.02 (s, 1H), 7.94 (s, 1H),

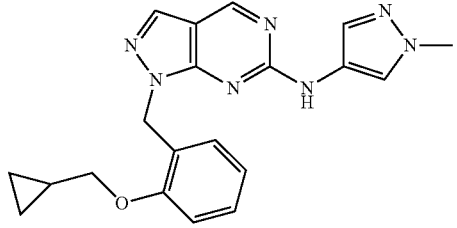 [SMILES: Cn1cc(Nc2ncc3cnn(Cc4ccccc4OCC4CC4)c3n2)cn1]

7.58 (s, 1H), 7.27-7.19 (m, 1H), 7.00-6.89 (m, 2H), 6.84 (m, 1H), 5.52 (s, 2H), 3.83-3.81 (m, 2H), 3.80 (s, 3H), 1.12-1.00 (m, 1H), 0.46-0.36 (m, 2H), 0.23-0.14 (m, 2H); LC-MS method B, (ES+) 376.0, RT=9.12 min.

Example 174

N-(1-Methyl-1H-pyrazol-4-yl)-1-((6-morpholinopyridin-2-yl)methyl)-1H-pyrazolo[3,4-d]pyrimidin-6-amine

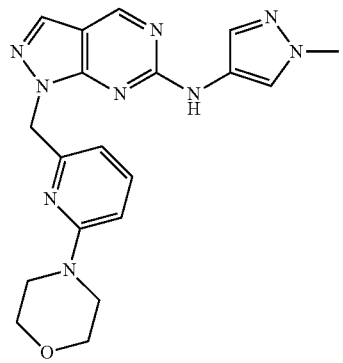 [SMILES: Cn1cc(Nc2ncc3cnn(Cc4cccc(N5CCOCC5)n4)c3n2)cn1]

1-((6-fluoropyridin-2-yl)methyl)-N-(1-methyl-1H-pyrazol-4-yl)-1H-pyrazolo[3,4-d]pyrimidin-6-amine (Example 170) (27 mg, 0.08 mmol) was dissolved in morpholine (0.6 ml) in a microwave tube under Nitrogen which was sealed and heated at 180° C. for 1 h. The mixture was diluted with DCM, washed with water and the water re-extracted with DCM. The combined organics were dried over Na$_2$SO$_4$, filtered and the solvent evaporated to give the title compound as a yellowish solid (20 mg, 64% yield). $^1$H NMR (d$_6$-DMSO) δ 9.78 (br s, 1H), 8.91 (s, 1H), 8.05 (s, 1H), 7.91 (s, 1H), 7.52 (s, 1H), 7.46 (t, 1H), 6.68 (d, 1H), 6.28 (br s, 1H), 5.46 (s, 2H), 3.78 (s, 3H), 3.62 (t, 4H), 3.35 (t, 4H); LC-MS method B, (ES+) 392.0, RT=6.84 min.

Example 175

1-(3-((2S,6R)-2,6-Dimethylmorpholino)benzyl)-N-(1-methyl-1H-pyrazol-4-yl)-1H-pyrazolo[3,4-d]pyrimidin-6-amine The following compound was made according to the procedure in Example 162 using (3S,5R)-3,5-dimethylmorpholine:

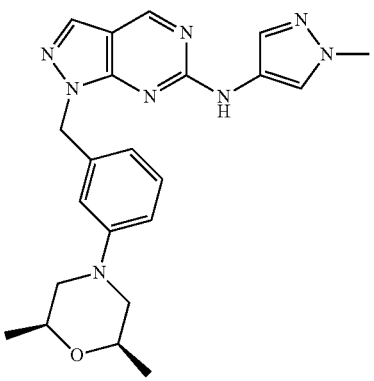

¹H NMR (d₆-DMSO) δ 9.86 (s, 1H), 8.90 (s, 1H), 8.12-7.96 (m, 2H), 7.62 (s, 1H), 7.17-7.11 (m, 1H), 7.09 (s, 1H), 6.84 (dd, J=8.3, 2.0 Hz, 1H), 6.71-6.63 (m, 1H), 5.48 (s, 2H), 3.84 (s, 3H), 3.68-3.55 (m, 2H), 3.49 (m, 2H), 2.24-2.11 (m, 2H), 1.18-0.97 (m, 6H); LC-MS method B, (ES+) 419.0, RT=8.45 min.

Example 176

N-(1-(2,2-Difluoroethyl)-1H-pyrazol-4-yl)-1-(3-(2-methoxyethoxy)benzyl)-1H-pyrazolo[3,4-d]pyrimidin-6-amine

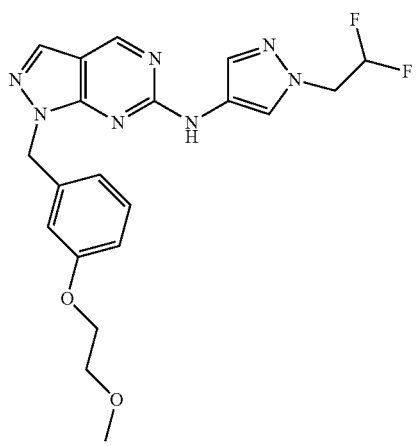 [SMILES: COCCOc1cccc(Cn2ncc3cnc(Nc4cnn(CC(F)F)c4)nc32)c1]

Step (i)

3-(2-methoxyethoxy)benzaldehyde was prepared following the procedure of Example 172 using 1-bromo-2-methoxyethane as alkylating agent.

Step (ii)

3-(2-methoxyethoxy)benzyl methanesulfonate was prepared as in Example 45 (Steps i and ii) using 3-(2-methoxyethoxy)benzaldehyde.

Step (iii)

The title compound was made according to the procedure in Example 1, using 1-(2,2-difluoroethyl)-1H-pyrazol-4-amine and 3-(2-methoxyethoxy)benzyl methanesulfonate. 1-(2,2-difluoroethyl)-1H-pyrazol-4-amine was prepared by Procedure A using 2,2-difluoromethane sulfonate as alkylating agent (see Example 39). ¹H NMR (d₆-DMSO) δ 9.93 (s, 1H), 8.93 (s, 1H), 8.21 (s, 1H), 8.06 (s, 1H), 7.67 (s, 1H), 7.21 (t, 1H), 6.85-6.89 (m, 3H), 6.20-6.48 (m, 1H), 5.52 (s, 2H), 4.62 (td, 2H), 3.99-4.01 (m, 2H), 3.57-3.59 (m, 2H), 3.25 (s, 3H); LC-MS method B, (ES+) 430.0, RT=8.45 min.

Example 177

N-(1-(3-(Azetidin-1-yl)propyl)-1H-pyrazol-4-yl)-1-(2-fluorobenzyl)-1H-pyrazolo[3,4-d]pyrimidin-6-amine The following compound was made according to the procedure in Example 1, using 1-(3-(azetidin-1-yl)propyl)-1H-pyrazol-4-amine and 1-(bromomethyl)-2-fluorobenzene. 1-(3-(azetidin-1-yl)propyl)-1H-pyrazol-4-amine was prepared as in Example 165 using 3-(azetidin-1-yl)propan-1-ol.

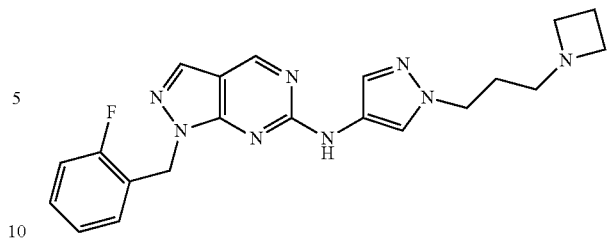

¹H NMR (d₆-DMSO) δ 8.78 (s, 1H), 8.00 (s, 1H), 7.93 (s, 1H), 7.57 (s, 1H), 7.32-7.23 (m, 1H), 7.16-7.04 (m, 3H), 5.61 (s, 2H), 4.16 (t, J=7.1 Hz, 2H), 3.16 (t, J=7.0 Hz, 4H), 2.41 (t, J=7.1 Hz, 2H), 2.11-1.99 (m, 2H), 1.98-1.85 (m, 2H); LC-MS method B, (ES+) 407, RT=5.55 min.

Example 178

1-(2,3-Dichlorobenzyl)-N-(1-methyl-1H-pyrazol-4-yl)-1H-pyrazolo[3,4-d]pyrimidin-6-amine The following compound was made according to the procedures in Example 1 (Step ii) using 1-(bromomethyl)-2,3-dichlorobenzene and 6-chloro-1H-pyrazolo[3,4-d]pyrimidine, followed by Example 1 (Step i) using 1-methyl-1H-pyrazol-4-amine.

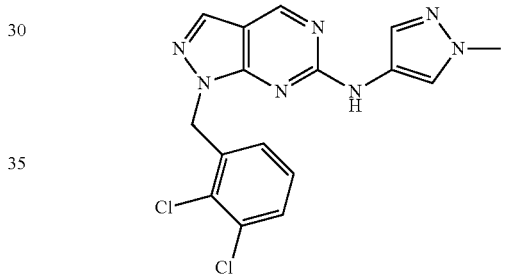

¹H NMR (d₆-DMSO) δ 9.89 (s, 1H), 8.94 (s, 1H), 8.09 (s, 1H), 7.98 (s, 1H), 7.61 (dd, 1H), 7.53 (s, 1H), 7.32 (t, 1H), 7.09 (br s, 1H), 5.69 (s, 2H), 3.81 (s, 3H); LC-MS method B, (ES+) 374/376, RT=9.21 min.

Example 179

2-Methyl-3-46-((1-methyl-1H-pyrazol-4-yl)amino)-1H-pyrazolo[3,4-d]pyrimidin-1-yl)methyl)phenol

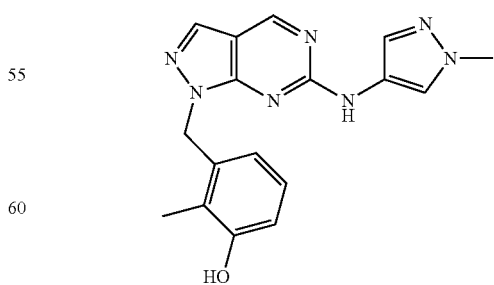

Step (i)

Borane-tetrahydrofuran (1M in THF, 4.6 mL, 1.4 eq) was added to a solution of 2-methyl-3-hydroxybenzoic acid (0.50 g, 3.3 mmol) in THF (30 mL). The reaction mixture was stirred overnight at rt before addition of saturated sodium hydrogencarbonate. The aqueous phase was extracted with DCM. The combined organic phases were dried over sodium sulfate and concentrated in vacuo to afford 3-(hydroxymethyl)-2-methylphenol in a quantitative yield.

Step (ii)

2-methyl-3-(((methylsulfonyl)oxy)methyl)phenyl methanesulfonate was prepared as in Example 45 (Step ii).

Step (iii)

2-methyl-3-46-((1-methyl-1H-pyrazol-4-yl)amino)-1H-pyrazolo[3,4-d]pyrimidin-1-yl)methyl)phenyl methanesulfonate was synthesized following the procedure in Example 1 (Step ii) using 2-methyl-3-(((methylsulfonyl)oxy)methyl)phenyl methanesulfonate Step (iv)

The residue from the previous step (0.24 mmol) was dissolved in ethanol (2 mL) and sodium hydroxide (0.5 mL, 10% in water). The reaction mixture was stirred under reflux until completion (several days) with regular additions of 10% sodium hydroxide. After evaporation, the residue was purified by preparative HPLC to afford the title compound. $^1$H NMR (d$_6$-DMSO) δ 9.81 (s, 1H), 9.33 (s, 1H), 8.91 (s, 1H), 8.06-7.97 (m, 2H), 7.54 (s, 1H), 6.91 (t, J=7.8 Hz, 1H), 6.73 (d, J=7.8 Hz, 1H), 6.52 (s, 1H), 5.49 (s, 2H), 3.82 (s, 3H), 2.17 (s, 3H); LC-MS method B, (ES+) 336.0, RT=7.05 min.

Example 180

N-(1-Methyl-1H-pyrazol-4-yl)-1-(2-morpholinobenzyl)-1H-pyrazolo[3,4-d]pyrimidin-6-amine

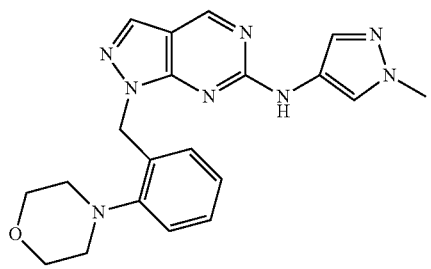 [SMILES: Cn1cc(Nc2ncc3cnn(Cc4ccccc4N4CCOCC4)c3n2)cn1]

Step (i)

A mixture of 2-fluorobenzaldehyde (0.5 mL, 4.8 mmol), morpholine (0.6 mL, 1.5 eq) and potassium carbonate (1.3 g, 2 eq) was heated in the microwave at 125° C. for 2.5 h. After evaporation, the residue was partitioned between water and DCM, the aqueous phase extracted with DCM. The combined organic phases were dried over sodium sulfate and concentrated in vacuo to afford 2-morpholinobenzaldehyde (0.57 g, 63%).

Step (ii)

The title compound was prepared as in Example 45 (Steps i-iii) using 2-morpholinobenzaldehyde. $^1$H NMR (d$_6$-DMSO) δ 9.82 (s, 1H), 8.93 (s, 1H), 8.05 (s, 1H), 7.87 (s, 1H), 7.65-7.59 (m, 1H), 7.32-7.21 (m, 2H), 7.03-6.97 (m, 1H), 6.90 (m, 1H), 5.65 (s, 2H), 3.78 (s, 3H), 3.75-3.69 (m, 4H), 2.92-2.86 (m, 4H); LC-MS method B, (ES+) 391.1, RT=8.04 min.

Example 181

N-(1-Methyl-1H-pyrazol-4-yl)-1-(3-((tetrahydrofuran-3-yl)oxy)benzyl)-1H-pyrazolo[3,4-d]pyrimidin-6-amine The following compound was made according to the procedure in Example 162 using tetrahydrofuran-3-ol:

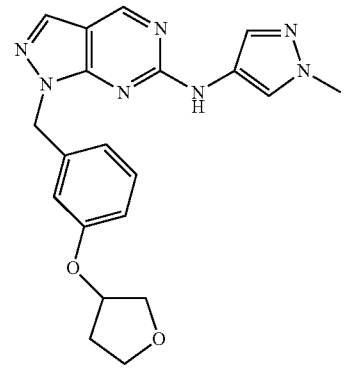 [SMILES: Cn1cc(Nc2ncc3cnn(Cc4cccc(OC5CCOC5)c4)c3n2)cn1]

$^1$H NMR (d$_6$-Acetone) δ 8.93 (br s and s, 2H), 8.14 (br s, 1H), 7.98 (s, 1H), 7.64 (s, 1H), 7.25 (t, 1H), 6.98 (s, 1H), 6.97 (s, 1H), 6.83 (dd, 1H), 5.56 (s, 2H), 4.98-4.91 (m, 1H), 3.98-3.60 (m, 7H), 2.25-2.12 (m, 1H), 2.02-1.93 (m, 1H); LC-MS method B, (ES+) 392.1, RT=7.73 min.

Example 182

1-(2-Fluorobenzyl)-N-(1-(2-(piperazin-1-yl)ethyl)-1H-pyrazol-4-yl)-1H-pyrazolo[3,4-d]pyrimidin-6-amine

Step (i)

tert-butyl 4-(2-(4-amino-1H-pyrazol-1-yl)ethyl)piperazine-1-carboxylate was prepared as in Example 165 using tert-butyl 4-(2-hydroxyethyl)piperazine-1-carboxylate Step (ii)

tert-butyl 4-(2-(4-(1-(2-fluorobenzyl)-1H-pyrazolo[3,4-d]pyrimidin-6-yl)-1H-pyrazol-1-yl)ethyl)piperazine-1-carboxylate was made according to the procedure in Example 1, using tert-butyl 4-(2-(4-amino-1H-pyrazol-1-yl)ethyl)piperazine-1-carboxylate.

Step (iii)

An excess of hydrochloride acid solution (4N in Dioxane, 2 ml) was added to a solution of 4-(2-(4-(1-(2-fluorobenzyl)-1H-pyrazolo[3,4-d]pyrimidin-6-yl)-1H-pyrazol-1-yl)ethyl)piperazine-1-carboxylate (117 mg, 0.225 mmol) in Dioxane (2 mL). The reaction mixture was stirred at rt for 18 h and concentrated in vacuo. The resultant residue was purified by preparative HPLC at high pH to give the title product. $^1$H NMR (CDCl$_3$) δ 8.78 (s, 1H), 8.06 (s, 1H), 7.93 (s, 1H), 7.58

(s, 1H), 7.29 (dd, J=4.9, 3.1 Hz, 1H), 7.24 (d, J=2.6 Hz, 1H), 7.19 (s, 1H), 7.08 (ddd, J=8.3, 6.1, 3.3 Hz, 2H), 5.61 (s, 2H), 4.26 (t, J=6.9 Hz, 2H), 2.92-2.82 (m, 3H), 2.50 (d, J=4.1 Hz, 4H), 1.69-1.50 (m, 4H); LC-MS method B, (ES+) 422, RT=5.19 min.

Example 183

1-46-(Dimethylamino)pyridin-2-yl)methyl)-N-(1-methyl-1H-pyrazol-4-yl)-1H-pyrazolo[3,4-d]pyrimidin-6-amine

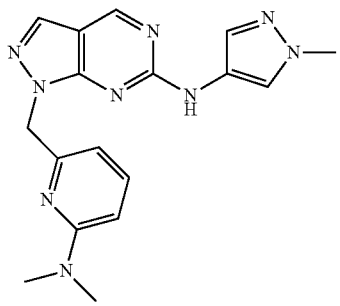

1-((6-fluoropyridin-2-yl)methyl)-N-(1-methyl-1H-pyrazol-4-yl)-1H-pyrazolo[3,4-d]pyrimidin-6-amine (Example 170) (45 mg, 0.138 mmol) was dissolved in DMF (0.6 ml) in a microwave tube under Nitrogen. This was sealed and heated at 180° C. for 1 h. The mixture was concentrated and purified by prep HPLC to afford 1-46-(dimethylamino)pyridin-2-yl)methyl)-N-(1-methyl-1H-pyrazol-4-yl)-1H-pyrazolo[3,4-d]pyrimidin-6-amine as yellowish solid (20 mg, 42% yield). $^1$H NMR (d$_6$-Acetone) δ 8.88 (s and br s, 2H), 8.06 (s, 1H), 7.99 (s, 1H), 7.61 (s, 1H), 7.40 (t, 1H), 6.49 (d, 1H), 6.24 (br s, 1H), 5.51 (s, 2H), 3.83 (s, 3H), 3.02 (s, 6H); LC-MS method B, (ES+) 350.1, RT=5.06 min.

Example 184

N-(1-(3-(Dimethylamino)propyl)-1H-pyrazol-4-yl)-1-(3-(2-methoxyethoxy)benzyl)-1H-pyrazolo[3,4-d]pyrimidin-6-amine

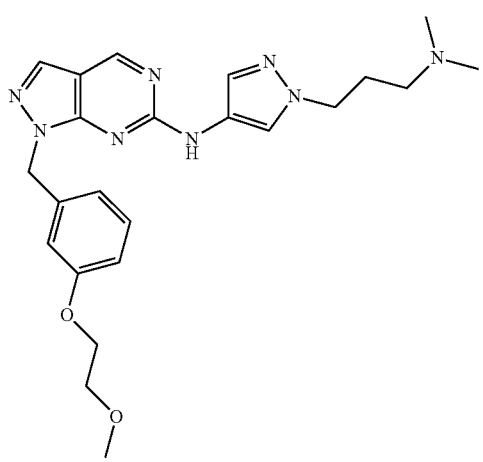 [SMILES: COCCOc1cccc(Cn2ncc3cnc(Nc4cnn(CCCN(C)C)c4)nc32)c1]

Step (i)
3-(2-methoxyethoxy)benzaldehyde was prepared following the procedure of Example 102 using 1-bromo-2-methoxyethane as alkylating agent.

Step (ii)
3-(2-hydroxyethoxy)benzyl methanesulfonate was prepared as in Example 45 (Steps i and ii) using 3-(2-methoxyethoxy)benzaldehyde.

Step (iii)
1-(3-(dimethylamino)propyl)-1H-pyrazol-4-amine was prepared by Procedure A using 3-chloro-N,N-dimethylpropan-1-amine, HCl as alkylating agent.

Step (iv)
The title compound was made according to the procedure in Example 1 (Step ii), using 3-(2-hydroxyethoxy)benzyl methanesulfonate and 6-chloro-1H-pyrazolo[3,4-d]pyrimidine followed by Example 1 (Step i) using 1-(3-(dimethylamino)propyl)-1H-pyrazol-4-amine. $^1$H NMR (d$_6$-DMSO) δ 9.86 (s, 1H), 8.92 (s, 1H), 8.20 (s, 1H), 8.10-8.01 (m, 2H), 7.59 (s, 1H), 7.23 (t, J=8.1 Hz, 1H), 6.90-6.81 (m, 2H), 5.52 (s, 2H), 4.10 (t, J=6.9 Hz, 2H), 4.03-3.96 (m, 2H), 3.64-3.55 (m, 2H), 3.26 (s, 3H), 2.18 (t, J=7.0 Hz, 2H), 2.12 (s, 6H), 1.93-1.83 (m, 2H); LC-MS method B, (ES+) 451.1, RT=5.32 min.

Example 185

1-(3-(2-Methoxyethoxy)-2-methylbenzyl)-N-(1-methyl-1H-pyrazol-4-yl)-1H-pyrazolo[3,4-d]pyrimidin-6-amine

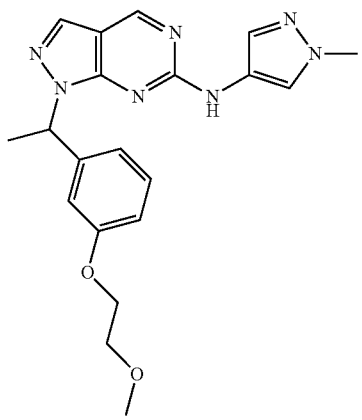 [SMILES: COCCOc1cccc(C(C)n2ncc3cnc(Nc4cnn(C)c4)nc32)c1]

Step (i)
To a solution of 3-hydroxy-2-methylbenzoic acid (0.50 g, 3.3 mmol) in DMF (6 mL) at 0° C. was slowly added potassium carbonate (1.4 g, 3 eq) under a nitrogen atmosphere. After stirring for 30 min at 0° C., 1-bromo-2-methoxyethane (1.4 mL, 4.5 eq) was added dropwise. The reaction mixture was stirred at rt for 1 h, then overnight at 80° C. After cooling down to rt, the reaction mixture was partitioned between ethyl acetate and water and the aqueous phase extracted with ethyl acetate. The combined organic phases were dried over sodium sulfate and concentrated in vacuo to afford 2-methoxyethyl 3-(2-methoxyethoxy)-2-methylbenzoate (0.83 g, 3.1 mmol, 94%).

Step (ii)
To a solution of 2-methoxyethyl 3-(2-methoxyethoxy)-2-methylbenzoate (0.83 g, 3.1 mmol) in DCM (50 mL) at 0° C. was added DIBAL (1M in THF, 13.6 mL, 4.4 eq) dropwise under inert atmosphere. After stirring for 24 h at rt, the reaction was quenched with saturated ammonium chloride until dissolution of the jelly precipitate. The aqueous phase was extracted with DCM, and the combined organic phases dried over sodium sulfate and concentrated in vacuo to afford (3-(2-methoxyethoxy)-2-methylphenyl)methanol in a quantitative yield.

Step (iii)

The title compound was prepared according to the procedure in Example 45 (Steps ii and iii) using (3-(2-methoxyethoxy)-2-methylphenyl)methanol. $^1$H NMR (d$_6$-DMSO) δ 9.82 (s, 1H), 8.92 (s, 1H), 8.07-7.95 (m, 2H), 7.54 (s, 1H), 7.07 (t, J=7.9 Hz, 1H), 6.90 (d, J=8.1 Hz, 1H), 6.67 (s, 1H), 5.53 (s, 2H), 4.11-4.00 (m, 2H), 3.82 (s, 3H), 3.72-3.62 (m, 2H), 3.32 (s, 3H), 2.23 (s, 3H); LC-MS method B, (ES+) 394.1, RT=8.32 min.

Example 186

N-(1-(3-(Dimethylamino)propyl)-1H-pyrazol-4-yl)-1-(3-morpholinobenzyl)-1H-pyrazolo[3,4-d]pyrimidin-6-amine

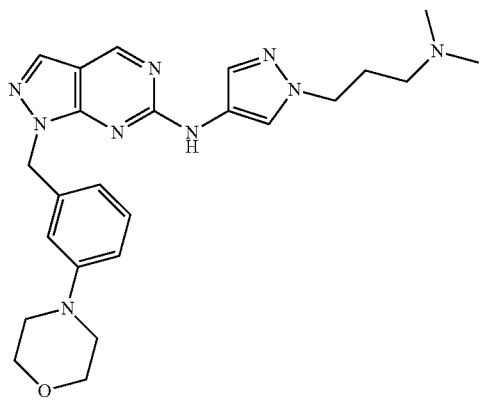 [SMILES: CN(C)CCCn1cc(Nc2ncc3cnn(Cc4cccc(N5CCOCC5)c4)c3n2)cn1]

Step (i)

3-morpholinobenzyl methanesulfonate was prepared according to the procedure in Example 45 (Step ii) using (3-morpholinophenyl)methanol.

Step (ii)

1-(3-(dimethylamino)propyl)-1H-pyrazol-4-amine was prepared by Procedure A using 3-chloro-N,N-dimethylpropan-1-amine, HCl as alkylating agent.

Step (iii)

The title compound was made according to the procedure in Example 1 (Step ii), using 3-morpholinobenzyl methanesulfonate and 6-chloro-1H-pyrazolo[3,4-d]pyrimidine followed by Example 1 (Step i) using 1-(3-(dimethylamino)propyl)-1H-pyrazol-4-amine. $^1$H NMR (d$_6$-DMSO) δ 9.83 (s, 1H), 8.91 (s, 1H), 8.08-8.00 (m, 2H), 7.62 (s, 1H), 7.19-7.10 (m, 1H), 7.00 (s, 1H), 6.84 (m, 1H), 6.75-6.65 (m, 1H), 5.49 (s, 2H), 4.10 (t, J=6.9 Hz, 2H), 3.70-3.64 (m, 4H), 3.04-2.98 (m, 4H), 2.17 (t, J=7.0 Hz, 2H), 2.11 (s, 6H), 1.92-1.82 (m, 2H); LC-MS method B, (ES+) 462.2, RT=5.21 min.

Example 187

(R)—N-(1-Methyl-1H-pyrazol-4-yl)-1-((6-(((tetrahydrofuran-3-yl)amino)pyridin-2-yl)methyl)-1H-pyrazolo[3,4-d]pyrimidin-6-amine The following compound was made according to the procedure in Example 183 using (S)-tetrahydrofuran-3-amine. tosylate:

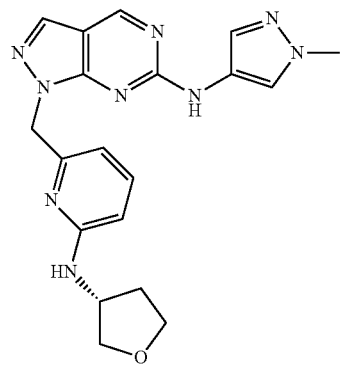 [SMILES: Cn1cc(Nc2ncc3cnn(Cc4cccc(N[C@@H]5CCOC5)n4)c3n2)cn1]

$^1$H NMR (d$_6$-Acetone) δ 8.86 (s and br s, 2H), 8.04 (s, 1H), 7.97 (s, 1H), 7.60 (s, 1H), 7.30 (t, 1H), 6.39 (d, 1H), 6.28 (br s, 1H), 5.92 (d, 1H), 5.47 (s, 2H), 4.29 (m, 1H), 3.85 (s, 3H), 3.80 (m, 2H), 3.67 (m, 1H), 3.48 (m, 1H), 2.12 (m, 1H), 1.75 (m, 1H); LC-MS method B, (ES+) 392.1, RT=5.02 min.

Example 188

N-(1-Methyl-1H-pyrazol-4-yl)-1-((6-(pyrrolidin-1-yl)pyridin-2-yl)methyl)-1H-pyrazolo[3,4-d]pyrimidin-6-amine

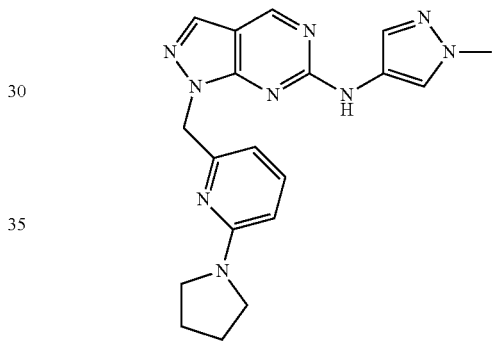

1-((6-fluoropyridin-2-yl)methyl)-N-(1-methyl-1H-pyrazol-4-yl)-1H-pyrazolo[3,4-d]pyrimidin-6-amine (Example 170) (45 mg, 0.138 mmol) was dissolved in dioxane/pyrrolidine (0.6 mL, 1:1) in a microwave tube under nitrogen. This was sealed and heated at 160° C. for 1 h. The mixture was concentrated in vacuo and re-dissolved in MeOH (2 mL). A solid precipitated over 16 h and was collected by filtration, and triturated with more MeOH to give N-(1-methyl-1H-pyrazol-4-yl)-1-((6-(pyrrolidin-1-yl)pyridin-2-yl)methyl)-1H-pyrazolo[3,4-d]pyrimidin-6-amine as a white solid (17 mg, 33% yield). $^1$H NMR (d$_6$-Acetone) δ 8.86 (s and br s, 2H), 8.05 (s, 1H), 7.98 (s, 1H), 7.60 (s, 1H), 7.35 (t, 1H), 6.28 (d, 1H), 6.18 (d, 1H), 5.47 (s, 2H), 3.82 (s, 3H), 3.38 (m, 4H), 1.95 (m, 4H); LC-MS method B, (ES+) 376.2, RT=4.95 min.

Example 189

4-Methyl-3-46-(((1-methyl-1H-pyrazol-4-yl)amino)-1H-pyrazolo[3,4-d]pyrimidin-1-yl)methyl)phenol

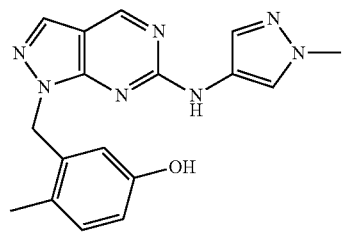

Step (i)

5-hydroxy-2-methylbenzoic acid (0.50 g, 3.3 mmol) was reduced to 3-(hydroxymethyl)-4-methylphenol as in Example 179 (step i) in a quantitative yield.

Step (ii)

Phosphorous tribromide (0.70 mL, 2.25 eq) was added dropwise to a solution of the alcohol in 20 mL DCM at 0° C. After stirring overnight at rt, the reaction was quenched with saturated sodium hydrogencarbonate, the aqueous phase extracted with DCM. The combined organic phases were dried over sodium sulfate and evaporated to yield the benzylbromide (0.56 mg, 2.8 mmol, 85%).

Step (iii)

The title compound was made as described in Example 1 using 3-(bromomethyl)-4-methylphenol. $^1$H NMR ($d_6$-DMSO) δ 9.92 (s, 1H), 9.16 (s, 1H), 9.02 (s, 1H), 8.15 (s, 1H), 8.09 (s, 1H), 7.62 (s, 1H), 7.07 (d, J=8.2 Hz, 1H), 6.65 (dd, J=8.2, 2.6 Hz, 1H), 6.54-6.43 (m, 1H), 5.52 (s, 2H), 3.91 (s, 3H), 2.35 (s, 3H); LC-MS method B, (ES+) 336.1, RT=7.15 min.

Example 190

2-(4-((1-(3-Morpholinobenzyl)-1H-pyrazolo[3,4-d]pyrimidin-6-yl)amino)-1H-pyrazol-1-yl)ethanol

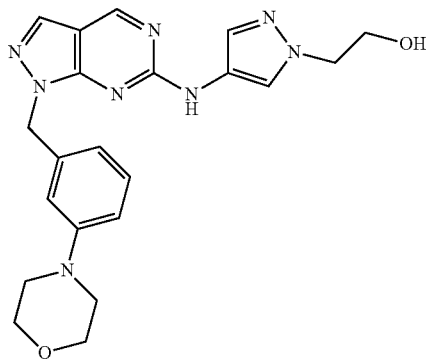 [SMILES: OCCn1cc(Nc2ncc3cnn(Cc4cccc(N5CCOCC5)c4)c3n2)cn1]

Step (i)

3-morpholinobenzyl methanesulfonate was prepared according to the procedure in Example 45 (Step ii) using (3-morpholinophenyl)methanol.

Step (ii)

2-(4-amino-1H-pyrazol-1-yl)ethanol was prepared according to Procedure A using 2-bromoethanol as alkylating agent.

Step (iii)

The title compound was made according to the procedure in Example 1 (Step ii), using 3-morpholinobenzyl methanesulfonate and 6-chloro-1H-pyrazolo[3,4-d]pyrimidine followed by Example 1 (Step i) using 2-(4-amino-1H-pyrazol-1-yl)ethanol. $^1$H NMR ($d_6$-DMSO) δ 9.82 (s, 1H), 8.90 (s, 1H), 8.10 (s, 1H), 8.03 (s, 1H), 7.63 (s, 1H), 7.20-7.09 (m, 1H), 7.00 (s, 1H), 6.83 (dd, J=8.2, 2.0 Hz, 1H), 6.71 (s, 1H), 5.46 (s, 2H), 4.89 (t, J=5.3 Hz, 1H), 4.13 (t, J=5.7 Hz, 2H), 3.73 (q, J=5.6 Hz, 2H), 3.70-3.64 (m, 4H), 3.07-2.97 (m, 4H); LC-MS method B, (ES+) 421.2, RT=6.73 min.

Example 191

(3-((6-((1-Methyl-1H-pyrazol-4-yl)amino)-1H-pyrazolo[3,4-d]pyrimidin-1-yl)methyl)phenyl)(morpholino)methanone

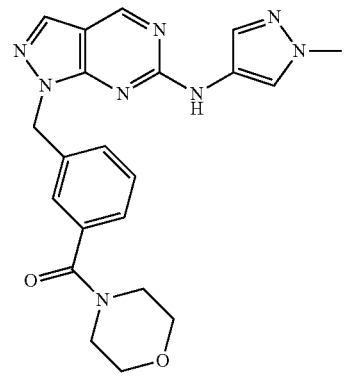 [SMILES: Cn1cc(Nc2ncc3cnn(Cc4cccc(C(=O)N5CCOCC5)c4)c3n2)cn1]

Step (i)

1-(3-iodobenzyl)-N-(1-methyl-1H-pyrazol-4-yl)-1H-pyrazolo[3,4-d]pyrimidin-6-amine was made according to Example 1 using 1-(bromomethyl)-3-iodobenzene.

Step (ii)

A mixture of 1-(3-iodobenzyl)-N-(1-methyl-1H-pyrazol-4-yl)-1H-pyrazolo[3,4-d]pyrimidin-6-amine (54 mg, 0.13 mmol), palladium acetate (1.4 mg, 0.05 eq), Xantphos (7.2 mg, 0.1 eq) and potassium phosphate (106 mg, 4 eq) was purged several times with carbon monoxide before addition of toluene (1 mL) and morpholine (334, 3 eq). After stirring for 2 h at 80° C., the reaction mixture was partitioned between water and DCM. The aqueous phase was extracted with DCM, the combined organic phases dried over sodium sulfate and evaporated. The residue was purified with the preparative HPLC to yield the title compound (40 mg, 96 μmol, 74%). $^1$H NMR ($d_6$-DMSO) δ 9.87 (s, 1H), 8.93 (s, 1H), 8.07 (s, 1H), 8.01 (s, 1H), 7.54 (s, 1H), 7.46-7.36 (m, 2H), 7.35-7.25 (m, 2H), 5.62 (s, 2H), 3.82 (s, 3H), 3.68-3.08 (m, 8H); LC-MS method B, (ES+) 419.2, RT=6.42 min.

Example 192

1-(2-Fluorobenzyl)-N-(1-((1-methylpiperidin-3-yl)methyl)-1H-pyrazol-4-yl)-1H-pyrazolo[3,4-d]pyrimidin-6-amine The title compound was made according to the procedure in Example 1 (Step ii), using 1-(bromo methyl)-2-fluorobenzene and 6-chloro-1H-pyrazolo[3,4-d]pyrimidine followed by Example 1 (Step i) using 1-((1-methylpiperidin-3-yl)methyl)-1H-pyrazol-4-amine. 1-((1-methylpiperidin-3-yl)methyl)-1H-pyrazol-4-amine was prepared by Procedure A using 3-(bromomethyl)-1-methylpiperidine as alkylating agent:

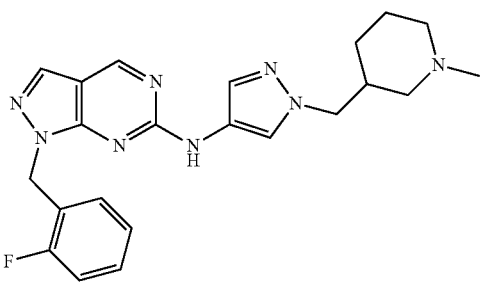 [SMILES: CN1CCCC(Cn2cc(Nc3ncc4cnn(Cc5ccccc5F)c4n3)cn2)C1]

¹H NMR (d₆-DMSO) δ 9.88 (s, 1H), 8.91 (s, 1H), 8.13-7.98 (m, 2H), 7.58 (s, 1H), 7.41-7.30 (m, 1H), 7.30-7.19 (m, 2H), 7.18-7.12 (m, 1H), 5.60 (s, 2H), 4.01-3.92 (m, 2H), 2.61-2.42 (m, 2H), 2.09 (s, 3H), 2.08-1.97 (m, 1H), 1.93-1.77 (m, 1H), 1.74-1.64 (m, 1H), 1.63-1.55 (m, 1H), 1.55-1.48 (m, 1H), 1.47-1.33 (m, 1H), 1.01-0.83 (m, 1H); LC-MS method B, (ES+) 421.2, RT=5.29 min.

Example 193

(R)—N-(1-Methyl-1H-pyrazol-4-yl)-1-((6-(((tetrahydrofuran-2-yl)methoxy)pyridin-2-yl)methyl)-1H-pyrazolo[3,4-d]pyrimidin-6-amine

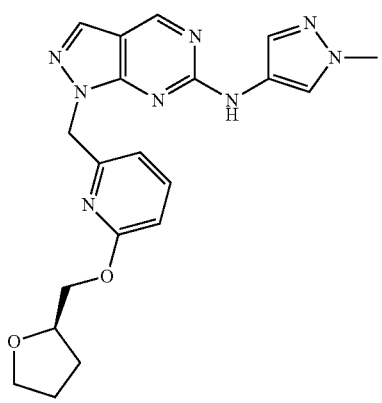 [SMILES: Cn1cc(Nc2ncc3cnn(Cc4cccc(OC[C@H]5CCCO5)n4)c3n2)cn1]

(R)-(Tetrahydrofuran-2-yl)methanol (22 mg, 0.214 mmol) was added to a solution of NaH (10 mg, 0.246 mmol) in dry DMF (1 mL) in a 2-necked flask under Nitrogen. Another portion of NaH (10 mg, 0.246 mmol) was added to a stirring solution of 1-((6-fluoropyridin-2-yl)methyl)-N-(1-methyl-1H-pyrazol-4-yl)-1H-pyrazolo[3,4-d]pyrimidin-6-amine (Example 170) (50 mg, 0.154 mmol) in DMF (1 ml). This solution was added to the 2-necked flask and stirred for 16 h at rt. The reaction was quenched with NH₄Cl (sat. solution, 1 mL) and diluted with Ethyl Acetate (20 mL). The organics were separated and washed with NaHCO₃ (sat. solution, 20 mL). The aqueous phase was re-extracted with Ethyl Acetate (2×10 mL). The combined organics were dried over Na₂SO₄, filtered and the solvent evaporated to give a crude product that was purified by prep HPLC. (R)—N-(1-methyl-1H-pyrazol-4-yl)-1-((6-(((tetrahydrofuran-2-yl)methoxy)pyridin-2-yl)methyl)-1H-pyrazolo[3,4-d]pyrimidin-6-amine was obtained as a white solid (24 mg, 38% yield). ¹H NMR (d₆-Acetone) δ 8.87 (s, 1H), 8.04 (s, 1H), 7.99 (s, 1H), 7.61 (s and t, 2H), 6.70 (d, 1H), 6.64 (d, 1H), 5.54 (s, 2H), 4.07 (m, 3H), 3.82 (s, 3H), 3.75 (m, 1H), 3.61 (m, 1H), 1.84 (m, 3H), 1.54 (m, 1H); LC-MS method B, (ES+) 407.1, RT=7.65 min.

Example 194

1-(2-Fluorobenzyl)-N-(1-(3-(4-methylpiperazin-1-yl)propyl)-1H-pyrazol-4-yl)-1H-pyrazolo[3,4-d]pyrimidin-6-amine The following compound was made according to the procedure in Example 1 using 1-(3-(4-methylpiperazin-1-yl)propyl)-1H-pyrazol-4-amine and 1-(bromomethyl)-2-fluorobenzene: 1-(3-(4-methylpiperazin-1-yl)propyl)-1H-pyrazol-4-amine was prepared as in Example 165 using 3-(4-methylpiperazin-1-yl)propan-1-ol:

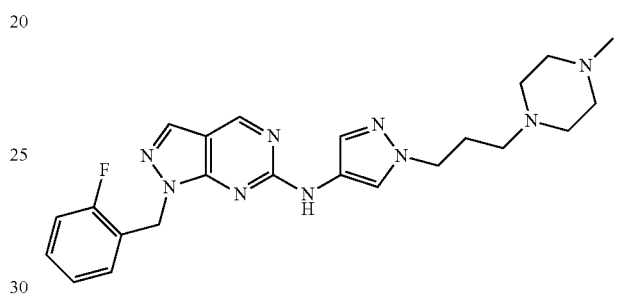

¹H NMR (d₆-DMSO) δ 8.91 (s, 1H), 8.46-8.44 (m, 2H), 8.04-8.00 (m, 2H), 7.71-7.56 (m, 2H), 7.47-7.29 (m, 2H), 4.72 (s, 2H), 4.13 (t, J=6.6 Hz, 2H), 3.65-3.28 (m, 4H), 2.98 (s, 3H), 2.94-2.82 (m, 2H), 2.64 (t, J=10.9 Hz, 2H), 2.38 (t, J=6.8 Hz, 2H), 1.95 (dd, J=13.2, 6.6 Hz, 2H); LC-MS method B, (ES+) 450.2, RT=4.18 min.

Example 195

N-(1-Methyl-1H-pyrazol-4-yl)-1-(3-(morpholinomethyl)benzyl)-1H-pyrazolo[3,4-d]pyrimidin-6-amine The following compound was made according to the procedure in Example 45 (Steps ii-iii) using (3-(morpholinomethyl)phenyl)methanol:

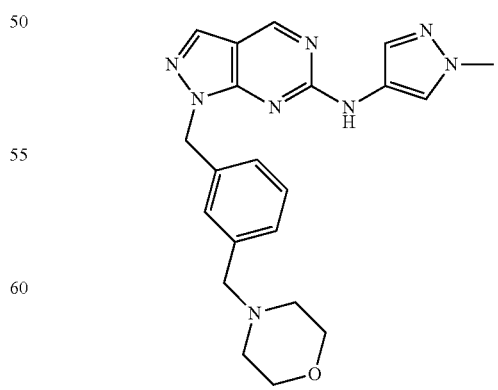

¹H NMR (d₆-DMSO) δ 9.83 (s, 1H), 8.92 (s, 1H), 8.05 (s, 1H), 8.00 (s, 1H), 7.56 (s, 1H), 7.31-7.22 (m, 2H), 7.22-7.14

(m, 2H), 5.55 (s, 2H), 3.83 (s, 3H), 3.50-3.44 (m, 4H), 3.39 (s, 2H), 2.30-2.21 (m, 4H); LC-MS method B, (ES+) 405.2, RT=4.52 min.

Example 196

2-(4-((1-(2,3,5,6-Tetrafluorobenzyl)-1H-pyrazolo[3,4-d]pyrimidin-6-yl)amino)-1H-pyrazol-1-yl)ethanol The following compound was made according to the procedure in Example 1, using 2-(4-amino-1H-pyrazol-1-yl)ethanol and 3-(bromomethyl)-1,2,4,5-tetrafluorobenzene. 2-(4-amino-1H-pyrazol-1-yl)ethano 1 was prepared as in Procedure A using 2-bromoethanol as alkylating agent

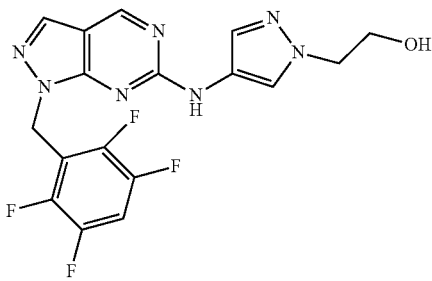 [SMILES: OCCn1cc(Nc2ncc3cnn(Cc4c(F)c(F)cc(F)c4F)c3n2)cn1]

$^1$H NMR (CDCl$_3$) δ 8.78 (s, 1H), 8.08 (s, 1H), 7.91 (s, 1H), 7.64 (s, 1H), 7.00-7.09 (m, 2H), 5.65 (s, 2H), 4.28-4.30 (m, 2H), 4.05-4.07 (m, 2H), 3.04 (br s, 1H); LC-MS method B, (ES+) 408, RT=7.68 min.

Example 197

N-(1-Methyl-1H-pyrazol-4-yl)-1-(3-(piperidin-1-yl)benzyl)-1H-pyrazolo[3,4-d]pyrimidin-6-amine The following compound was made according to the procedure in Example 162 using piperidine in Step (ii):

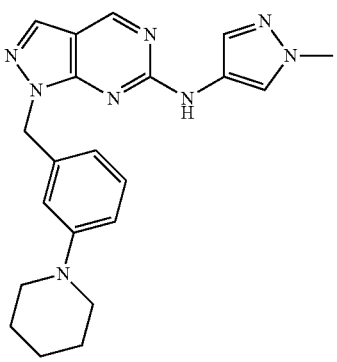 [SMILES: Cn1cc(Nc2ncc3cnn(Cc4cccc(N5CCCCC5)c4)c3n2)cn1]

$^1$H NMR (d$_6$-DMSO) δ 9.89-9.73 (m, 1H), 8.90 (s, 1H), 8.12-7.99 (m, 2H), 7.58 (s, 1H), 7.16-7.06 (m, 1H), 7.00 (s, 1H), 6.83-6.75 (m, 1H), 6.69-6.57 (m, 1H), 5.47 (s, 2H), 3.84 (s, 3H), 3.09-2.99 (m, 4H), 1.59-1.42 (m, 6H); LC-MS method B, (ES+) 389.2, RT=5.67 min.

Example 198

N-(1-Methyl-1H-pyrazol-4-yl)-1-(3-(tetrahydro-2H-pyran-4-yl)benzyl)-1H-pyrazolo[3,4-d]pyrimidin-6-amine

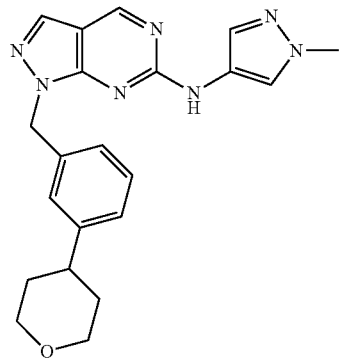 [SMILES: Cn1cc(Nc2ncc3cnn(Cc4cccc(C5CCOCC5)c4)c3n2)cn1]

Step (i)
1-(3-iodobenzyl)-N-(1-methyl-1H-pyrazol-4-yl)-1H-pyrazolo[3,4-d]pyrimidin-6-amine was made according to Example 1 using 1-(bromomethyl)-3-iodobenzene.

Step (ii)
1-(3-iodobenzyl)-N-(1-methyl-1H-pyrazol-4-yl)-1H-pyrazolo[3,4-d]pyrimidin-6-amine (50 mg, 0.12 mmol), 3,6-dihydro-2H-pyran-4-boronic acid pinacol ester (29 mg, 1.2 eq), sodium carbonate (31 mg, 2.5 eq) and bis(diphenylphosphino)-ferrocenedichloropalladium(II)-DCM-complex (5 mg, 0.05 eq) in ACN/water (1:1, 2 mL) were heated in the microwave for 30 min at 130° C. The reaction mixture was diluted with methanol, passed through a thiol column, washed with methanol and evaporated. The residue was dissolved in DCM, the organic phase washed with water, dried over sodium sulfate and concentrated in vacuo to afford 1-(3-(3,6-dihydro-2H-pyran-4-yl)benzyl)-N-(1-methyl-1H-pyrazol-4-yl)-1H-pyrazolo[3,4-d]pyrimidin-6-amine.

Step (iii)
1-(3-(3,6-dihydro-2H-pyran-4-yl)benzyl)-N-(1-methyl-1H-pyrazol-4-yl)-1H-pyrazolo[3,4-d]pyrimidin-6-amine was dissolved in methanol (8 mL) and palladium on carbon was added under an inert atmosphere. The reaction mixture was stirred overnight at rt under a hydrogen atmosphere. The mixture was filtered over Celite, then evaporated, and the residue was purified by preparative HPLC to afford the title compound (13 mg, 32 μmol, 38% over two steps). $^1$H NMR (d$_6$-DMSO) δ 9.84 (s, 1H), 8.91 (s, 1H), 8.11-8.02 (m, 2H), 7.58 (s, 1H), 7.31-7.22 (m, 2H), 7.19-7.14 (m, 1H), 7.13-7.07 (m, 1H), 5.54 (s, 2H), 3.94-3.86 (m, 2H), 3.85 (s, 3H), 3.44-3.35 (m, 2H), 2.75-2.65 (m, 1H), 1.66-1.54 (m, 4H); LC-MS method B, (ES+) 390.2, RT=8.40 min.

Example 199

N-(1-Methyl-1H-pyrazol-4-yl)-1-(3-(4-methylpiperazin-1-yl)benzyl)-1H-pyrazolo[3,4-d]pyrimidin-6-amine The following compound was made according to the procedure in Example 162 using N-methylpiperazine in Step (ii):

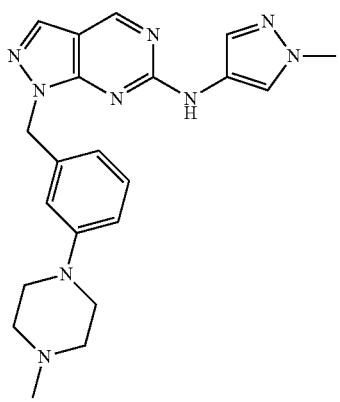 [SMILES: CN1CCN(c2cccc(Cn3ncc4cnc(Nc5cnn(C)c5)nc43)c2)CC1]

¹H NMR (d₆-DMSO) δ 9.84 (s, 1H), 8.91 (s, 1H), 8.07 (s, 1H), 8.04 (s, 1H), 7.59 (s, 1H), 7.16-7.09 (m, 1H), 7.03 (s, 1H), 6.85-6.79 (m, 1H), 6.69-6.61 (m, 1H), 5.48 (s, 2H), 3.84 (s, 3H), 3.08-3.00 (m, 4H), 2.43-2.34 (m, 4H), 2.19 (s, 3H); LC-MS method B, (ES+) 404.2, RT=5.00 min.

Example 200

N-(2-Methoxyethyl)-3-46-((1-methyl-1H-pyrazol-4-yl)amino)-1H-pyrazolo[3,4-d]pyrimidin-1-yl)methyl)benzamide The following compound was made according to the procedure in Example 191 using 2-methoxyethanamine:

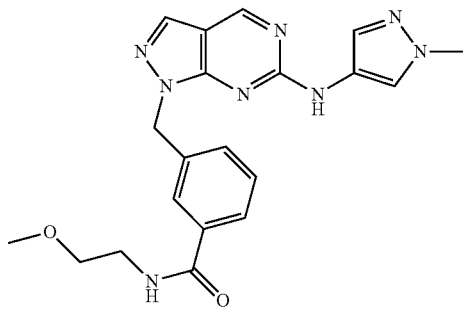

¹H NMR (d₆-DMSO) δ 9.85 (s, 1H), 8.92 (s, 1H), 8.51 (t, J=5.1 Hz, 1H), 8.07 (s, 1H), 8.02 (s, 1H), 7.82 (s, 1H), 7.78-7.72 (m, 1H), 7.53 (s, 1H), 7.45-7.37 (m, 2H), 5.60 (s, 2H), 3.83 (s, 3H), 3.46-3.35 (m, 4H), 3.32 (s, 3H); LC-MS method B, (ES+) 407.1, RT=6.65 min.

Example 201

N-(1-Methyl-1H-pyrazol-4-yl)-1-(2-methyl-3-morpholino benzyl)-1H-pyrazolo[3,4-d]pyrimidin-6-amine

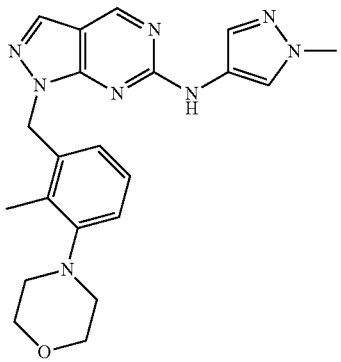

Step (i)

2-methyl-3-morpholinobenzoic acid (0.5 g, 2.26 mmol) was dissolved in dry THF (12 mL) under Nitrogen and the solution was cooled at 0° C. with an ice bath. A solution of BH₃ (1M in THF, 3.39 mL, 3.39 mmol) was added dropwise and the reaction was allowed to reach rt overnight. The mixture was quenched with NH₄Cl (sat. solution, 2 mL) and diluted with ethyl acetate (20 mL). The organics were separated, washed with water (10 mL) and brine (10 mL) and dried over Na₂SO₄. The filtered solution was evaporated under vacuum to give (2-methyl-3-morpholinophenyl)methanol as a crude oil which crystallized over 2 h (0.5 g, quantitative).

Step (ii)

(2-methyl-3-morpholinophenyl)methanol (0.468 g, 2.26 mmol) was dissolved in dry DCM (14 mL) with triethylamine (0.669 mL, 4.82 mmol) and this stirred solution was cooled at 0° C. in an ice bath. Mesyl chloride (0.415 g, 3.62 mmol) was added dropwise and the reaction was allowed to reach rt overnight. The mixture was diluted in DCM (25 mL), washed with water (20 mL) and the water re-extracted with DCM (20 mL). The combined organics were dried over Na₂SO₄, filtered and the solvent removed under vacuum to afford 4-(3-(chloromethyl)-2-methylphenyl)morpholine as a crude oil (0.5 g, 98% yield).

Step (iii)

The title compound was made according to the procedure in Example 1 (Step ii), using 4-(3-(chloromethyl)-2-methylphenyl)morpholine and 6-chloro-1H-pyrazolo[3,4-d]pyrimidine followed by Example 1 (Step i) using 4-(3-((6-chloro-1H-pyrazolo[3,4-d]pyrimidin-1-yl)methyl)-2-methylphenyl)morpholine and 1-methyl-1H-pyrazol-4-amine. ¹H NMR (d₆-Acetone) δ 8.86 (s and br s, 2H), 8.11 (s, 1H), 7.95 (s, 1H), 7.61 (s, 1H), 7.11 (t, 1H), 7.02 (d, 1H), 6.88 (bs, 1H), 5.57 (s, 2H), 3.85 (s, 3H), 3.78 (t, 4H), 2.82 (m, 4H), 2.44 (s, 3H). LC-MS method B, (ES+) 405.2, RT=8.33 min.

Example 202

N-Methyl-2-(4-((1-(3-morpholinobenzyl)-1H-pyrazolo[3,4-d]pyrimidin-6-yl)amino)-1H-pyrazol-1-yl)acetamide

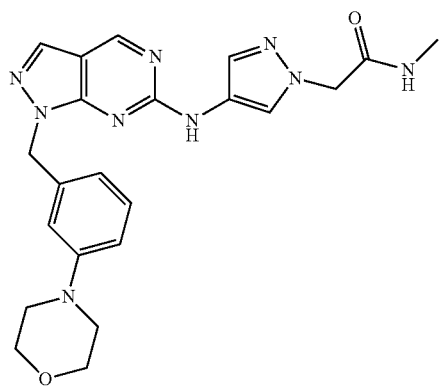 [SMILES: CNC(=O)Cn1cc(Nc2ncc3cnn(Cc4cccc(N5CCOCC5)c4)c3n2)cn1]

Step (i)

3-morpholinobenzyl methanesulfonate was prepared according to the procedure in Example 45 (Step ii) using (3-morpholinophenyl)methanol.

Step (ii)

2-(4-amino-1H-pyrazol-1-yl)acetamide was prepared according to Procedure A using 2-bromo-N-methylacetamide.

Step (iii)

The title compound was made according to the procedure in Example 1 (Step ii), using 3-morpholinobenzyl methanesulfonate and 6-chloro-1H-pyrazolo[3,4-d]pyrimidine followed by Example 1 (Step i) using 2-(4-amino-1H-pyrazol-1-yl)acetamide. $^1$H NMR (d$_6$-DMSO) δ 9.88 (s, 1H), 8.91 (s, 1H), 8.15 (s, 1H), 8.04 (s, 1H), 7.92-7.85 (m, 1H), 7.66 (s, 1H), 7.15 (t, J=7.9 Hz, 1H), 7.01 (s, 1H), 6.86-6.79 (m, 1H), 6.76-6.66 (m, 1H), 5.48 (s, 2H), 4.77 (s, 2H), 3.72-3.63 (m, 4H), 3.06-2.97 (m, 4H), 2.62 (d, J=4.6 Hz, 3H); LC-MS method B, (ES+) 448.2, RT=6.63 min.

Example 203

Ethyl 1-(3-((6-((1-methyl-1H-pyrazol-4-yl)amino)-1H-pyrazolo[3,4-d]pyrimidin-1-yl)methyl)phenyl)piperidine-3-carboxylate The following compound was made according to the procedure in Example 162 using ethyl piperidine-3-carboxylate in Step (ii):

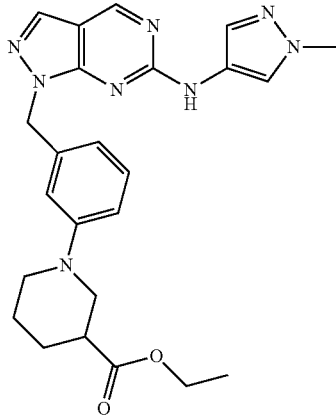 [SMILES: CCOC(=O)C1CCCN(c2cccc(Cn3ncc4cnc(Nc5cnn(C)c5)nc43)c2)C1]

$^1$H NMR (CD$_2$Cl$_2$) δ 8.78 (s, 1H), 7.92-7.87 (m, 2H), 7.55 (s, 1H), 7.32 (s, 1H), 7.18 (t, J=7.9 Hz, 1H), 6.97 (s, 1H), 6.90-6.82 (m, 1H), 6.80-6.72 (m, 1H), 5.47 (s, 2H), 4.11 (q, J=7.1 Hz, 2H), 3.86 (s, 3H), 3.67-3.59 (m, 1H), 3.44-3.35 (m, 1H), 3.03-2.94 (m, 1H), 2.84-2.72 (m, 1H), 2.61 (s, 1H), 1.96 (s, 1H), 1.75 (s, 1H), 1.63 (s, 2H), 1.23 (t, J=7.1 Hz, 3H); LC-MS method B, (ES+) 461.2, RT=8.95 min.

Example 204

3-(4-((1-(3-Morpholinobenzyl)-1H-pyrazolo[3,4-d]pyrimidin-6-yl)amino)-1H-pyrazol-1-yl)propanamide

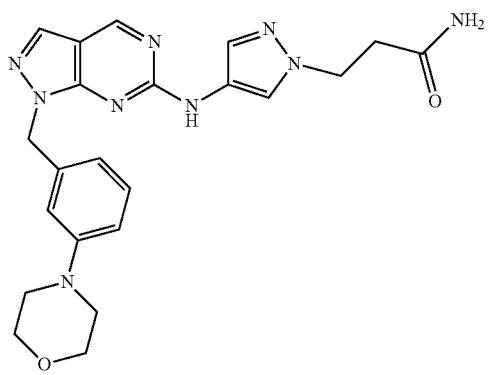 [SMILES: NC(=O)CCn1cc(Nc2ncc3cnn(Cc4cccc(N5CCOCC5)c4)c3n2)cn1]

The following compound was made according to the procedure in Example 186 using 3-chloropropanamide in Step (ii):

$^1$H NMR (d$_6$-DMSO) δ 9.83 (s, 1H), 8.90 (s, 1H), 8.13-8.00 (m, 2H), 7.62 (s, 1H), 7.41 (s, 1H), 7.16 (t, J=7.9 Hz, 1H), 7.04 (s, 1H), 6.89 (s, 1H), 6.86-6.79 (m, 1H), 6.72 (s, 1H), 5.49 (s, 2H), 4.30 (t, J=6.8 Hz, 2H), 3.72-3.63 (m, 4H), 3.06-2.98 (m, 4H), 2.61 (t, J=6.9 Hz, 2H); LC-MS method B, (ES+) 448.1, RT=6.41 min.

Example 205

1-(2-Fluoro-5-morpholinobenzyl)-N-(1-methyl-1H-pyrazol-4-yl)-1H-pyrazolo[3,4-d]pyrimidin-6-amine

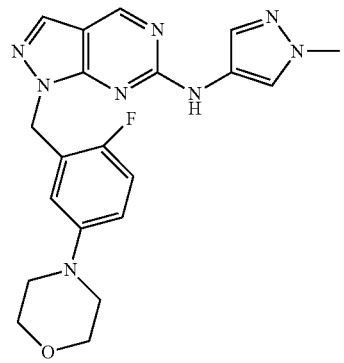 [SMILES: Cn1cc(Nc2ncc3cnn(Cc4cc(N5CCOCC5)ccc4F)c3n2)cn1]

Step (i)

To a solution of 5-Amino-2-fluoro benzyl alcohol (500 mg, 3.5 mmol) in toluene (12 mL) was added DIEA (2 eq) and 2-bromoethylether (1.5 eq) and the reaction heated to 90° C. for 18 h. The solvent was removed in vacuo and the residue partitioned between EtOAc and H$_2$O. The organic phase was dried (Na$_2$SO$_4$), filtered and concentrated in vacuo. The resultant residue was purified by column chromatography (petroleum ether: EtOAc) to give 2(2-fluoro-5-morpholinophenyl)methanol (550 mg, 74%) as a yellow oil.

Step (ii)

4-(3-(bromomethyl)-4-fluorophenyl)morpholine was prepared from 2(2-fluoro-5-morpholinophenyl)methanol using a method analogous to Example 209, (Step ii).

Step (iii)

The title compound was made according to the procedure in Example 1 (Step ii) using 4-(3-(bromomethyl)-4-fluorophenyl)morpholine. $^1$H NMR (CDCl$_3$) δ 8.77 (s, 1H), 8.03 (s, 1H), 7.93 (s, 1H), 7.56 (s, 1H), 7.16 (br s, 1H), 7.00 (t, 1H), 6.76-6.86 (m, 2H), 5.57 (s, 2H), 3.94 (s, 3H), 3.77 (t, 4H), 2.98 (t, 4H); LC-MS method B, (ES+) 409, RT=7.67 min.

Example 206

1-(3-(2-Aminopyridin-4-yl)benzyl)-N-(1-methyl-1H-pyrazol-4-yl)-1H-pyrazolo[3,4-d]pyrimidin-6-amine

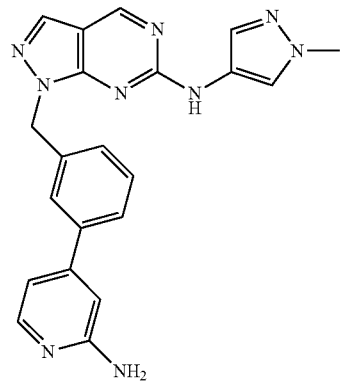 [SMILES: Cn1cc(Nc2ncc3cnn(Cc4cccc(-c5ccnc(N)c5)c4)c3n2)cn1]

Step (i)

2-amino-4-bromopyridine (0.50 g, 2.9 mmol), bis(pinacolato)diboron (1.1 g, 1.5 eq), tris(dibenzylideneacetone)dipalladium (0) (0.13 g, 0.05 eq), X-phos (0.14 g, 0.1 eq) and potassium acetate (0.57 mg, 2 eq) were mixed in dioxane (2.5 ml) under nitrogen before being heated at 110° C. for 4 h. After cooling to rt, the reaction mixture was diluted with methanol, passed through a thiol cartridge and evaporated to afford 4-(4,4,5,5-tetramethyl-1,3,2-dioxaborolan-2-yl)pyridin-2-amine which was used without further purification.

Step (ii)

The Suzuki reaction was carried out as described in Example 198 (Step ii) using 4-(4,4,5,5-tetramethyl-1,3,2-dioxaborolan-2-yl)pyridin-2-amine to afford the title compound after purification with the preparative HPLC (5.6 mg, 14 μmol, 12%). $^1$H NMR (d$_6$-DMSO) δ 9.86 (s, 1H), 8.92 (s, 1H), 8.07 (s, 2H), 7.93 (d, J=5.3 Hz, 1H), 7.66 (s, 1H), 7.60-7.50 (m, 2H), 7.44 (t, J=7.7 Hz, 1H), 7.38-7.28 (m, 1H), 6.70-6.65 (m, 1H), 6.63 (s, 1H), 5.96 (s, 2H), 5.64 (s, 2H), 3.81 (s, 3H); LC-MS method B, (ES+) 398.1, RT=4.98 min.

Example 207

N,N-Dimethyl-3-(4-41-(3-morpholinobenzyl)-1H-pyrazolo[3,4-d]pyrimidin-6-yl)amino)-1H-pyrazol-1-yl)propanamide

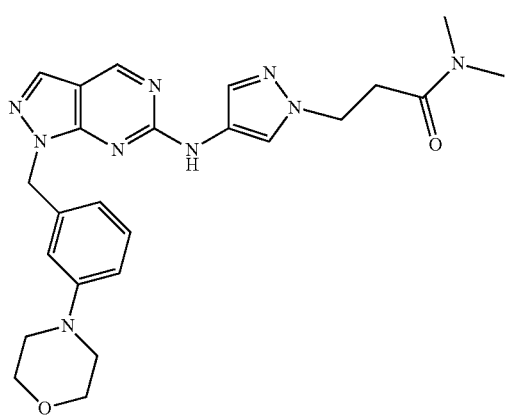 [SMILES: CN(C)C(=O)CCn1cc(Nc2ncc3cnn(Cc4cccc(N5CCOCC5)c4)c3n2)cn1]

Step (i)

3-(4-amino-1H-pyrazol-1-yl)-N,N-dimethylpropanamide was made according to the procedure in Example 165 using 3-hydroxy-N,N-dimethylpropanamide.

Step (ii)

3-morpholinobenzyl methanesulfonate was prepared according to the procedure in Example 45 (Step ii) using (3-morpholinophenyl)methanol.

Step (iii)

The title compound was made according to the procedure in Example 1 (Step ii), using 3-morpholinobenzyl methanesulfonate and 6-chloro-1H-pyrazolo[3,4-d]pyrimidine followed by Example 1 (Step i) using 3-(4-amino-1H-pyrazol-1-yl)-N,N-dimethylpropanamide. $^1$H NMR (d$_6$-DMSO) δ 9.83 (s, 1H), 8.90 (s, 1H), 8.17 (s, 1H), 8.03 (s, 1H), 7.60 (s, 1H), 7.18-7.11 (m, 1H), 7.06 (s, 1H), 6.87-6.79 (m, 1H), 6.77-6.68 (m, 1H), 5.49 (s, 2H), 4.32 (t, J=6.8 Hz, 2H), 3.70-3.63 (m, 4H), 3.05-2.98 (m, 4H), 2.89 (s, 3H), 2.84 (t, J=6.9 Hz, 2H), 2.80 (s, 3H); LC-MS method B, (ES+) 476.2, RT=7.15 min.

Example 208

(R)-1-(6-(((6-((1-Methyl-1H-pyrazol-4-yl)amino)-1H-pyrazolo[3,4-d]pyrimidin-1-yl)methyl)pyridin-2-yl)pyrrolidin-3-ol The following compound was made according to the procedure in Example 188 using pyrrolidin-3-ol:

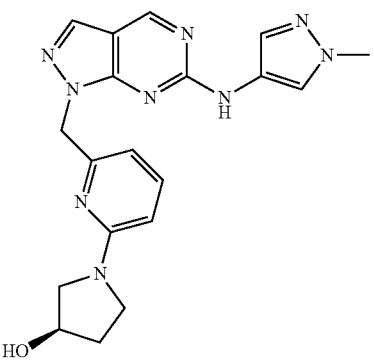 [SMILES: Cn1cc(Nc2ncc3cnn(Cc4cccc(N5CC[C@@H](O)C5)n4)c3n2)cn1]

$^1$H NMR (d$_6$-DMSO) δ 9.77 (br s, 1H), 8.93 (s, 1H), 8.07 (s, 1H), 7.94 (s, 1H), 7.53 (s, 1H), 7.37 (t, 1H), 6.29 (d, 1H), 6.14 (br s, 1H), 5.44 (s, 2H), 4.90 (d, 1H), 4.34 (s, 1H), 3.79 (s, 3H), 3.38 (m, 3H), 3.24 (m, 1H), 1.97 (m, 1H), 1.85 (m, 1H); LC-MS method B, (ES+) 392.1, RT=4.51 min.

Example 209

2-(3-((64(1-Methyl-1H-pyrazol-4-yl)amino)-1H-pyrazolo[3,4-d]pyrimidin-1-yl)methyl)phenoxy)acetamide

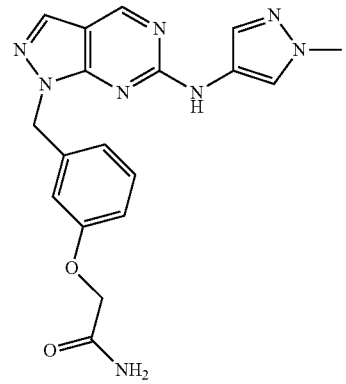 [SMILES: Cn1cc(Nc2ncc3cnn(Cc4cccc(OCC(N)=O)c4)c3n2)cn1]

Step (i)

To a solution of 3-hydroxybenzyl alcohol (500 mg, 4 mmol) in acetonitrile (10 mL) was added 2-bromoacetamide (1 eq) and potassium carbonate (1 eq). The resulting suspension was stirred at rt for 18 h. The solvent was removed in vacuo and the residue partitioned between EtOAc and H$_2$O. The aqueous layer was acidified with dilute HCl (2M) and then re-extracted with EtOAc (3×50 mL). The organic phases were combined, dried (Na$_2$SO$_4$), filtered and concentrated in vacuo. The resultant residue was purified by column chromatography (EtOAc: methanol) to give 2-(3-(hydroxymethyl)phenoxy)acetamide (320 mg, 43%).

Step (ii)

2-(3-(hydroxymethyl)phenoxy)acetamide (320 mg, 1.76 mmol) was suspended in dichloromethane (12 mL) and the suspension cooled to 0° C. (ice bath). Phosphorus tribromide (1.5 eq) was added slowly and the reaction allowed to warm to rt. After stirring for 18 h the reaction was quenched by addition of NaHCO₃ (sat., aq). The product was extracted with dichloromethane, dried (Na₂SO₄), filtered and concentrated in vacuo to afford 2-(3-(bromomethyl)phenoxy)acetamide as a white solid.

Step (iii)

The title compound was made according to the procedure in Example 1 (Step ii) using 2-(3-(bromomethyl)phenoxy)acetamide. $^1$H NMR (d$_6$-DMSO) δ 9.84 (br s, 1H), 8.92 (s, 1H), 8.06 (s, 1H), 8.02 (s, 1H), 7.56 (s, 1H), 7.50 (s, 1H), 7.27 (s, 1H), 7.24 (t, 1H), 6.83-6.91 (m, 3H), 5.52 (s, 2H), 4.36 (s, 2H), 3.83 (s, 3H); LC-MS method B, (ES+) 379, RT=6.37 min Example 210

N-(1-Methyl-1H-pyrazol-4-yl)-1-(2,3,6-trifluoro-5-morpholinobenzyl)-1H-pyrazolo[3,4-d]pyrimidin-6-amine

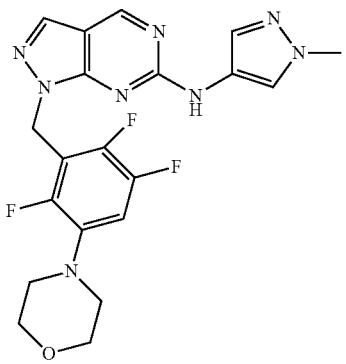 [SMILES: Cn1cc(Nc2ncc3cnn(Cc4c(F)c(F)cc(N5CCOCC5)c4F)c3n2)cn1]

Step (i)

A solution of 3-Amino-2,5,6-trifluoro benzoic acid (500 mg, 2.6 mmol) in THF (4 mL) was cooled to 0° C. (ice bath). Borane (2.5 eq., 1M in THF) was added dropwise over 20 min. The reaction was allowed to warm slowly to rt and stirred at rt for 18 h. The reaction was quenched by addition of saturated NH₄Cl (aq) and extracted with EtOAc. The organic phase was washed with H₂O then brine, dried (Na₂SO₄), filtered and concentrated in vacuo to give (3-amino-2,5,6-trifluorophenyl)methanol as a pale brown solid (425 mg, 92%)

Step (ii)

To a solution of (3-amino-2,5,6-trifluorophenyl)methanol (200 mg, 1.1 mmol) in DMF (3 mL) was added DIEA (1.6 mL) and 2-bromoethylether (5 eq) and the reaction heated to 80° C. for 18 h. The reaction was allowed to cool to rt, diluted with EtOAc and washed with H₂O then saturated NH₄Cl (aq). The organic phase was dried (Na₂SO₄), filtered and concentrated in vacuo. The resultant residue was purified by column chromatography (petroleum ether: EtOAc) to give (2,3,6-trifluoro-5-morpholinophenyl)methanol (110 mg, 48%).

Step (iii)

4-(3-(bromomethyl)-2,4,5-trifluorophenyl)morpholine was prepared from (2,3,6-trifluoro-5-morpholinophenyl)methanol using a method analogous to Example 209, step (ii).

Step (iv)

The title compound was made according to the procedure in Example 1 (Step ii), using 4-(3-(bromomethyl)-2,4,5-trifluorophenyl)morpholine. $^1$H NMR (CDCl₃) δ 8.70 (s, 1H), 8.00 (s, 1H), 7.86 (s, 1H), 7.57 (s, 1H), 6.70-6.77 (m, 1H), 5.57 (s, 2H), 3.90 (s, 3H), 3.78 (t, 4H), 2.95 (t, 4H); LC-MS method B, (ES+) 445, RT=8.28 min.

Example 211

3-(4-((1-(3-Morpholinobenzyl)-1H-pyrazolo[3,4-d]pyrimidin-6-yl)amino)-1H-pyrazol-1-yl)propan-1-ol The following compound was made according to the procedure in Example 202 using 3-bromopropan-1-ol in Step (ii):

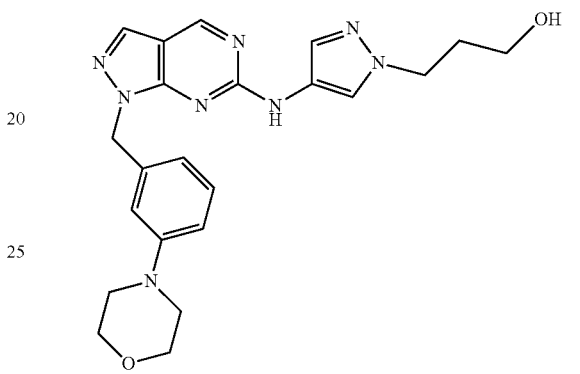

$^1$H NMR (d$_6$-DMSO) δ 9.82 (s, 1H), 8.90 (s, 1H), 8.10-7.99 (m, 2H), 7.62 (s, 1H), 7.18-7.09 (m, 1H), 6.99 (s, 1H), 6.85-6.81 (m, 1H), 6.75-6.68 (m, 1H), 5.47 (s, 2H), 4.57 (t, 1H), 4.14 (t, J=7.0 Hz, 2H), 3.71-3.62 (m, 4H), 3.41 (dd, 2H), 3.05-2.96 (m, 4H), 1.95-1.85 (m, 2H); LC-MS method B, (ES+) 435.2, RT=6.84 min.

Example 212

1-(3-(4,4-Difluoropiperidin-1-yl)benzyl)-N-(1-methyl-1H-pyrazol-4-yl)-1H-pyrazolo[3,4-d]pyrimidin-6-amine The following compound was made according to the procedure in Example 162 using 4,4-difluoropiperidine in Step (ii):

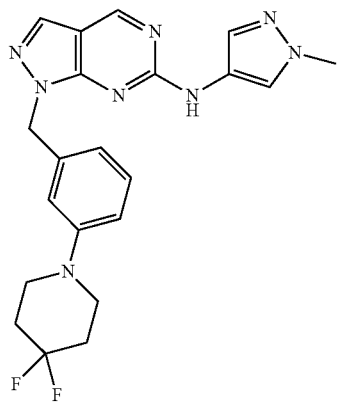 [SMILES: Cn1cc(Nc2ncc3cnn(Cc4cccc(N5CCC(F)(F)CC5)c4)c3n2)cn1]

$^1$H NMR (CD₂Cl₂) δ 8.68 (s, 1H), 7.84 (s, 1H), 7.78 (s, 1H), 7.52 (s, 2H), 7.16-7.04 (m, 1H), 6.89 (s, 1H), 6.81-6.68 (m, 2H), 5.39 (s, 2H), 3.79 (s, 3H), 3.26-3.12 (m, 4H), 2.02-1.85 (m, 4H); LC-MS method B, (ES+) 425.1, RT=9.06 min.

Example 213

3-(4-((1-(3-Morpholinobenzyl)-1H-pyrazolo[3,4-d]pyrimidin-6-yl)amino)-1H-pyrazol-1-yl)-1-(piperidin-1-yl)propan-1-one

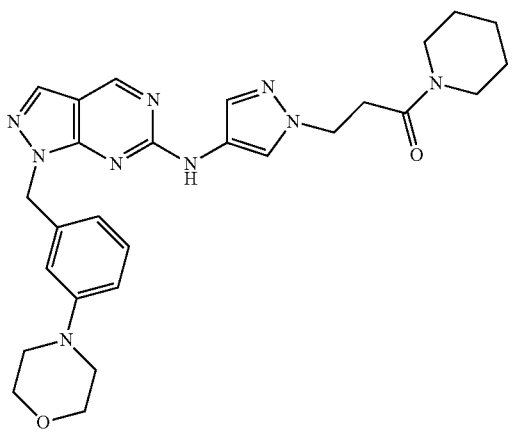 [SMILES: O=C(CCn1cc(Nc2ncc3cnn(Cc4cccc(N5CCOCC5)c4)c3n2)cn1)N1CCCCC1]

Step (i)

4-Nitro-1H-pyrazole (0.50 g, 4.4 mmol) was dissolved in DMF (5 mL). After addition of methyl-3-bromopropionate (0.72 mL, 1.5 eq) and potassium carbonate (0.92 g, 1.5 eq), the reaction mixture was stirred at 50° C. for 3 h, then partitioned between water and DCM. The aqueous phase was extracted with DCM, the combined organic phases dried over sodium sulfate and evaporated. The residue was hydrolyzed at rt over 30 min with lithium hydroxide (3M, aqueous) (4.4 mL, 3 eq) in methanol (5 mL) and the reaction mixture evaporated to dryness to afford 3-(4-nitro-1H-pyrazol-1-yl)propanoic acid in a quantitative yield.

Step (ii)

To a solution of 3-(4-nitro-1H-pyrazol-1-yl)propanoic acid (4.4 mmol) in 5 mL DMF were added diisopropylethylamine (1.2 mL, 1.5 eq), piperidine (0.66 mL, 1.5 eq), 1-hydroxybenzotriazole (0.90 g, 1.5 eq) and N-(3-Dimethylaminopropyl)-N'-ethylcarbodiimide (1.27 g, 1.5 eq). After stirring at rt for 17 h, saturated sodium bicarbonate was added and the aqueous phase extracted with DCM. The combined organic phases were dried over sodium sulfate and evaporated to afford 3-(4-nitro-1H-pyrazol-1-yl)-1-(piperidin-1-yl)propan-1-one in quantitative yield.

Step (iii)

3-(4-nitro-1H-pyrazol-1-yl)-1-(piperidin-1-yl)propan-1-one (4.4 mmol) was dissolved in 5 mL methanol and palladium on carbon added under an inert atmosphere. The reaction mixture was stirred overnight at rt under hydrogen atmosphere. The resulting mixture was filtered through Celite and the filtrate concentrated in vacuo to give 3-(4-amino-1H-pyrazol-1-yl)-1-(piperidin-1-yl)propan-1-one in a quantitative yield.

Step (iv)

The title compound was made according to the procedure in Example 186 (Steps i and iii) using 3-(4-amino-1H-pyrazol-1-yl)-1-(piperidin-1-yl)propan-1-one. $^1$H NMR (d$_6$-DMSO) δ 9.82 (s, 1H), 8.90 (s, 1H), 8.18 (s, 1H), 8.03 (s, 1H), 7.60 (s, 1H), 7.18-7.12 (m, 1H), 7.06 (s, 1H), 6.83 (dd, J=8.2, 2.0 Hz, 1H), 6.77-6.70 (m, 1H), 5.49 (s, 2H), 4.33 (t, J=6.8 Hz, 2H), 3.75-3.61 (m, 5H), 3.43-3.36 (m, 2H), 3.08-2.96 (m, 5H), 2.84 (t, J=6.9 Hz, 2H), 1.59-1.48 (m, 2H), 1.45-1.32 (m, 4H); LC-MS method B, (ES+) 516.2, RT=8.22 min.

Example 214

1-(2-Fluoro-3-morpholinobenzyl)-N-(1-methyl-1H-pyrazol-4-yl)-1H-pyrazolo[3,4-d]pyrimidin-6-amine

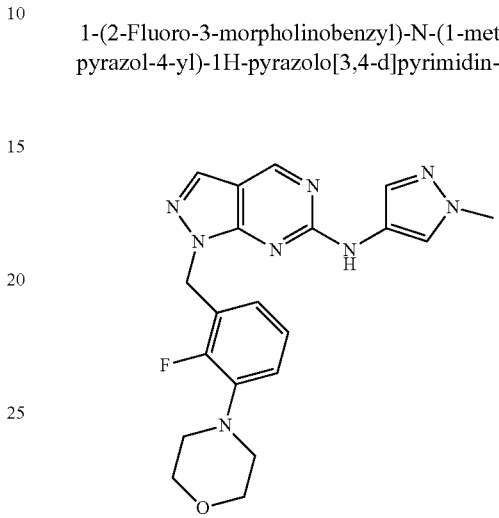

Step (i)

To a solution of 3-amino-2-fluoro benzoic acid (500 mg, 3.1 mmol) in DMF (10 mL) was added DIEA (4.5 mL) and 2-bromoethylether (5 eq) and the reaction heated to 80° C. for 18 h. The reaction was allowed to cool to rt, diluted with EtOAc and washed with saturated NH$_4$Cl (aq). The organic phase was dried (Na$_2$SO$_4$), filtered and concentrated in vacuo. The resultant residue was purified by column chromatography (petroleum ether: EtOAc) to give 2-(2-bromoethoxy)ethyl 2-fluoro-3-morpholinobenzoate (450 mg, 38%) as a yellow oil.

Step (ii)

To a solution of 2-(2-bromoethoxy)ethyl 2-fluoro-3-morpholinobenzoate (450 mg, 1.2 mmol) in THF (5 mL) was added lithium borohydride (1.5 eq) and the reaction stirred at rt for 18 h. The reaction was quenched by addition of saturated NH$_4$Cl (aq) and extracted with EtOAc. The organic phase was dried (Na$_2$SO$_4$), filtered and concentrated in vacuo. The resultant residue was purified by column chromatography (petroleum ether: EtOAc) to give (2-fluoro-3-morpholinophenyl)methanol.

Step (iii)

4-(3-(bromo methyl)-2-fluorophenyl)morpholine was prepared from (2-fluoro-3-morpholinophenyl)methanol using a method analogous to Example 209, (Step ii).

Step (iv)

The title compound was made according to the procedure in Example 1 (Step ii), using 443-(bromomethyl)-2-fluorophenyl)morpholine. $^1$H NMR (d$_4$-Methanol) δ 8.86 (s, 1H), 8.10 (s, 1H), 8.00 (s, 1H), 7.65 (s, 1H), 6.97-7.07 (m, 2H), 6.87 (br t, 1H), 5.63 (s, 2H), 3.92 (s, 3H), 3.84 (t, 4H), 3.06 (t, 4H); LC-MS method B, (ES+) 409, RT=7.92 min.

Example 215

N-(1-Methyl-1H-pyrazol-4-yl)-1-(3-(piperazin-1-yl)benzyl)-1H-pyrazolo[3,4-d]pyrimidin-6-amine

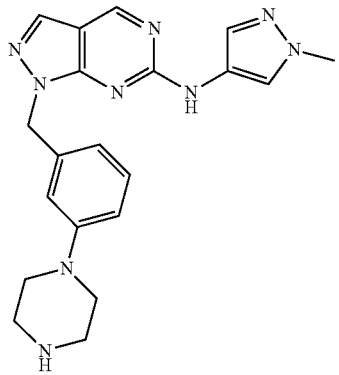 [SMILES: Cn1cc(Nc2ncc3cnn(Cc4cccc(N5CCNCC5)c4)c3n2)cn1]

Step (i)
tert-Butyl-4-(3-(ethoxycarbonyl)phenyl)piperazine-1-carboxylate (0.20 g, 0.60 mmol) was dissolved in THF (1 mL) and lithium borohydride (0.10 g, 7.5 eq) was added in three portions. The reaction mixture stirred at rt for 48 h then quenched with saturated ammonium chloride under ice-cooling. The aqueous phase was extracted with DCM and the combined organic phases dried over sodium sulfate and evaporated to afford tert-butyl 4-(3-(hydroxymethyl)phenyl)piperazine-1-carboxylate (0.16 mg, 0.54 mmol, 90%).

Step (ii)
tert-Butyl-4-(3-(((methylsulfonyl)oxy)methyl)phenyl)piperazine-1-carboxylate was made according to Example 45 (Step ii) using tert-butyl 4-(3-(hydroxymethyl)phenyl)piperazine-1-carboxylate.

Step (iii)
tert-Butyl-4-(3-((6-((1-methyl-1H-pyrazol-4-yl)amino)-1H-pyrazolo[3,4-d]pyrimidin-1-yl)methyl)phenyl)piperazine-1-carboxylate was made according to Example 1 using tert-Butyl 4-(3-(((methylsulfonyl)oxy)methyl)phenyl)piperazine-1-carboxylate.

Step (iv)
tert-Butyl-4-(3-((6-((1-methyl-1H-pyrazol-4-yl)amino)-1H-pyrazolo[3,4-d]pyrimidin-1-yl)methyl)phenyl)piperazine-1-carboxylate (1.10 g, 2.25 mmol) was treated with TFA/DCM (1:2, 12 mL) for 1 h at rt. After evaporation to dryness, the residue was purified by preparative HPLC to afford the title compound (103 mg, 0.26 mmol, 12% over two steps). $^1$H NMR (d$_6$-DMSO) δ 9.83 (s, 1H), 8.90 (s, 1H), 8.08 (s, 1H), 8.04 (s, 1H), 7.58 (s, 1H), 7.18-7.06 (m, 1H), 7.00 (s, 1H), 6.84-6.75 (m, 1H), 6.73-6.58 (m, 1H), 5.48 (s, 2H), 3.84 (s, 3H), 2.99-2.91 (m, 4H), 2.79-2.71 (m, 4H), 2.22 (br s, 1H); LC-MS method B, (ES+) 390.1, RT=4.93 min.

Example 216

N-(1-(2,2-Difluoroethyl)-1H-pyrazol-4-yl)-1-(3-morpholinobenzyl)-1H-pyrazolo[3,4-d]pyrimidin-6-amine The following compound was made according to the procedure in Example 202 using 2,2-difluoromethane sulfonate as alkylating agent in Step (ii):

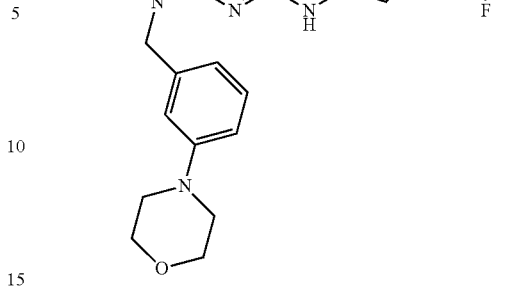

$^1$H NMR (d$_6$-DMSO) δ 9.90 (s, 1H), 8.92 (s, 1H), 8.21 (s, 1H), 8.05 (s, 1H), 7.70 (s, 1H), 7.21-7.07 (m, 1H), 7.00 (s, 1H), 6.83 (dd, J=8.2, 2.0 Hz, 1H), 6.72 (s, 1H), 6.34 (tt, J=55.1, 3.8 Hz, 1H), 5.49 (s, 2H), 4.62 (td, J=15.0, 3.8 Hz, 2H), 3.76-3.60 (m, 4H), 3.09-2.93 (m, 4H); LC-MS method B, (ES+) 441.2, RT=8.22 min.

Example 217

N-Methyl-3-(4-41-(3-morpholinobenzyl)-1H-pyrazolo[3,4-d]pyrimidin-6-yl)amino)-1H-pyrazol-1-yl)propanamide The following compound was made according to the procedure in Example 202, using 3-chloro-N-methylpropanamide in Step (ii):

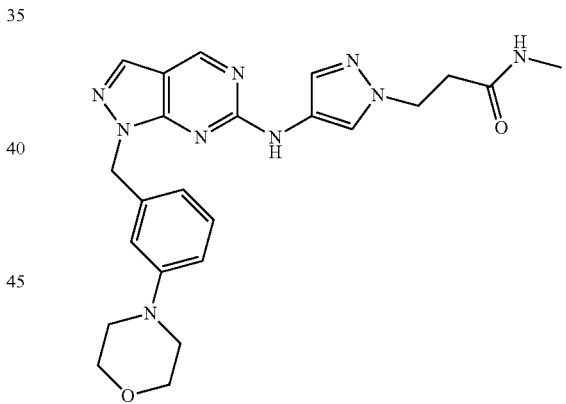

$^1$H NMR (d$_6$-DMSO) δ 9.82 (s, 1H), 8.90 (s, 1H), 8.07 (s, 1H), 8.03 (s, 1H), 7.86 (m, 1H), 7.60 (s, 1H), 7.15 (m, 1H), 7.03 (s, 1H), 6.83 (m, 1H), 6.72 (m, 1H), 5.49 (s, 2H), 4.30 (t, J=6.9 Hz, 2H), 3.71-3.64 (m, 4H), 3.06-2.98 (m, 4H), 2.60 (t, J=6.9 Hz, 2H), 2.55 (d, J=4.6 Hz, 3H); LC-MS method B, (ES+) 462.2, RT=6.72 min.

Example 218

1-(3-(3,6-Dihydro-2H-pyran-4-yl)benzyl)-N-(1-methyl-1H-pyrazol-4-yl)-1H-pyrazolo[3,4-d]pyrimidin-6-amine The following compound was made according to the procedure in Example 198 (Steps i and ii):

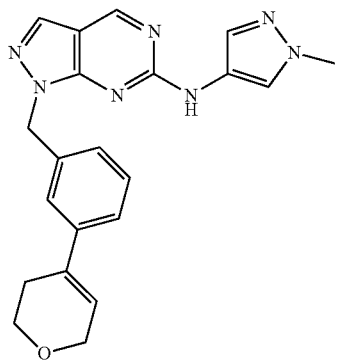 [SMILES: Cn1cc(Nc2ncc3cnn(Cc4cccc(C5=CCOCC5)c4)c3n2)cn1]

¹H NMR (d₆-DMSO) δ 9.84 (s, 1H), 8.91 (s, 1H), 8.11-8.03 (m, 2H), 7.58 (s, 1H), 7.51 (s, 1H), 7.38-7.26 (m, 2H), 7.20-7.13 (m, 1H), 6.20-6.13 (m, 1H), 5.57 (s, 2H), 4.17 (m, 2H), 3.83 (s, 3H), 3.77 (m, 2H), 2.36 (m, 2H); LC-MS method B, (ES+) 388.1, RT=8.19 min.

Example 219

6-(6-((1-Methyl-1H-pyrazol-4-yl)amino)-1H-pyrazolo[3,4-d]pyrimidin-1-yl)-2H-benzo[b][1,4]oxazin-3(4H)-one The following compound was made according to the procedure in Example 17 (Step iii), using 6-bromo-2H-benzo[b][1,4]oxazin-3(4H)-one:

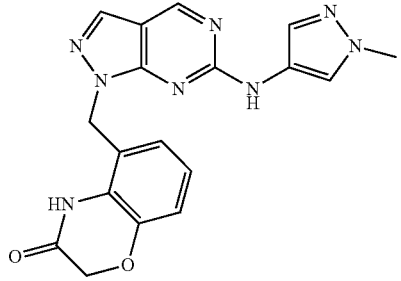 [SMILES: Cn1cc(Nc2ncc3cnn(Cc4cccc5c4NC(=O)CO5)c3n2)cn1]

¹H NMR (d₆-DMSO) δ 10.96 (s, 1H), 10.01 (s, 1H), 9.00 (s, 1H), 8.26 (s, 1H), 8.00 (s, 1H), 7.65-7.69 (m, 1H), 7.62 (s, 1H), 7.54 (s, 1H), 7.19 (d, 1H), 4.67 (s, 2H), 3.82 (s, 3H); LC-MS method B, (ES+) 363.0, RT=6.97 min.

Example 220

N-(1-Methyl-1H-pyrazol-4-yl)-1-(naphthalen-1-ylmethyl)-1H-pyrazolo[3,4-d]pyrimidin-6-amine The title compound was made according to the procedure in Example 1 (Step ii), using 1-(bromomethyl)naphthalene in Step (ii):

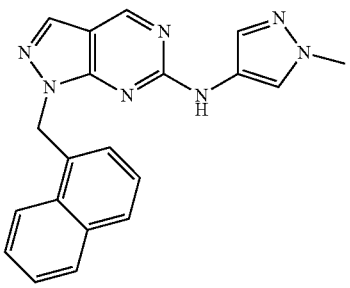 [SMILES: Cn1cc(Nc2ncc3cnn(Cc4cccc5ccccc45)c3n2)cn1]

¹H NMR (d₆-DMSO) δ 9.92 (br s, 1H), 8.94 (s, 1H), 8.40 (d, J=7.0 Hz, 1H), 8.06 (s and s, 2H), 7.95 (d, 1H), 7.90 (d, J=8.5 Hz, 1H), 7.61-7.33 (m, 5H), 6.01 (s, 2H), 3.78 (s, 3H); LC-MS method B, (ES+) 356.0, RT=8.91 min.

Example 221

1-(2-(2-(Benzyloxy)ethoxy)benzyl)-N-(1-methyl-1H-pyrazol-4-yl)-1H-pyrazolo[3,4-d]pyrimidin-6-amine The title compound was made according to the procedure in Example 171 using 2-hydroxybenzaldehyde and 2-benzyloxyethanol:

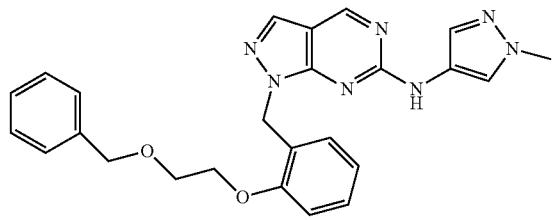 [SMILES: Cn1cc(Nc2ncc3cnn(Cc4ccccc4OCCOCc4ccccc4)c3n2)cn1]

¹H NMR (d₆-DMSO) δ 9.85 (s, 1H), 8.91 (s, 1H), 8.15-7.95 (m, 2H), 7.56 (s, 1H), 7.39-7.14 (m, 6H), 6.91 (s, 1H), 6.88-6.81 (m, 2H), 5.52 (s, 2H), 4.51 (s, 2H), 4.14-4.01 (m, 2H), 3.82 (s, 3H), 3.75-3.67 (m, 2H); LC-MS method B, (ES+) 456.1, RT=9.68 min.

Example 222

1-(3-(2-(Benzyloxy)ethoxy)benzyl)-N-(1-methyl-1H-pyrazol-4-yl)-1H-pyrazolo[3,4-d]pyrimidin-6-amine The title compound was made according to the procedure in Example 166 (Steps i-ii):

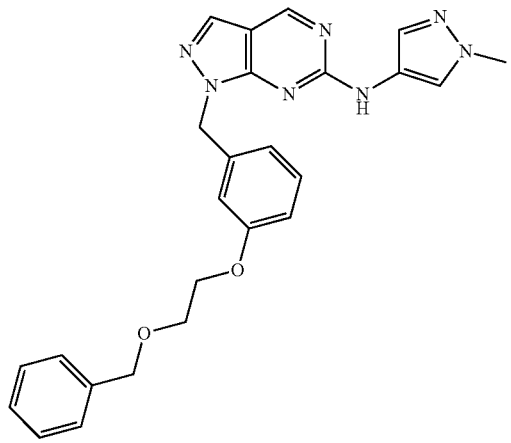 [SMILES: Cn1cc(Nc2ncc3cnn(Cc4cccc(OCCOCc5ccccc5)c4)c3n2)cn1]

¹H NMR (d₆-DMSO) δ 9.85 (s, 1H), 8.91 (s, 1H), 8.15-7.95 (m, 2H), 7.56 (s, 1H), 7.39-7.14 (m, 6H), 6.91 (s, 1H), 6.88-6.81 (m, 2H), 5.52 (s, 2H), 4.51 (s, 2H), 4.14-4.01 (m, 2H), 3.82 (s, 3H), 3.75-3.67 (m, 2H); LC-MS method B, (ES+) 456.1, RT=9.68 min.

Example 223

4-(3-((6-((1-Methyl-1H-pyrazol-4-yl)amino)-1H-pyrazolo[3,4-d]pyrimidin-1-yl)methyl)phenyl)thiomorpholine 1,1-dioxide The title compound was made according to the procedure in Example 162 using thiomorpholine 1,1-dioxide in Step (ii):

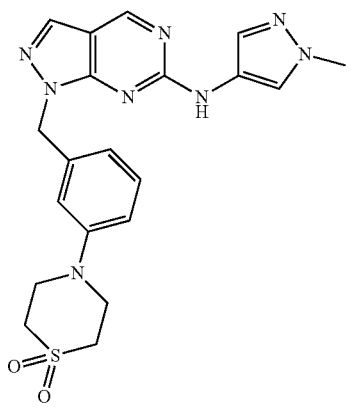 [SMILES: Cn1cc(Nc2ncc3cnn(Cc4cccc(N5CCS(=O)(=O)CC5)c4)c3n2)cn1]

¹H NMR (d₆-Acetone) δ 8.90 (s, 1H), 8.86 (s, 1H), 8.15 (s, 1H), 7.96 (s, 1H), 7.70 (s, 1H), 7.28-7.18 (m, 2H), 6.98 (dd, J=8.0, 2.4 Hz, 1H), 6.85 (d, J=7.2 Hz, 1H), 5.55 (s, 2H), 3.90 (s, 3H), 3.86-3.76 (m, 4H), 3.07-2.97 (m, 4H). LC-MS method B, (ES+) 439.0, RT=7.05 min.

Example 224

N-(1-Methyl-1H-pyrazol-4-yl)-1-(2-phenoxybenzyl)-1H-pyrazolo[3,4-d]pyrimidin-6-amine The title compound was made according to the procedure in Example 1 (Step ii), using 1-(bromomethyl)-2-phenoxybenzene:

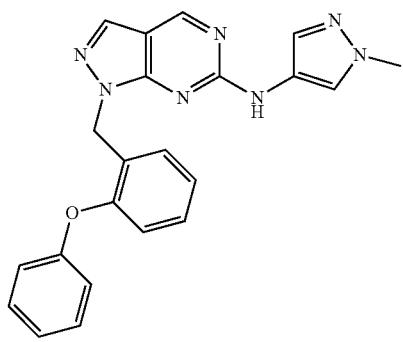 [SMILES: Cn1cc(Nc2ncc3cnn(Cc4ccccc4Oc4ccccc4)c3n2)cn1]

¹H NMR (d₆-DMSO) δ 9.77 (br s, 1H), 8.85 (s, 1H), 8.01 (s, 1H), 7.94 (s, 1H), 7.54 (s, 1H), 7.37-7.26 (m, 3H), 7.22 (s, 1H), 7.13 (t, J=7.0 Hz, 1H), 7.06 (t, J=7.0 Hz, 1H), 6.90 (d, J=7.9 Hz, 1H), 6.84 (d, J=7.9 Hz, 2H), 5.58 (s, 2H), 3.75 (s, 3H). LC-MS method B, (ES+) 398.0, RT=9.40 min.

Example 225

1-(2-(3-((6-((1-Methyl-1H-pyrazol-4-yl)amino)-1H-pyrazolo[3,4-d]pyrimidin-1-yl)methyl)phenoxy)ethyl)pyrrolidin-2-one The following compound was made according to the procedure in Example 45 (Steps i-iii) using 3-(2-(2-oxopyrrolidin-1-yl)ethoxy)benzaldehyde, which was prepared as in Example 171 using 1-(2-hydroxyethyl)pyrrolidin-2-one.

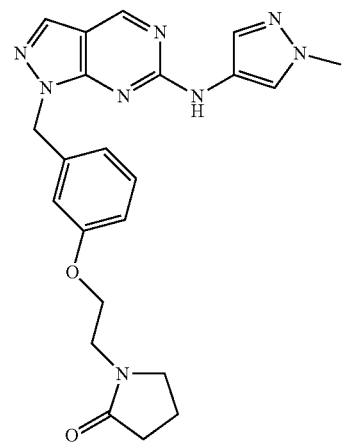 [SMILES: Cn1cc(Nc2ncc3cnn(Cc4cccc(OCCN5CCCC5=O)c4)c3n2)cn1]

¹H NMR (d₆-DMSO) δ 9.85 (s, 1H), 8.91 (s, 1H), 8.10-7.98 (m, 2H), 7.57 (s, 1H), 7.24 (t, J=8.0 Hz, 1H), 6.93 (s, 1H), 6.85 (dd, J=8.0, 2.2 Hz, 2H), 5.52 (s, 2H), 4.00 (t, J=5.5 Hz, 2H), 3.83 (s, 3H), 3.49 (t, J=5.5 Hz, 2H), 3.38 (m, 2H), 2.18 (t, J=8.0 Hz, 2H), 1.93-1.81 (m, 2H); LC-MS method B, (ES+) 433.0, RT=7.14 min.

Example 226

1-(3-(2-Oxa-5-azabicyclo[2.2.2]octan-5-yl)benzyl)-N-(1-methyl-1H-pyrazol-4-yl)-1H-pyrazolo[3,4-d]pyrimidin-6-amine The following compound was made according to the procedure in Example 162 using 8-oxa-3-azabicyclo[3.2.1]octane in Step (ii):

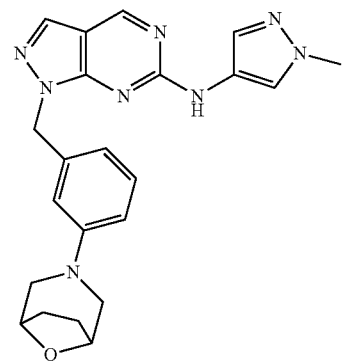 [SMILES: Cn1cc(Nc2ncc3cnn(Cc4cccc(N5CC6CCC(C5)O6)c4)c3n2)cn1]

¹H NMR (d₆-DMSO) δ 9.63 (s, 1H), 8.70 (s, 1H), 7.92-7.79 (m, 2H), 7.41 (s, 1H), 6.95-6.86 (m, 1H), 6.75 (s, 1H), 6.59-6.50 (m, 1H), 6.48-6.38 (m, 1H), 5.27 (s, 2H), 4.16 (s, 2H), 3.64 (s, 3H), 3.11-3.03 (m, 2H), 2.58-2.49 (m, 2H), 1.66-1.48 (m, 4H); LC-MS method B, (ES+) 417.1, RT=8.25 min.

Example 227

4-(3-((6-((1-Methyl-1H-pyrazol-4-yl)amino)-1H-pyrazolo[3,4-d]pyrimidin-1-yl)methyl)phenyl)morpholin-3-one

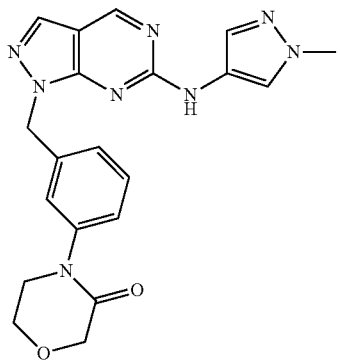 [SMILES: Cn1cc(Nc2ncc3cnn(Cc4cccc(N5CCOCC5=O)c4)c3n2)cn1]

Step (i)
1-(3-iodobenzyl)-N-(1-methyl-1H-pyrazol-4-yl)-1H-pyrazolo[3,4-d]pyrimidin-6-amine was made according to the procedure in Example 1, using 1-(bromomethyl)-3-iodobenzene.

Step (ii)
To a solution of 1-(3-iodobenzyl)-N-(1-methyl-1H-pyrazol-4-yl)-1H-pyrazolo[3,4-d]pyrimidin-6-amine (50 mg, 0.12 mmol) in dioxane (1 mL) were added morpholin-3-one (15 mg, 1.25 eq), copper iodide (4.4 mg, 0.2 eq), potassium phosphate (49 mg, 2 eq) and N,N'-dimethylethylene diamine (5 μl, 0.4 eq). After stirring for 16 h at 90° C., the reaction mixture was partitioned between 0.5M EDTA and DCM. The aqueous phase was extracted with DCM, the combined organic phases dried over sodium sulfate and evaporated. The residue was purified by preparative HPLC to yield the title compound (23 mg, 56 μmol, 47%). $^1$H NMR (d$_6$-DMSO) δ 9.85 (s, 1H), 8.92 (s, 1H), 8.06 (s, 2H), 7.56 (s, 1H), 7.43 (s, 1H), 7.39-7.35 (m, 1H), 7.33-7.29 (m, 1H), 7.20-7.13 (m, 1H), 5.57 (s, 2H), 4.17 (s, 2H), 3.96-3.91 (m, 2H), 3.84 (s, 3H), 3.69-3.64 (m, 2H); LC-MS method B, (ES+) 405.1, RT=6.31 min.

Example 228

1-(Benzo[d][1,3]dioxol-4-ylmethyl)-N-(1-methyl-1H-pyrazol-4-yl)-1H-pyrazolo[3,4-d]pyrimidin-6-amine The following compound was made according to the procedure in Example 209 (Steps ii-iii) using benzo[d][1,3]dioxol-4-ylmethanol:

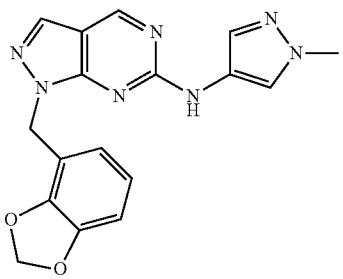 [SMILES: Cn1cc(Nc2ncc3cnn(Cc4cccc5c4OCO5)c3n2)cn1]

$^1$H NMR (CDCl$_3$) δ 8.78 (s, 1H), 7.91-7.92 (m, 2H), 7.62 (s, 1H), 7.11 (br s, 1H), 6.76-6.79 (m, 3H), 5.99 (s, 2H), 5.52 (s, 2H), 3.92 (s, 3H); LC-MS method B, (ES+) 350.1, RT=7.88 min.

Example 229

1-((2,3-Dihydrobenzo[b][1,4]dioxin-5-yl)methyl)-N-(1-methyl-1H-pyrazol-4-yl)-1H-pyrazolo[3,4-d]pyrimidin-6-amine The following compound was made according to the procedure in Example 209 (Steps ii-iii) using (2,3-dihydrobenzo[b][1,4]dioxin-5-yl)methanol:

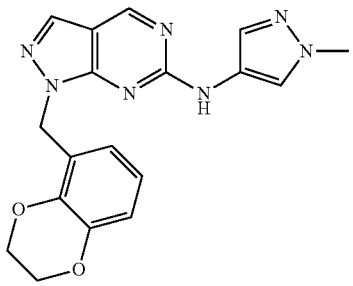 [SMILES: Cn1cc(Nc2ncc3cnn(Cc4cccc5c4OCCO5)c3n2)cn1]

$^1$H NMR (CDCl$_3$) δ 8.78 (s, 1H), 7.93 (s, 1H), 7.86 (s, 1H), 7.64 (s, 1H), 7.09 (br s, 1H), 6.81 (dd, 1H), 6.75 (t, 1H), 6.65 (d, 1H), 5.55 (s, 2H), 4.26-4.33 (m, 4H), 3.91 (s, 3H); LC-MS method B, (ES+) 364.1, RT=7.95 min.

Example 230

N-(1-Methyl-1H-pyrazol-4-yl)-1-(3-(pyridin-4-yl)benzyl)-1H-pyrazolo[3,4-d]pyrimidin-6-amine The following compound was made according to the procedure in Example 198 (Steps i and ii) using 4-(4,4,5,5-tetramethyl-1,3,2-dioxaborolan-2-yl)pyridine in Step (iii):

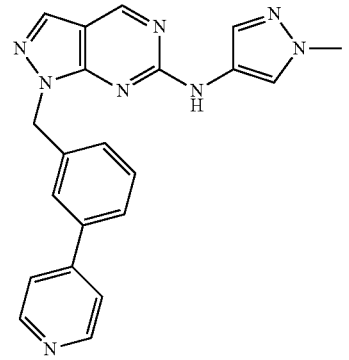 [SMILES: Cn1cc(Nc2ncc3cnn(Cc4cccc(-c5ccncc5)c4)c3n2)cn1]

$^1$H NMR (d$_6$-DMSO) δ 9.86 (s, 1H), 8.92 (s, 1H), 8.61 (dd, J=4.5, 1.6 Hz, 2H), 8.13-8.04 (m, 2H), 7.87 (s, 1H), 7.74-7.69 (m, 1H), 7.62 (dd, J=4.5, 1.6 Hz, 2H), 7.58 (s, 1H), 7.48 (t, J=7.7 Hz, 1H), 7.38-7.32 (m, 1H), 5.67 (s, 2H), 3.80 (s, 3H); LC-MS method B, (ES+) 383.1, RT=5.15 min.

Example 231

4-(3-((6-((1-(3-(Dimethylamino)propyl)-1H-pyrazol-4-yl)amino)-1H-pyrazolo[3,4-d]pyrimidin-1-yl)methyl)phenyl)morpholin-3-one

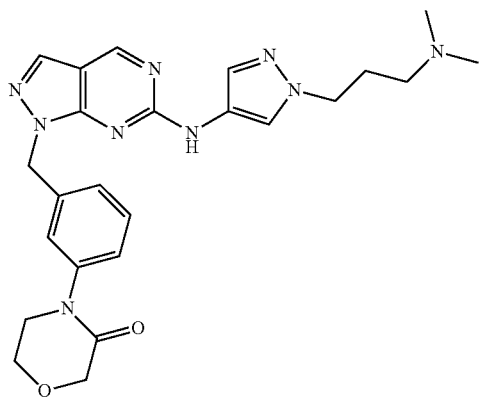 [SMILES: CN(C)CCCn1cc(Nc2ncc3cnn(Cc4cccc(N5CCOCC5=O)c4)c3n2)cn1]

Step (i)

4-(3-(hydroxymethyl)phenyl)morpholin-3-one was prepared according to the procedure in Example 227 (Step ii) using (3-iodophenyl)methanol.

Step (ii)

4-(3-(bromomethyl)phenyl)morpholin-3-one was prepared according to the procedure in Example 189 (Step ii) using 4-(3-(hydroxymethyl)phenyl)morpholin-3-one.

Step (iii)

1-(3-(dimethylamino)propyl)-1H-pyrazol-4-amine was prepared by Procedure A using 3-chloro-N,N-dimethylpropan-1-amine, HCl as alkylating agent.

Step (iv)

The title compound was made according to the procedure in Example 1 (Step ii), using 4-(3-(bromo methyl)phenyl)morpholin-3-one and 6-chloro-1H-pyrazolo[3,4-d]pyrimidine followed by Example 1 (Step i) using 1-(3-(dimethylamino)propyl)-1H-pyrazol-4-amine. $^1$H NMR ($d_6$-DMSO) δ 9.83 (s, 1H), 8.91 (s, 1H), 8.10-8.00 (m, 2H), 7.59 (s, 1H), 7.41 (s, 1H), 7.38-7.27 (m, 2H), 7.23-7.12 (m, 1H), 5.55 (s, 2H), 4.17 (s, 2H), 4.10 (t, J=7.0 Hz, 2H), 3.96-3.89 (m, 2H), 3.70-3.62 (m, 2H), 2.16 (t, J=7.0 Hz, 2H), 2.10 (s, 6H), 1.93-1.82 (m, 2H); LC-MS method B, (ES+) 476.2, RT=4.74 min.

Example 232

4-(3-((6-((1-(2-Hydroxyethyl)-1H-pyrazol-4-yl)amino)-1H-pyrazolo[3,4-d]pyrimidin-1-yl)methyl)phenyl)morpholin-3-one The title compound was made according to the procedure in Example 231 using 2-bromoethanol in Step (iii):

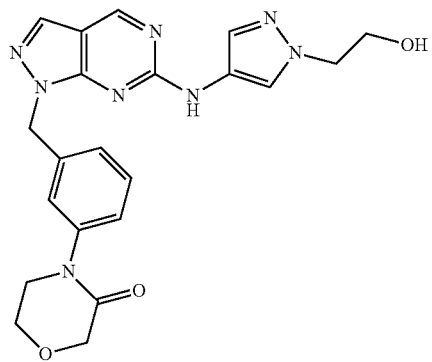 [SMILES: O=C1COCCN1c1cccc(Cn2ncc3cnc(Nc4cnn(CCO)c4)nc32)c1]

$^1$H NMR ($d_6$-DMSO) δ 9.84 (s, 1H), 8.91 (s, 1H), 8.12 (s, 1H), 8.05 (s, 1H), 7.60 (s, 1H), 7.42 (s, 1H), 7.39-7.33 (m, 1H), 7.32-7.28 (m, 1H), 7.19 (s, 1H), 5.54 (s, 2H), 4.88 (t, J=5.3 Hz, 1H), 4.17 (s, 2H), 4.13 (t, J=5.7 Hz, 2H), 3.95-3.90 (m, 2H), 3.73 (q, J=5.6 Hz, 2H), 3.69-3.63 (m, 2H); LC-MS method B, (ES+) 435.1, RT=5.91 min.

Example 233

1-(3-(4-((1-(3-Morpholinobenzyl)-1H-pyrazolo[3,4-d]pyrimidin-6-yl)amino)-1H-pyrazol-1-yl)propyl)pyrrolidin-2-one The following compound was made according to the procedure in Example 45 (Steps ii and iii), using (3-morpholinophenyl)methanol in Step (ii) and 1-(3-(4-amino-1H-pyrazol-1-yl)propyl)pyrrolidin-2-one in Step (iii). 1-(3-(4-amino-1H-pyrazol-1-yl)propyl)pyrrolidin-2-one was prepared as in Example 165 using 1-(3-hydroxypropyl)pyrrolidin-2-one:

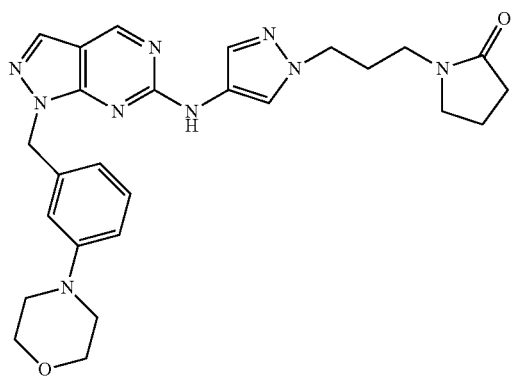 [SMILES: O=C1CCCN1CCCn1cc(Nc2ncc3cnn(Cc4cccc(N5CCOCC5)c4)c3n2)cn1]

$^1$H NMR ($d_6$-DMSO) δ 9.84 (s, 1H), 8.90 (s, 1H), 8.14 (s, 1H), 8.03 (s, 1H), 7.62 (s, 1H), 7.20-7.08 (m, 1H), 6.99 (s, 1H), 6.83 (dd, J=8.0, 2.1 Hz, 1H), 6.70 (d, J=5.4 Hz, 1H), 5.50 (s, 2H), 4.11-4.03 (m, 2H), 3.72-3.60 (m, 4H), 3.28 (t, J=7.0 Hz, 2H), 3.22-3.14 (m, 2H), 3.06-2.96 (m, 4H), 2.18 (t, J=8.0 Hz, 2H), 2.02-1.79 (m, 4H); LC-MS method B, (ES+) 502.3, RT=7.29 min.

Example 234

N-(1-((3-((Dimethylamino)methyl)oxetan-3-yl)methyl)-1H-pyrazol-4-yl)-1-(3-morpholinobenzyl)-1H-pyrazolo[3,4-d]pyrimidin-6-amine

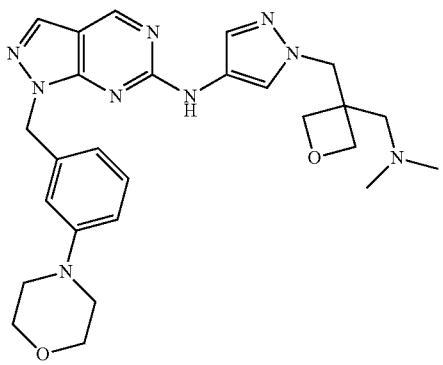 [SMILES: CN(C)CC1(Cn2cc(Nc3ncc4cnn(Cc5cccc(N6CCOCC6)c5)c4n3)cn2)COC1]

Step (i)

4-nitro-1H-pyrazole (0.5 g, 4.42 mmol) and $K_2CO_3$ (1.22 g, 8.84 mmol) were suspended in acetonitrile (30 mL) in a 2-necked flask under Nitrogen and (3-(bromomethyl)oxetan-3-yl)methanol (1.36 g, 7.52 mmol) was added dropwise. The reaction was heated at 60° C. for 16 h and the solution was concentrated to about ⅓ of the volume under vacuum and then partitioned between DCM (50 mL) and water (50 mL). The organics were dried over $Na_2SO_4$, filtered and the solvent evaporated to give (34(4-nitro-1H-pyrazol-1-yl)methyl)oxetan-3-yl)methanol as a transparent oil (0.94 g, quantitative yield).

Step (ii)

(3-((4-nitro-1H-pyrazol-1-yl)methyl)oxetan-3-yl)methanol (0.6 g, 2.8 mmol) was dissolved in DCM (16 ml) with triethylamine (0.778 mL, 5.6 mmol) and the reaction was cooled at 0° C. Mesyl chloride (0.415 g, 3.62 mmol) was added dropwise and the reaction was allowed to reach rt overnight. The mixture was diluted in DCM (25 mL), washed with water (20 mL) and the water re-extracted with DCM (20 mL). The combined organics were dried over $Na_2SO_4$, filtered and the solvent removed under vacuum. (3-((4-nitro-1H-pyrazol-1-yl)methyl)oxetan-3-yl)methyl methanesulfonate was obtained as a yellowish oil (0.9 g, quantitative yield).

Step (iii)

(3-((4-nitro-1H-pyrazol-1-yl)methyl)oxetan-3-yl)methyl methanesulfonate (0.225 g, 0.935 mmol) was suspended in acetonitrile (6 mL) with $K_2CO_3$ (0.297 g, 2.15 mmol) and dimethylamine (2M in MeOH, 1.87 mL, 3.75 mmol) in a microwave vial and sealed under Nitrogen. This was heated at 70° C. for 36 h then diluted with DCM (20 mL), washed with water (20 mL) and brine (20 mL). The organics were dried over $Na_2SO_4$, filtered and the solvent removed under vacuum. The crude product was purified by prep HPLC to give N,N-dimethyl-1-(3-((4-nitro-1H-pyrazol-1-yl)methyl)oxetan-3-yl)methanamine as a white so lid (33 mg, 15% yield).

Step (iv)

N,N-dimethyl-1-(3-((4-nitro-1H-pyrazol-1-yl)methyl)oxetan-3-yl)methanamine (33 mg, 0.137 mmol) was hydrogenated according to conditions in Example 213 (Step iii), to afford 1-((3-((dimethylamino)methyl)oxetan-3-yl)methyl)-1H-pyrazol-4-amine (29 mg, quantitative yield).

Step (v)

The title compound was made according to the procedure in Example 1 (Step ii), using 3-morpholinobenzyl methanesulfonate (Example 202, Step (i)) and 6-chloro-1H-pyrazolo[3,4-d]pyrimidine followed by Example 1 (Step i) using 1-((3-((dimethylamino)methyl)oxetan-3-yl)methyl)-1H-pyrazol-4-amine. $^1$H NMR ($d_6$-Acetone) δ 8.91 (br s, 1H), 8.84 (s, 1H), 8.21 (s, 1H), 7.94 (s, 1H), 7.73 (s, 1H), 7.16 (t, 1H), 7.02 (s, 1H), 6.84 (dd, 1H), 6.79 (d, 1H), 5.51 (s, 2H), 4.64 (d, 2H), 4.54 (s, 2H), 4.36 (d, 2H), 3.71 (t, 4H), 3.05 (t, 4H), 2.39 (s, 2H), 2.15 (s, 6H). LC-MS method B, (ES+) 504.3, RT=5.09 min.

Example 235

4-(3-((6-((1-Methyl-1H-pyrazol-4-yl)amino)-1H-pyrazolo[3,4-d]pyrimidin-1-yl)methyl)phenyl)morpholin-3-ol

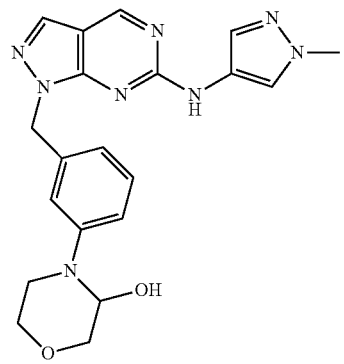 [SMILES: Cn1cc(Nc2ncc3cnn(Cc4cccc(N5CCOCC5O)c4)c3n2)cn1]

Step (i)

4-(3-((6-(1-methyl-1H-pyrazol-4-ylamino)-1H-pyrazolo[3,4-d]pyrimidin-1-yl)methyl)phenyl) morpholin-3-one was synthesized as in Example 227.

Step (ii)

To a solution of 4-(3-((6-(1-methyl-1H-pyrazol-4-ylamino)-1H-pyrazolo[3,4-d]pyrimidin-1-yl)methyl)phenyl)morpholin-3-one (45 mg, 0.12 mmol) in 4 mL methanol was added lithium borohydride (170 mg, 70 eq in seven portions every 10 min). The reaction mixture was evaporated and the residue partitioned between ethyl acetate and water. The aqueous phase was extracted with ethyl acetate, the combined organic phases dried over sodium sulfate and evaporated. The residue was purified with the preparative HPLC to yield the title compound (5 mg, 12 μmol, 10%). $^1$H NMR ($d_6$-DMSO) δ 8.22 (s, 1H), 7.78 (s, 1H), 7.37-7.32 (m, 3H), 7.29-7.24 (m, 1H), 7.12-7.08 (m, 1H), 7.01 (s, 1H), 6.06 (s, 1H), 5.16 (s, 2H), 4.45 (s, 2H), 4.18 (s, 2H), 3.96-3.91 (m, 2H), 3.76 (s, 3H), 3.68-3.63 (m, 2H); LC-MS method B, (ES+) 407.2, RT=4.04 min.

Example 236

3-((1-(2-Fluorobenzyl)-1H-pyrazolo[3,4-d]pyrimidin-6-yl)amino)-1-methyl-1H-pyrazole-5-carboxylic acid The title compound was made according to the procedure in Example 1 (Step ii), using 1-(bromo methyl)-2-fluorobenzene and 6-chloro-1H-pyrazolo[3,4-d]pyrimidine followed by Example 1 (Step i) using 3-amino-1-methyl-1H-pyrazole-5-carboxylic acid:

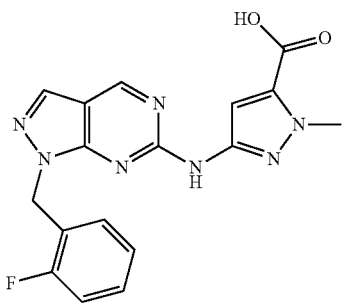 [SMILES: Cn1nc(Nc2ncc3cnn(Cc4ccccc4F)c3n2)cc1C(=O)O]

¹H NMR (d₆-DMSO) δ 10.36 (s, 1H), 8.98 (s, 1H), 8.11 (s, 1H), 7.12-7.37 (m, 6H), 5.53 (s, 2H), 4.00 (s, 3H); LC-MS method B, (ES+) 368.0, RT=7.82 min.

Example 237

1-(2-Fluorobenzyl)-N-(1-methyl-1H-imidazol-4-yl)-1H-pyrazolo[3,4-d]pyrimidin-6-amine The title compound was made according to the procedure in Example 1 (Step ii), using 1-(bromomethyl)-2-fluorobenzene and 6-chloro-1H-pyrazolo[3,4-d]pyrimidine followed by Example 1 (Step i) using 1-methyl-1H-imidazol-4-amine. 1-methyl-1H-imidazol-4-amine was prepared by Procedure A using 4-nitro-1H-imidazole and methyl iodide:

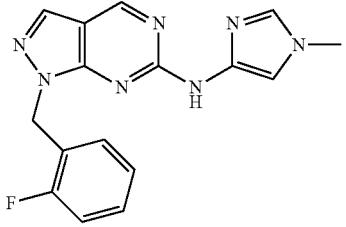 [SMILES: Cn1cnc(Nc2ncc3cnn(Cc4ccccc4F)c3n2)c1]

¹H NMR (d₆-DMSO) δ 9.99 (s, 1H), 8.92 (s, 1H), 8.06 (s, 1H), 7.46 (s, 1H), 7.41-7.40 (m, 1H), 7.39-7.33 (m, 1H), 7.31-7.21 (m, 2H), 7.19-7.13 (m, 1H), 5.61 (s, 2H), 3.67 (s, 3H); LC-MS method B, (ES+) 324.0, RT=5.50 min.

Example 238

2-(3-((1-(2-Fluorobenzyl)-1H-pyrazolo[3,4-d]pyrimidin-6-yl)amino)-1H-pyrazol-1-yl)ethanol The title compound was made according to the procedure in Example 1 (Step ii), using 1-(bromo methyl)-2-fluorobenzene and 6-chloro-1H-pyrazolo[3,4-d]pyrimidine followed by Example 1 (Step i) using 2-(3-amino-1H-pyrazol-1-yl)ethanol. 2-(3-amino-1H-pyrazol-1-yl)ethanol was prepared by Procedure A using 3-nitro-1H-pyrazole and 2-bromoethanol:

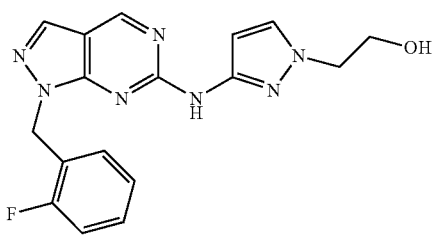 [SMILES: OCCn1ccc(Nc2ncc3cnn(Cc4ccccc4F)c3n2)n1]

¹H NMR (d₆-DMSO) δ 10.12 (s, 1H), 8.94 (s, 1H), 8.07 (s, 1H), 7.60 (d, 1H), 7.35 (dd, 1H), 7.20-7.24 (m, 2H), 7.14 (t, 1H), 5.55 (s, 2H), 4.88 (t, 1H), 4.04 (t, 2H), 3.70-3.74 (m, 2H); LC-MS method B (ES+) 354, RT=7.38 min.

Example 239

4-((1-(2-Fluorobenzyl)-1H-pyrazolo[3,4-d]pyrimidin-6-yl)amino)-N-methyl-1H-pyrrole-2-carboxamide

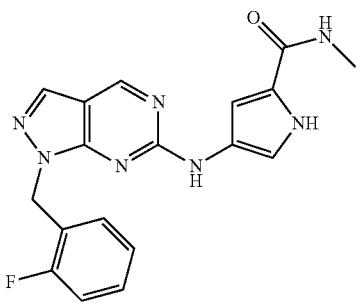 [SMILES: CNC(=O)c1cc(Nc2ncc3cnn(Cc4ccccc4F)c3n2)c[nH]1]

Step (i)

A solution of 4-nitropyrrole-2-carboxylic acid hydrate (200 mg, 1.28 mmol), methylamine (1.28 mmol, 2M in THF), hydroxybenzotriazole (1.41 mmol), 1-ethyl-3-(3-dimethylaminopropyl)carbodiimide (1.41 mmol) and diisopropylethylamine (2.56 mmol) in DMF was stirred at rt for 24 h. The resultant mixture was washed with H₂O, extracted with DCM then dried using a hydrophobic frit. The organic phase was concentrated in vacuo to afford N-methyl-4-nitro-1H-pyrrole-2-carboxamide as a yellow gum.

Step (ii)

A solution of N-methyl-4-nitro-1H-pyrrole-2-carboxamide (75 mg, 0.44 mmol) in methanol was degassed and flushed with N₂ (g). 10% Pd on activated carbon was added and the mixture degassed and flushed with N₂ (g). H₂ (g) was applied and the reaction mixture stirred at rt for 14 h. The resultant mixture was filtered through celite then concentrated in vacuo to afford 4-amino-N-methyl-1H-pyrrole-2-carboxamide as a green solid.

Step (iii)

The title compound was made according to the procedure in Example 1 (Step ii), using 1-(bromo methyl)-2-fluorobenzene and 6-chloro-1H-pyrazolo[3,4-d]pyrimidine followed by Example 1 (Step i) using 3-amino-N-methyl-1H-pyrazole-5-carboxamide. ¹H NMR (d₆-DMSO) δ 11.11 (s, 1H), 9.86 (s, 1H), 8.89 (s, 1H), 8.02 (s, 1H), 7.95 (dd, 1H), 7.41 (s, 1H), 7.20-7.34 (m, 1H), 7.20-7.24 (m, 2H), 7.16 (td, 1H), 6.79 (dd, 1H), 5.55 (s, 2H), 2.73 (d, 3H); LC-MS method B, (ES+) 366, RT=7.44 min.

Example 240

2-(4-((1-(2-Fluorobenzyl)-1H-pyrazolo[3,4-d]pyrimidin-6-yl)amino)-1H-imidazol-1-yl)ethanol

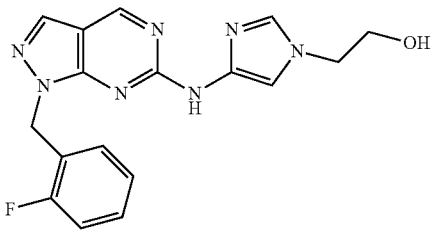 [SMILES: OCCn1cnc(Nc2ncc3cnn(Cc4ccccc4F)c3n2)c1]

Step (i)
2-(4-amino-1H-imidazol-1-yl)ethanol was prepared by Procedure A using 4-nitro-1H-imidazole and 2-bromoethanol in DMF instead of ACN.
Step (ii)
6-chloro-1-(2-fluorobenzyl)-1H-pyrazolo[3,4-d]pyrimidine was prepared as in Example 1
(Step ii), using 1-(bromomethyl)-2-fluorobenzene and 6-chloro-1H-pyrazolo[3,4-d]pyrimidine.
Step (iii)
The title compound was made according to the procedure in Example 1 (Step i) using 6-chloro-1-(2-fluorobenzyl)-1H-pyrazolo[3,4-d]pyrimidine and 2-(4-amino-1H-imidazol-1-yl)ethanol. $^1$H NMR (d$_6$-DMSO) δ 9.98 (s, 1H), 8.92 (s, 1H), 8.06 (s, 1H), 7.54 (s, 1H), 7.43 (s, 1H), 7.40-7.27 (m, 2H), 7.27-7.12 (m, 2H), 5.61 (s, 2H), 4.97 (t, 1H), 4.00 (t, 2H), 3.81-3.56 (m, 2H); LC-MS method B, (ES+) 354.0, RT=5.20 min.

Example 241

1-(2-Fluorobenzyl)-N-(1-methyl-1H-pyrrol-3-yl)-1H-pyrazolo[3,4-d]pyrimidin-6-amine The title compound was made according to the procedure in Example 1 (Step ii), using 1-(bromomethyl)-2-fluorobenzene and 6-chloro-1H-pyrazolo[3,4-d]pyrimidine followed by Example 1 (Step i) using 1-methyl-1H-pyrrol-3-amine. 1-methyl-1H-pyrrol-3-amine was prepared by Procedure A using 3-nitro-1H-pyrrole and methyl iodide:

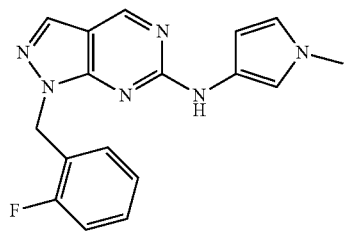 [SMILES: Cn1ccc(Nc2ncc3cnn(Cc4ccccc4F)c3n2)c1]

$^1$H NMR (d$_6$-DMSO) δ 9.66 (s, 1H), 8.85 (s, 1H), 8.00 (s, 1H), 7.32-7.38 (m, 1H), 7.21-7.26 (m, 3H), 7.13-7.17 (m, 1H), 6.54 (t, 1H), 6.08 (t, 1H), 5.56 (s, 2H), 3.60 (s, 3H); LC-MS method B, (ES+) 323, RT=9.26 min.

Example 242

4-((1-(2-Fluorobenzyl)-1H-pyrazolo[3,4-d]pyrimidin-6-yl)amino)-N,1-dimethyl-1H-pyrrole-2-carboxamide The title compound was made according to the procedure in Example 239 using 1-methyl-4-nitro-1H-pyrrole-2-carboxylic acid in Step (i):

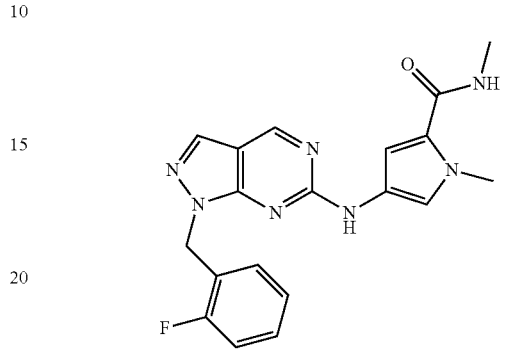

$^1$H NMR (d$_6$-DMSO) δ 9.86 (s, 1H), 8.89 (s, 1H), 8.03 (s, 1H), 7.92 (s, 1H) 7.46 (s, 1H), 7.32-7.35 (m, 1H), 7.23-7.25 (m, 2H), 7.15 (t, 1H), 6.70 (s, 1H), 5.60 (s, 2H), 3.84 (s, 3H), 2.70 (d, 3H); LC-MS method B, (ES+) 380, RT=8.10 min.

Example 243

4-((1-(2-Fluorobenzyl)-1H-pyrazolo[3,4-d]pyrimidin-6-yl)amino)-1-methyl-N-(2-morpholinoethyl)-1H-pyrrole-2-carboxamide The title compound was made according to the procedure in Example 239 using 1-methyl-4-nitro-1H-pyrrole-2-carboxylic acid and 2-morpholinoethanamine in Step (i):

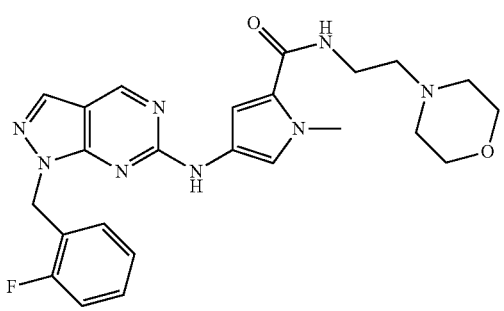 [SMILES: Cn1cc(Nc2ncc3cnn(Cc4ccccc4F)c3n2)cc1C(=O)NCCN1CCOCC1]

$^1$H NMR (d$_6$-DMSO) δ 9.86 (s, 1H), 8.89 (s, 1H), 8.03 (s, 1H), 7.88 (t, 1H), 7.46 (s, 1H), 7.32-7.37 (m, 1H), 7.21-7.25 (m, 2H), 7.15 (td, 1H), 6.74 (d, 1H), 5.60 (s, 2H), 3.83 (s, 3H), 3.56 (4H), 3.27-3.30 (m, 2H), 2.40-2.44 (m, 6H); LC-MS method B, (ES+) 479, RT=5.62 min.

Example 244

(4-((1-(2-Fluorobenzyl)-1H-pyrazolo[3,4-d]pyrimidin-6-yl)amino)-1-methyl-1H-pyrrol-2-yl)(morpholino)methanone The title compound was made according to the procedure in Example 239 using 1-methyl-4-nitro-1H-pyrrole-2-carboxylic acid and morpholine:

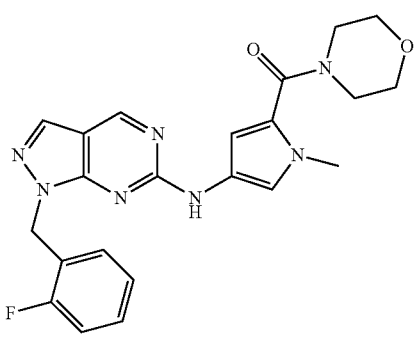 [SMILES: Cn1cc(Nc2ncc3cnn(Cc4ccccc4F)c3n2)cc1C(=O)N1CCOCC1]

¹H NMR (d₆-DMSO) δ 9.76 (s, 1H), 8.88 (s, 1H), 8.03 (s, 1H), 7.32-7.38 (m, 2H), 7.21-7.26 (m, 2H), 7.15 (td, 1H), 6.50 (s, 1H), 5.58 (s, 2H), 3.68 (s, 3H), 3.62-3.63 (m, 4H), 3.58-3.59 (m, 4H); LC-MS method B, (ES+) 436, RT=8.15 min.

Example 245

N-(Cyanomethyl)-4-((1-(2-fluorobenzyl)-1H-pyrazolo[3,4-d]pyrimidin-6-yl)amino)-1-methyl-1H-pyrrole-2-carboxamide The title compound was made according to the procedure in Example 239 using 1-methyl-4-nitro-1H-pyrrole-2-carboxylic acid and 2-aminoacetonitrile in Step (i):

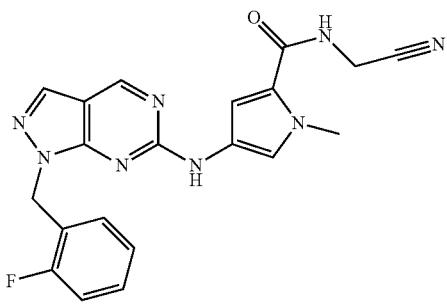 [SMILES: Cn1cc(Nc2ncc3cnn(Cc4ccccc4F)c3n2)cc1C(=O)NCC#N]

¹H NMR (d₆-DMSO) δ 9.93 (s, 1H), 8.90 (s, 1H), 8.66 (t, 1H), 8.04 (s, 1H), 7.56 (s, 1H), 7.32-7.36 (m, 1H), 7.23-7.25 (m, 2H), 7.15 (td, 1H), 6.84 (d, 1H), 5.61 (s, 2H), 4.20 (d, 2H), 3.88 (s, 3H); LC-MS method B, (ES+) 405, RT=8.44 min.

Example 246

4-((1-(2-Fluorobenzyl)-1H-pyrazolo[3,4-d]pyrimidin-6-yl)amino)-N,N,1-trimethyl-1H-pyrrole-2-carboxamide The title compound was made according to the procedure in Example 239 using 1-methyl-4-nitro-1H-pyrrole-2-carboxylic acid and dimethylamine in Step (i):

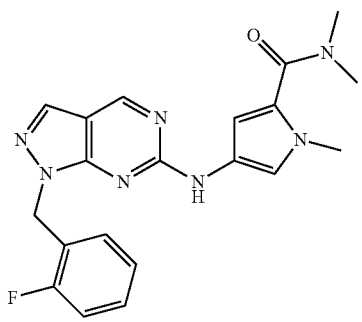 [SMILES: CN(C)C(=O)c1cc(Nc2ncc3cnn(Cc4ccccc4F)c3n2)cn1C]

¹H NMR (d₆-DMSO) δ 9.75 (s, 1H), 8.88 (s, 1H), 8.03 (s, 1H), 7.32-7.38 (m, 2H), 7.23-7.26 (m, 2H), 7.15 (td, 1H), 6.49 (s, 1H), 5.58 (s, 2H), 3.67 (s, 3H), 3.04 (s, 6H); LC-MS method B, (ES+) 394, RT=8.30 min.

Example 247

2-(3-((1-(2-Fluorobenzyl)-1H-pyrazolo[3,4-d]pyrimidin-6-yl)amino)-1H-pyrrol-1-yl)ethanol The title compound was made according to the procedure in Example 1 (Step ii), using 1-(bromo methyl)-2-fluorobenzene and 6-chloro-1H-pyrazolo[3,4-d]pyrimidine followed by Example 1 (Step i) using 2-(3-amino-1H-pyrrol-1-yl)ethanol. 2-(3-amino-1H-pyrrol-1-yl)ethanol was prepared by Procedure A using 3-nitro-1H-pyrrole and 2-bromoethanol:

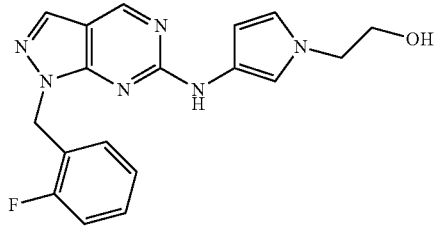

¹H NMR (d₆-DMSO) δ 9.66 (s, 1H), 8.84 (s, 1H), 8.00 (s, 1H), 7.32-7.35 (m, 2H), 7.22-7.28 (m, 2H), 7.15 (td, 1H), 6.61 (t, 1H), 6.08-6.10 (m, 1H), 5.56 (s, 2H), 4.85 (t, 1H), 3.88 (t, 2H), 3.62-3.67 (m, 2H); LC-MS method B, (ES+) 353, RT=7.67 min.

Example 248

(1-Methyl-4-41-(3-morpholinobenzyl)-1H-pyrazolo[3,4-d]pyrimidin-6-yl)amino)-1H-pyrrol-2-yl)(morpholino)methanone

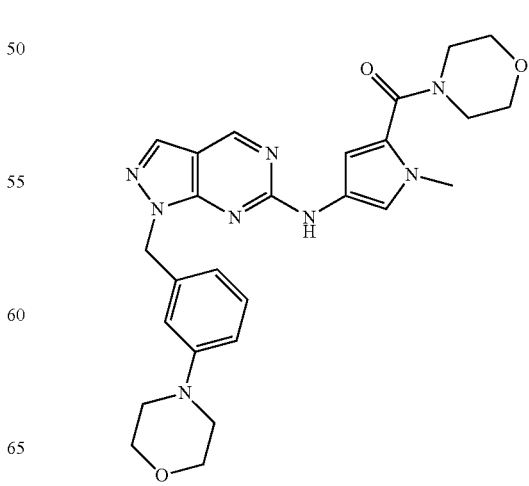

Step (i)

(4-amino-1-methyl-1H-pyrrol-2-yl)(morpholino)methanone was prepared as in Example 239 (Steps i-ii) using 1-methyl-4-nitro-1H-pyrrole-2-carboxylic acid and morpholine:

Step (ii)

3-morpholinobenzyl methanesulfonate was prepared according to the procedure in Example 202 (Step i).

Step (iii)

The title compound was made according to the procedure in Example 1 using (4-amino-1-methyl-1H-pyrrol-2-yl)(morpholino)methanone in Step (i) and 3-morpholinobenzyl methanesulfonate in Step (ii). $^1$H NMR (d$_6$-DMSO) δ 9.73 (s, 1H), 8.88 (s, 1H), 8.02 (s, 1H), 7.36 (s, 1H), 7.19-7.11 (m, 1H), 7.04 (s, 1H), 6.87-6.80 (m, 1H), 6.73-6.66 (m, 1H), 6.55 (s, 1H), 5.47 (s, 2H), 3.69 (s, 3H), 3.68-3.65 (m, 4H), 3.65-3.60 (m, 4H), 3.59-3.55 (m, 4H), 3.04-2.98 (m, 4H); LC-MS method B, (ES+) 503.2, RT=7.87 min.

Example 249

N-(1-(3-(Dimethylamino)-2-methylpropyl)-1H-pyrazol-4-yl)-1-(3-morpholinobenzyl)-1H-pyrazolo[3,4-d]pyrimidin-6-amine The title compound was made according to the procedure in Example 45 (Steps ii and iii), using (3-morpholinophenyl)methanol and 1-(3-(dimethylamino)-2-methylpropyl)-1H-pyrazol-4-amine. 1-(3-(dimethylamino)-2-methylpropyl)-1H-pyrazol-4-amine was prepared as in Example 165 using 3-(dimethylamino)-2-methylpropan-1-ol

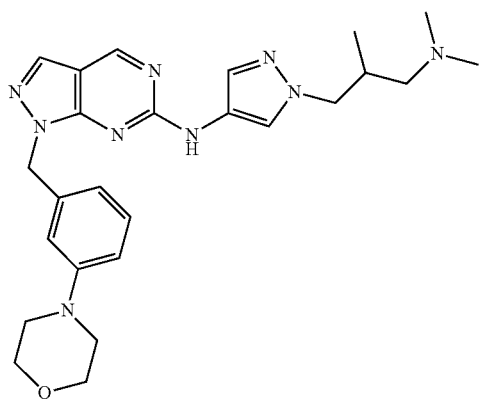 [SMILES: CC(CN(C)C)Cn1cc(Nc2ncc3cnn(Cc4cccc(N5CCOCC5)c4)c3n2)cn1]

Step (i)

1-(3-(dimethylamino)-2-methylpropyl)-1H-pyrazol-4-amine was prepared as in Example 165 using 3-(dimethylamino)-2-methylpropan-1-ol:

Step (ii)

3-morpholinobenzyl methanesulfonate was prepared according to the procedure in Example 202 (Step i).

Step (iii)

The title compound was made according to the procedure in Example 1 using 1-(3-(dimethylamino)-2-methylpropyl)-1H-pyrazol-4-amine in Step (i) and 3-morpholinobenzyl methanesulfonate in Step (ii). $^1$H NMR (CDCl$_3$) δ 8.80 (s, 1H), 7.93 (s, 2H), 7.68 (s, 1H), 7.47 (s, 1H), 7.26-7.20 (m, 1H), 6.96 (s, 1H), 6.93-6.86 (m, 1H), 6.83 (dd, J=8.0, 2.0 Hz, 1H), 5.50 (s, 2H), 4.25 (dd, J=13.6, 4.8 Hz, 1H), 3.89 (dd, J=13.6, 8.0 Hz, 1H), 3.85-3.79 (m, 4H), 3.15-3.07 (m, 4H), 2.32-2.05 (m, 9H), 0.93 (d, J=6.5 Hz, 3H); LC-MS method B, (ES+) 476, RT=5.17 min.

Example 250

1-(Dimethylamino)-3-(4-((1-(3-morpholinobenzyl)-1H-pyrazolo[3,4-d]pyrimidin-6-yl)amino)-1H-pyrazol-1-yl)propan-2-ol

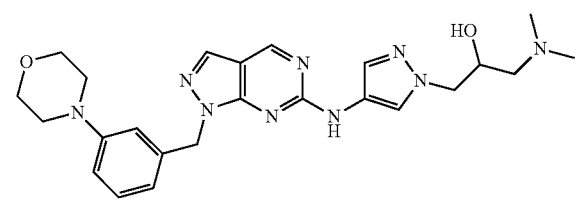 [SMILES: CN(C)CC(O)Cn1cc(Nc2ncc3cnn(Cc4cccc(N5CCOCC5)c4)c3n2)cn1]

Step (i)

To a stirred, cooled (0° C.) solution of 4-nitro-1H-pyrazole (1.0 g, 8.8 mmol), glycidol (0.58 mL, 8.8 mmol) and triphenylphosphine (2.14 g, 10.6 mmol) in THF (40 mL) was added DIAD (2.25 mL, 11.4 mmol). After 24 h the reaction mixture was diluted with ethyl acetate and water. The aqueous layer was extracted with ethyl acetate and the combined organic layers were washed (brine), dried (anhydrous MgSO$_4$) and concentrated. Flash chromatography (Isolera, silica, 50 g, 0-90% ethyl acetate in petroleum ether) afforded 4-nitro-1-(oxiran-2-ylmethyl)-1H-pyrazole as an off-white solid (0.71 g, 48% yield). LCMS (UPLC, low pH), RT=0.74 min.

Step (ii)

4-nitro-1-(oxiran-2-ylmethyl)-1H-pyrazole (200 mg, 1.2 mmol) was stirred overnight at rt in dimethylamine (2M in methanol, 5 mL). The solution was concentrated to give 1-(dimethylamino)-3-(4-nitro-1H-pyrazol-1-yl)propan-2-ol as a yellow solid (quantitative). LC-MS (UPLC, high pH), (ES+) 215.2, RT=0.75 min.

Step (iii)

1-(dimethylamino)-3-(4-nitro-1H-pyrazol-1-yl)propan-2-ol (253 mg, 1.18 mmol) and palladium on carbon (10%, 25 mg) were stirred in ethanol (5 mL) under a balloon of hydrogen for 24 h. The palladium was removed by filtration through celite and the solution was concentrated to afford 1-(4-amino-1H-pyrazol-1-yl)-3-(dimethylamino)propan-2-ol as a brown oil (200 mg), which was used crude in the following reaction.

Step (iv)

3-morpholinobenzyl methanesulfonate was prepared according to the procedure in Example 202 (Step i).

Step (v)

The title compound was made according to the procedure in Example 1, using 1-(4-amino-1H-pyrazol-1-yl)-3-(dimethylamino)propan-2-ol in Step (i) and (3-3-morpholinobenzyl methanesulfonate in Step (ii) $^1$H NMR (d$_6$-DMSO) δ 9.83 (s, 1H), 8.90 (s, 1H), 8.10 (br s, 1H), 8.03 (s, 1H), 7.65 (br s, 1H), 7.15 (t, 1H), 6.99 (br s, 1H), 6.83 (dd, 1H), 6.72 (br s, 1H), 5.45 (s, 2H), 4.86 (d, 1H), 4.18 (dd, 1H), 3.99-3.90 (m, 2H), 3.68 (t, 4H), 3.02 (t, 4H), 2.20 (dd, 2H), 2.16 (s, 6H); LC-MS method B, (ES+) 478.3, RT=4.96 min.

Example 251

N-(1-(3-Aminopropyl)-1H-pyrazol-4-yl)-1-(3-morpholinobenzyl)-1H-pyrazolo[3,4-d]pyrimidin-6-amine

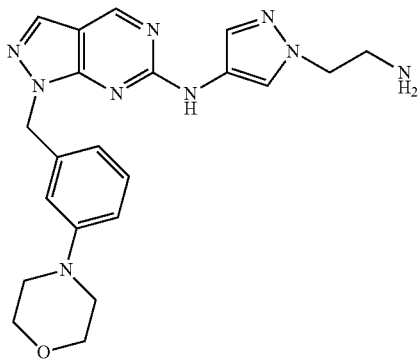 [SMILES: NCCn1cc(Nc2ncc3cnn(Cc4cccc(N5CCOCC5)c4)c3n2)cn1]

Step (i)

tert-butyl (3-(4-amino-1H-pyrazol-1-yl)propyl)carbamate was prepared as in Procedure A using tert-butyl (3-bromopropyl)carbamate.

Step (ii)

3-morpholinobenzyl methanesulfonate was prepared according to the procedure in Example 202 (Step i).

Step (iii)

tert-butyl (3-(4-((1-(3-morpholino benzyl)-1H-pyrazolo[3,4-d]pyrimidin-6-yl)amino)-1H-pyrazol-1-yl)propyl)carbamate was made according to the procedure in Example 1 using tert-butyl (3-(4-amino-1H-pyrazol-1-yl)propyl)carbamate in Step (i) and 3-morpholinobenzyl methanesulfonate in Step (ii).

Step (iii)

The title compound was made by Boc deprotection following the procedure in Example 215 (Step iv). $^1$H NMR (d$_6$-DMSO) δ 9.83 (s, 1H), 8.91 (s, 1H), 8.12 (s, 1H), 8.05 (s, 1H), 7.62 (s, 1H), 7.16 (t, J=7.9 Hz, 1H), 7.00 (s, 1H), 6.90-6.79 (m, 1H), 6.71 (s, 1H), 5.49 (s, 2H), 4.23-4.02 (m, 2H), 3.76-3.63 (m, 5H), 3.01 (d, J=4.2 Hz, 4H), 2.97-2.88 (m, 1H), 1.94-1.74 (m, 2H); LC-MS method B, (ES+) 434, RT=4.97 min.

Example 252

N-Cyclopropyl-3-(4-((1-(3-morpholinobenzyl)-1H-pyrazolo[3,4-d]pyrimidin-6-yl)amino)-1H-pyrazol-1-yl)propanamide The title compound was made according to the procedure in Example 202 using 3-chloro-N-cyclopropylpropanamide in Step (ii):

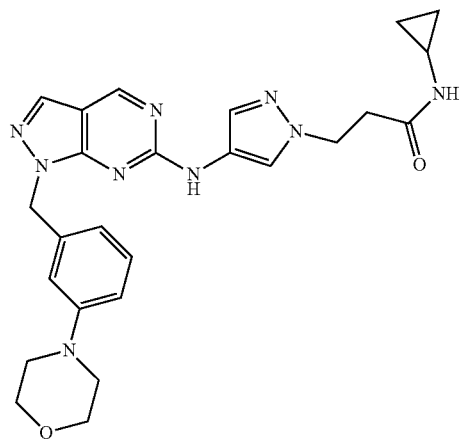 [SMILES: O=C(CCn1cc(Nc2ncc3cnn(Cc4cccc(N5CCOCC5)c4)c3n2)cn1)NC1CC1]

$^1$H NMR (d$_6$-DMSO) δ 9.70 (s, 1H), 8.77 (s, 1H), 7.99-7.89 (m, 2H), 7.85 (m, 1H), 7.47 (s, 1H), 7.03 (m, 1H), 6.92 (s, 1H), 6.70 (m, 1H), 6.60 (s, 1H), 5.37 (s, 2H), 4.17 (t, J=6.8 Hz, 2H), 3.59-3.51 (m, 4H), 2.97-2.85 (m, 4H), 2.49-2.40 (m, 3H), 0.46-0.36 (m, 2H), 0.24-0.14 (m, 2H); LC-MS method B, (ES+) 488.3, RT=7.18 min.

Example 253

1-(3-46-(((1-Methyl-1H-pyrazol-4-yl)amino)-1H-pyrazolo[3,4-d]pyrimidin-1-yl)methyl)phenyl)piperazin-2-one

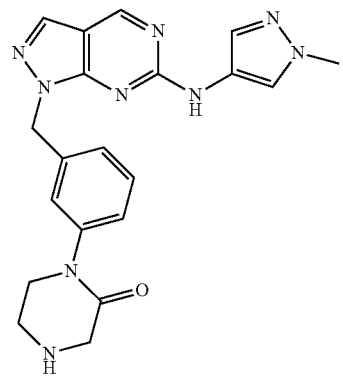 [SMILES: Cn1cc(Nc2ncc3cnn(Cc4cccc(N5CCNCC5=O)c4)c3n2)cn1]

Step (i)

tert-butyl 4-(3-((6-((1-methyl-1H-pyrazol-4-yl)amino)-1H-pyrazolo[3,4-d]pyrimidin-1-yl)methyl)phenyl)-3-oxopiperazine-1-carboxylate was made according to the procedure in Example 227 using tert-butyl 3-oxopiperazine-1-carboxylate in Step (ii).

Step (ii)

The title compound was deprotected according to the procedure in Example 215 (Step iv). $^1$H NMR (d$_6$-DMSO) δ 9.84 (s, 1H), 8.92 (s, 1H), 8.06 (s, 2H), 7.56 (s, 1H), 7.38-7.29 (m, 2H), 7.26-7.20 (m, 1H), 7.20-7.10 (m, 1H), 5.56 (s, 2H), 3.84 (s, 3H), 3.52 (t, J=5.4 Hz, 2H), 3.36-3.33 (m, 2H), 3.01-2.91 (m, 2H), 2.72 (br s, 1H); LC-MS method B, (ES+) 404.2, RT=4.49 min.

Example 254

2-(4-((1-(2,3,6-Trifluorobenzyl)-1H-pyrazolo[3,4-d]pyrimidin-6-yl)amino)-1H-pyrazol-1-yl)ethanol The title compound was made according to the procedure in Example 1 using 2-(bromo methyl)-1,3,4-trifluorobenzene and 2-(4-amino-1H-pyrazol-1-yl)ethanol. 2-(4-amino-1H-pyrazol-1-yl)ethano 1 was prepared as in Procedure A using 2-bromoethanol as alkylating agent:

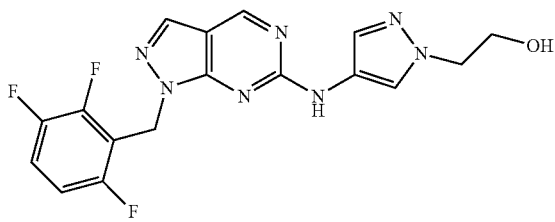 [SMILES: OCCn1cc(Nc2ncc3cnn(Cc4c(F)ccc(F)c4F)c3n2)cn1]

$^1$H NMR (d$_6$-DMSO) δ 9.89 (s, 1H), 8.90 (s, 1H), 8.14 (s, 1H), 8.02 (s, 1H), 7.66 (s, 1H), 7.49-7.55 (m, 1H), 7.17-7.22 (m, 1H), 5.63 (m, 2H), 4.88 (t, 1H), 4.13-4.16 (m, 2H), 3.73-3.77 (m, 2H); LC-MS method B, (ES+) 390.1, RT=7.30 min.

Example 255

1-(2,3-Difluoro-5-morpholinobenzyl)-N-(1-methyl-1H-pyrazol-4-yl)-1H-pyrazolo[3,4-d]pyrimidin-6-amine

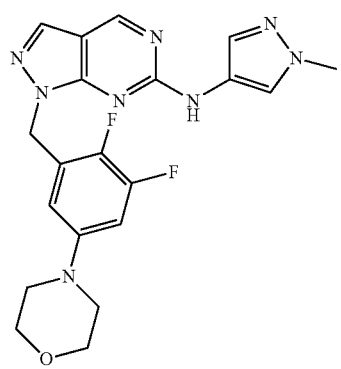 [SMILES: Cn1cc(Nc2ncc3cnn(Cc4cc(N5CCOCC5)cc(F)c4F)c3n2)cn1]

Step (i)
2-(2-bromoethoxy)ethyl 2,3-difluoro-5-morpholinobenzoate was formed following the procedure in Example 205 (Step i) using 5-amino-2,3-difluorobenzoic acid.
Step (ii)
(2,3-difluoro-5-morpholinophenyl)methanol was formed following the procedure in Example 45 (Step i) using 2-(2-bromoethoxy)ethyl 2,3-difluoro-5-morpholinobenzoate.
Step (iii)
4-(3-(bromomethyl)-4,5-difluorophenyl)morpholine was made following the procedure in Example 189 (Step ii).
Step (iv)
The title compound was made according to the procedure in Example 1 (Step ii) using 4-(3-(bromomethyl)-4,5-difluorophenyl)morpholine. $^1$H NMR (CDCl$_3$) δ 8.78 (s, 1H), 8.02 (s, 1H), 7.93 (s, 1H), 7.54 (s, 1H), 7.28 (s, 1H), 6.65-6.56 (m, 2H), 5.57 (s, 2H), 3.94 (s, 3H), 3.80-3.73 (m, 4H), 3.01-2.94 (m, 4H); LC-MS method B, (ES+) 427, RT=8.25 min.

Example 256

1-(2,6-Difluoro-3-morpholinobenzyl)-N-(1-methyl-1H-pyrazol-4-yl)-1H-pyrazolo[3,4-d]pyrimidin-6-amine The title compound was made according to the procedure in Example 255 using 3-amino-2,6-difluorobenzoic acid:

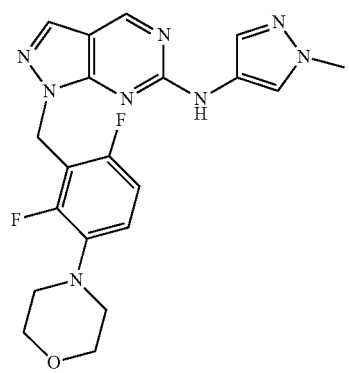 [SMILES: Cn1cc(Nc2ncc3cnn(Cc4c(F)ccc(N5CCOCC5)c4F)c3n2)cn1]

$^1$H NMR (CDCl$_3$) δ 8.75 (s, 1H), 8.06 (s, 1H), 7.90 (s, 1H), 7.59 (s, 1H), 7.14 (s, 1H), 6.95-6.83 (m, 2H), 5.60 (s, 2H), 3.96 (s, 3H), 3.87-3.79 (m, 4H), 3.04-2.97 (m, 4H); LC-MS method B, (ES+) 427, RT=7.88 min.

Example 257

2-(4-((1-(2-Flluoro-3-morpholinobenzyl)-1H-pyrazolo[3,4-d]pyrimidin-6-yl)amino)-1H-pyrazol-1-yl)ethanol The title compound was made according to the procedure in Example 214 using 2-(4-amino-1H-pyrazol-1-yl)ethanol. 2-(4-amino-1H-pyrazol-1-yl)ethanol was prepared as in Procedure A using 2-bromoethanol as alkylating agent:

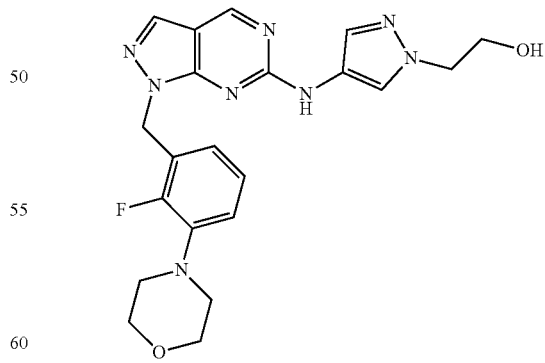

$^1$H NMR (d$_6$-DMSO) δ 9.87 (s, 1H), 8.91 (s, 1H), 8.12 (s, 1H), 8.04 (s, 1H), 7.62 (s, 1H), 7.08-7.02 (m, 1H), 7.01-6.95 (m, 1H), 6.87 (s, 1H), 5.56 (s, 2H), 4.88 (t, J=5.5 Hz, 1H), 4.13 (t, J=5.5 Hz, 2H), 3.77-3.68 (m, 6H), 3.02-2.94 (m, 4H); LC-MS method B, (ES+) 439.2, RT=7.00 min.

Example 258

4-(2-Fluoro-3-(((6-((1-methyl-1H-pyrazol-4-yl)amino)-1H-pyrazolo[3,4-d]pyrimidin-1-yl)methyl)phenyl)morpholin-3-one

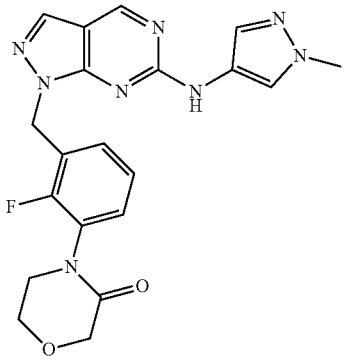 [SMILES: Cn1cc(Nc2ncc3cnn(Cc4cccc(N5CCOCC5=O)c4F)c3n2)cn1]

Step (i)

1-bromo-3-(bromomethyl)-2-fluorobenzene was synthesised following in the procedure in Example 45 (Step i) using 3-bromo-2-fluorobenzoic acid to form 4-(2-fluoro-3-(hydroxymethyl)phenyl)morpholin-3-one followed by the bromination procedure in Example 189 (Step ii).

Step (ii)

1-(3-bromo-2-fluorobenzyl)-N-(1-methyl-1H-pyrazol-4-yl)-1H-pyrazolo[3,4-d]pyrimidin-6-amine was formed following the procedure in Example 1 using 1-bromo-3-(bromomethyl)-2-fluorobenzene.

Step (iii)

The title compound was made following the procedure in Example 227 (step ii) using 1-(3-bromo-2-fluorobenzyl)-N-(1-methyl-1H-pyrazol-4-yl)-1H-pyrazolo[3,4-d]pyrimidin-6-amine. $^1$H NMR (d$_6$-DMSO) δ 9.88 (s, 1H), 8.92 (s, 1H), 8.16-7.99 (m, 2H), 7.56 (s, 1H), 7.47-7.36 (m, 1H), 7.29-7.16 (m, 2H), 5.63 (s, 2H), 4.23 (s, 2H), 4.01-3.93 (m, 2H), 3.83 (s, 3H), 3.69-3.58 (m, 2H); LC-MS method B, (ES+) 423.2, RT=6.64 min.

Example 259

N-(1-((3-(((Methylamino)methyl)oxetan-3-yl)methyl)-1H-pyrazol-4-yl)-1-(3-morpholinobenzyl)-1H-pyrazolo[3,4-d]pyrimidin-6-amine

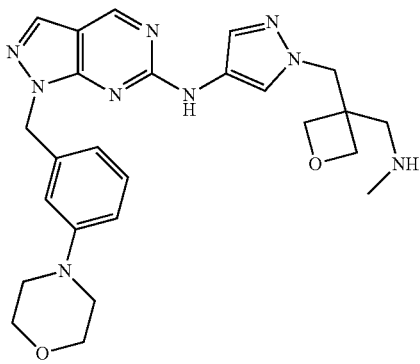 [SMILES: CNCC1(Cn2cc(Nc3ncc4cnn(Cc5cccc(N6CCOCC6)c5)c4n3)cn2)COC1]

Step (i)

N-methyl-1-(3-((4-nitro-1H-pyrazol-1-yl)methyl)oxetan-3-yl)methanamine was formed following the procedure in Example 234 (Steps i-iii) using methylamine.

Step (ii)

N-methyl-1-(3-((4-nitro-1H-pyrazol-1-yl)methyl)oxetan-3-yl)methanamine (0.13 g, 0.575 mmol) was dissolved in DCM (6 mL) with Et$_3$N (0.24 mL, 1.72 mmol) in a 2-neck flask under Nitrogen. The stirred solution was cooled at −10° C. in an acetone/dry ice bath then a solution of trifluoroacetic anhydride (0.241 g, 1.15 mmol) in DCM (3 mL) was added. The reaction was then allowed to reach rt over 3 h. The reaction was quenched with NH$_4$Cl (sat. solution, 2 mL), diluted with DCM (20 mL) and washed with H$_2$O (20 mL). The aqueous phase was extracted once with DCM (10 mL) and the combined organics were washed with brine, dried (Na$_2$SO$_4$) and filtered. The solvent was evaporated to give 2,2,2-trifluoro-N-methyl-N-((3-((4-nitro-1H-pyrazol-1-yl)methyl)oxetan-3-yl)methyl)acetamide compound as a yellowish oil (0.198 g, quantitative yield).

Step (iii)

N-((3-((4-amino-1H-pyrazol-1-yl)methyl)oxetan-3-yl)methyl)-2,2,2-trifluoro-N-methylacetamide was synthesised following the procedure in Example 213 (Step iii) using 2,2,2-trifluoro-N-methyl-N-((3-((4-nitro-1H-pyrazol-1-yl)methyl)oxetan-3-yl)methyl)acetamide.

Step (iv)

2,2,2-trifluoro-N-methyl-N-((3-((4-((1-(3-morpholinobenzyl)-1H-pyrazolo[3,4-d]pyrimidin-6-yl)amino)-1H-pyrazol-1-yl)methyl)oxetan-3-yl)methyl)acetamide was made according to the procedure in Example 1 (Step ii) using 3-morpholinobenzyl methanesulfonate (see Example 202, Step (i)) and 6-chloro-1H-pyrazolo[3,4-d]pyrimidine followed by Example 1 (Step i) using N-((3-((4-amino-1H-pyrazol-1-yl)methyl)oxetan-3-yl)methyl)-2,2,2-trifluoro-N-methylacetamide.

Step (v)

2,2,2-trifluoro-N-methyl-N-((3-((4-((1-(3-morpholinobenzyl)-1H-pyrazolo[3,4-d]pyrimidin-6-yl)amino)-1H-pyrazol-1-yl)methyl)oxetan-3-yl)methyl)acetamide (22 mg, 37.5 µmol) was dissolved in MeOH (1 mL) in a small vial. A solution of K$_2$CO$_3$ (26 mg, 187 µmol) in H$_2$O (60 µL) was added to the solution, and the closed vial was heated at 55° C. for 1.5 h. The mixture was then diluted with EtOAc (7 mL) and washed with H$_2$O (5 ml). The aqueous was extracted with a mixture of CHCl$_3$/IPA=2:1 (3 mL×2). The organics were dried on Na$_2$SO$_4$, filtered and the solvent evaporated. The crude (22 mg) was purified by prep HPLC to give the title compound (2 mg). $^1$H NMR (d$_6$-Acetone): δ 8.93 (s, 1H), 8.85 (s, 1H), 8.26 (s, 1H), 8.14 (s, 1H), 7.95 (s, 1H), 7.71 (s, 1H), 7.17 (t, 1H), 7.05 (s, 1H), 6.85 (dd, J=8.0, 2.2 Hz, 1H), 6.80 (d, J=7.4 Hz, 1H), 5.52 (s, 2H), 4.59 (d, J=6.1 Hz, 2H), 4.50 (s, 2H), 4.34 (d, J=6.1 Hz, 2H), 3.72 (t, 4H), 3.06 (m, 4H), 2.52 (s, 2H), 2.38 (s, 3H); LC-MS method B, (ES+) 490.2, RT=5.08 min.

Example 260

2-(4-((1-(2-Cyclopropylbenzyl)-1H-pyrazolo[3,4-d]pyrimidin-6-yl)amino)-1H-pyrazol-1-yl)ethanol The title compound was made according to the procedure in Example 1 using 1-(bromomethyl)-2-cyclopropylbenzene and 2-(4-amino-1H-pyrazol-1-yl)ethanol. 2-(4-amino-1H-pyrazol-1-yl)ethanol was prepared as in Procedure A using 2-bromoethanol as alkylating agent:

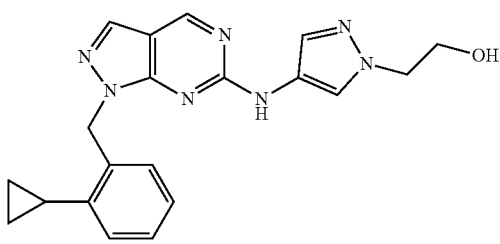 [SMILES: OCCn1cc(Nc2ncc3cnn(Cc4ccccc4C4CC4)c3n2)cn1]

¹H NMR (d₆-DMSO) δ 9.81 (s, 1H), 8.92 (s, 1H), 8.05 (s, 1H), 8.01 (s, 1H), 7.60 (s, 1H), 7.19 (td, 1H), 7.10 (td, 1H), 7.02-7.03 (m, 2H), 5.71 (s, 2H), 4.86 (t, 1H), 4.10 (t, 2H), 3.68-3.72 (m, 2H), 2.19 (s, 1H), 0.86 (d, 2H), 0.61-0.65 (m, 2H); LC-MS method B, (ES+) 376, RT=8.07 min Example 261

2-(4-((1-(2-Fluoro-6-(trifluoromethyl)benzyl)-1H-pyrazolo[3,4-d]pyrimidin-6-yl)amino)-1H-pyrazol-1-yl)ethanol The title compound was made according to the procedure in Example 1 using 2-(bromomethyl)-1-fluoro-3-(trifluoromethyl)benzene and 2-(4-amino-1H-pyrazol-1-yl)ethanol. 2-(4-amino-1H-pyrazol-1-yl)ethanol was prepared as in Procedure A using 2-bromoethanol as alkylating agent:

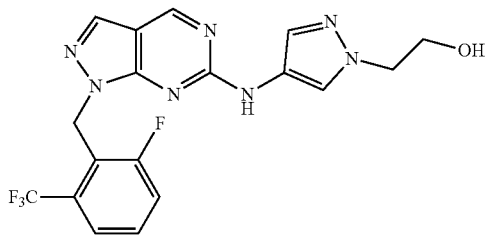 [SMILES: OCCn1cc(Nc2ncc3cnn(Cc4c(F)cccc4C(F)(F)F)c3n2)cn1]

¹H NMR (d₆-DMSO) δ 9.86 (s, 1H), 8.89 (s, 1H), 8.13 (s, 1H), 7.95 (s, 1H), 7.58-7.69 (m, 4H), 5.66 (s, 2H), 4.86 (t, 1H), 4.13 (t, 2H), 3.74 (q, 2H); LC-MS method B, (ES+) 422, RT=7.87 min.

Example 262

N-(1-(3-(Dimethylamino)propyl)-1H-pyrazol-4-yl)-1-(2,3,6-trifluoro-5-morpholinobenzyl)-1H-pyrazolo[3,4-d]pyrimidin-6-amine

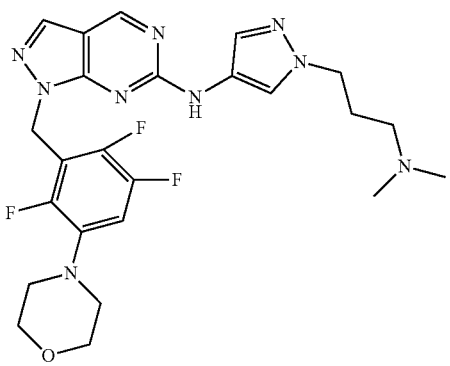 [SMILES: CN(C)CCCn1cc(Nc2ncc3cnn(Cc4c(F)c(F)cc(N5CCOCC5)c4F)c3n2)cn1]

Step (i)
1-(3-(dimethylamino)propyl)-1H-pyrazol-4-amine was prepared by Procedure A using 3-chloro-N,N-dimethylpropan-1-amine.HCl as alkylating agent.

Step (ii)
1-(3-(dimethylamino)propyl)-1H-pyrazol-4-amine was formed following Procedure A using 3-chloro-N,N-dimethylpropan-1-amine as alkylating agent Step (iii)
4-(3-(bromomethyl)-2,4,5-trifluorophenyl)morpholine was made following the procedure in Example 210 (Steps i-iii).

Step (iii)
The title compound was made according to the procedure in Example 1 using 1-(3-(dimethylamino)propyl)-1H-pyrazol-4-amine in Step (i) and 4-(3-(bromomethyl)-2,4,5-trifluorophenyl)morpholine in Step (ii). ¹H NMR (d₆-Acetone) δ 8.97 (s, 1H), 8.86 (s, 1H), 8.29 (s, 1H), 7.94 (s, 1H), 7.72 (s, 1H), 7.16-6.94 (m, 1H), 5.69 (s, 2H), 4.20 (t, J=6.9 Hz, 2H), 3.86-3.67 (m, 4H), 3.13-2.96 (m, 4H), 2.26 (t, J=6.8 Hz, 2H), 2.18 (s, 6H), 2.01 (t, J=6.9 Hz, 2H); LC-MS method B, (ES+) 516.2, RT=5.37 min.

Example 263

N-(1-(3-(Dimethylamino)propyl)-1H-pyrazol-4-yl)-1-(2-fluoro-3-morpholinobenzyl)-1H-pyrazolo[3,4-d]pyrimidin-6-amine The title compound was made according to the procedure in Example 214 using 1-(3-(dimethylamino)propyl)-1H-pyrazol-4-amine in Step (iv). 1-(3-(dimethylamino)propyl)-1H-pyrazol-4-amine was prepared as in Procedure A using 3-chloro-N,N-dimethylpropan-1-amine.HCl as alkylating agent:

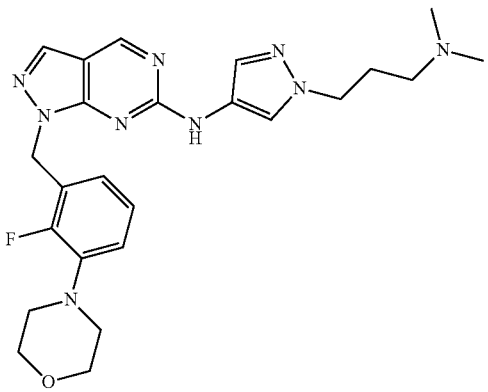 [SMILES: CN(C)CCCn1cc(Nc2ncc3cnn(Cc4cccc(N5CCOCC5)c4F)c3n2)cn1]

¹H NMR (d₆-DMSO) δ 9.85 (s, 1H), 8.91 (s, 1H), 8.13-8.00 (m, 2H), 7.59 (s, 1H), 7.12-6.92 (m, 2H), 6.84 (s, 1H), 5.57 (s, 2H), 4.16-4.04 (m, 2H), 3.76-3.67 (m, 4H), 3.00-2.91 (m, 4H), 2.19-2.14 (m, 2H), 2.11 (s, 6H), 1.93-1.85 (m, 2H); LC-MS method B, (ES+) 480.2, RT=5.28 min.

Example 264

2-(4-((1-(2-Fluoro-5-morpholinobenzyl)-1H-pyrazolo[3,4-d]pyrimidin-6-yl)amino)-1H-pyrazol-1-yl)ethanol The title compound was formed following the procedure in Example 205 using 2-(4-amino-1H-pyrazol-1-yl)ethanol in Step (iii). 2-(4-amino-1H-pyrazol-1-yl)ethanol was synthesized following Procedure A using 2-bromoethanol as alkylating agent:

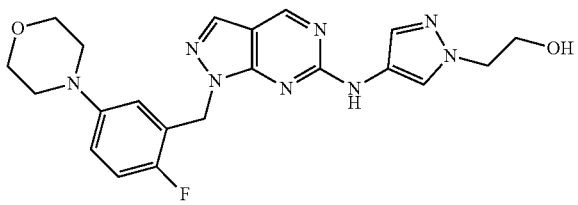 [SMILES: OCCn1cc(Nc2ncc3cnn(Cc4cc(N5CCOCC5)ccc4F)c3n2)cn1]

¹H NMR (d₆-DMSO) δ 9.83 (br s, 1H), 8.90 (s, 1H), 8.12 (br s, 1H), 8.03 (s, 1H), 7.66 (s, 1H), 7.07 (t, 1H), 6.96 (br s, 1H), 6.91-6.86 (m, 1H), 5.52 (s, 2H), 4.87 (s, 1H), 4.13 (t, 2H), 3.73 (t, 2H), 3.64 (t, 4H), 2.91 (t, 4H); LC-MS method B, (ES+) 439.2, RT=6.86 min.

Example 265

2-(4-((1-(2,3,6-Trifluoro-5-morpholinobenzyl)-1H-pyrazolo[3,4-d]pyrimidin-6-yl)amino)-1H-pyrazol-1-yl)ethanol

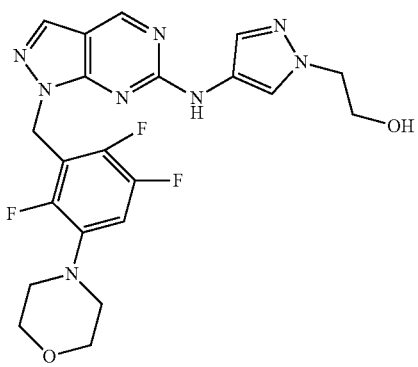 [SMILES: OCCn1cc(Nc2ncc3cnn(Cc4c(F)c(F)cc(N5CCOCC5)c4F)c3n2)cn1]

Step (i)
2-(4-amino-1H-pyrazol-1-yl)ethanol was synthesisied following Procedure A using 2-bromoethanol as alkylating agent.
Step (ii)
The title compound was formed following the procedure in Example 210 using 2-(4-amino-1H-pyrazol-1-yl)ethanol in Step (iv).
¹H NMR (d₆-Acetone) δ 8.95 (s, 1H), 8.84 (s, 1H), 8.32 (s, 1H), 7.92 (s, 1H), 7.73 (s, 1H), 7.04 (dt, J=12.3, 8.2 Hz, 1H), 5.67 (s, 2H), 4.23 (m, 2H), 4.01 (s, 1H), 3.93 (t, J=5.5 Hz, 2H), 3.74 (dd, J=5.5, 3.8 Hz, 4H), 3.10-2.93 (m, 4H); LC-MS method B, (ES+) 474.2, RT=7.47 min.

Example 266

4-(2-Fluoro-3-((6-((1-(2-hydroxyethyl)-1H-pyrazol-4-yl)amino)-1H-pyrazolo[3,4-d]pyrimidin-1-yl)methyl)phenyl)morpholin-3-one

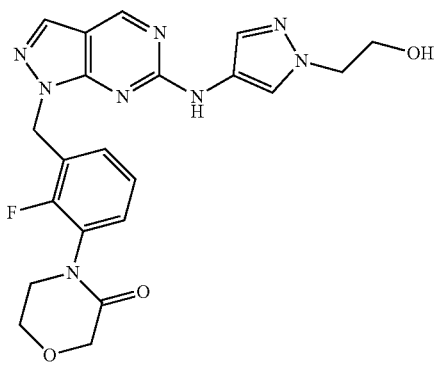 [SMILES: O=C1COCCN1c1cccc(Cn2ncc3cnc(Nc4cnn(CCO)c4)nc32)c1F]

Step (i)
1-bromo-3-(bromomethyl)-2-fluorobenzene was formed following the procedure in Example (Step i) using 3-bromo-2-fluorobenzoic acid to form 4-(2-fluoro-3-(hydroxymethyl)phenyl)morpholin-3-one followed by the bromination procedure as in Example 189 (Step ii).
Step (ii)
2-(4-amino-1H-pyrazol-1-yl)ethanol was made following Procedure A using 2-bromoethanol as alkylating agent.
Step (iii)
2-(4-((1-(3-bromo-2-fluorobenzyl)-1H-pyrazolo[3,4-d]pyrimidin-6-yl)amino)-1H-pyrazol-1-yl)ethano 1 was formed following the procedure in Example 1 using 1-bromo-3-(bromo methyl)-2-fluorobenzene and 2-(4-amino-1H-pyrazol-1-yl)ethanol.
Step (iv)
The title compound was made following the procedure in Example 227 (Step ii) using 2-(4-((1-(3-bromo-2-fluorobenzyl)-1H-pyrazolo[3,4-d]pyrimidin-6-yl)amino)-1H-pyrazol-1-yl)ethano 1. ¹H NMR (d₆-DMSO) δ 10.01 (s, 1H), 9.04 (s, 1H), 8.25 (s, 1H), 8.18 (s, 1H), 7.74 (s, 1H), 7.56-7.50 (m, 1H), 7.43-7.29 (m, 2H), 5.73 (s, 2H), 4.98 (t, J=5.5 Hz, 1H), 4.35 (s, 2H), 4.24 (t, J=5.5 Hz, 2H), 4.13-4.05 (m, 2H), 3.89-3.81 (m, 2H), 3.81-3.72 (m, 2H); LC-MS method B, (ES+) 453.1, RT=6.04 min.

Example 267

2-(4-((1-(3-(piperazin-1-yl)benzyl)-1H-pyrazolo[3,4-d]pyrimidin-6-yl)amino)-1H-pyrazol-1-yl)ethanol

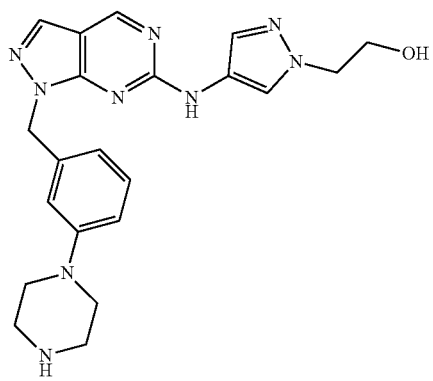 [SMILES: OCCn1cc(Nc2ncc3cnn(Cc4cccc(N5CCNCC5)c4)c3n2)cn1]

Step (i)
2-(4-amino-1H-pyrazol-1-yl)ethanol was made following Procedure A using 2-bromoethanol as alkylating agent.
Step (ii)
The title compound was made following the procedure in Example 215 using 2-(4-amino-1H-pyrazol-1-yl)ethanol in Step (iii). ¹H NMR (d₆-DMSO) δ 9.83 (s, 1H), 8.90 (s, 1H), 8.13 (s, 1H), 8.04 (s, 1H), 7.64 (s, 1H), 7.16-7.08 (m, 1H), 6.98 (s, 1H), 6.81 (dd, J=8.3, 2.0 Hz, 1H), 6.70 (s, 1H), 5.46 (s, 2H), 4.92 (br s, 1H), 4.14 (t, J=5.5 Hz, 2H), 3.74 (t, J=5.5 Hz, 2H), 3.18 (d, 1H), 3.00-2.91 (m, 4H), 2.79-2.72 (m, 4H); LC-MS method B, (ES+) 420.2, RT=4.51 min.

Example 268

1-(3-Morpholinobenzyl)-N-(1-(piperidin-3-ylmethyl)-1H-pyrazol-4-yl)-1H-pyrazolo[3,4-d]pyrimidin-6-amine

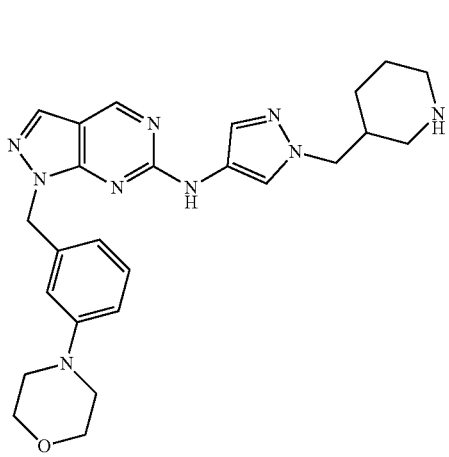 [SMILES: c1cc(Cn2ncc3cnc(Nc4cnn(CC5CCCNC5)c4)nc32)cc(N2CCOCC2)c1]

Step (i)

3-morpholinobenzyl methanesulfonate was prepared according to the procedure in Example 45 (Step ii) using (3-morpholinophenyl)methanol.

Step (ii)

tert-butyl 3-(hydroxymethyl)piperidine-1-carboxylate was prepared following the procedure in Example 45 (Step i) using 1-(tert-butoxycarbonyl)piperidine-3-carboxylic acid.

Step (iii)

tert-butyl 3-((4-amino-1H-pyrazol-1-yl)methyl)piperidine-1-carboxylate was prepared following the procedure in Example 165 using tert-butyl 3-(hydroxymethyl)piperidine-1-carboxylate.

Step (iv)

tert-butyl 3-((4-((1-(3-morpholino benzyl)-1H-pyrazolo[3,4-d]pyrimidin-6-yl)amino)-1H-pyrazol-1-yl)methyl)piperidine-1-carboxylate was made according to the procedure in Example 1 (Step ii), using 3-morpholinobenzyl methanesulfonate and 6-chloro-1H-pyrazolo[3,4-d]pyrimidine followed by Example 1 (Step i) using tert-butyl 3-((4-amino-1H-pyrazol-1-yl)methyl)piperidine-1-carboxylate.

Step (v)

The title compound was made following the procedure in Example 215 (Step iv) using tert-butyl 3-((4-((1-(3-morpholinobenzyl)-1H-pyrazolo[3,4-d]pyrimidin-6-yl)amino)-1H-pyrazol-1-yl)methyl)piperidine-1-carboxylate. $^1$H NMR (CDCl$_3$) δ 8.78 (s, 1H), 7.91 (s, 1H), 7.87 (s, 1H), 7.63 (s, 1H), 7.25-7.19 (m, 1H), 7.18 (s, 1H), 6.95-6.92 (m, 1H), 6.89-6.84 (m, 1H), 6.84-6.79 (m, 1H), 5.48 (s, 2H), 4.04-3.92 (m, 2H), 3.83-3.78 (m, 4H), 3.12-3.08 (m, 4H), 3.02-2.92 (m, 2H), 2.61-2.53 (m, 1H), 2.44-2.34 (m, 1H), 2.14-2.02 (m, 1H), 1.81-1.37 (m, 3H), 1.29-1.11 (m, 2H); LC-MS method B, (ES+) 474, RT=5.19 min.

Example 269

1-(3-Fluoro-5-morpholinobenzyl)-N-(1-methyl-1H-pyrazol-4-yl)-1H-pyrazolo[3,4-d]pyrimidin-6-amine Step (i)

(3-fluoro-5-morpholinophenyl)methanol was formed following the procedure in Example 214 (Steps i-iii) using 3-amino-5-fluorobenzoic acid.

Step (ii)

The title compound was formed following the procedure in Example 1 using 4-(3-(bromomethyl)-5-fluorophenyl)morpholine in Step (ii). $^1$H NMR (d$_6$-DMSO) δ 9.84 (s, 1H), 8.91 (s, 1H), 8.05 (s, 2H), 7.57 (s, 1H), 6.84 (s, 1H), 6.70-6.62 (m, 1H), 6.47-6.36 (m, 1H), 5.49 (s, 2H), 3.83 (s, 3H), 3.71-3.61 (m, 4H), 3.11-3.01 (m, 4H); LC-MS method B, (ES+) 409, RT=8.19 min.

Example 270

4-(3-((6-((1-(3-(Dimethylamino)propyl)-1H-pyrazol-4-yl)amino)-1H-pyrazolo[3,4-d]pyrimidin-1-yl)methyl)-2-fluorophenyl)morpholin-3-one

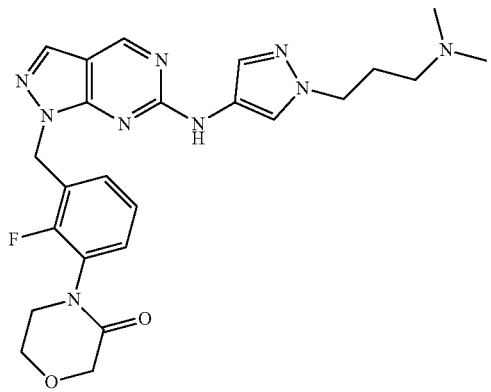 [SMILES: CN(C)CCCn1cc(Nc2ncc3cnn(Cc4cccc(N5CCOCC5=O)c4F)c3n2)cn1]

Step (i)

1-bromo-3-(bromomethyl)-2-fluorobenzene was formed following in the procedure in Example 45 (Step i) using 3-bromo-2-fluorobenzoic acid to form (3-bromo-2-fluorophenyl)methanol followed by the bromination procedure in Example 189 (Step ii).

Step (ii)

1-(3-(dimethylamino)propyl)-1H-pyrazol-4-amine was prepared by Procedure A using 3-chloro-N,N-dimethylpropan-1-amine.HCl as alkylating agent.

Step (iii)
1-(3-bromo-2-fluorobenzyl)-N-(1-(3-(dimethylamino)propyl)-1H-pyrazol-4-yl)-1H-pyrazolo[3,4-d]pyrimidin-6-amine was formed following the procedure in Example 1 using 1-(3-(dimethylamino)propyl)-1H-pyrazol-4-amine and 1-bromo-3-(bromo methyl)-2-fluorobenzene.

Step (iv)
The title compound was made following the procedure in Example 227 (step ii) using 1-(3-amino-2-fluorobenzyl)-N-(1-(3-(dimethylamino)propyl)-1H-pyrazol-4-yl)-1H-pyrazolo[3,4-d]pyrimidin-6-amine. $^1$H NMR (d$_6$-DMSO) δ 9.88 (s, 1H), 8.92 (s, 1H), 8.13-8.04 (m, 2H), 7.59 (s, 1H), 7.41 (m, 1H), 7.25-7.18 (m, 2H), 5.62 (s, 2H), 4.23 (s, 2H), 4.10 (t, J=6.9 Hz, 2H), 4.02-3.93 (m, 2H), 3.69-3.59 (m, 2H), 2.17 (t, J=6.9 Hz, 2H), 2.11 (s, 6H), 1.92-1.85 (m, 2H); LC-MS method B, (ES+) 494.2, RT=4.68 min.

Example 271

2-(4-((1-(3-Fluoro-5-morpholinobenzyl)-1H-pyrazolo[3,4-d]pyrimidin-6-yl)amino)-1H-pyrazol-1-yl)ethanol The title compound was made following the procedure in Example 269 using 2-(4-amino-1H-pyrazol-1-yl)ethanol. 2-(4-amino-1H-pyrazol-1-yl)ethanol was made following Procedure A using 2-bromoethanol as alkylating agent:

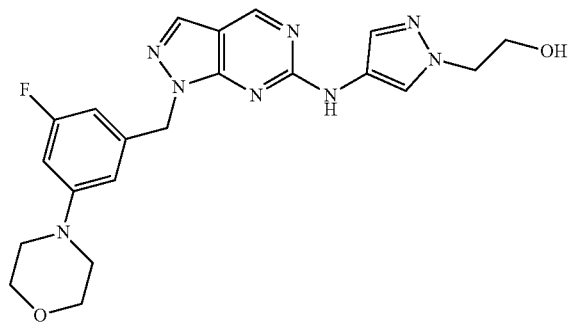 [SMILES: OCCn1cc(Nc2ncc3cnn(Cc4cc(F)cc(N5CCOCC5)c4)c3n2)cn1]

$^1$H NMR (d$_6$-DMSO) δ 9.85 (br s, 1H), 8.91 (s, 1H), 8.10 (br s, 1H), 8.05 (s, 1H), 7.63 (s, 1H), 6.83 (s, 1H), 6.66 (dt, 1H), 6.42 (br d, 1H), 5.48 (s, 2H), 4.88 (t, 1H), 4.13 (t, 2H), 3.73 (q, 2H), 3.66 (t, 4H), 3.06 (t, 4H); LC-MS method B, (ES+) 439.2, RT=7.26 min.

Example 272

4-(3-Fluoro-5-(((6-((1-methyl-1H-pyrazol-4-yl)amino)-1H-pyrazolo[3,4-d]pyrimidin-1-yl)methyl)phenyl)morpholin-3-one

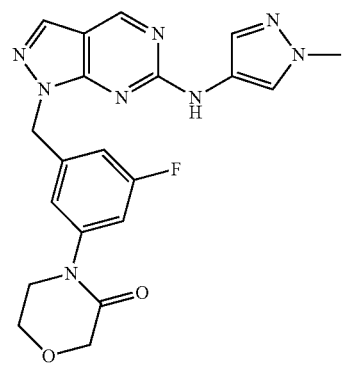 [SMILES: Cn1cc(Nc2ncc3cnn(Cc4cc(F)cc(N5CCOCC5=O)c4)c3n2)cn1]

Step (i)
1-(3-bromo-5-fluorobenzyl)-N-(1-methyl-1H-pyrazol-4-yl)-1H-pyrazolo[3,4-d]pyrimidin-6-amine was made following the procedure in Example 1 using 1-bromo-3-(bromomethyl)-5-fluorobenzene.

Step (ii)
The title compound was made following the procedure in Example 227 (Step ii) using 1-(3-bromo-5-fluorobenzyl)-N-(1-methyl-1H-pyrazol-4-yl)-1H-pyrazolo[3,4-d]pyrimidin-6-amine. $^1$H NMR (d$_6$-DMSO) δ 9.62 (s, 1H), 8.68 (s, 1H), 7.85-7.78 (m, 2H), 7.30 (s, 1H), 7.09-7.00 (m, 2H), 6.79-6.72 (m, 1H), 5.34 (s, 2H), 3.93 (s, 2H), 3.71-3.64 (m, 2H), 3.59 (s, 3H), 3.46-3.40 (m, 2H); LC-MS method B, (ES+) 423.1, RT=6.80 min.

Example 273

4-(3,4-Difluoro-5-(((6-((1-methyl-1H-pyrazol-4-yl)amino)-1H-pyrazolo[3,4-d]pyrimidin-1-yl)methyl)phenyl)morpholin-3-one

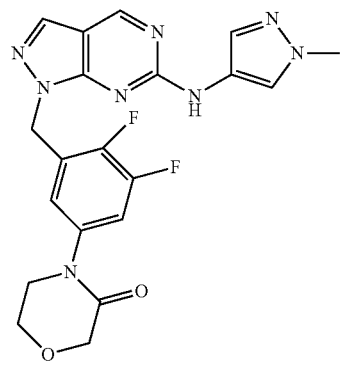 [SMILES: Cn1cc(Nc2ncc3cnn(Cc4cc(N5CCOCC5=O)cc(F)c4F)c3n2)cn1]

Step (i)
1-(5-bromo-2,3-difluorobenzyl)-N-(1-methyl-1H-pyrazol-4-yl)-1H-pyrazolo[3,4-d]pyrimidin-6-amine was made following the procedure in Example 45 (Steps ii-iii) using (5-bromo-2,3-difluorophenyl)methanol.

Step (ii)
The title compound was made following the procedure in Example 227 (Step ii) using 1-(5-bromo-2,3-difluorobenzyl)-N-(1-methyl-1H-pyrazol-4-yl)-1H-pyrazolo[3,4-d]pyrimidin-6-amine. $^1$H NMR (d$_6$-DMSO) δ 9.90 (s, 1H), 8.93 (s, 1H), 8.12 (s, 1H), 8.08 (s, 1H), 7.62-7.53 (m, 2H), 7.31 (s, 1H), 5.66 (s, 2H), 4.18 (s, 2H), 3.95-3.89 (m, 2H), 3.86 (s, 3H), 3.69-3.62 (m, 2H); LC-MS method B, (ES+) 441.2, RT=7.05 min.

Example 274

1-(2-Fluoro-3-((6-((1-methyl-1H-pyrazol-4-yl)amino)-1H-pyrazolo[3,4-d]pyrimidin-1-yl)methyl)phenyl)piperazin-2-one 1

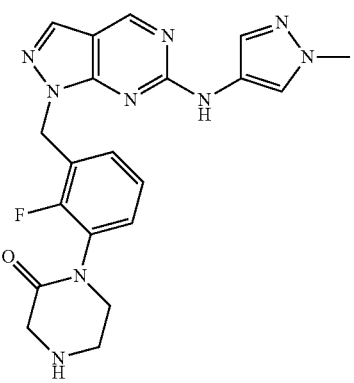 [SMILES: Cn1cc(Nc2ncc3cnn(Cc4cccc(N5CCNCC5=O)c4F)c3n2)cn1]

Step (i)

Tert-butyl 4-(2-fluoro-3-((6-((1-methyl-1H-pyrazol-4-yl)amino)-1H-pyrazolo[3,4-d]pyrimidin-1-yl)methyl)phenyl)-3-oxopiperazine-1-carboxylate was made following the procedure in Example 258 using 1-(3-bromo-2-fluorobenzyl)-N-(1-methyl-1H-pyrazol-4-yl)-1H-pyrazolo[3,4-d]pyrimidin-6-amine and tert-butyl 3-oxopiperazine-1-carboxylate in Step (iii).

Step (ii)

The title compound was made following the procedure in Example 215 (Step iv) using tert-butyl 4-(2-fluoro-3-((6-((1-methyl-1H-pyrazol-4-yl)amino)-1H-pyrazolo[3,4-d]pyrimidin-1-yl)methyl)phenyl)-3-oxopiperazine-1-carboxylate. $^1$H NMR (CDCl$_3$) δ 8.79 (s, 1H), 7.98 (s, 1H), 7.93 (s, 1H), 7.54 (s, 1H), 7.25-7.09 (m, 5H), 5.62 (s, 2H), 3.94 (s, 3H), 3.71 (s, 2H), 3.64-3.59 (m, 2H), 3.24-3.18 (m, 2H); LC-MS method B, (ES+) 422, RT=4.54 min.

Example 275

1-(2-Fluoro-3-((6-((1-(2-hydroxyethyl)-1H-pyrazol-4-yl)amino)-1H-pyrazolo[3,4-d]pyrimidin-1-yl)methyl)phenyl)piperazin-2-one

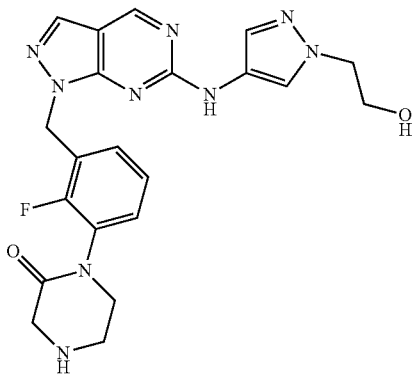 [SMILES: O=C1CNCCN1c1cccc(Cn2ncc3cnc(Nc4cnn(CCO)c4)nc32)c1F]

Step (i)

2-(4-amino-1H-pyrazol-1-yl)ethanol was made following Procedure A using 2-bromoethanol as alkylating agent.

Step (ii)

tert-butyl 4-(2-fluoro-3-((64(1-(2-hydroxyethyl)-1H-pyrazol-4-yl)amino)-1H-pyrazolo[3,4-d]pyrimidin-1-yl)methyl)phenyl)-3-oxopiperazine-1-carboxylate was made following the procedure in Example 258 using tert-butyl 3-oxopiperazine-1-carboxylate and 2-(4-amino-1H-pyrazol-1-yl)ethano 1.

Step (iii)

The title compound was deprotected following the procedure in Example 215 (Step iv) using tert-butyl 4-(2-fluoro-3-46-((1-methyl-1H-pyrazol-4-yl)amino)-1H-pyrazolo[3,4-d]pyrimidin-1-yl)methyl)phenyl)-3-oxopiperazine-1-carboxylate. $^1$H NMR (CDCl$_3$) δ 8.79 (s, 1H), 8.22 (s, 1H), 7.95 (s, 1H), 7.47 (s, 1H), 7.24-7.07 (m, 5H), 5.65 (s, 2H), 4.28-4.21 (m, 2H), 3.98-3.94 (m, 2H), 3.72 (s, 2H), 3.67-3.60 (m, 2H), 3.23 (t, J=5.4 Hz, 2H), 2.61 (s, 1H); LC-MS method B, (ES+) 452, RT=4.29 min.

Example 276

2-(4-((1-(2,3-Difluoro-5-morpholinobenzyl)-1H-pyrazolo[3,4-d]pyrimidin-6-yl)amino)-1H-pyrazol-1-yl)ethanol

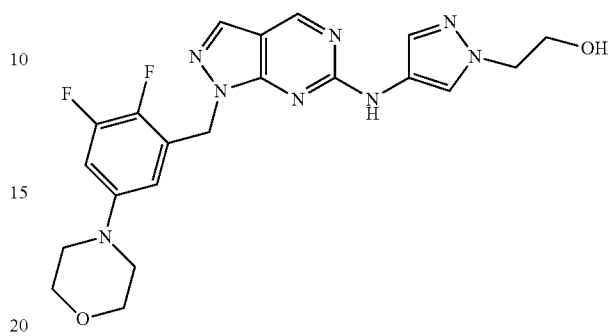

Step (i)

2-(4-amino-1H-pyrazol-1-yl)ethanol was made following Procedure A using 2-bromoethanol as alkylating agent.

Step (ii)

The title compound was made following the procedure in Example 255 using 2-(4-amino-1H-pyrazol-1-yl)ethanol in Step (iv). $^1$H NMR (d$_6$-DMSO) δ 9.70 (s, 1H), 8.74 (s, 1H), 7.97 (s, 1H), 7.88 (s, 1H), 7.51 (s, 1H), 6.88-6.73 (m, 1H), 6.62 (s, 1H), 5.41 (s, 2H), 4.71 (t, 1H), 3.97 (t, 2H), 3.61-3.55 (m, 2H), 3.47 (t, 4H), 2.80 (t, 4H); LC-MS method 50, (ES+) 457.2, RT=7.28 min.

Example 277

1-(3-((6-((1-(2-Hydroxyethyl)-1H-pyrazol-4-yl)amino)-1H-pyrazolo[3,4-d]pyrimidin-1-yl)methyl)phenyl)piperazin-2-one

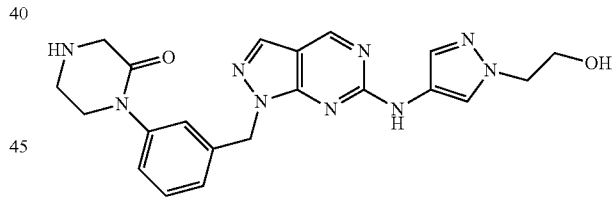

Step (i)

2-(4-amino-1H-pyrazol-1-yl)ethanol was made following Procedure A using 2-bromoethanol as alkylating agent Step (ii)

tert-butyl 4-(3-((6-((1-(2-hydroxyethyl)-1H-pyrazol-4-yl)amino)-1H-pyrazolo[3,4-d]pyrimidin-1-yl)methyl)phenyl)-3-oxopiperazine-1-carboxylate was made according to the procedure in Example 227 using tert-butyl 3-oxopiperazine-1-carboxylate and 2-(4-amino-1H-pyrazol-1-yl)ethano 1.

Step (iii)

The title compound was made according to the procedure in Example 215 (Step iv). $^1$H NMR (d$_6$-DMSO) δ 9.85 (br s, 1H), 8.91 (s, 1H), 8.12 (br s, 1H), 8.05 (s, 1H), 7.59 (s, 1H), 7.36-7.32 (m, 2H), 7.24-7.19 (m, 2H), 5.54 (s, 2H), 4.87 (br s, 1H), 4.13 (t, 2H), 3.73 (t, 2H), 3.53 (t, 2H), 3.38 (s, 2H), 3.00 (s, 2H); LC-MS method B, (ES+) 434.0, RT=4.20 min.

Example 278

4-(3-Fluoro-5-((6-((1-(2-hydroxyethyl)-1H-pyrazol-4-yl)amino)-1H-pyrazolo[3,4-d]pyrimidin-1-yl)methyl)phenyl)morpholin-3-one The title compound was made following the procedure in Example 272 using 2-(4-amino-1H-pyrazol-1-yl)ethanol. 2-(4-amino-1H-pyrazol-1-yl)ethanol was made following Procedure A using 2-bromoethanol as alkylating agent:

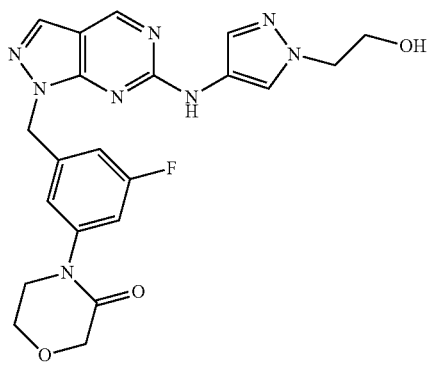 [SMILES: O=C1COCCN1c1cc(F)cc(Cn2ncc3cnc(Nc4cnn(CCO)c4)nc32)c1]

$^1$H NMR (d$_6$-DMSO) δ 9.87 (s, 1H), 8.93 (s, 1H), 8.17-8.03 (m, 2H), 7.60 (s, 1H), 7.34-7.24 (m, 2H), 7.04-6.94 (m, 1H), 5.57 (s, 2H), 4.88 (t, J=5.3 Hz, 1H), 4.18 (s, 2H), 4.14 (t, J=5.7 Hz, 2H), 3.93 (m, 2H), 3.76-3.71 (m, 2H), 3.71-3.67 (m, 2H); LC-MS method B, (ES+) 453.2, RT=6.10 min.

Example 279

4-(3,4-Difluoro-5-((6-((1-(2-hydroxyethyl)-1H-pyrazol-4-yl)amino)-1H-pyrazolo[3,4-d]pyrimidin-1-yl)methyl)phenyl)morpholin-3-one The title compound was made following the procedure in Example 273 using 2-(4-amino-1H-pyrazol-1-yl)ethanol. 2-(4-amino-1H-pyrazol-1-yl)ethanol was made following Procedure A using 2-bromoethanol as alkylating agent:

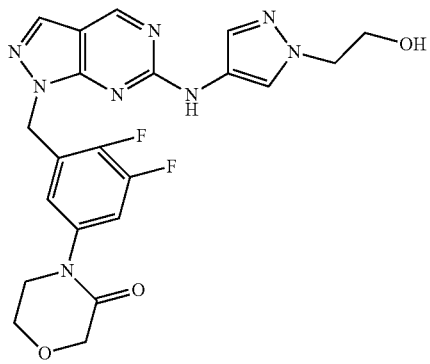 [SMILES: O=C1COCCN1c1cc(F)c(F)c(Cn2ncc3cnc(Nc4cnn(CCO)c4)nc32)c1]

$^1$H NMR (d$_6$-DMSO) δ 9.88 (s, 1H), 8.92 (s, 1H), 8.12 (s, 1H), 8.06 (s, 1H), 7.64 (s, 1H), 7.60-7.52 (m, 1H), 7.29 (s, 1H), 5.63 (s, 2H), 4.87 (t, J=5.3 Hz, 1H), 4.16 (s, 2H), 4.14 (t, J=5.8 Hz, 2H), 3.93-3.88 (m, 2H), 3.77-3.71 (m, 2H), 3.66-3.62 (m, 2H); LC-MS method B, (ES+) 470.8, RT=6.26 min.

Example 280

1-(3-Morpholinobenzyl)-N-(1-(pyrrolidin-3-ylmethyl)-1H-pyrazol-4-yl)-1H-pyrazolo[3,4-d]pyrimidin-6-amine

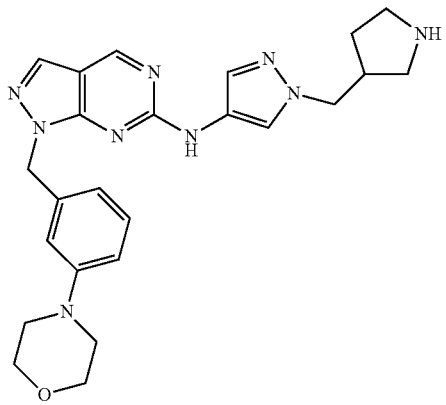 [SMILES: c1cc(Cn2ncc3cnc(Nc4cnn(CC5CCNC5)c4)nc32)cc(N2CCOCC2)c1]

Step (i)
tert-butyl 3-((4-amino-1H-pyrazol-1-yl)methyl)pyrrolidine-1-carboxylate was prepared as in Example 165 using tert-butyl 3-(hydroxymethyl)pyrrolidine-1-carboxylate
Step (ii)
tert-butyl 3-((4-((1-(3-morpholino benzyl)-1H-pyrazolo[3,4-d]pyrimidin-6-yl)amino)-1H-pyrazol-1-yl)methyl)pyrrolidine-1-carboxylate was made according to the procedure in Example 202, using tert-butyl 3-((4-amino-1H-pyrazol-1-yl)methyl)pyrrolidine-1-carboxylate in Step (ii).
Step (iii)
The title compound was made by Boc deprotection following the procedure in Example 215 (Step iv). $^1$H NMR (d$_6$-DMSO) δ 9.83 (s, 1H), 8.90 (s, 1H), 8.08 (s, 1H), 8.03 (s, 1H), 7.68-7.55 (m, 1H), 7.14 (t, J=7.9 Hz, 1H), 6.97 (s, 1H), 6.83 (d, J=8.1 Hz, 1H), 6.70 (s, 1H), 5.48 (s, 2H), 4.11 (d, J=7.8 Hz, 1H), 4.02 (d, J=7.1 Hz, 1H), 3.71-3.63 (m, 4H), 3.63-3.56 (m, 2H), 3.05-2.95 (m, 4H), 2.85-2.60 (m, 3H). 1.90-1.60 (m, 3H); LC-MS method B, (ES+) 460, RT=5.17 min.

Example 281

4-(2,4,5-Trifluoro-3-((6-((1-methyl-1H-pyrazol-4-yl)amino)-1H-pyrazolo[3,4-d]pyrimidin-1-yl)methyl)phenyl)morpholin-3-one

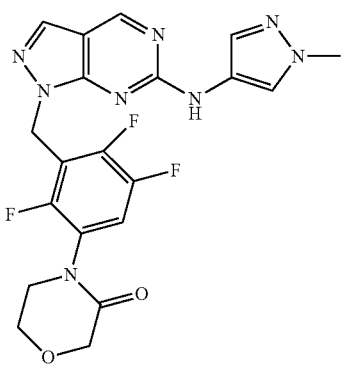 [SMILES: Cn1cc(Nc2ncc3cnn(Cc4c(F)c(F)cc(N5CCOCC5=O)c4F)c3n2)cn1]

Step (i) n-Butyllithium (2.5M in hexane, 10.5 mL, 1.1 eq.) was added dropwise over 15 min to a solution of diisopropylamine (4.0 mL, 1.2 eq.) in THF (25 mL) at 0° C. After stirring for 15 min, the LDA solution was added dropwise over 40 min to a solution of 2,4,5-trifluorobromobenzene (5.0 g, 24 mmol) in THF (50 mL) at −78° C. The solution was stirred for 10 min and then transferred to a slurry of dry ice (50 g) in diethylether (65 mL). The reaction was allowed to warm to rt and treated with 1M HCl. The phases were separated and the organic layer extracted with 0.5M NaOH. The basic extracts were acidified to pH 1 with 6M HCl and extracted with diethylether. The combined organic phases were dried over sodium sulfate and evaporated to yield 3-bromo-2,5,6-trifluorobenzoic acid as a white solid (3.2 g, 52%).

Step (ii)

3-bromo-2,5,6-trifluorobenzoic acid was reduced to (3-bromo-2,5,6-trifluorophenyl)methanol as in Example 179 (Step i).

Step (iii)

4-(2,4,5-trifluoro-3-(hydroxymethyl)phenyl)morpholin-3-one was prepared following the procedure in Example 227 (Step ii) using (3-bromo-2,5,6-trifluorophenyl)methanol.

Step (iv)

4-(3-(bromomethyl)-2,4,5-trifluorophenyl)morpholin-3-one was prepared according to Example 189 (Step ii).

Step (v)

The title compound was made according to Example 1 using 4-(3-(bromomethyl)-2,4,5-trifluorophenyl)morpholin-3-one. $^1$H NMR (d$_6$-DMSO) δ 9.91 (s, 1H), 8.91 (s, 1H), 8.15 (s, 1H), 8.03 (s, 1H), 7.86-7.76 (m, 1H), 7.60 (s, 1H), 5.67 (s, 2H), 4.21 (s, 2H), 3.98-3.92 (m, 2H), 3.85 (s, 3H), 3.66-3.61 (m, 2H); LC-MS method B, (ES+) 459.0, RT=6.97 min.

Example 282

4-(2,4,5-Trifluoro-3-((6-((1-(2-hydroxyethyl)-1H-pyrazol-4-yl)amino)-1H-pyrazolo[3,4-d]pyrimidin-1-yl)methyl)phenyl)morpholin-3-one The title compound was made according to the procedure in Example 281, using 2-(4-amino-1H-pyrazol-1-yl)ethanol which was prepared by Procedure A using 2-bromoethanol as alkylating agent:

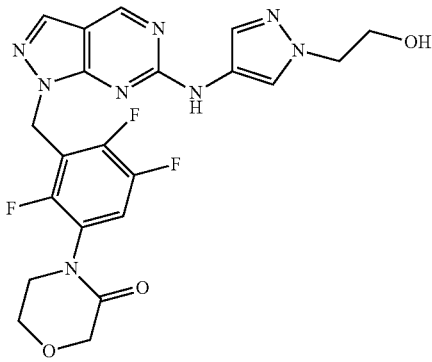 [SMILES: O=C1COCCN1c1cc(F)c(F)c(Cn2ncc3cnc(Nc4cnn(CCO)c4)nc32)c1F]

$^1$H NMR (d$_6$-DMSO) δ 9.91 (s, 1H), 8.91 (s, 1H), 8.16 (s, 1H), 8.03 (s, 1H), 7.87-7.73 (m, 1H), 7.67 (s, 1H), 5.65 (s, 2H), 4.87 (t, J=5.3 Hz, 1H), 4.22 (s, 2H), 4.17-4.12 (m, 2H), 3.98-3.93 (m, 2H), 3.78-3.72 (m, 2H), 3.67-3.62 (m, 2H), LC-MS method B, (ES+) 489.0, RT=6.30 min.

Example 283

2-(4-((1-(2,3,6-Trifluoro-5-(piperazin-1-yl)benzyl)-1H-pyrazolo[3,4-d]pyrimidin-6-yl)amino)-1H-pyrazol-1-yl)ethanol

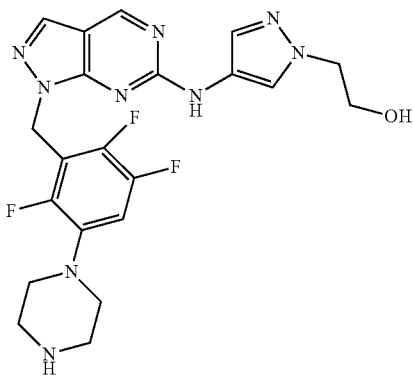 [SMILES: OCCn1cc(Nc2ncc3cnn(Cc4c(F)c(F)cc(N5CCNCC5)c4F)c3n2)cn1]

Step (i)

2,3,5,6-tetrafluoroterephthalonitrile (1 g, 5 mmol) was dissolved in acetone (15 mL) in a 2-necked flask under Nitrogen. A solution of tert-butyl piperazine-1-carboxylate (1.39 g, 7.5 mmol) in water (3 mL) was then added followed by triethylamine (1.01 g, 10 mmol). The solution was heated to 55° C. for 8 h then cooled to rt. The resulting solid was filtered then washed with acetone. The filtrate was concentrated under vacuum and the residue was dissolved again in DCM (30 mL) and washed once with 1M HCl (30 mL) and once with brine (30 mL). The organics were dried over Na$_2$SO$_4$, filtered and the solvent removed in vacuo to give tert-butyl 4-(2,5-dicyano-3,4,6-trifluorophenyl)piperazine-1-carboxylate as a bright yellow solid (0.938 g, 51% yield).

Step (ii)

tert-butyl 4-(2,5-dicyano-3,4,6-trifluorophenyl)piperazine-1-carboxylate (0.52 g, 1.42 mmol) was added in small portions to a stirred solution of 77% H$_2$SO$_4$ (1.5 ml) in a round bottomed vial. The vial was sealed under Nitrogen and then slowly heated to 165° C. The mixture was stirred at this temperature for 16 h then cooled to rt., diluted with MeOH (10 mL) and filtered over a celite cartridge. The filtrate was evaporated and redissolved in THF (10 mL) and triethylamine (3.4 mL, 25 mmol). A solution of Boc anhydride 1M in THF (1.68 mL, 1.68 mmol) was then added to the flask and the mixture was allowed to stir at rt for 3 h. The solution was diluted with Ethyl acetate (30 mL), washed with an aqueous buffer solution at pH=3 (30 mL) and the aqueous phase was then extracted with Ethyl acetate (2×10 mL). The combined organics were dried over Na$_2$SO$_4$, filtered and the solvent removed in vacuo to afford 3-(4-(tert-butoxycarbonyl)piperazin-1-yl)-2,5,6-trifluorobenzoic acid as a brown oil (0.84 g)

Step (iii)

3-(4-(tert-butoxycarbonyl)piperazin-1-yl)-2,5,6-trifluorobenzoic acid (0.84 g) was reacted in the standard reduction conditions with Borane in THF (see Example 179, Step i). The crude product was purified by Flash chromatography using a gradient of Hexane/Ethyl acetate (from 9:1 to 1:4) to give tert-butyl 4-(2,4,5-trifluoro-3-(hydroxymethyl)phenyl)piperazine-1-carboxylate as a white solid (0.18 g, 37% yield from beginning of step ii)

Step (iv)

tert-butyl 4-(2,4,5-trifluoro-3-(hydroxymethyl)phenyl)piperazine-1-carboxylate (180 mg, 0.52 mmol) was reacted under the standard conditions with PBr₃ in DCM (see Example 189, Step ii) to give tert-butyl 4-(3-(bromomethyl)-2,4,5-trifluorophenyl)piperazine-1-carboxylate (57 mg).

Step (v)

2-(4-amino-1H-pyrazol-1-yl)ethanol which was prepared by Procedure A using 2-bromoethanol as alkylating agent:

Step (vi)

tert-butyl 4-(2,4,5-trifluoro-3-46-41-(2-hydroxyethyl)-1H-pyrazol-4-yl)amino)-1H-pyrazolo[3,4-d]pyrimidin-1-yl)methyl)phenyl)piperazine-1-carboxylate.was made according to the procedure in Example 1 (Step i) using 2-(4-amino-1H-pyrazol-1-yl)ethanol followed by Example 1 (Step ii), using (tert-butyl 4-(3-(bromomethyl)-2,4,5-trifluorophenyl)piperazine-1-carboxylate and 2-(4-((1H-pyrazolo[3,4-d]pyrimidin-6-yl)amino)-1H-pyrazol-1-yl)ethanol to afford tert-butyl 4-(2,4,5-trifluoro-3-46-41-(2-hydroxyethyl)-1H-pyrazol-4-yl)amino)-1H-pyrazolo[3,4-d]pyrimidin-1-yl)methyl)phenyl)piperazine-1-carboxylate.

Step (vii)

tert-butyl 4-(2,4,5-trifluoro-3-46-41-(2-hydroxyethyl)-1H-pyrazol-4-yl)amino)-1H-pyrazolo[3,4-d]pyrimidin-1-yl)methyl)phenyl)piperazine-1-carboxylate was dissolved in dioxane (1.5 mL) and MeOH (0.7 mL) and a solution of HCl (4.0M dioxane, 0.5 mL) was added. The mixture was stirred at rt for 4 h. The solvent was then evaporated and the residue dissolved in DMSO (0.5 mL) and purified by prep HPLC to give 2-(4-((1-(2,3,6-trifluoro-5-(piperazin-1-yl)benzyl)-1H-pyrazolo[3,4-d]pyrimidin-6-yl)amino)-1H-pyrazol-1-yl)ethanol as yellow solid (3 mg). ¹H NMR (d₆-Acetone): δ 8.95 (s, 1H), 8.84 (s, 1H), 8.33 (s, 1H), 7.92 (s, 1H), 7.72 (s, 1H), 6.99 (dt, J=12.4, 8.2 Hz, 1H), 5.67 (s, 2H), 4.24 (t, J=5.5 Hz, 2H), 4.07 (s, 1H), 3.93 (t, J=5.5 Hz, 2H), 2.97-2.85 (m, 8H). LC-MS method B, (ES+) 474.00, RT=4.81 min.

Example 284

1-(3-Fluoro-5-((6-((1-(2-hydroxyethyl)-1H-pyrazol-4-yl)amino)-1H-pyrazolo[3,4-d]pyrimidin-1-yl)methyl)phenyl)piperazin-2-one

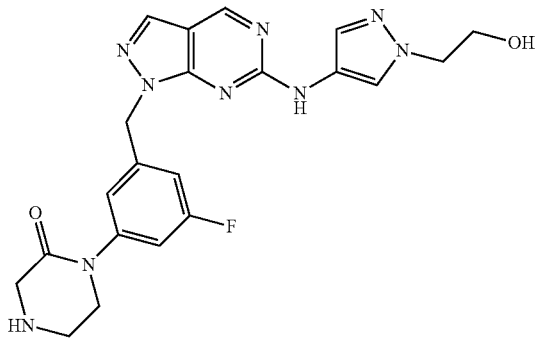 [SMILES: O=C1CNCCN1c1cc(F)cc(Cn2ncc3cnc(Nc4cnn(CCO)c4)nc32)c1]

Step (i)

2-(4-amino-1H-pyrazol-1-yl)ethanol was made following Procedure A using 2-bromoethanol as alkylating agent.

Step (ii)

2-(4-((1-(3-bromo-5-fluorobenzyl)-1H-pyrazolo[3,4-d]pyrimidin-6-yl)amino)-1H-pyrazol-1-yl)ethano 1 was made according to the procedure in Example 1, using 2-(4-amino-1H-pyrazol-1-yl)ethanol in Step (i) and 1-bromo-3-(bromomethyl)-5-fluorobenzene in Step (ii).

Step (iii)

tert-butyl 4-(3-fluoro-5-46-41-(2-hydroxyethyl)-1H-pyrazol-4-yl)amino)-1H-pyrazolo[3,4-d]pyrimidin-1-yl)methyl)phenyl)-3-oxopiperazine-1-carboxylate was made according to the procedure in Example 227 (Step ii) using tert-butyl 3-oxopiperazine-1-carboxylate and 2-(4-((1-(3-bromo-5-fluorobenzyl)-1H-pyrazolo[3,4-d]pyrimidin-6-yl)amino)-1H-pyrazol-1-yl)ethanol.

Step (iv)

The title compound was made according to the procedure in Example 215 (Step iv) using tert-butyl 4-(3-fluoro-5-46-41-(2-hydroxyethyl)-1H-pyrazol-4-yl)amino)-1H-pyrazolo[3,4-d]pyrimidin-1-yl)methyl)phenyl)-3-oxopiperazine-1-carboxylate. ¹H NMR (d₆-DMSO) δ 9.87 (s, 1H), 8.92 (s, 1H), 8.12 (s, 1H), 8.07 (s, 1H), 7.59 (s, 1H), 7.29-7.12 (m, 2H), 6.99 (d, J=5.8 Hz, 1H), 5.56 (s, 2H), 4.88 (s, 1H), 4.20-4.00 (m, 3H), 3.73 (t, J=5.8 Hz, 2H), 3.54 (t, J=5.4 Hz, 2H), 3.17 (s, 2H), 2.98 (t, J=5.4 Hz, 2H); LC-MS method B, (ES+) 452.2, RT=4.39 min.

Example 285

1-(3-Fluoro-5-((6-((1-methyl-1H-pyrazol-4-yl)amino)-1H-pyrazolo[3,4-d]pyrimidin-1-yl)methyl)phenyl)piperazin-2-one

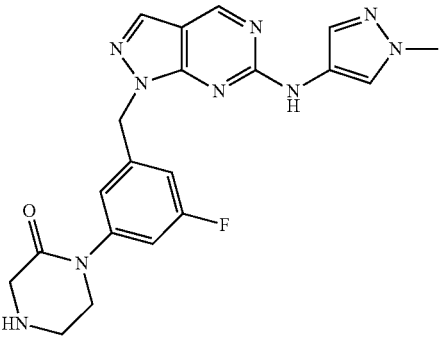 [SMILES: Cn1cc(Nc2ncc3cnn(Cc4cc(F)cc(N5CCNCC5=O)c4)c3n2)cn1]

Step (i)

1-(3-bromo-5-fluorobenzyl)-N-(1-methyl-1H-pyrazol-4-yl)-1H-pyrazolo[3,4-d]pyrimidin-6-amine was made according to the procedure in Example 1, using 1-bromo-3-(bromomethyl)-5-fluorobenzene in Step (ii).

Step (ii)

tert-butyl 4-(3-fluoro-5-46-((1-methyl-1H-pyrazol-4-yl)amino)-1H-pyrazolo[3,4-d]pyrimidin-1-yl)methyl)phenyl)-3-oxopiperazine-1-carboxylate was made according to the procedure in Example 227 (Step ii) using tert-butyl 3-oxopiperazine-1-carboxylate.

Step (iii)

The title compound was made according to the procedure in Example 215 (Step iv) using tert-butyl 4-(3-fluoro-5-((6-((1-methyl-1H-pyrazol-4-yl)amino)-1H-pyrazolo[3,4-d]pyrimidin-1-yl)methyl)phenyl)-3-oxopiperazine-1-carboxylate. ¹H NMR (d₆-DMSO) δ 9.86 (s, 1H), 8.92 (s, 1H), 8.07 (s, 2H), 7.54 (s, 1H), 7.18 (m, 2H), 6.99 (s, 1H), 5.57 (s, 2H), 3.83 (s, 3H), 3.61-3.47 (m, 2H), 3.37 (s, 2H), 3.07-2.88 (m, 2H); LC-MS method B, (ES+) 422.2, RT=4.61 min.

Example 286

1-(3-(3-Methoxyazetidin-1-yl)benzyl)-N-(1-methyl-1H-pyrazol-4-yl)-1H-pyrazolo[3,4-d]pyrimidin-6-amine

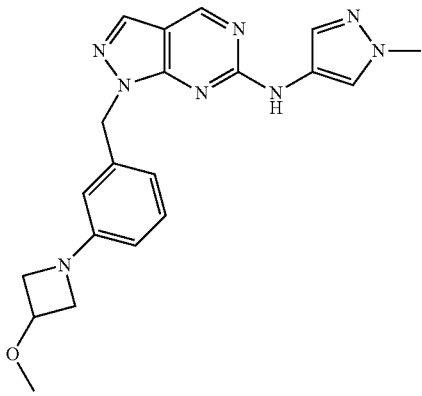 [SMILES: COC1CN(c2cccc(Cn3ncc4cnc(Nc5cnn(C)c5)nc43)c2)C1]

Step (i)

1-(3-iodobenzyl)-N-(1-methyl-1H-pyrazol-4-yl)-1H-pyrazolo[3,4-d]pyrimidin-6-amine was made according to the procedure in Example 1, using 1-(bromomethyl)-3-iodobenzene in Step (ii).

Step (ii)

The title compound was made according to the procedure in Example 162 (Step ii) using 1-(3-iodobenzyl)-N-(1-methyl-1H-pyrazol-4-yl)-1H-pyrazolo[3,4-d]pyrimidin-6-amine and 3-methoxyazetidine. $^1$H NMR ($d_6$-DMSO) δ 9.85 (s, 1H), 8.88 (s, 1H), 8.10-7.97 (m, 2H), 7.58 (s, 1H), 7.09 (t, J=7.8 Hz, 1H), 6.57 (d, J=6.6 Hz, 1H), 6.49 (s, 1H), 6.37-6.28 (m, 1H), 5.45 (s, 2H), 4.26 (tt, J=6.1, 4.3 Hz, 1H), 4.00-3.89 (m, 2H), 3.84 (s, 3H), 3.49 (m, 4.3 Hz, 2H), 3.20 (s, 3H); LC-MS method B, (ES+) 391.2, RT=7.99 min.

Example 287

N-(1-Methyl-1H-pyrazol-4-yl)-1-(2,3,6-trifluoro-5-(piperazin-1-yl)benzyl)-1H-pyrazolo[3,4-d]pyrimidin-6-amine The title compound was made according to the procedure in Example 283, using N-(1-methyl-1H-pyrazol-4-yl)-1H-pyrazolo[3,4-d]pyrimidin-6-amine in Step (vi):

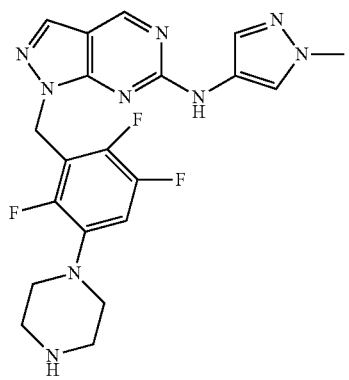 [SMILES: Cn1cc(Nc2ncc3cnn(Cc4c(F)c(F)cc(N5CCNCC5)c4F)c3n2)cn1]

$^1$H NMR ($d_6$-Acetone) δ 8.94 (s, 1H), 8.84 (s, 1H), 8.26 (s, 1H), 7.92 (s, 1H), 7.65 (s, 1H), 6.99 (dd, J=8.2, 4.2 Hz, 1H), 5.67 (s, 2H), 3.89 (s, 3H), 2.91 (m, 8H); LC-MS method B, (ES+) 444.20, RT=5.18 min.

Example 288

1-(2-Fluoro-3-(piperazin-1-yl)benzyl)-N-(1-methyl-1H-pyrazol-4-yl)-1H-pyrazolo[3,4-d]pyrimidin-6-amine

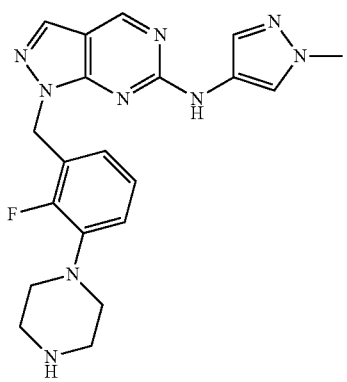 [SMILES: Cn1cc(Nc2ncc3cnn(Cc4cccc(N5CCNCC5)c4F)c3n2)cn1]

Step (i)

3-(4-(tert-butoxycarbonyl)piperazin-1-yl)-2-fluorobenzoic acid was synthesised following the procedure in Example 162 (Step ii) using 3-bromo-2-fluorobenzoic acid and tert-butyl piperazine-1-carboxylate.

Step (ii)

tert-butyl 4-(2-fluoro-3-(hydroxymethyl)phenyl)piperazine-1-carboxylate was formed following the procedure in Example 179 (Step i) using 3-(4-(tert-butoxycarbonyl)piperazin-1-yl)-2-fluorobenzoic acid.

Step (iii)

tert-butyl 4-(3-(chloromethyl)-2-fluorophenyl)piperazine-1-carboxylate was synthesized following the procedure in Example 201 (Step ii) using tert-butyl 4-(2-fluoro-3-(hydroxymethyl)phenyl)piperazine-1-carboxylate.

Step (iv)

tert-butyl 4-(2-fluoro-3-46-((1-methyl-1H-pyrazol-4-yl)amino)-1H-pyrazolo[3,4-d]pyrimidin-1-yl)methyl)phenyl)piperazine-1-carboxylate was synthesized following the procedure in Example 1 using tert-butyl 4-(3-(chloromethyl)-2-fluorophenyl)piperazine-1-carboxylate in Step (ii).

Step (v)

The title product was formed by deprotection following a procedure analogous to Example 215 (Step iv) using tert-butyl 4-(2-fluoro-3-((6-((1-methyl-1H-pyrazol-4-yl)amino)-1H-pyrazolo[3,4-d]pyrimidin-1-yl)methyl)phenyl)piperazine-1-carboxylate. $^1$H NMR ($d_6$-Acetone) δ 8.91 (br s, 1H), 8.85 (s, 1H), 8.19 (s, 1H), 7.96 (s, 1H), 7.61 (d, J=3.2 Hz, 1H), 7.06-6.91 (m, 2H), 6.82 (s, 1H), 5.62 (s, 2H), 3.88 (s, 3H), 3.12-3.03 (m, 2H), 3.03-2.91 (m, 6H); LC-MS method B, (ES+) 408.20, RT=4.78 min.

Example 289

2-(4-((1-(3-Fluoro-5-(3-oxomorpholino)benzyl)-1H-pyrazolo[3,4-d]pyrimidin-6-yl)amino)-1H-pyrazol-1-yl)-N-methylacetamide

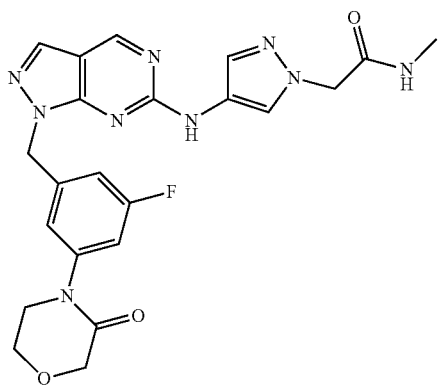 [SMILES: CNC(=O)Cn1cc(Nc2ncc3cnn(Cc4cc(F)cc(N5CCOCC5=O)c4)c3n2)cn1]

Step (i)

To a stirred solution of 1-H nitropyrazole (2.0 g, 17.6 mmol) and triethylamine (2.5 mL, 2 eq) in THF (20 mL) was added Boc anhydride (1.2 eq, 2.3 mL, 2M in THF). After stirring for 18 h at 20° C., the reaction mixture was diluted with EtOAc, washed with water then brine, dried (sat. MgSO$_4$) and concentrated. Purification (silica, Isolera) with a gradient of 0-50% EtOAc in petroleum ether 40-60 gave tert-butyl 4-nitro-1H-pyrazole-1-carboxylate as a white solid (1.7 g, 45% yield). $^1$H NMR (d$_6$-DMSO) δ 9.30 (d, 1H), 8.53 (d, 1H), 1.61 (s, 9H).

Step (ii)

tert-butyl 4-nitro-1H-pyrazole-1-carboxylate was stirred with palladium on carbon (10%, 170 mg) in ethanol (20 mL) under an atmosphere of hydrogen at 20° C. for 18 h. The palladium was removed by filtration and the solvent was removed in vacuo to give tert-butyl 4-amino-1H-pyrazole-1-carboxylate (1.48 g). $^1$H NMR (d$_6$-DMSO) δ 7.35 (d, 1H), 7.33 (d, 1H), 4.40 (s, 2H), 1.54 (s, 9H).

Step (iii) (3-bromo-5-fluorophenyl)methanol was formed by reducing 3-bromo-5-fluorobenzoic acid using the procedure in Example 179 (Step i).

Step (iv)

4-(3-fluoro-5-(hydroxymethyl)phenyl)morpholin-3-one was made as in Example 227 (Step ii) using (3-bromo-5-fluorophenyl)methanol.

Step (v)

4-(3-(bromomethyl)-5-fluorophenyl)morpholin-3-one was made as in Example 189 (Step ii) using 4-(3-fluoro-5-(hydroxymethyl)phenyl)morpholin-3-one.

Step (vi)

4-(3-((6-chloro-1H-pyrazolo[3,4-d]pyrimidin-1-yl)methyl)-5-fluorophenyl)morpholin-3-one was made following the procedure in Example 1 (Step ii) using 6-chloro-1H-pyrazolo[3,4-d]pyrimidine and 4-(3-(bromomethyl)-5-fluorophenyl)morpholin-3-one.

Step (vii)

4-(3-((6-((1H-pyrazol-4-yl)amino)-1H-pyrazolo[3,4-d]pyrimidin-1-yl)methyl)-5-fluorophenyl)morpholin-3-one was made following the procedure in Example 1 (Step i) using 4-(3-((6-chloro-1H-pyrazolo[3,4-d]pyrimidin-1-yl)methyl)-5-fluorophenyl)morpholin-3-one Step (iii) and tert-butyl 4-amino-1H-pyrazole-1-carboxylate.

Step (viii)

The title compound was made following the conditions in Procedure A using 4-(3-((6-((1H-pyrazol-4-yl)amino)-1H-pyrazolo[3,4-d]pyrimidin-1-yl)methyl)-5-fluorophenyl)morpholin-3-one and 2-bromo-N-methylacetamide. $^1$H NMR (d$_6$-DMSO) δ 9.94 (s, 1H), 8.94 (s, 1H), 8.17 (s, 1H), 8.09 (s, 1H), 7.87 (d, J=4.2 Hz, 1H), 7.62 (s, 1H), 7.36-7.23 (m, 2H), 7.00 (s, 1H), 5.58 (s, 2H), 4.77 (s, 2H), 4.18 (s, 2H), 3.92 (dd, J=5.8, 4.3 Hz, 2H), 3.75-3.61 (m, 2H), 2.61 (d, J=4.9 Hz, 3H); LC-MS method B, (ES+) 480.20, RT=6.18 min.

Example 290

2-(4-((1-(2-Fluorobenzyl)-1H-pyrazolo[3,4-d]pyrimidin-6-yl)amino)-1H-pyrazol-1-yl)-N-methylacetamide

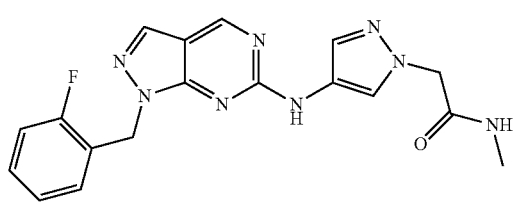 [SMILES: CNC(=O)Cn1cc(Nc2ncc3cnn(Cc4ccccc4F)c3n2)cn1]

Step (i)

2-(4-amino-1H-pyrazol-1-yl)-N-methylacetamide was made according to Procedure A using 2-bromo-N-methylacetamide.

Step (ii)

The title compound was made according to the procedure in Example 1 (Step ii) using 6-chloro-1H-pyrazolo[3,4-d]pyrimidine and 1-(chloromethyl)-2-fluorobenzene followed by Example 1 (Step i) using 2-(4-amino-1H-pyrazol-1-yl)-N-methylacetamide. $^1$H NMR (d$_6$-DMSO) δ 9.91 (s, 1H), 8.92 (s, 1H), 8.13 (s, 1H), 8.05 (s, 1H), 7.86 (br s, 1H), 7.64 (s, 1H), 7.36-7.12 (m, 4H), 5.59 (s, 2H), 4.74 (s, 2H), 2.61 (d, J=4 Hz, 3H); LC-MS method B, (ES+) 381, RT=6.87 min.

Example 291

2-(4-((1-((6-Fluoropyridin-2-yl)methyl)-1H-pyrazolo[3,4-d]pyrimidin-6-yl)amino)-1H-pyrazol-1-yl)-N-methylacetamide

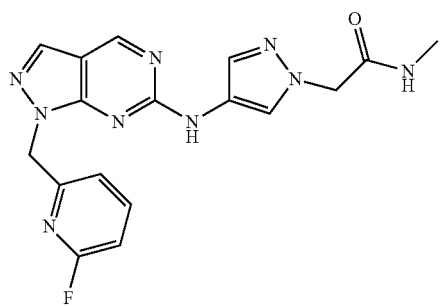 [SMILES: CNC(=O)Cn1cc(Nc2ncc3cnn(Cc4cccc(F)n4)c3n2)cn1]

Step (i)

2-(4-amino-1H-pyrazol-1-yl)-N-methylacetamide was made according to Procedure A using 2-bromo-N-methylacetamide.

Step (ii)

The title compound was made according to the procedure in Example 1 (Step ii) using 6-chloro-1H-pyrazolo[3,4-d]pyrimidine and 2-(chloromethyl)-6-fluoropyridine followed by Example 1 (Step i) using 2-(4-amino-1H-pyrazol-1-yl)-N-methylacetamide. $^1$H NMR (d$_6$-DMSO) 9.93 (s, 1H), 8.95 (s, 1H), 8.10 (s, 1H), 8.07 (s, 1H), 7.92-7.98 (m, 1H), 7.85 (s, 1H), 7.85 (s, 1H), 7.08-7.11 (m, 2H) 5.62 (s, 2H), 4.73 (s, 2H), 2.60 (d, 3H); LC-MS method B, (ES+) 382.1, RT=6.12 min.

Example 292

4-(2,4-Difluoro-3-((6-((1-methyl-1H-pyrazol-4-yl)amino)-1H-pyrazolo[3,4-d]pyrimidin-1-yl)methyl)phenyl)morpholin-3-one The title compound was formed following the procedure in Example 281 using 1-bromo-2,4-difluorobenzene in Step (i):

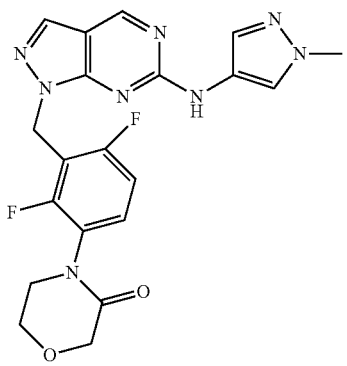 [SMILES: Cn1cc(Nc2ncc3cnn(Cc4c(F)ccc(N5CCOCC5=O)c4F)c3n2)cn1]

$^1$H NMR (d$_6$-DMSO) δ 9.88 (s, 1H), 8.90 (s, 1H), 8.16 (s, 1H), 8.01 (s, 1H), 7.62-7.50 (m, 2H), 7.27-7.19 (m, 1H), 5.62 (s, 2H), 4.21 (s, 2H), 3.99-3.93 (m, 2H), 3.85 (s, 3H), 3.65-3.58 (m, 2H); LC-MS method B, (ES+) 441, RT=6.58 min.

Example 293

4-(2,4-Difluoro-3-((6-((1-(2-hydroxyethyl)-1H-pyrazol-4-yl)amino)-1H-pyrazolo[3,4-d]pyrimidin-1-yl)methyl)phenyl)morpholin-3-one

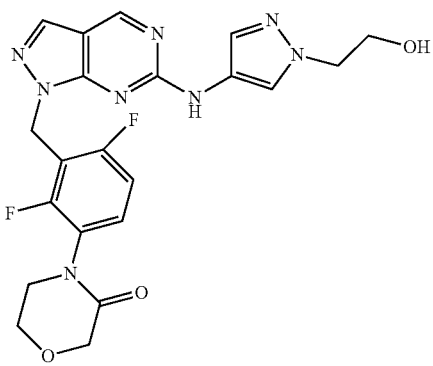 [SMILES: O=C1COCCN1c1ccc(F)c(Cn2ncc3cnc(Nc4cnn(CCO)c4)nc32)c1F]

Step (i)

4-(3-(bromomethyl)-2,4-difluorophenyl)morpholin-3-one was formed following the procedure in Example 281 (Steps i-iv) using 1-bromo-2,4-difluorobenzene in Step (i).

Step (ii)

2-(4-amino-1H-pyrazol-1-yl)ethanol was prepared by Procedure A using 2-bromoethanol as alkylating agent.

Step (iii)

The title compound was formed following the procedure in Example 1 using 6-chloro-1H-pyrazolo[3,4-d]pyrimidine and 4-(3-(bromomethyl)-2,4-difluorophenyl)morpholin-3-one in Step (ii) followed by 2-(4-amino-1H-pyrazol-1-yl)ethanol in Step (i). $^1$H NMR (d$_6$-DMSO) δ 9.88 (s, 1H), 8.90 (s, 1H), 8.17 (s, 1H), 8.01 (s, 1H), 7.66 (s, 1H), 7.58-7.51 (m, 1H), 7.26-7.19 (m, 1H), 5.60 (s, 2H), 4.87 (t, J=5.5 Hz, 1H), 4.21 (s, 2H), 4.17-4.12 (m, 2H), 3.98-3.94 (m, 2H), 3.78-3.72 (m, 2H), 3.64-3.60 (m, 2H); LC-MS method B, (ES+) 471, RT=5.99 min.

Example 294

4-(3-((6-((1-(3-(Dimethylamino)propyl)-1H-pyrazol-4-yl)amino)-1H-pyrazolo[3,4-d]pyrimidin-1-yl)methyl)-2,4,5-trifluorophenyl)morpholin-3-one

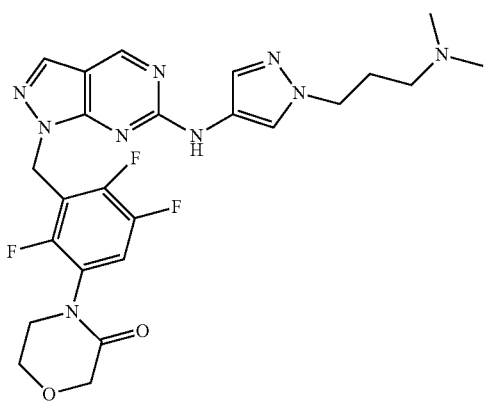 [SMILES: CN(C)CCCn1cc(Nc2ncc3cnn(Cc4c(F)c(F)cc(N5CCOCC5=O)c4F)c3n2)cn1]

Step (i)

4-(3-(bromomethyl)-2,4,5-trifluorophenyl)morpholin-3-one was formed as in Example 281 (Steps i-iv).

Step (ii)

1-(3-(dimethylamino)propyl)-1H-pyrazol-4-amine was formed following Procedure A using 3-chloro-N,N-dimethylpropan-1-amine.HCl as alkylating agent.

Step (iii)

The title compound was made according to the procedure in Example 1 using 1-(3-(dimethylamino)propyl)-1H-pyrazol-4-amine in Step (i) and 4-(3-(bromomethyl)-2,4,5-trifluorophenyl)morpholin-3-one in Step (ii). $^1$H NMR (d$_6$-DMSO) δ 9.92 (s, 1H), 8.91 (s, 1H), 8.19 (s, 1H), 8.03 (s, 1H), 7.86-7.77 (m, 1H), 7.64 (s, 1H), 5.66 (s, 2H), 4.21 (s, 2H), 4.16-4.09 (m, 2H), 3.99-3.91 (m, 2H), 3.68-3.61 (m, 2H), 2.30-2.24 (m, 2H), 2.18 (s, 6H), 1.98-1.88 (m, 2H); LC-MS method B, (ES+) 530, RT=4.83 min.

Example 295

1-(3,4-Difluoro-5-((6-((1-methyl-1H-pyrazol-4-yl)amino)-1H-pyrazolo[3,4-d]pyrimidin-1-yl)methyl)phenyl)piperazin-2-one

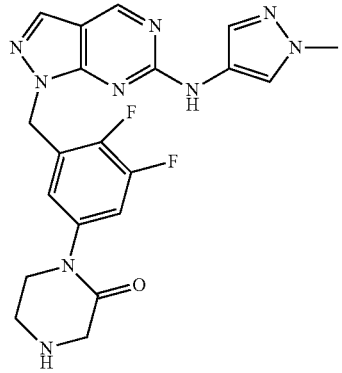 [SMILES: Cn1cc(Nc2ncc3cnn(Cc4cc(N5CCNCC5=O)cc(F)c4F)c3n2)cn1]

Step (i)

(5-bromo-2,3-difluorophenyl)methanol was synthesized following the procedure in Example 179 (Step i) using 5-bromo-2,3-difluorobenzoic acid.

Step (ii)

tert-butyl 4-(3,4-difluoro-5-(hydroxymethyl)phenyl)-3-oxopiperazine-1-carboxylate was prepared following the procedure in Example 227 (Step ii) using (5-bromo-2,3-difluorophenyl)methanol.

Step (iii)

tert-butyl 4-(3,4-difluoro-5-(((methylsulfonyl)oxy)methyl)phenyl)-3-oxopiperazine-1-carboxylate was prepared following the procedure of Example 45, Step (ii) using tert-butyl 4-(3,4-difluoro-5-(hydroxymethyl)phenyl)-3-oxopiperazine-1-carboxylate.

Step (iv)

N-(1-methyl-1H-pyrazol-4-yl)-1H-pyrazolo[3,4-d]pyrimidin-6-amine was prepared as in Example 1 (Step i) followed by Example 1 (Step ii) using tert-butyl 4-(3,4-difluoro-5-(((methylsulfonyl)oxy)methyl)phenyl)-3-oxopiperazine-1-carboxylate to afford tert-butyl 4-(3,4-difluoro-5-((6-((1-methyl-1H-pyrazol-4-yl)amino)-1H-pyrazolo[3,4-d]pyrimidin-1-yl)methyl)phenyl)-3-oxopiperazine-1-carboxylate.

Step (v)

The title compound was formed by deprotection following a procedure analogous to Example 215 (Step iv) using tert-butyl 4-(3,4-difluoro-5-((6-((1-methyl-1H-pyrazol-4-yl)amino)-1H-pyrazolo[3,4-d]pyrimidin-1-yl)methyl)phenyl)-3-oxopiperazine-1-carboxylate. $^1$H NMR (d$_6$-DMSO) δ 9.89 (s, 1H), 8.92 (s, 1H), 8.11 (s, 1H), 8.07 (s, 1H), 7.58 (s, 1H), 7.51-7.42 (m, 1H), 7.19 (s, 1H), 5.64 (s, 2H), 3.84 (s, 3H), 3.53-3.46 (m, 2H), 3.34 (s, 2H), 2.97-2.90 (m, 2H), 2.85 (br s, 1H); LC-MS method B, (ES+) 440, RT=4.84 min.

Example 296

1-(3,4-Difluoro-5-((6-((1-(2-hydroxyethyl)-1H-pyrazol-4-yl)amino)-1H-pyrazolo[3,4-d]pyrimidin-1-yl)methyl)phenyl)piperazin-2-one

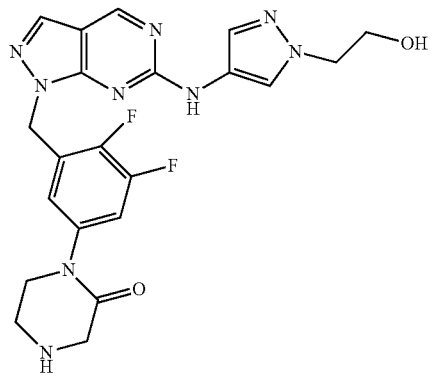 [SMILES: O=C1CNCCN1c1cc(F)c(F)c(Cn2ncc3cnc(Nc4cnn(CCO)c4)nc32)c1]

Step (i)

2-(4-amino-1H-pyrazol-1-yl)ethanol was prepared according to Procedure A using 2-bromoethanol as alkylating agent.

Step (ii)

2-(4-((1H-pyrazolo[3,4-d]pyrimidin-6-yl)amino)-1H-pyrazol-1-yl)ethanol was prepared as in Example 1 (Step i) using 2-(4-amino-1H-pyrazol-1-yl)ethanol.

Step (iii)

The title compound was made following the procedure in Example 295 using 2-(4-((1H-pyrazolo[3,4-d]pyrimidin-6-yl)amino)-1H-pyrazol-1-yl)ethanol in Step (iv). $^1$H NMR (d$_6$-DMSO) δ 9.88 (s, 1H), 8.92 (s, 1H), 8.13 (s, 1H), 8.06 (s, 1H), 7.64 (s, 1H), 7.50-7.43 (m, 1H), 7.19 (s, 1H), 5.63 (s, 2H), 4.89 (t, J=5.3 Hz, 1H), 4.14 (t, J=5.5 Hz, 2H), 3.78-3.70 (m, 2H), 3.49 (t, J=5.5 Hz, 2H), 3.33 (s, 2H), 2.97-2.91 (m, 2H), 2.68 (s, 1H); LC-MS method B, (ES+) 470, RT=4.66 min.

Example 297

4-(2,5-Difluoro-3-((6-((1-methyl-1H-pyrazol-4-yl)amino)-1H-pyrazolo[3,4-d]pyrimidin-1-yl)methyl)phenyl)morpholin-3-one

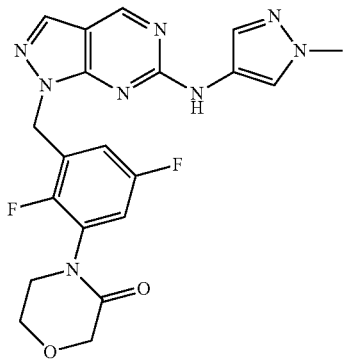 [SMILES: Cn1cc(Nc2ncc3cnn(Cc4cc(F)cc(N5CCOCC5=O)c4F)c3n2)cn1]

Step (i)

Raney nickel (5.3 g, 50% slurry in water) was added to a solution of 4-amino-3-bromo-2,5-difluoro-benzonitrile (4.0 g, 17.2 mmol) in formic acid (60 mL). After heating for 1 h at 85° C., the reaction mixture was filtered through Celite, washed with DCM and evaporated to dryness. The residue was suspended in DCM and neutralized carefully with saturated sodium hydrogencarbonate. The aqueous phase was extracted with DCM and the combined organic phases were dried over sodium sulfate and evaporated to yield 4-amino-3-bromo-2,5-difluorobenzaldehyde (3.4 g, 14.3 mmol, 83%). $^1$H NMR (d$_6$-DMSO) δ 9.91 (d, J=3.0 Hz, 1H), 7.45 (dd, J=11.0, 6.0 Hz, 1H), 6.96 (br s, 2H).

Step (ii)

4-amino-3-bromo-2,5-difluorobenzaldehyde (3.4 g, 14.3 mmol) was dissolved in acetic acid (18 mL) before addition of hypophosphoric acid (50% in water, 39 mL). A solution of sodium nitrite (1.4 eq, 1.4 g) in water (8 mL) was then added dropwise under ice-cooling. After stirring at rt for 2 h, the reaction mixture was poured onto a mixture ice/water and the aqueous phase extracted with DCM. The combined organic phases were dried over sodium sulfate and evaporated. A column chromatography (0 to 10% ethyl acetate in petroleum ether) afforded 3-bromo-2,5-difluorobenzaldehyde (1.3 g, 6.3 mmol, 44%). $^1$H NMR (d$_6$-DMSO) δ 10.15-10.12 (m, 1H), 8.13 (ddd, J=8.0, 5.0, 3.0 Hz, 1H), 7.66 (ddd, J=8.0, 5.0, 3.0 Hz, 1H).

Step (iii)

(3-bromo-2,5-difluorophenyl)methanol was prepared as in Example 45 (Step i) using 3-bromo-2,5-difluorobenzaldehyde.

Step (iv)

4-(2,5-difluoro-3-(hydroxymethyl)phenyl)morpholin-3-one was prepared following the procedure in Example 227 (Step ii) using (3-bromo-2,5-difluorophenyl)methanol.

Step (v)

4-(3-(bromomethyl)-2,5-difluorophenyl)morpholin-3-one was prepared according to Example 189 (Step ii).

Step (vi)

The title compound was prepared as in Example 1 (Step ii) using 4-(3-(bromomethyl)-2,5-difluorophenyl)morpholin-3-one and N-(1-methyl-1H-pyrazol-4-yl)-1H-pyrazolo[3,4-d]pyrimidin-6-amine. $^1$H NMR (d$_6$-DMSO) δ 9.90 (s, 1H), 8.93 (s, 1H), 8.13-8.05 (m, 2H), 7.56 (s, 1H), 7.48-7.42 (m, 1H), 7.14 (s, 1H), 5.63 (s, 2H), 4.23 (s, 2H), 3.99-3.93 (m, 2H), 3.83 (s, 3H), 3.70-3.63 (m, 2H); LC-MS method B, (ES+) 441, RT=6.82 min.

Example 298

4-(2,5-Difluoro-3-((6-((1-(2-hydroxyethyl)-1H-pyrazol-4-yl)amino)-1H-pyrazolo[3,4-d]pyrimidin-1-yl)methyl)phenyl)morpholin-3-one

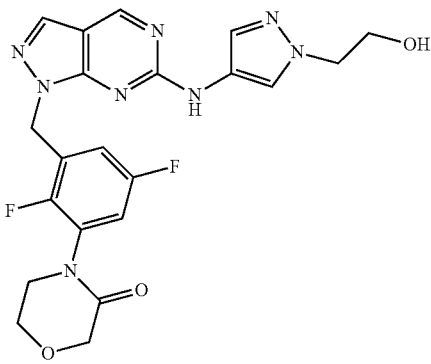 [SMILES: O=C1COCCN1c1cc(F)cc(Cn2ncc3cnc(Nc4cnn(CCO)c4)nc32)c1F]

Step (i)

2-(4-amino-1H-pyrazol-1-yl)ethanol was prepared according to Procedure A using 2-bromoethanol as alkylating agent.

Step (ii)

2-(4-((1H-pyrazolo[3,4-d]pyrimidin-6-yl)amino)-1H-pyrazol-1-yl)ethanol was prepared as in Example 1 (Step i) using 2-(4-amino-1H-pyrazol-1-yl)ethanol.

Step (iii)

The title compound was made following the procedure in Example 297 using 2-(4-((1H-pyrazolo[3,4-d]pyrimidin-6-yl)amino)-1H-pyrazol-1-yl)ethanol in Step (vi). $^1$H NMR (d$_6$-DMSO) δ 9.91 (s, 1H), 8.93 (s, 1H), 8.17-8.05 (m, 2H), 7.63 (s, 1H), 7.49-7.41 (m, 1H), 7.15 (s, 1H), 5.62 (s, 2H), 4.87 (t, J=5.5 Hz, 1H), 4.24 (s, 2H), 4.13 (m, 2H), 3.97 (m, 2H), 3.79-3.71 (m, 2H), 3.71-3.64 (m, 2H); LC-MS method B, (ES+) 471, RT=6.26 min.

Example 299

4-(3-((6-((1-(3-(Dimethylamino)propyl)-1H-pyrazol-4-yl)amino)-1H-pyrazolo[3,4-d]pyrimidin-1-yl)methyl)-2,4-difluorophenyl)morpholin-3-one

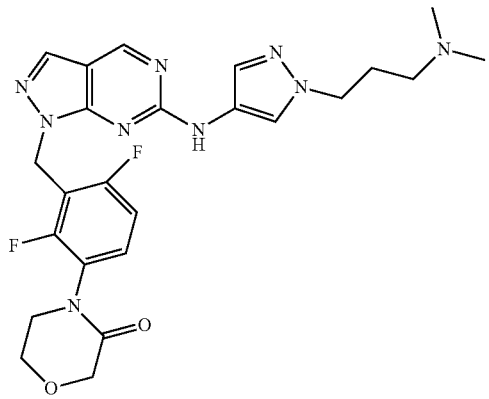 [SMILES: CN(C)CCCn1cc(Nc2ncc3cnn(Cc4c(F)ccc(N5CCOCC5=O)c4F)c3n2)cn1]

Step (i)

4-(3-(bromomethyl)-2,4-difluorophenyl)morpholin-3-one was formed following the procedure in Example 281 (Steps i-iv) using 1-bromo-2,4-difluorobenzene in Step (i).

Step (ii)

1-(3-(dimethylamino)propyl)-1H-pyrazol-4-amine was prepared by Procedure A using 3-chloro-N,N-dimethylpropan-1-amine.HCl as alkylating agent.

Step (iii)

The title compound was formed following the procedure in Example 1 (Step ii) using 6-chloro-1H-pyrazolo[3,4-d]pyrimidine and 4-(3-(bromomethyl)-2,4-difluorophenyl)morpholin-3-one followed by the procedure in Example 1 (Step i) using 1-(3-(dimethylamino)propyl)-1H-pyrazol-4-amine. $^1$H NMR (d$_6$-DMSO) δ 9.88 (s, 1H), 8.89 (s, 1H), 8.21 (s, 1H), 8.15 (s, 1H), 8.01 (s, 1H), 7.63 (s, 1H), 7.59-7.50 (m, 1H), 7.22 (m, 1H), 5.60 (s, 2H), 4.20 (s, 2H), 4.12 (t, J=7.0 Hz, 2H), 3.98-3.92 (m, 2H), 3.63-3.58 (m, 2H), 2.20 (t, J=7.0 Hz, 2H), 2.13 (s, 6H), 1.95-1.85 (m, 2H); LC-MS method B, (ES+) 512, RT=4.73 min.

Example 300

1-(2,4-Difluoro-3-((6-((1-methyl-1H-pyrazol-4-yl)amino)-1H-pyrazolo[3,4-d]pyrimidin-1-yl)methyl)phenyl)piperazin-2-one

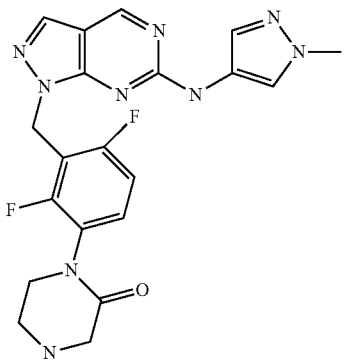 [SMILES: Cn1cc(Nc2ncc3cnn(Cc4c(F)ccc(N5CCNCC5=O)c4F)c3n2)cn1]

Step (i)
3-bromo-2,6-difluorobenzoic acid was prepared following the procedure in Example 281 (Step i) using 1-bromo-2,4-difluorobenzene.
Step (ii)
The title compound was made following the procedure in Example 295 using 3-bromo-2,6-difluorobenzoic acid in Step (i). $^1$H NMR (d$_6$-DMSO) δ 9.88 (s, 1H), 8.90 (s, 1H), 8.16 (s, 1H), 8.01 (s, 1H), 7.60 (s, 1H), 7.51-7.38 (m, 1H), 7.26-7.15 (m, 1H), 5.61 (s, 2H), 3.85 (s, 3H), 3.48 (t, J=5.5 Hz, 2H), 3.39 (s, 2H), 3.00 (t, J=5.5 Hz, 2H); LC-MS method B, (ES+) 440, RT=4.48 min.

Example 301

1-(2,6-Difluoro-3-(piperazin-1-yl)benzyl)-N-(1-methyl-1H-pyrazol-4-yl)-1H-pyrazolo[3,4-d]pyrimidin-6-amine

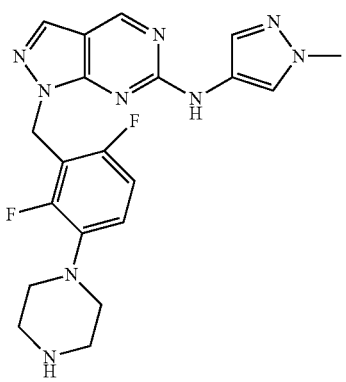 [SMILES: Cn1cc(Nc2ncc3cnn(Cc4c(F)ccc(N5CCNCC5)c4F)c3n2)cn1]

Step (i)
3-bromo-2,6-difluorobenzoic acid was prepared as in Example 281 (Step i) using 1-bromo-2,4-difluorobenzene.
Step (ii)
3-(4-(tert-butoxycarbonyl)piperazin-1-yl)-2,6-difluorobenzoic acid was prepared as in Example 162 (Step ii) using 3-bromo-2,6-difluorobenzoic acid and tert-butyl piperazine-1-carboxylate.

Step (iii)
tert-butyl 4-(2,4-difluoro-3-(hydroxymethyl)phenyl)piperazine-1-carboxylate was formed following the procedure in Example 179 (Step i) using 3-(4-(tert-butoxycarbonyl)piperazin-1-yl)-2,6-difluorobenzoic acid.
Step (iv)
tert-butyl 4-(2,4-difluoro-3-(((methylsulfonyl)oxy)methyl)phenyl)piperazine-1-carboxylate was synthesized following the procedure in Example 45 (Step ii) using tert-butyl 4-(2,4-difluoro-3-(hydroxymethyl)phenyl)piperazine-1-carboxylate.
Step (v)
tert-butyl 4-(2,4-difluoro-3-((6-((1-methyl-1H-pyrazol-4-yl)amino)-1H-pyrazolo[3,4-d]pyrimidin-1-yl)methyl)phenyl)piperazine-1-carboxylate was synthesized following the procedure in Example 1 (Step i) then Step (ii) using tert-butyl 4-(2,4-difluoro-3-(((methylsulfonyl)oxy)methyl)phenyl)piperazine-1-carboxylate and N-(1-methyl-1H-pyrazol-4-yl)-1H-pyrazolo[3,4-d]pyrimidin-6-amine.
Step (vi)
The title product was formed by deprotection following a procedure analogous to Example 215 (Step iv) using tert-butyl tert-butyl 4-(2,4-difluoro-3-((6-((1-methyl-1H-pyrazol-4-yl)amino)-1H-pyrazolo[3,4-d]pyrimidin-1-yl)methyl)phenyl)piperazine-1-carboxylate. $^1$H NMR (d$_6$-DMSO) δ 9.87 (s, 1H), 8.89 (s, 1H), 8.15 (s, 1H), 7.99 (s, 1H), 7.59 (s, 1H), 7.07-6.99 (m, 2H), 5.57 (s, 2H), 3.86 (s, 3H), 2.87-2.74 (m, 9H); LC-MS method B, (ES+) 426, RT=4.81 min.

Example 302

1-(2,4-Difluoro-3-((6-((1-(2-hydroxyethyl)-1H-pyrazol-4-yl)amino)-1H-pyrazolo[3,4-d]pyrimidin-1-yl)methyl)phenyl)piperazin-2-one

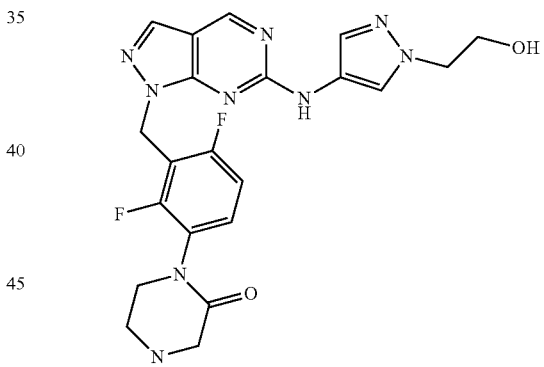

Step (i)
2-(4-amino-1H-pyrazol-1-yl)ethanol was prepared according to Procedure A using 2-bromoethanol as alkylating agent.
Step (ii)
2-(4-((1H-pyrazolo[3,4-d]pyrimidin-6-yl)amino)-1H-pyrazol-1-yl)ethanol was prepared as in Example 1 (Step i) using 2-(4-amino-1H-pyrazol-1-yl)ethanol.
Step (iii)
3-bromo-2,6-difluorobenzoic acid was prepared following the procedure in Example 281 (Step i) using 1-bromo-2,4-difluorobenzene.
Step (iv)
The title compound was made following the procedure in Example 295 using 3-bromo-2,6-difluorobenzoic acid in Step (i) and 2-(4-((1H-pyrazolo[3,4-d]pyrimidin-6-yl)amino)-1H-pyrazol-1-yl)ethanol in Step (iv). $^1$H NMR (d$_6$-DMSO) δ 9.88 (s, 1H), 8.90 (s, 1H), 8.18 (s, 1H), 8.01 (s, 1H), 7.66 (s, 1H), 7.49-7.41 (m, 1H), 7.23-7.16 (m, 1H), 5.60 (s, 2H), 4.87 (s, 1H), 4.15 (t, J=5.5 Hz, 2H), 3.75 (t, J=6.0 Hz, 2H), 3.49 (t, J=5.5 Hz, 2H), 3.39 (s, 2H), 3.01 (t, J=5.5 Hz, 2H); LC-MS method B, (ES+) 470, RT=4.31 min.

Example 303

1-(3-(4-Methoxypiperidin-1-yl)benzyl)-N-(1-methyl-1H-pyrazol-4-yl)-1H-pyrazolo[3,4-d]pyrimidin-6-amine The following compound was made according to the procedure in Example 162 using 4-methoxypiperidine in Step (ii):

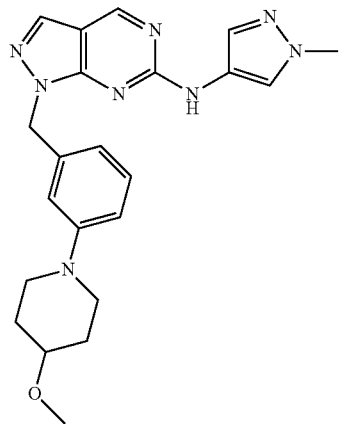 [SMILES: COC1CCN(c2cccc(Cn3ncc4cnc(Nc5cnn(C)c5)nc43)c2)CC1]

$^1$H NMR (d$_6$-DMSO) δ 9.83 (s, 1H), 8.90 (s, 1H), 8.08 (s, 1H), 8.03 (s, 1H), 7.58 (s, 1H), 7.15-7.09 (m, 1H), 7.03 (s, 1H), 6.85-6.80 (m, 1H), 6.67-6.61 (m, 1H), 5.48 (s, 2H), 3.84 (s, 3H), 3.44-3.36 (m, 2H), 3.28-3.26 (m, 1H), 3.24 (s, 3H), 2.86-2.76 (m, 2H), 1.89-1.79 (m, 2H), 1.48-1.36 (m, 2H); LC-MS method B, (ES+) 419, RT=6.21 min.

Example 304

2-(4-((1-(2,6-Difluoro-3-(piperazin-1-yl)benzyl)-1H-pyrazolo[3,4-d]pyrimidin-6-yl)amino)-1H-pyrazol-1-yl)ethanol The following compound was made according to Example 301 using 2-(4-((1H-pyrazolo[3,4-d]pyrimidin-6-yl)amino)-1H-pyrazol-1-yl)ethanol (see Example 302, Step (ii)) in Step (v):

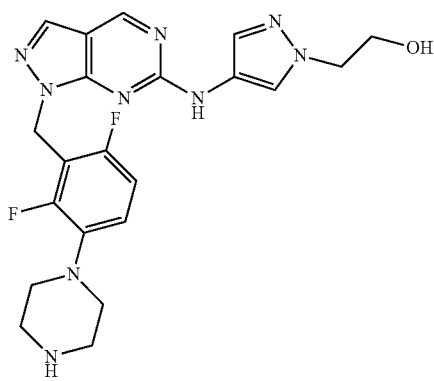 [SMILES: OCCn1cc(Nc2ncc3cnn(Cc4c(F)ccc(N5CCNCC5)c4F)c3n2)cn1]

$^1$H NMR (d$_6$-DMSO) δ 9.87 (s, 1H), 8.89 (s, 1H), 8.17 (s, 1H), 7.99 (s, 1H), 7.65 (s, 1H), 7.09-6.99 (m, 2H), 5.56 (s, 2H), 4.15 (t, J=6.0 Hz, 2H), 3.75 (t, J=6.0 Hz, 2H), 2.90-2.81 (m, 8H); LC-MS method B, (ES+) 456, RT=4.56 min.

Example 305

2-(4-((1-(2,3-Difluoro-5-(piperazin-1-yl)benzyl)-1H-pyrazolo[3,4-d]pyrimidin-6-yl)amino)-1H-pyrazol-1-yl)ethanol The following compound was made according to Example 301 using 5-bromo-2,3-difluorobenzoic acid in Step (i) and 2-(4-((1H-pyrazolo[3,4-d]pyrimidin-6-yl)amino)-1H-pyrazol-1-yl)ethanol (see Example 302, Step (ii)) in Step (v):

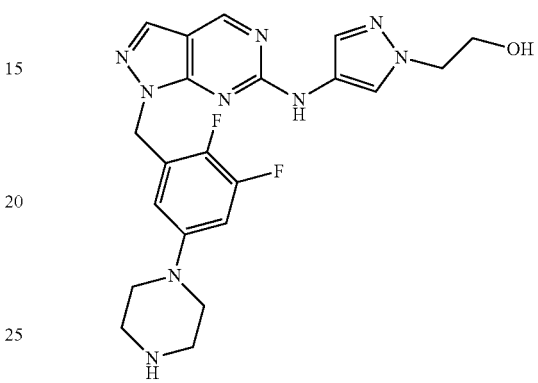

$^1$H NMR (d$_6$-DMSO) δ 9.87 (s, 1H), 8.90 (s, 1H), 8.14 (s, 1H), 8.04 (s, 1H), 7.66 (s, 1H), 6.96-6.85 (m, 1H), 6.75 (s, 1H), 5.56 (s, 2H), 4.13 (t, J=6.0 Hz, 2H), 3.74 (t, J=6.0 Hz, 2H), 2.93-2.85 (m, 4H), 2.76-2.69 (m, 4H); LC-MS method B, (ES+) 456, RT=4.77 min.

Example 306

1-(2-Fluorobenzyl)-N-(1-(pyrrolidin-3-ylmethyl)-1H-pyrazol-4-yl)-1H-pyrazolo[3,4-d]pyrimidin-6-amine

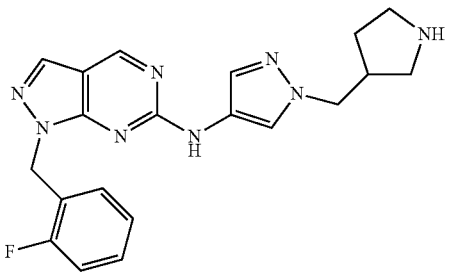 [SMILES: Fc1ccccc1Cn1ncc2cnc(Nc3cnn(CC4CCNC4)c3)nc21]

Step (i)
tert-butyl 34(4-amino-1H-pyrazol-1-yl)methyl)pyrrolidine-1-carboxylate was prepared as in Example 165 using tert-butyl 3-(hydroxymethyl)pyrrolidine-1-carboxylate
Step (ii)
tert-butyl 3-((4-((1-(2-fluorobenzyl)-1H-pyrazolo[3,4-d]pyrimidin-6-yl)amino)-1H-pyrazol-1-yl)methyl)pyrrolidine-1-carboxylate was prepared as in Example 1 (Step ii) using 1-(bromo methyl)-2-fluorobenzene and 6-chloro-1H-pyrazolo[3,4-d]pyrimidine followed by Example 1 (Step i) using 142-fluorobenzyl)-N-(1H-pyrazol-4-yl)-1H-pyrazolo[3,4-d]pyrimidin-6-amine and tert-butyl 34(4-amino-1H-pyrazol-1-yl)methyl)pyrrolidine-1-carboxylate.

Step (iii)
The title compound was made by Boc deprotection according to the procedure in Example 215 (Step iv) using tert-butyl 3-((4-((142-fluorobenzyl)-1H-pyrazolo[3,4-d]pyrimidin-6-yl)amino)-1H-pyrazol-1-yl)methyl)pyrrolidine-1-carboxylate.
¹H NMR (d₆-DMSO) δ 9.88 (s, 1H), 8.92 (s, 1H), 8.10 (s, 1H), 8.06 (s, 1H), 7.62-7.54 (m, 1H), 7.40-7.31 (m, 1H), 7.30-7.19 (m, 2H), 7.18-7.11 (m, 1H), 5.61 (s, 2H), 4.10 (d, J=7.0 Hz, 1H), 4.02 (d, J=7.0 Hz, 1H), 2.85-2.63 (m, 3H), 2.48-2.42 (m, 2H), 1.75-1.63 (m, 1H), 1.41-1.30 (m, 1H); LC-MS method B, (ES+) 393, RT=5.26 min.

Example 307

(3-Fluoro-5-46-((1-methyl-1H-pyrazol-4-yl)amino)-1H-pyrazolo[3,4-d]pyrimidin-1-yl)methyl)phenyl)(morpholino)methanone The following compound was made according to Example 191 using 1-bromo-3-(bromomethyl)-5-fluorobenzene in Step (i):

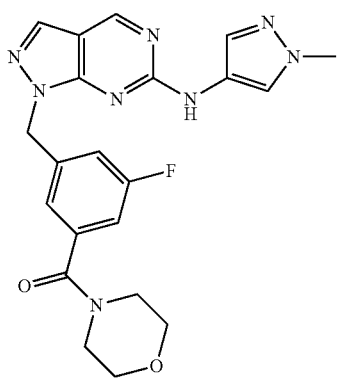 [SMILES: Cn1cc(Nc2ncc3cnn(Cc4cc(F)cc(C(=O)N5CCOCC5)c4)c3n2)cn1]

¹H NMR (d₆-DMSO) δ 9.87 (s, 1H), 8.93 (s, 1H), 8.09 (s, 1H), 8.01 (s, 1H), 7.54 (s, 1H), 7.28-7.22 (m, 1H), 7.22-7.18 (m, 1H), 7.10 (s, 1H), 5.64 (s, 2H), 3.82 (s, 3H), 3.63-3.50 (m, 4H), 3.48-3.34 (m, 4H); LC-MS method B, (ES+) 437, RT=6.84 min.

Example 308

(3-Fluoro-5-46-((1-methyl-1H-pyrazol-4-yl)amino)-1H-pyrazolo[3,4-d]pyrimidin-1-yl)methyl)phenyl)(piperazin-1-yl)methanone

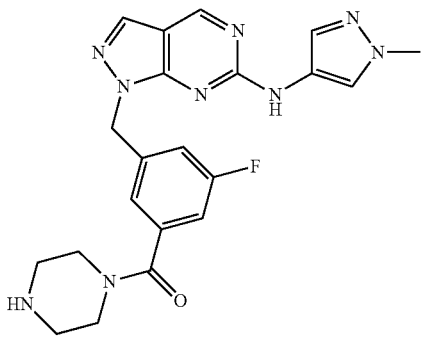 [SMILES: Cn1cc(Nc2ncc3cnn(Cc4cc(F)cc(C(=O)N5CCNCC5)c4)c3n2)cn1]

Step (i)
tert-butyl 4-(3-fluoro-5-((6-((1-methyl-1H-pyrazol-4-yl)amino)-1H-pyrazolo[3,4-d]pyrimidin-1-yl)methyl)benzoyl)piperazine-1-carboxylate was made according to Example 191 using 1-bromo-3-(bromomethyl)-5-fluorobenzene in Step (i) and tert-butyl piperazine-1-carboxylate in Step (ii).
Step (ii)
The title compound was made according to the procedure in Example 215 (Step iv) using tert-butyl 4-(3-fluoro-5-((6-((1-methyl-1H-pyrazol-4-yl)amino)-1H-pyrazolo[3,4-d]pyrimidin-1-yl)methyl)benzo yl)piperazine-1-carboxylate. ¹H NMR (d₆-DMSO) δ 9.88 (s, 1H), 8.93 (s, 1H), 8.09 (s, 1H), 8.00 (s, 1H), 7.52 (s, 1H), 7.26-7.19 (m, 1H), 7.18-7.12 (m, 1H), 7.03 (s, 1H), 5.63 (s, 2H), 3.81 (s, 3H), 3.50-3.38 (m, 2H), 3.11-3.01 (m, 2H), 2.70-2.59 (m, 2H), 2.48-2.40 (m, 2H); LC-MS method B, (ES+) 436, RT=4.69 min.

Example 309

N-(1H-Pyrazol-4-yl)-1-(2,3,6-trifluoro-5-morpholinobenzyl)-1H-pyrazolo[3,4-d]pyrimidin-6-amine

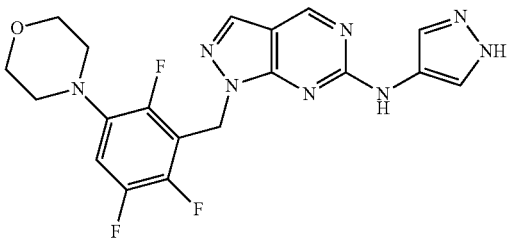 [SMILES: Fc1cc(N2CCOCC2)c(F)c(Cn2ncc3cnc(Nc4cn[nH]c4)nc32)c1F]

Step (i)
tert-butyl 4-amino-1H-pyrazole-1-carboxylate was formed according to Example 289 (Steps i-ii).
Step (ii)
4-(3-(bromomethyl)-2,4,5-trifluorophenyl)morpholine was prepared following Example 210 (Steps i-iii).
Step (v)
4-(3-(bromo methyl)-2,4,5-trifluorophenyl)morpholine and 6-chloro-1H-pyrazolo[3,4-d]pyrimidine were coupled as in Example 1 (Step ii) to afford 4-(3-((6-chloro-1H-pyrazolo[3,4-d]pyrimidin-1-yl)methyl)-2,4,5-trifluorophenyl)morpholine followed by Example 1 (Step i) using tert-butyl 4-amino-1H-pyrazole-1-carboxylate to afford the title product. ¹H NMR (d₆-DMSO) δ 12.55 (s, 1H), 9.87 (br s, 1H), 8.89 (s, 1H), 8.15 (br s, 1H), 8.00 (s, 1H), 7.70 (s, 1H), 7.21-7.14 (m, 1H), 5.58 (s, 2H), 3.68 (t, 4H), 2.93 (t, 4H); LC-MS method B, (ES+) 431.1, RT=7.59 min.

Example 310

2-(4-((1-(2,6-Difluoro-3-morpholinobenzyl)-1H-pyrazolo[3,4-d]pyrimidin-6-yl)amino)-1H-pyrazol-1-yl)ethanol

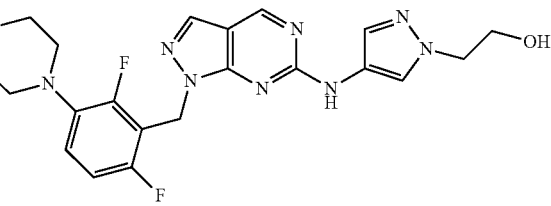

Step (i)

4-(3-(bromomethyl)-2,4-difluorophenyl)morpholine was made according to Example 255 (Steps i-iii) using 3-amino-2,6-difluorobenzoic acid in Step (i).

Step (ii)

2-(4-amino-1H-pyrazol-1-yl)ethanol was formed following Procedure A using 2-bromoethanol as alkylating agent.

Step (iii)

The title compound was made following the procedure in Example 1 (Step ii) using 2-(4-amino-1H-pyrazol-1-yl)ethanol and 6-chloro-1H-pyrazolo[3,4-d]pyrimidine to form 2-(4-((1H-pyrazolo[3,4-d]pyrimidin-6-yl)amino)-1H-pyrazol-1-yl)ethanol. This was followed by the procedure in Example 1 (Step i) using 4-(3-(bromomethyl)-2,4-difluorophenyl)morpholine. $^1$H NMR (d$_6$-DMSO) δ 9.86 (s, 1H), 8.88 (s, 1H), 8.17 (br s, 1H), 7.98 (s, 1H), 7.65 (s, 1H), 7.14-6.97 (m, 2H), 5.56 (s, 2H), 4.88 (t, 1H), 4.18-4.09 (m, 2H), 3.77-3.73 (m, 2H), 3.70 (t, 4H), 2.92 (t, 4H); LC-MS method B, (ES+) 457.2, RT=6.98 min.

Example 311

2-(4-((1-(2-Fluoro-3-(piperazin-1-yl)benzyl)-1H-pyrazolo[3,4-d]pyrimidin-6-yl)amino)-1H-pyrazol-1-yl)ethanol The following compound was made according to Example 288 using 2-(4-amino-1H-pyrazol-1-yl)ethanol in Step (iv):

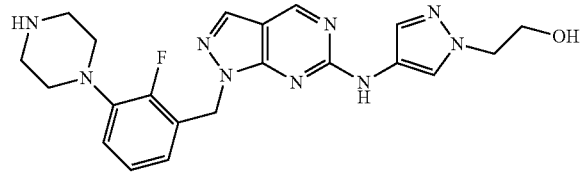 [SMILES: OCCn1cc(Nc2ncc3cnn(Cc4cccc(N5CCNCC5)c4F)c3n2)cn1]

$^1$H NMR (d$_6$-DMSO) δ 9.87 (s, 1H), 8.91 (s, 1H), 8.23 (s, 1H), 8.12 (s, 1H), 8.05 (s, 1H), 7.62 (s, 1H), 7.04 (t, 1H), 6.97 (dd, 1H), 6.86 (br s, 1H), 5.56 (s, 2H), 4.13 (t, 2H), 3.74 (t, 2H), 2.92-2.89 (m, 8H); LC-MS method B, (ES+) 438.2, RT=4.52 min.

Example 312

4-(3-((6-((1H-Pyrazol-4-yl)amino)-1H-pyrazolo[3,4-d]pyrimidin-1-yl)methyl)-5-fluorophenyl)morpholin-3-one The following compound was made according to Example 289 Steps (i-vii):

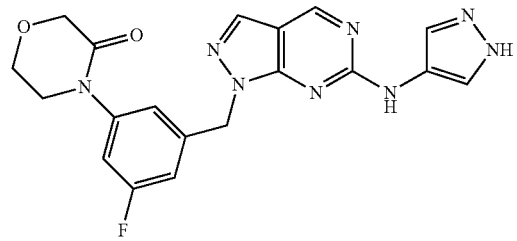 [SMILES: O=C1COCCN1c1cc(F)cc(Cn2ncc3cnc(Nc4cn[nH]c4)nc32)c1]

$^1$H NMR (d$_6$-DMSO) δ 12.51 (s, 1H), 9.86 (s, 1H), 8.93 (s, 1H), 8.08 (s, 1H), 7.67 (s, 1H), 7.30-7.27 (m, 2H), 6.96 (d, 1H), 5.57 (s, 2H), 4.19 (s, 2H), 3.97-3.88 (m, 2H), 3.69-3.67 (m, 2H); LC-MS method B, (ES+) 409.1, RT=6.32 min.

Example 313

(2-Fluoro-3-((6-((1-(2-hydroxyethyl)-1H-pyrazol-4-yl)amino)-1H-pyrazolo[3,4-d]pyrimidin-1-yl)methyl)phenyl)(morpholino)methanone

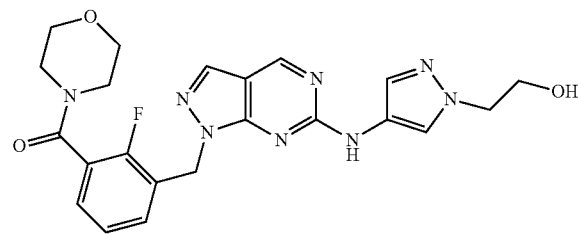 [SMILES: O=C(c1cccc(Cn2ncc3cnc(Nc4cnn(CCO)c4)nc32)c1F)N1CCOCC1]

Step (i)

2-(4-((1-(3-bromo-2-fluorobenzyl)-1H-pyrazolo[3,4-d]pyrimidin-6-yl)amino)-1H-pyrazol-1-yl)ethano 1 was made as in Example 1 (Step ii) using 6-chloro-1H-pyrazolo[3,4-d]pyrimidine and 1-bromo-3-(bromomethyl)-2-fluorobenzene followed by Example 1 (Step ii) using 2-(4-amino-1H-pyrazol-1-yl)ethanol.

Step (ii)

The title compound was made according to Example 191 (Step ii) using 2-(4-41-(3-bromo-2-fluorobenzyl)-1H-pyrazolo[3,4-d]pyrimidin-6-yl)amino)-1H-pyrazol-1-yl)ethanol. $^1$H NMR (d$_6$-DMSO) δ 9.88 (s, 1H), 8.92 (s, 1H), 8.08 (br s, 1H), 8.06 (s, 1H), 7.61 (s, 1H), 7.37-7.33 (m, 2H), 7.24 (t, 1H), 5.63 (s, 2H), 4.87 (t, 1H), 4.12 (t, 2H), 3.73 (q, 2H), 3.63 (br s, 4H), 3.48 (br s, 2H), 3.18 (t, 2H); LC-MS method B, (ES+) 467.2, RT=6.09 min.

Example 314

2-(4-((1-((6-Fluoropyridin-2-yl)methyl)-1H-pyrazolo[3,4-d]pyrimidin-6-yl)amino)-1H-pyrazol-1-yl)ethanol The following compound was made according to the procedure in Example 45 using 6-fluoropicolinaldehyde in Step (i) and 2-(4-amino-1H-pyrazol-1-yl)ethanol in Step (iii). 2-(4-amino-1H-pyrazol-1-yl)ethanol was prepared by Procedure A using 2-bromoethanol as ablating agent:

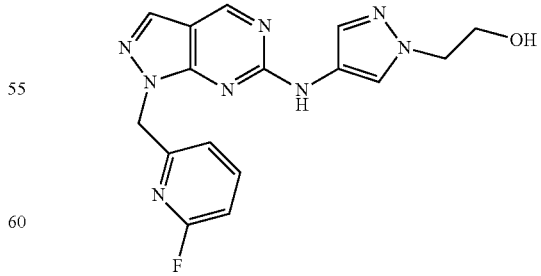

$^1$H NMR (d$_6$-DMSO) δ 9.86 (s, 1H), 8.93 (s, 1H), 8.08 (s, 1H), 8.01 (s, 1H), 7.92-7.98 (m, 1H), 7.55 (s, 1H), 7.08-7.11 (m, 2H), 5.60 (s, 2H), 4.10 (t, 2H), 3.71 (t, 2H); LC-MS method B, (ES+) 355.1, RT=6.18 min.

Example 315

1-(2,3-Difluoro-5-(piperazin-1-yl)benzyl)-N-(1-methyl-1H-pyrazol-4-yl)-1H-pyrazolo[3,4-d]pyrimidin-6-amine The following compound was made according to Example 301 using 5-bromo-2,3-difluorobenzoic acid in Step (i):

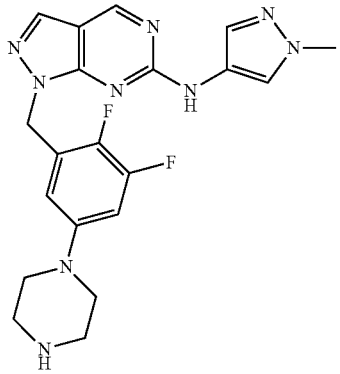 [SMILES: Cn1cc(Nc2ncc3cnn(Cc4cc(N5CCNCC5)cc(F)c4F)c3n2)cn1]

$^1$H NMR (d$_6$-DMSO) δ 9.88 (s, 1H), 8.91 (s, 1H), 8.13 (s, 1H), 8.04 (s, 1H), 7.60 (s, 1H), 6.96-6.85 (m, 1H), 6.77 (s, 1H), 5.58 (s, 2H), 3.84 (s, 3H), 2.94-2.83 (m, 4H), 2.77-2.68 (m, 4H); LC-MS method B, (ES+) 426, RT=5.07 min.

Example 316

(2-Fluoro-3-((6-((1-methyl-1H-pyrazol-4-yl)amino)-1H-pyrazolo[3,4-d]pyrimidin-1-yl)methyl)phenyl)(morpholino)methanone The following compound was made according to Example 191 using 1-bromo-3-(bromomethyl)-2-fluorobenzene in Step (i):

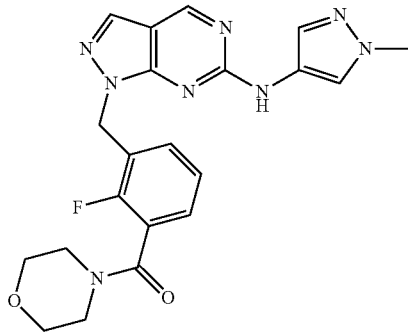 [SMILES: Cn1cc(Nc2ncc3cnn(Cc4cccc(C(=O)N5CCOCC5)c4F)c3n2)cn1]

$^1$H NMR (d$_6$-DMSO) δ 9.88 (s, 1H), 8.92 (s, 1H), 8.06 (s, 1H), 8.03 (s, 1H), 7.55 (s, 1H), 7.38-7.32 (m, 2H), 7.28-7.21 (m, 1H), 5.64 (s, 2H), 3.83 (s, 3H), 3.63 (s, 4H), 3.47 (s, 2H), 3.17 (s, 2H); LC-MS method B, (ES+) 437, RT=6.65 min.

Example 317

Biology Assays

Determination of the Effect of the Compounds According to the Invention on JAK

The compounds of the present invention as described in the previous examples were tested in a Kinobeads™ assay as described for ZAP-70 (WO-A 2007/137867). Briefly, test compounds (at various concentrations) and the affinity matrix with the immobilized aminopyrido-pyrimidine ligand 24 were added to cell lysate aliquots and allowed to bind to the proteins in the lysate sample. After the incubation time the beads with captured proteins were separated from the lysate. Bound proteins were then eluted and the presence of JAK2 and JAK3 was detected and quantified using specific antibodies in a dot blot procedure and the Odyssey infrared detection system. Dose response curves for individual kinases were generated and IC$_{50}$ values calculated. Kinobeads™ assays for ZAP-70 (WO-A 2007/137867) and for kinase selectivity profiling (WO-A 2006/134056) have been previously described.

Protocols

Washing of Affinity Matrix

The affinity matrix was washed two times with 15 mL of 1×DP buffer containing 0.2% NP40 (IGEPAL® CA-630, Sigma, #13021) and then resuspended in 1×DP buffer containing 0.2% NP40 (3% beads slurry).

5×DP buffer: 250 mM Tris-HCl pH 7.4, 25% Glycerol, 7.5 mM MgCl$_2$, 750 mM NaCl, 5 mM Na$_3$VO$_4$; filter the 5×DP buffer through a 0.22 μm filter and store in aliquots at −80° C. The 5×DP buffer is diluted with H$_2$O to 1×DP buffer containing 1 mM DTT and 25 mM NaF.

Preparation of Test Compounds

Stock solutions of test compounds were prepared in DMSO. In a 96 well plate 30 μL solution of diluted test compounds at 5 mM in DMSO were prepared. Starting with this solution a 1:3 dilution series (9 steps) was prepared. For control experiments (no test compound) a buffer containing 2% DMSO was used.

Cell culture and preparation of cell lysates

Molt4 cells (ATCC catalogue number CRL-1582) and Ramos cells (ATCC catalogue number CRL-1596) were grown in 1 L Spinner flasks (Integra Biosciences, #182101) in suspension in RPMI 1640 medium (Invitrogen, #21875-034) supplemented with 10% Fetal Bovine Serum (Invitrogen) at a density between 0.15×10$^6$ and 1.2×10$^6$ cells/mL. Cells were harvested by centrifugation, washed once with 1×PBS buffer (Invitrogen, #14190-094) and cell pellets were frozen in liquid nitrogen and subsequently stored at −80° C. Cells were homogenized in a Potter S homogenizer in lysis buffer: 50 mM Tris-HCl, 0.8% NP40, 5% glycerol, 150 mM NaCl, 1.5 mM MgCl$_2$, 25 mM NaF, 1 mM sodium vanadate, 1 mM DTT, pH 7.5. One complete EDTA-free tablet (protease inhibitor cocktail, Roche Diagnostics, 1873580) per 25 mL buffer was added. The material was dounced 10 times using a mechanized POTTER S, transferred to 50 mL falcon tubes, incubated for 30 minutes on ice and spun down for 10 minutes at 20,000 g at 4° C. (10,000 rpm in Sorvall SLA600, precooled). The supernatant was transferred to an ultracentrifuge (UZ)-polycarbonate tube (Beckmann, 355654) and spun for 1 hour at 100.000 g at 4° C. (33.500 rpm in Ti50.2, precooled). The supernatant was transferred again to a fresh 50 mL falcon tube, the protein concentration was determined by a Bradford assay (BioRad) and samples containing 50 mg of protein per aliquot were prepared. The samples were immediately used for experiments or frozen in liquid nitrogen and stored frozen at −80° C.

Dilution of Cell Lysate

Cell lysate (approximately 50 mg protein per plate) was thawed in a water bath at room temperature and then stored on ice. To the thawed cell lysate 1×DP 0.8% NP40 buffer containing protease inhibitors (1 tablet for 25 mL buffer; EDTA-free protease inhibitor cocktail; Roche Diagnostics 1873580) was added in order to reach a final protein concentration of 10 mg/mL total protein. The diluted cell lysate was stored on ice. Mixed Molt4/Ramos lysate was prepared by combining one volume of Molt4 lysate and two volumes of Ramos lysate (ratio 1:2).

Incubation of Lysate with Test Compound and Affinity Matrix

To a 96 well filter plate (Multiscreen HTS, BV Filter Plates, Millipore #MSBVN1250) were added per well: 100 μL affinity matrix (3% beads slurry), 34, of compound solution, and 50 μL of diluted lysate. Plates were sealed and incubated for 3 hours in a cold room on a plate shaker (Heidolph tiramax 1000) at 750 rpm. Afterwards the plate was washed 3 times with 230 μL washing buffer (1×DP 0.4% NP40). The filter plate was placed on top of a collection plate (Greiner bio-one, PP-microplate 96 well V-shape, 65120) and the beads were then eluted with 20 μL of sample buffer (100 mM Tris, pH 7.4, 4% SDS, 0.00025% bromophenol blue, 20% glycerol, 50 mM DTT). The eluate was frozen quickly at −80° C. and stored at −20° C.

Detection and Quantification of Eluted Kinases

The kinases in the eluates were detected and quantified by spotting on nitrocellulose membranes and using a first antibody directed against the kinase of interest and a fluorescently labelled secondary antibody (anti-rabbit IRDye™ antibody 800 (Licor, #926-32211). The Odyssey Infrared Imaging system from LI-COR Biosciences (Lincoln, Neb., USA) was operated according to instructions provided by the manufacturer (Schutz-Geschwendener et al., 2004. Quantitative, two-color Western blot detection with infrared fluorescence. Published May 2004 by LI-COR Biosciences, www.licor.com).

After spotting of the eluates the nitrocellulose membrane (BioTrace NT; PALL, #BTNT30R) was first blocked by incubation with Odyssey blocking buffer (LICOR, 927-40000) for 1 hour at room temperature. Blocked membranes were then incubated for 16 hours at the temperature shown in table 4 with the first antibody diluted in Odyssey blocking buffer (LICOR #927-40000). Afterwards the membrane was washed twice for 10 minutes with PBS buffer containing 0.2% Tween 20 at room temperature. The membrane was then incubated for 60 minutes at room temperature with the detection antibody (anti-rabbit IRDye™ antibody 800, Licor, #926-32211) diluted in Odyssey blocking buffer (LICOR #927-40000). Afterwards the membrane was washed twice for 10 minutes each with 1×PBS buffer containing 0.2% Tween 20 at room temperature. Then the membrane was rinsed once with PBS buffer to remove residual Tween 20. The membrane was kept in PBS buffer at 4° C. and scanned with the Odyssey instrument. Fluorescence signals were recorded and analysed according to the instructions of the manufacturer.

TABLE 4

Sources and dilutions of antibodies

| Target kinase | Primary antibody (dilution) | Temp of Primary incubation | Secondary antibody (dilution) |
|---|---|---|---|
| Jak2 | Cell signaling #3230 (1:100) | Room temperature | Licor anti-rabbit 800 (1:15000) |
| Jak3 | Cell signaling #3775 (1:100) | 4° C. | Licor anti-rabbit 800 (1:5000) |

Results

TABLE 5

Inhibition values ($IC_{50}$ in μM) as determined in the Kinobeads™ assay (Activity level: A < 0.1 μM; 0.1 μM ≤ B < 1 μM; 1 μM ≤ C < 10 μM; D ≥ 10 μM).

| Example | JAK2 IC50 (μM) | JAK3 IC50 (μM) |
|---|---|---|
| 1 | C | A |
| 2 | C | A |
| 3 | D | B |
| 4 | B | A |
| 8 | D | C |
| 9 | D | B |

TABLE 5-continued

Inhibition values ($IC_{50}$ in μM) as determined in the Kinobeads™ assay (Activity level: A < 0.1 μM; 0.1 μM ≤ B < 1 μM; 1 μM ≤ C < 10 μM; D ≥ 10 μM).

| Example | JAK2 IC50 (μM) | JAK3 IC50 (μM) |
|---|---|---|
| 10 | B | A |
| 11 | C | A |
| 12 | C | A |
| 13 | B | A |
| 14 | B | A |
| 15 | C | A |
| 16 | C | A |
| 17 | B | B |
| 18 | B | A |
| 19 | D | C |
| 20 | C | A |
| 21 | D | B |
| 22 | D | A |
| 23 | D | B |
| 24 | D | A |
| 25 | C | A |
| 26 | D | B |
| 27 | C | A |
| 28 | C | A |
| 29 | C | A |
| 30 | A | A |
| 31 | C | A |
| 32 | A | A |
| 33 | B | A |
| 34 | B | A |
| 35 | C | A |
| 36 | D | B |
| 37 | D | B |
| 38 | D | B |
| 39 | C | A |
| 40 | C | B |
| 41 | C | B |
| 42 | C | A |
| 43 | C | B |
| 44 | C | A |
| 45 | C | A |
| 46 | C | B |
| 47 | C | B |
| 48 | C | B |
| 49 | C | A |
| 50 | C | A |
| 51 | C | A |
| 52 | A | A |
| 53 | A | A |
| 54 | C | B |
| 55 | C | B |
| 56 | C | B |
| 57 | D | B |
| 58 | D | B |
| 59 | D | A |
| 60 | C | B |
| 61 | C | B |
| 62 | A | A |
| 63 | B | A |
| 64 | B | A |
| 65 | C | A |
| 66 | D | B |
| 67 | B | A |
| 68 | C | A |
| 69 | C | A |
| 70 | B | A |
| 71 | D | B |
| 72 | C | A |
| 73 | B | A |
| 74 | C | B |
| 75 | B | A |
| 76 | C | A |
| 77 | D | B |
| 78 | C | B |
| 79 | B | A |
| 80 | C | A |
| 81 | C | B |
| 82 | C | B |

TABLE 5-continued

Inhibition values (IC$_{50}$ in μM) as determined in the Kinobeads ™ assay (Activity level: A < 0.1 μM; 0.1 μM ≤ B < 1 μM; 1 μM ≤ C < 10 μM; D ≥ 10 μM).

| Example | JAK2 IC50 (μM) | JAK3 IC50 (μM) |
|---|---|---|
| 83 | C | A |
| 84 | C | A |
| 85 | C | A |
| 86 | D | B |
| 87 | C | A |
| 88 | C | A |
| 89 | B | A |
| 90 | B | A |
| 91 | B | A |
| 92 | C | A |
| 93 | D | B |
| 94 | C | A |
| 95 | C | A |
| 96 | D | B |
| 97 | D | B |
| 98 | B | A |
| 99 | D | B |
| 100 | D | B |
| 101 | C | B |
| 102 | C | B |
| 103 | C | B |
| 104 | B | A |
| 105 | D | A |
| 106 | C | A |
| 107 | C | A |
| 108 | C | B |
| 109 | D | B |
| 110 | D | B |
| 111 | C | A |
| 112 | C | A |
| 113 | C | A |
| 114 | D | B |
| 115 | C | A |
| 116 | B | A |
| 117 | C | A |
| 118 | C | A |
| 119 | D | B |
| 120 | D | B |
| 121 | B | A |
| 122 | C | B |
| 123 | B | A |
| 124 | B | A |
| 125 | B | A |
| 126 | C | A |
| 127 | C | B |
| 128 | C | A |
| 129 | B | A |
| 130 | B | A |
| 131 | B | A |
| 132 | D | A |
| 133 | C | A |
| 134 | C | A |
| 135 | C | B |
| 136 | C | B |
| 137 | B | A |
| 138 | C | B |
| 139 | C | B |
| 140 | C | A |
| 141 | D | B |
| 142 | B | A |
| 143 | C | A |
| 144 | B | A |
| 145 | B | A |
| 146 | C | B |
| 147 | D | B |
| 148 | C | B |
| 149 | C | B |
| 150 | C | A |
| 151 | B | A |
| 152 | C | A |
| 153 | B | A |
| 154 | C | B |
| 155 | C | A |
| 156 | C | B |
| 157 | B | A |
| 158 | A | A |
| 159 | C | A |
| 160 | C | A |
| 161 | C | B |
| 162 | D | A |
| 163 | B | A |
| 164 | C | A |
| 165 | C | A |
| 166 | C | A |
| 167 | D | A |
| 168 | C | A |
| 169 | D | B |
| 170 | C | A |
| 171 | D | A |
| 172 | D | B |
| 173 | C | B |
| 174 | D | A |
| 175 | D | B |
| 176 | D | B |
| 177 | B | A |
| 178 | C | A |
| 179 | C | A |
| 180 | B | B |
| 181 | D | A |
| 182 | B | A |
| 183 | D | B |
| 184 | C | A |
| 185 | D | A |
| 186 | C | A |
| 187 | D | A |
| 188 | D | B |
| 189 | D | B |
| 190 | D | A |
| 191 | D | A |
| 192 | B | A |
| 193 | D | A |
| 194 | D | B |
| 195 | D | A |
| 196 | B | A |
| 197 | D | B |
| 198 | D | A |
| 199 | D | A |
| 200 | D | A |
| 201 | D | A |
| 202 | D | A |
| 203 | D | B |
| 204 | D | A |
| 205 | D | B |
| 206 | D | B |
| 207 | C | A |
| 208 | D | A |
| 209 | C | A |
| 210 | C | A |
| 211 | D | A |
| 212 | D | B |
| 213 | D | A |
| 214 | C | A |
| 215 | C | A |
| 216 | D | A |
| 217 | D | A |
| 218 | D | A |
| 219 | B | A |
| 220 | C | B |
| 221 | C | B |
| 222 | D | B |
| 223 | D | A |
| 224 | D | B |
| 225 | D | A |
| 226 | D | A |
| 227 | C | A |
| 228 | B | A |

TABLE 5-continued

Inhibition values (IC$_{50}$ in μM) as determined in the Kinobeads ™ assay (Activity level: A < 0.1 μM; 0.1 μM ≤ B < 1 μM; 1 μM ≤ C < 10 μM; D ≥ 10 μM).

| Example | JAK2 IC50 (μM) | JAK3 IC50 (μM) |
|---|---|---|
| 229 | B | A |
| 230 | D | A |
| 231 | D | A |
| 232 | D | A |
| 233 | D | A |
| 234 | D | A |
| 235 | D | B |
| 236 | D | B |
| 237 | D | B |
| 238 | D | B |
| 239 | A | A |
| 240 | C | A |
| 241 | C | A |
| 242 | B | A |
| 243 | A | A |
| 244 | A | A |
| 245 | B | A |
| 246 | B | A |
| 247 | B | A |
| 248 | C | A |
| 249 | D | A |
| 250 | D | A |
| 251 | D | A |
| 252 | D | A |
| 253 | D | A |
| 254 | B | A |
| 255 | D | B |
| 256 | D | A |
| 257 | C | A |
| 258 | C | A |
| 259 | D | A |
| 260 | C | A |
| 261 | C | A |
| 262 | C | A |
| 263 | C | A |
| 264 | D | A |
| 265 | C | A |
| 266 | C | A |
| 267 | C | A |
| 268 | C | A |
| 269 | C | A |
| 270 | C | A |
| 271 | C | A |
| 272 | C | A |
| 273 | D | A |
| 274 | C | A |
| 275 | C | A |
| 276 | D | A |
| 277 | D | A |
| 278 | C | A |
| 279 | D | A |
| 280 | D | A |
| 281 | C | A |
| 282 | C | A |
| 283 | C | A |
| 284 | C | A |
| 285 | C | A |
| 286 | D | A |
| 287 | C | A |
| 288 | C | A |
| 289 | C | A |
| 290 | B | A |
| 291 | C | A |
| 292 | C | A |
| 293 | C | A |
| 294 | C | A |
| 295 | D | A |
| 296 | D | A |
| 297 | B | A |
| 298 | B | A |
| 299 | C | A |
| 300 | C | A |
| 301 | C | A |
| 302 | C | A |
| 303 | D | A |
| 304 | C | A |
| 305 | C | A |
| 306 | B | A |
| 307 | B | A |
| 308 | C | A |
| 309 | C | A |
| 310 | D | A |
| 311 | C | A |
| 312 | B | A |
| 313 | D | A |
| 314 | B | A |
| 315 | C | A |
| 316 | C | A |

The invention claimed is:

1. A compound of formula (I)

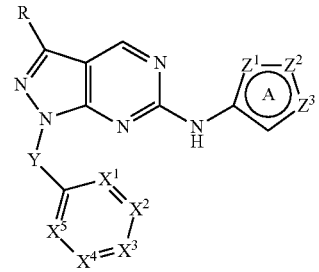

or a pharmaceutically acceptable salt thereof, wherein
R is H or F;
Ring A is a 5 membered aromatic heterocycle in which $Z^1$, $Z^2$ and $Z^3$ are independently selected from the group consisting of C($R^1$), N, N($R^1$), O and S, provided that at least one of $Z^1$, $Z^2$, $Z^3$ is N;
Each $R^1$ is independently H, halogen; CN; C(O)O$R^2$; O$R^2$; C(O)$R^2$; C(O)N($R^2R^{2a}$); S(O)$_2$N($R^2R^{2a}$); S(O)N($R^2R^{2a}$); S(O)$_2R^2$; S(O)$R^2$; N($R^2$)S(O)$_2$N($R^{2a}R^{2b}$); N($R^2$)S(O)N($R^{2a}R^{2b}$); S$R^2$; N($R^2R^{2a}$); NO$_2$; OC(O)$R^2$; N($R^2$)C(O)$R^{2a}$; N($R^2$)S(O)$_2R^{2a}$; N($R^2$)S(O)$R^{2a}$; N($R^2$)C(O)N($R^{2a}R^{2b}$); N($R^2$)C(O)O$R^{2a}$; OC(O)N($R^2R^{2a}$); $T^1$; C$_{1-6}$ alkyl; C$_{2-6}$ alkenyl; or C$_{2-6}$ alkynyl, wherein C$_{1-6}$ alkyl; C$_{2-6}$ alkenyl; and C$_{2-6}$ alkynyl are optionally substituted with one or more $R^3$, which are the same or different;
$R^2$, $R^{2a}$, $R^{2b}$ are independently selected from the group consisting of H; $T^1$; C$_{1-6}$ alkyl; C$_{2-6}$ alkenyl; and C$_{2-6}$ alkynyl, wherein C$_{1-6}$ alkyl; C$_{2-6}$ alkenyl; and C$_{2-6}$ alkynyl are optionally substituted with one or more $R^3$, which are the same or different;
$R^3$ is halogen; CN; C(O)O$R^4$; O$R^4$; C(O)$R^4$; C(O)N($R^4R^{4a}$); S(O)$_2$N($R^4R^{4a}$); S(O)N($R^4R^{4a}$); S(O)$_2R^4$; S(O)$R^4$; N($R^4$)S(O)$_2$N($R^{4a}R^{4b}$); N($R^4$)S(O)N($R^{4a}R^{4b}$); S$R^4$; N($R^4R^{4a}$); NO$_2$; OC(O)$R^4$; N($R^4$)C(O)$R^{4a}$; N($R^4$)S(O)$_2R^{4a}$; N($R^4$)S(O)$R^{4a}$; N($R^4$)C(O)N($R^{4a}R^{4b}$); N($R^4$)C(O)O$R^{4a}$; OC(O)N($R^4R^{4a}$); or $T^1$;
$R^4$, $R^{4a}$, $R^{4b}$ are independently selected from the group consisting of H; $T^1$; C$_{1-6}$ alkyl; C$_{2-6}$ alkenyl; and C$_{2-6}$ alkynyl, wherein $C_{1-6}$ alkyl; $C_{2-6}$ alkenyl; and $C_{2-6}$ alkynyl are optionally substituted with one or more halogen, which are the same or different;

$T^1$ is $C_{3-7}$ cycloalkyl; or saturated 4 to 7 membered heterocyclyl, wherein $T^1$ is optionally substituted with one or more $R^{10}$, which are the same or different;

Y is $(C(R^5R^{5a}))_n$;

n is 0, 1, 2, 3 or 4;

$R^5$, $R^{5a}$ are independently selected from the group consisting of H; and unsubstituted $C_{1-6}$ alkyl; or jointly form oxo (=O);

Optionally, $R^5$ and $R^{5a}$ are joined to form an unsubstituted $C_{3-7}$ cycloalkyl;

$X^1$ is $C(R^6)$ or N; $X^2$ is $C(R^{6a})$ or N; $X^3$ is $C(R^{6b})$ or N; $X^4$ is $C(R^{6c})$ or N; $X^5$ is $C(R^{6d})$ or N, provided that at most two of $X^1$, $X^2$, $X^3$, $X^4$, or $X^5$ are N;

$R^6$, $R^{6a}$, $R^{6b}$, $R^{6c}$, $R^{6d}$ are independently selected from the group consisting of H; halogen; CN; C(O)OR$^7$; OR$^7$; C(O)R$^7$; C(O)N(R$^7$R$^{7a}$); S(O)$_2$N(R$^7$R$^{7a}$); S(O)N(R$^7$R$^{7a}$); S(O)$_2$R$^7$; S(O)R$^7$; N(R$^7$)S(O)$_2$N(R$^{7a}$R$^7$); N(R$^7$)S(O)N(R$^{7a}$R$^{7b}$); SR$^7$; N(R$^7$R$^{7a}$); NO$_2$; OC(O)R$^7$; N(R$^7$)C(O)R$^{7a}$; N(R$^7$)S(O)$_2$R$^{7a}$; N(R$^7$)S(O)R$^{7a}$; N(R$^7$)C(O)N(R$^{7a}$R$^{7b}$); N(R$^7$)C(O)OR$^{7a}$; OC(O)N(R$^7$R$^{7a}$); $T^2$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{11}$, which are the same or different;

Optionally one of the pairs $R^6/R^{6a}$ or $R^{6a}/R^{6b}$ is joined to form a ring $T^3$;

$R^7$, $R^{7a}$, $R^{7b}$ are independently selected from the group consisting of H; $T^2$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^8$, which are the same or different;

$R^8$ is halogen; CN; C(O)OR$^9$; OR$^9$; C(O)R$^9$; C(O)N(R$^9$R$^{9a}$); S(O)$_2$N(R$^9$R$^{9a}$); S(O)N(R$^9$R$^{9a}$); S(O)$_2$R$^9$; S(O)R$^9$; N(R$^9$)S(O)$_2$N(R$^{9a}$R$^{9b}$); N(R$^9$)S(O)N(R$^{9a}$R$^{9b}$); SR$^9$; N(R$^9$R$^{9a}$); NO$_2$; OC(O)R$^9$; N(R$^9$)C(O)R$^{9a}$; N(R$^9$)S(O)$_2$R$^{9a}$; N(R$^9$)S(O)R$^{9a}$; N(R$^9$)C(O)N(R$^{9a}$R$^{9b}$); N(R$^9$)C(O)OR$^{9a}$; OC(O)N(R$^9$R$^{9a}$); or $T^2$;

$R^9$, $R^{9a}$, $R^{9b}$ are independently selected from the group consisting of H; $T^2$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{12}$, which are the same or different;

$R^{10}$ is halogen; CN; C(O)OR$^{13}$; OR$^{13}$; oxo (=O), where the ring is at least partially saturated; C(O)R$^{13}$; C(O)N(R$^{13}$R$^{13a}$); S(O)$_2$N(R$^{13}$R$^{13a}$); S(O)N(R$^{13}$R$^{13a}$); S(O)$_2$R$^{13}$; S(O)R$^{13}$; N(R$^{13}$)S(O)$_2$N(R$^{13a}$R$^{13b}$); N(R$^{13}$)S(O)N(R$^{13a}$R$^{13b}$); SR$^{13}$; N(R$^{13}$R$^{13a}$); NO$_2$; OC(O)R$^{13}$; N(R$^{13}$)C(O)R$^{13a}$; N(R$^{13}$)S(O)$_2$R$^{13a}$; N(R$^{13}$)S(O)R$^{13a}$; N(R$^{13}$)C(O)N(R$^{13a}$R$^{13b}$); N(R$^{13}$)C(O)OR$^{13a}$; OC(O)N(R$^{13}$R$^{13a}$); $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more $R^{14}$, which are the same or different;

$R^{13}$, $R^{13a}$, $R^{13b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{14}$, which are the same or different;

$R^{11}$, $R^{12}$ are independently selected from the group consisting of halogen; CN; C(O)OR$^{15}$; OR$^{15}$; C(O)R$^{15}$; C(O)N(R$^{15}$R$^{15a}$); S(O)$_2$N(R$^{15}$R$^{15a}$); S(O)N(R$^{15}$R$^{15a}$); S(O)$_2$R$^{15}$; S(O)R$^{15}$; N(R$^{15}$)S(O)$_2$N(R$^{15a}$R$^{15b}$); N(R$^{15}$)S(O)N(R$^{15a}$R$^{15b}$); SR$^{15}$; N(R$^{15}$R$^{15a}$); NO$_2$; OC(O)R$^{15}$; N(R$^{15}$)C(O)R$^{15a}$; N(R$^{15}$)S(O)$_2$R$^{15a}$; N(R$^{15}$)S(O)R$^{15a}$; N(R$^{15}$)C(O)N(R$^{15a}$R$^{15b}$); N(R$^{15}$)C(O)OR$^{15a}$; OC(O)N(R$^{15}$R$^{15a}$); or $T^2$;

$R^{15}$, $R^{15a}$, $R^{15b}$ are independently selected from the group consisting of H; $T^2$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;

$R^{14}$ is halogen; CN; C(O)OR$^{16}$; OR$^{16}$; C(O)R$^{16}$; C(O)N(R$^{16}$R$^{16a}$); S(O)$_2$N(R$^{16}$R$^{16a}$); S(O)N(R$^{16}$R$^{16a}$); S(O)$_2$R$^{16}$; S(O)R$^{16}$; N(R$^{16}$)S(O)$_2$N(R$^{16a}$R$^{16b}$); N(R$^{16}$)S(O)N(R$^{16a}$R$^{16b}$); SR$^{16}$; N(R$^{16}$R$^{16a}$); NO$_2$; OC(O)R$^{16}$; N(R$^{16}$)C(O)R$^{16a}$; N(R$^{16}$)S(O)$_2$R$^{16a}$; N(R$^{16}$)S(O)R$^{16a}$; N(R$^{16}$)C(O)N(R$^{16a}$R$^{16b}$); N(R$^{16}$)C(O)OR$^{16a}$; or OC(O)N(R$^{16}$R$^{16a}$);

$R^{16}$, $R^{16a}$, $R^{16b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;

$T^2$ is phenyl; naphthyl; indenyl; indanyl; $C_{3-7}$ cycloalkyl; 4 to 7 membered heterocyclyl; or 7 to 11 membered heterobicyclyl, wherein $T^2$ is optionally substituted with one or more $R^{17}$, which are the same or different;

$T^3$ is phenyl; $C_{3-7}$ cycloalkyl; or 4 to 7 membered heterocyclyl, wherein $T^3$ is optionally substituted with one or more $R^{18}$, which are the same or different;

$R^{17}$, $R^{18}$ are independently selected from the group consisting of halogen; CN; C(O)OR$^{19}$; OR$^{19}$; oxo (=O), where the ring is at least partially saturated; C(O)R$^{19}$; C(O)N(R$^{19}$R$^{19a}$); S(O)$_2$N(R$^{19}$R$^{19a}$); S(O)N(R$^{19}$R$^{19a}$); S(O)$_2$R$^{19}$; S(O)R$^{19}$; N(R$^{19}$)S(O)$_2$N(R$^{19a}$R$^{19b}$); N(R$^{19}$)S(O)N(R$^{19a}$R$^{19b}$); SR$^{19}$; N(R$^{19}$R$^{19a}$); NO$_2$; OC(O)R$^{19}$; N(R$^{19}$)C(O)R$^{19a}$; N(R$^{19}$)S(O)$_2$R$^{19a}$; N(R$^{19}$)S(O)R$^{19a}$; N(R$^{19}$)C(O)N(R$^{19a}$R$^{19b}$); N(R$^{19}$)C(O)OR$^{19a}$; OC(O)N(R$^{19}$R$^{19a}$); $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{20}$, which are the same or different;

$R^{19}$, $R^{19a}$, $R^{19b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{20}$, which are the same or different;

$R^{20}$ is halogen; CN; C(O)OR$^{21}$; OR$^{21}$; C(O)R$^{21}$; C(O)N(R$^{21}$R$^{21a}$); S(O)$_2$N(R$^{21}$R$^{21a}$); S(O)N(R$^{21}$R$^{21a}$); S(O)$_2$R$^{21}$; S(O)R$^{21}$; N(R$^{21}$)S(O)$_2$N(R$^{21a}$R$^{21b}$); N(R$^{21}$)S(O)N(R$^{21a}$R$^{21b}$); SR$^{21}$; N(R$^{21}$R$^{21a}$); NO$_2$; OC(O)R$^{21}$; N(R$^{21}$)C(O)R$^{21a}$; N(R$^{21}$)S(O)$_2$R$^{21a}$; N(R$^{21}$)S(O)R$^{21a}$; N(R$^{21}$)C(O)N(R$^{21a}$R$^{21b}$); N(R$^{21}$)C(O)OR$^{21a}$; or OC(O)N(R$^{21}$R$^{21a}$);

$R^{21}$, $R^{21a}$, $R^{21b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different wherein the compound is not 1-(pyridin-3-yl)methyl)-N-(1-methyl-1H-pyrazol-4-yl)-1H-pyrazolo[3,4-d]pyrimidin-6-amine.

2. A compound of claim 1, wherein R is H.

3. A compound of claim 1, wherein ring A is a pyrazole, an oxazole or an isoxazole.

4. A compound of claim 1, wherein 0, 1, or 2 $R^1$, which are the same or different, are other than H.

5. A compound of claim 1, wherein $R^1$ is OR$^2$ or $C_{1-4}$ alkyl, which is optionally substituted with 1 or 2 $R^3$, which are the same or different.

6. A compound of claim 1, wherein $R^3$ is halogen; CN; OR$^4$; C(O)N(R$^4$R$^{4a}$); or C(O)T$^1$, wherein $T^1$ is an unsubstituted 4 to 7 membered heterocycle containing at least one ring nitrogen atom which is attached to C(O).

7. A compound of claim 1, wherein n is 0, 1 or 2.

8. A compound of claim 1, wherein $R^5$, $R^{5a}$ are H.

9. A compound of claim 1, wherein none or one of $X^1$, $X^2$, $X^3$, $X^4$, or $X^5$ is N.

10. A compound of claim 1, wherein $R^6$, $R^{6a}$, $R^{6b}$, $R^{6c}$, and $R^{6d}$ are H.

11. A compound of claim 1, wherein at least one of $R^6$, $R^{6a}$, $R^{6b}$, $R^{6c}$, or $R^{6d}$ is other than H.

12. A compound of claim 11, wherein $R^6$, $R^{6a}$, $R^{6b}$, $R^{6c}$, and $R^{6d}$ are independently selected from the group consisting of H; halogen; CN; $C(O)OR^7$; $C(O)N(R^7R^{7a})$; $S(O)_2NR^7R^{7a})$; and $N(R^7)S(O)_2R^{7a}$, provided that 1 or 2 of $R^6$, $R^{6a}$, $R^{6b}$, $R^{6c}$, or $R^{6d}$ are other than H.

13. A compound of claim 11, wherein $R^7$, $R^{7a}$, and $R^{7b}$ are independently selected from the group consisting of H; and unsubstituted $C_{1-4}$ alkyl.

14. A compound of claim 11, wherein in formula (I): Y, $X^1$, $X^2$, $X^3$, $X^4$, and $X^5$ are selected to give formula (Ia)

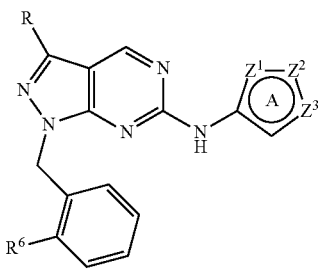

(Ia)

provided that $R^6$ is other than H.

15. A compound of claim 11, wherein in formula (I): Y, $X^1$, $X^2$, $X^3$, $X^4$, and $X^5$ are selected to give formula (Ib)

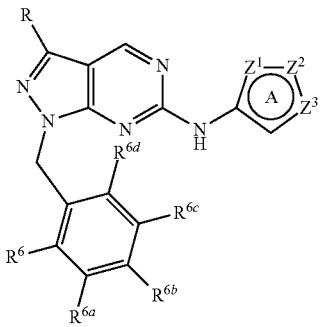

(Ib)

provided that $R^6$ and one of $R^{6a}$, $R^{6b}$, $R^{6c}$ or $R^{6d}$ are other than H.

16. A compound of claim 11, wherein in formula (I): Y, $X^1$, $X^2$, $X^3$, $X^4$, and $X^5$ are selected to give formula (Ic)

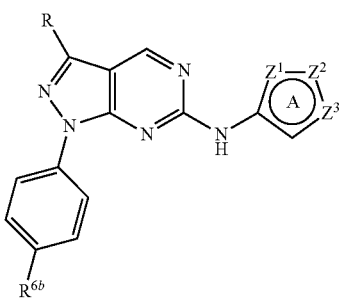

(Ic)

provided that $R^{6b}$ is other than H.

17. A compound of claim 1 selected from the group consisting of
- 2-((6-(1-Methyl-1H-pyrazol-4-ylamino)-1H-pyrazolo[3,4-d]pyrimidin-1-yl) methyl)benzonitrile;
- 1-(2-Fluorobenzyl)-N-(1-methyl-1H-pyrazol-4-yl)-1H-pyrazolo[3,4-d]pyrimidin-6-amine;
- 2-((6-(1-Methyl-1H-pyrazol-3-ylamino)-1H-pyrazolo[3,4-d]pyrimidin-1-yl)methyl)benzonitrile;
- 2-((6-(1H-Pyrazol-4-ylamino)-1H-pyrazolo[3,4-d]pyrimidin-1-yl)methyl)benzonitrile;
- 2-((6-(Isoxazol-4-ylamino)-1H-pyrazolo[3,4-d]pyrimidin-1-yl)methyl)benzonitrile;
- 2-((6-(1,3-Dimethyl-1H-pyrazol-4-ylamino)-1H-pyrazolo[3,4-d]pyrimidin-1-yl)methyl)benzonitrile;
- 2-((6-(1-Ethyl-3-methyl-1H-pyrazol-4-ylamino)-1H-pyrazolo[3,4-d]pyrimidin-1-yl)methyl)benzonitrile;
- 2-((6-(Isoxazol-3-ylamino)-1H-pyrazolo[3,4-d]pyrimidin-1-yl)methyl)benzonitrile;
- 2-((6-(1,5-Dimethyl-1H-pyrazol-3-ylamino)-1H-pyrazolo[3,4-d]pyrimidin-1-yl)methyl)benzonitrile;
- 2-((6-(1-(2-Methoxyethyl)-1H-pyrazol-4-ylamino)-1H-pyrazolo[3,4-d]pyrimidi-1-yl)methyl)benzonitrile;
- 2-((6-(1-Ethyl-1H-pyrazol-4-ylamino)-1H-pyrazolo[3,4-d]pyrimidin-1-yl) methyl)benzonitrile;
- 2-((6-(1-Isopropyl-1H-pyrazol-4-ylamino)-1H-pyrazolo[3,4-d]pyrimidin-1-yl)methyl)benzonitrile;
- 2-(4-(1-(2-Cyanobenzyl)-1H-pyrazolo[3,4-d]pyrimidin-6-ylamino)-1H-pyrazol-1-yl)-N-methylacetamide;
- 2-((6-(1-(2-Morpholino-2-oxoethyl)-1H-pyrazol-4-ylamino)-1H-pyrazolo[3,4-d]pyrimidin-1-yl)methyl) benzonitrile;
- 2-((6-(1-(2-Cyanoethyl)-1H-pyrazol-4-ylamino)-1H-pyrazolo[3,4-d]pyrimidin-1-yl)methyl)benzonitrile;
- 2-((6-(1-Methyl-1H-pyrazol-4-ylamino)-1H-pyrazolo[3,4-d]pyrimidin-1-yl)methyl)benzamide;
- N-Methyl-N-(4-(6-(1-methyl-1H-pyrazol-4-ylamino)-1H-pyrazolo[3,4-d]pyrimidin-1-yl)phenyl)methanesulfonamide;
- N-(4-(6-(1-Methyl-1H-pyrazol-4-ylamino)-1H-pyrazolo[3,4-d]pyrimidin-1-yl)phenyl)methanesulfonamide;
- 2-((6-(1-Isopropyl-1H-pyrazol-3-ylamino)-1H-pyrazolo[3,4-d]pyrimidin-1-yl)methyl)benzonitrile;
- 2-((6-(1-(3-Cyanopropyl)-1H-pyrazol-4-ylamino)-1H-pyrazolo[3,4-d]pyrimidin-1-yl)methyl)benzonitrile;
- 2-((6-(3-Methyl-1-propyl-1H-pyrazol-4-ylamino)-1H-pyrazolo[3,4-d]pyrimidin-1-yl)methyl)benzonitrile;
- 2-((6-(1-(2,2-Difluoroethyl)-3-methyl-1H-pyrazol-4-ylamino)-1H-pyrazolo[3,4-d]pyrimidin-1-yl)methyl) benzonitrile;
- 2-((6-(1-(2-methoxyethyl)-3-methyl-1H-pyrazol-4-ylamino)-1H-pyrazolo[3,4-d]pyrimidin-1-yl)methyl) benzonitrile;
- 2-((6-(1-(2,2-Difluoroethyl)-3-methoxy-1H-pyrazol-4-ylamino)-1H-pyrazolo[3,4-d]pyrimidin-1-yl)methyl) benzonitrile;
- 2-((6-(1-(2-Hydroxyethyl)-1H-pyrazol-4-ylamino)-1H-pyrazolo[3,4-d]pyrimidin-1-yl)methyl)benzonitrile;
- 1-(1-(2-Fluorophenyl)ethyl)-N-(1-methyl-1H-pyrazol-4-yl)-1H-pyrazolo[3,4-d]pyrimidin-6-amine;
- 1-(2-Chlorobenzyl)-N-(1-methyl-1H-pyrazol-4-yl)-1H-pyrazolo[3,4-d]pyrimidin-6-amine;
- 1-(2-fluorobenzyl)-N-(1-(2-methoxyethyl)-1H-pyrazol-4-yl)-1H-pyrazolo[3,4-d]pyrimidin-6-amine;
- 1-(2,6-Difluorobenzyl)-N-(1-methyl-1H-pyrazol-4-yl)-1H-pyrazolo[3,4-d]pyrimidin-6-amine;
- 1-(2,5-Difluorobenzyl)-N-(1-methyl-1H-pyrazol-4-yl)-1H-pyrazolo[3,4-d]pyrimidin-6-amine;

1-(2,3-Difluorobenzyl)-N-(1-methyl-1H-pyrazol-4-yl)-1H-pyrazolo[3,4-d]pyrimidin-6-amine;
2-(4-(1-(2,5-Difluorobenzyl)-1H-pyrazolo[3,4-d]pyrimidin-6-ylamino)-1H-pyrazol-1-yl)ethanol;
2-(4-(1-(2,3-Difluorobenzyl)-1H-pyrazolo[3,4-d]pyrimidin-6-ylamino)-1H-pyrazol-1-yl)ethanol;
2-(4-(1-(2-Fluorobenzyl)-1H-pyrazolo[3,4-d]pyrimidin-6-ylamino)-1H-pyrazol-1-yl)ethanol;
4-(6-(1-Methyl-1H-pyrazol-4-ylamino)-1H-pyrazolo[3,4-d]pyrimidin-1-yl)benzenesulfonamide;
2-((6-(1-(2,2-difluoroethyl)-3-methoxy-1H-pyrazol-4-ylamino)-1H-pyrazolo[3,4-d]pyrimidin-1-yl)methyl)benzamide;
2-((6-(1,5-Dimethyl-1H-pyrazol-4-ylamino)-1H-pyrazolo[3,4-d]pyrimidin-1-yl)methyl)benzonitrile;
2-((6-(3-methoxy-1-(2,2,2-trifluoroethyl)-1H-pyrazol-4-ylamino)-1H-pyrazolo[3,4-d]pyrimidin-1-yl)methyl)benzonitrile;
2-((6-(1-(2,2-Difluoroethyl)-1H-pyrazol-4-ylamino)-1H-pyrazolo[3,4-d]pyrimidin-1-yl)methyl)benzonitrile;
N-methyl-4-(6-(1-methyl-1H-pyrazol-4-ylamino)-1H-pyrazolo[3,4-d]pyrimidin-1-yl)benzenesulfonamide;
2-((6-(1-Methyl-1H-pyrazol-4-ylamino)-1H-pyrazolo[3,4-d]pyrimidin-1-yl)methyl)benzoic acid;
2-((6-(1-(2,2-Difluoroethyl)-1H-pyrazol-4-ylamino)-1H-pyrazolo[3,4-d]pyrimidin-1-yl)methyl)benzamide;
2-((6-(1-(2,2-Difluoroethyl)-3-methyl-1H-pyrazol-4-ylamino)-1H-pyrazolo[3,4-d]pyrimidin-1-yl)methyl)benzamide;
2-((6-(1-(2-Hydroxyethyl)-3-methoxy-1H-pyrazol-4-ylamino)-1H-pyrazolo[3,4-d]pyrimidin-1-yl)methyl)benzonitrile;
1-((2-Fluoropyridin-3-yl)methyl)-N-(1-methyl-1H-pyrazol-4-yl)-1H-pyrazolo[3,4-d]pyrimidin-6-amine;
1-((3-Fluoropyridin-4-yl)methyl)-N-(1-methyl-1H-pyrazol-4-yl)-1H-pyrazolo[3,4-d]pyrimidin-6-amine;
1-(2,4-Difluorobenzyl)-N-(1-methyl-1H-pyrazol-4-yl)-1H-pyrazolo[3,4-d]pyrimidin-6-amine;
N-(1-Methyl-1H-pyrazol-4-yl)-1-phenethyl-1H-pyrazolo[3,4-d]pyrimidin-6-amine;
2-(4-(1-(2-Fluorobenzyl)-1H-pyrazolo[3,4-d]pyrimidin-6-ylamino)-3-methoxy-1H-pyrazol-1-yl)ethanol;
2-(4-(1-(2,3-Difluorobenzyl)-1H-pyrazolo[3,4-d]pyrimidin-6-ylamino)-3-methoxy-1H-pyrazol-1-yl)ethanol;
2-(4-(1-(2,5-Difluorobenzyl)-1H-pyrazolo[3,4-d]pyrimidin-6-ylamino)-3-methoxy-1H-pyrazol-1-yl)ethanol;
4-Fluoro-2-((6-(1-methyl-1H-pyrazol-4-ylamino)-1H-pyrazolo[3,4-d]pyrimidin-1-yl)methyl)benzonitrile;
4-fluoro-2-((6-(1-methyl-1H-pyrazol-4-ylamino)-1H-pyrazolo[3,4-d]pyrimidin-1-yl)methyl)benzamide;
N-(6-(6-(1-methyl-1H-pyrazol-4-ylamino)-1H-pyrazolo[3,4-d]pyrimidin-1-yl)pyridin-3-yl)methanesulfonamide;
N-(2-methyl-6-(6-(1-methyl-1H-pyrazol-4-ylamino)-1H-pyrazolo[3,4-d]pyrimidin-1-yl)pyridin-3-yl)methanesulfonamide;
1-(4-fluorophenyl)-N-(1-methyl-1H-pyrazol-4-yl)-1H-pyrazolo[3,4-d]pyrimidin-6-amine;
1-(4-chlorophenyl)-N-(1-methyl-1H-pyrazol-4-yl)-1H-pyrazolo[3,4-d]pyrimidin-6-amine; and
1-(4-fluoro-3-methoxyphenyl)-N-(1-methyl-1H-pyrazol-4-yl)-1H-pyrazolo[3,4-d]pyrimidin-6-amine.

18. A pharmaceutical composition comprising a compound or a pharmaceutically acceptable salt thereof of claim 1 together with a pharmaceutically acceptable carrier, optionally in combination with one or more other pharmaceutical compositions.

19. A compound of claim 1 selected from the group consisting of
(R)-N-(1-methyl-1H-pyrazol-4-yl)-1-((6-(3-methylmorpholino)pyridin-2-yl)methyl)-1H-pyrazolo[3,4-d]pyrimidin-6-amine;
1-(4-fluoro-3-methylphenyl)-N-(1-methyl-1H-pyrazol-4-yl)-1H-pyrazolo[3,4-d]pyrimidin-6-amine;
N-(1-methyl-1H-pyrazol-4-yl)-1-(4-(methylsulfonyl)phenyl)-1H-pyrazolo[3,4-d]pyrimidin-6-amine;
1-(2-chloro-5-fluorobenzyl)-N-(1-methyl-1H-pyrazol-4-yl)-1H-pyrazolo[3,4-d]pyrimidin-6-amine;
1-(2-chloro-6-fluorobenzyl)-N-(1-methyl-1H-pyrazol-4-yl)-1H-pyrazolo[3,4-d]pyrimidin-6-amine;
1-(5-chloro-2-fluorobenzyl)-N-(1-methyl-1H-pyrazol-4-yl)-1H-pyrazolo[3,4-d]pyrimidin-6-amine;
N-(1-methyl-1H-pyrazol-4-yl)-1-(2-(trifluoromethyl)benzyl)-1H-pyrazolo[3,4-d]pyrimidin-6-amine;
N-(1-methyl-1H-pyrazol-4-yl)-1-(3-(trifluoromethyl)benzyl)-1H-pyrazolo[3,4-d]pyrimidin-6-amine;
1-(3-fluorobenzyl)-N-(1-methyl-1H-pyrazol-4-yl)-1H-pyrazolo[3,4-d]pyrimidin-6-amine;
3-((6-((1-methyl-1H-pyrazol-4-yl)amino)-1H-pyrazolo[3,4-d]pyrimidin-1-yl)methyl)benzonitrile;
1-(3-methoxybenzyl)-N-(1-methyl-1H-pyrazol-4-yl)-1H-pyrazolo[3,4-d]pyrimidin-6-amine;
1-(3-chlorobenzyl)-N-(1-methyl-1H-pyrazol-4-yl)-1H-pyrazolo[3,4-d]pyrimidin-6-amine;
4-(6-((1-(2,2-difluoroethyl)-3-methoxy-1H-pyrazol-4-yl)amino)-1H-pyrazolo[3,4-d]pyrimidin-1-yl)benzenesulfonamide;
1-(3-chloro-2-fluorobenzyl)-N-(1-methyl-1H-pyrazol-4-yl)-1H-pyrazolo[3,4-d]pyrimidin-6-amine;
2-(4-((1-(2,6-difluorobenzyl)-1H-pyrazolo[3,4-d]pyrimidin-6-yl)amino)-1H-pyrazol-1-yl)ethanol;
N-(1-methyl-1H-pyrazol-4-yl)-1-phenyl-1H-pyrazolo[3,4-d]pyrimidin-6-amine;
N-(2-((6-((1-methyl-1H-pyrazol-4-yl)amino)-1H-pyrazolo[3,4-d]pyrimidin-1-yl)methyl)phenyl)methanesulfonamide;
1-benzyl-N-(1-methyl-1H-pyrazol-4-yl)-1H-pyrazolo[3,4-d]pyrimidin-6-amine;
1-(2-fluorophenethyl)-N-(1-methyl-1H-pyrazol-4-yl)-1H-pyrazolo[3,4-d]pyrimidin-6-amine;
1-(3,4-difluorobenzyl)-N-(1-methyl-1H-pyrazol-4-yl)-1H-pyrazolo[3,4-d]pyrimidin-6-amine;
1-(3,5-difluorobenzyl)-N-(1-methyl-1H-pyrazol-4-yl)-1H-pyrazolo[3,4-d]pyrimidin-6-amine;
3-((6-((1-methyl-1H-pyrazol-4-yl)amino)-1H-pyrazolo[3,4-d]pyrimidin-1-yl)methyl)benzamide;
1-(3-fluorophenethyl)-N-(1-methyl-1H-pyrazol-4-yl)-1H-pyrazolo[3,4-d]pyrimidin-6-amine;
1-(4-fluorophenethyl)-N-(1-methyl-1H-pyrazol-4-yl)-1H-pyrazolo[3,4-d]pyrimidin-6-amine;
N-(1-methyl-1H-pyrazol-4-yl)-1-(3-methylbenzyl)-1H-pyrazolo[3,4-d]pyrimidin-6-amine;
N-(1-methyl-1H-pyrazol-4-yl)-1-(2-methylbenzyl)-1H-pyrazolo[3,4-d]pyrimidin-6-amine;
N-(1-methyl-1H-pyrazol-4-yl)-1-(2-(trifluoromethoxy)benzyl)-1H-pyrazolo[3,4-d]pyrimidin-6-amine;
N-(1-methyl-1H-pyrazol-4-yl)-1-(3-(trifluoromethoxy)benzyl)-1H-pyrazolo[3,4-d]pyrimidin-6-amine;
1-(2-methoxybenzyl)-N-(1-methyl-1H-pyrazol-4-yl)-1H-pyrazolo[3,4-d]pyrimidin-6-amine;
1-(2-fluorobenzyl)-N-(1H-pyrazol-4-yl)-1H-pyrazolo[3,4-d]pyrimidin-6-amine;
1-(4-((1-(2-fluorobenzyl)-1H-pyrazolo[3,4-d]pyrimidin-6-yl)amino)-1H-pyrazol-1-yl)propan-2-ol;

1-(2-fluoro-6-methoxybenzyl)-N-(1-methyl-1H-pyrazol-
4-yl)-1H-pyrazolo[3,4-d]pyrimidin-6-amine;
1-(5-fluoro-2-methoxybenzyl)-N-(1-methyl-1H-pyrazol-
4-yl)-1H-pyrazolo[3,4-d]pyrimidin-6-amine;
(2-((6-((1-methyl-1H-pyrazol-4-yl)amino)-1H-pyrazolo
[3,4-d]pyrimidin-1-yl)methyl)phenyl)methanol;
1-(2-fluoro-3-methoxybenzyl)-N-(1-methyl-1H-pyrazol-
4-yl)-1H-pyrazolo[3,4-d]pyrimidin-6-amine;
1-(2-fluoro-5-methoxybenzyl)-N-(1-methyl-1H-pyrazol-
4-yl)-1H-pyrazolo[3,4-d]pyrimidin-6-amine;
1-(4-((1-(2-fluorobenzyl)-1H-pyrazolo[3,4-d]pyrimidin-
6-yl)amino)-1H-pyrazol-1-yl)ethanone;
1-(2-fluorobenzyl)-N-(1-(methylsulfonyl)-1H-pyrazol-4-
yl)-1H-pyrazolo[3,4-d]pyrimidin-6-amine;
N-(3-chloro-1H-pyrazol-4-yl)-1-(2-fluorobenzyl)-1H-
pyrazolo[3,4-d]pyrimidin-6-amine;
N-(1-methyl-1H-pyrazol-4-yl)-1-(2,3,6-trifluorobenzyl)-
1H-pyrazolo[3,4-d]pyrimidin-6-amine;
1-(4-fluorobenzyl)-N-(1-methyl-1H-pyrazol-4-yl)-1H-
pyrazolo[3,4-d]pyrimidin-6-amine;
1-(3-isopropylbenzyl)-N-(1-methyl-1H-pyrazol-4-yl)-
1H-pyrazolo[3,4-d]pyrimidin-6-amine;
1-(2-isopropylbenzyl)-N-(1-methyl-1H-pyrazol-4-yl)-
1H-pyrazolo[3,4-d]pyrimidin-6-amine;
1-(2-(2-methoxyethoxy)benzyl)-N-(1-methyl-1H-pyra-
zol-4-yl)-1H-pyrazolo[3,4-d]pyrimidin-6-amine;
4-((1-(2-fluorobenzyl)-1H-pyrazolo[3,4-d]pyrimidin-6-
yl)amino)-1H-pyrazole-1-carboxamide;
1-(3-fluoro-5-methoxybenzyl)-N-(1-methyl-1H-pyrazol-
4-yl)-1H-pyrazolo[3,4-d]pyrimidin-6-amine;
1-benzyl-N-(3-methoxy-1-methyl-1H-pyrazol-4-yl)-1H-
pyrazolo[3,4-d]pyrimidin-6-amine;
2-(4-((1-benzyl-1H-pyrazolo[3,4-d]pyrimidin-6-yl)
amino)-3-methoxy-1H-pyrazol-1-yl)ethanol;
2-fluoro-3-((6-((1-methyl-1H-pyrazol-4-yl)amino)-1H-
pyrazolo[3,4-d]pyrimidin-1-yl)methyl)benzonitrile;
2-fluoro-6-((6-((1-methyl-1H-pyrazol-4-yl)amino)-1H-
pyrazolo[3,4-d]pyrimidin-1-yl)methyl)benzonitrile;
1-benzyl-N-(1,5-dimethyl-1H-pyrazol-4-yl)-1H-pyrazolo
[3,4-d]pyrimidin-6-amine;
1-benzyl-N-(1,3-dimethyl-1H-pyrazol-4-yl)-1H-pyrazolo
[3,4-d]pyrimidin-6-amine;
1-(2-cyclopropylbenzyl)-N-(1-methyl-1H-pyrazol-4-yl)-
1H-pyrazolo[3,4-d]pyrimidin-6-amine;
1-(4-((1-(2-fluorobenzyl)-1H-pyrazolo[3,4-d]pyrimidin-
6-yl)amino)-1H-pyrazol-1-yl)-2-methylpropan-2-ol;
2-(4-((1-benzyl-1H-pyrazolo[3,4-d]pyrimidin-6-yl)
amino)-3-methyl-1H-pyrazol-1-yl)ethanol;
1-(2-(benzyloxy)benzyl)-N-(1-methyl-1H-pyrazol-4-yl)-
1H-pyrazolo[3,4-d]pyrimidin-6-amine;
1-(3-fluoro-2-methylbenzyl)-N-(1-methyl-1H-pyrazol-4-
yl)-1H-pyrazolo[3,4-d]pyrimidin-6-amine;
1-(5-fluoro-2-methylbenzyl)-N-(1-methyl-1H-pyrazol-4-
yl)-1H-pyrazolo[3,4-d]pyrimidin-6-amine;
1-(2-fluoro-6-methylbenzyl)-N-(1-methyl-1H-pyrazol-4-
yl)-1H-pyrazolo[3,4-d]pyrimidin-6-amine;
1-benzyl-N-(1-(2,2-difluoroethyl)-1H-pyrazol-4-yl)-1H-
pyrazolo[3,4-d]pyrimidin-6-amine;
1-benzyl-N-(1-(2,2-difluoroethyl)-3-methoxy-1H-pyra-
zol-4-yl)-1H-pyrazolo[3,4-d]pyrimidin-6-amine;
1-benzyl-N-(1-(2,2-difluoroethyl)-3-methyl-1H-pyrazol-
4-yl)-1H-pyrazolo[3,4-d]pyrimidin-6-amine;
4-(6-((1-(2-hydroxyethyl)-1H-pyrazol-4-yl)amino)-1H-
pyrazolo[3,4-d]pyrimidin-1-yl)benzenesulfonamide;
3-(6-((1-methyl-1H-pyrazol-4-yl)amino)-1H-pyrazolo[3,
4-d]pyrimidin-1-yl)benzenesulfonamide;
N-(1-(2-(diethylamino)ethyl)-1H-pyrazol-4-yl)-1-(2-
fluorobenzyl)-1H-pyrazolo[3,4-d]pyrimidin-6-amine;
1-(2-fluorobenzyl)-N-(1-(2-morpholinoethyl)-1H-pyra-
zol-4-yl)-1H-pyrazolo[3,4-d]pyrimidin-6-amine;
N-(1-(3-(dimethylamino)propyl)-1H-pyrazol-4-yl)-1-(2-
fluorobenzyl)-1H-pyrazolo[3,4-d]pyrimidin-6-amine;
N-(2-((6-((1-methyl-1H-pyrazol-4-yl)amino)-1H-pyra-
zolo[3,4-d]pyrimidin-1-yl)methyl)phenyl)propane-2-
sulfonamide;
4-(6-((1-(2,2-difluoroethyl)-1H-pyrazol-4-yl)amino)-1H-
pyrazolo[3,4-d]pyrimidin-1-yl)benzenesulfonamide;
N-(1-(2,2-difluoroethyl)-1H-pyrazol-4-yl)-1-(2-fluo-
robenzyl)-1H-pyrazolo[3,4-d]pyrimidin-6-amine;
1-(2,5-difluorobenzyl)-N-(1-(2,2-difluoroethyl)-1H-pyra-
zol-4-yl)-1H-pyrazolo[3,4-d]pyrimidin-6-amine;
2-((6-((1-(2,2-difluoroethyl)-1H-pyrazol-4-yl)amino)-
1H-pyrazolo[3,4-d]pyrimidin-1-yl)methyl)-4-fluo-
robenzonitrile;
N-(2-((6-((1-(2,2-difluoroethyl)-1H-pyrazol-4-yl)amino)-
1H-pyrazolo[3,4-d]pyrimidin-1-yl)methyl)phenyl)
methanesulfonamide hydrochloride;
1-(3-(2-methoxyethoxy)benzyl)-N-(1-methyl-1H-pyra-
zol-4-yl)-1H-pyrazolo[3,4-d]pyrimidin-6-amine;
2-(4-((1-benzyl-1H-pyrazolo[3,4-d]pyrimidin-6-yl)
amino)-1H-pyrazol-1-yl)-N-methylacetamide;
2,2,2-trifluoro-N-(2-((6-((1-methyl-1H-pyrazol-4-yl)
amino)-1H-pyrazolo[3,4-d]pyrimidin-1-yl)methyl)
phenyl)ethanesulfonamide;
4-(6-((1-methyl-1H-pyrazol-4-yl)amino)-1H-pyrazolo[3,
4-d]pyrimidin-1-yl)benzamide;
N-methyl-4-(6-((1-methyl-1H-pyrazol-4-yl)amino)-1H-
pyrazolo[3,4-d]pyrimidin-1-yl)benzamide;
(4-(6-((1-methyl-1H-pyrazol-4-yl)amino)-1H-pyrazolo
[3,4-d]pyrimidin-1-yl)phenyl)(morpholino)metha-
none;
2-fluoro-4-(6-((1-methyl-1H-pyrazol-4-yl)amino)-1H-
pyrazolo[3,4-d]pyrimidin-1-yl)benzenesulfonamide;
N-(2-hydroxyethyl)-4-(6-((1-methyl-1H-pyrazol-4-yl)
amino)-1H-pyrazolo[3,4-d]pyrimidin-1-yl)benzene-
sulfonamide;
N-(3-((6-((1-methyl-1H-pyrazol-4-yl)amino)-1H-pyra-
zolo[3,4-d]pyrimidin-1-yl)methyl)phenyl)methane-
sulfonamide;
N-(3-((6-((1-methyl-1H-pyrazol-4-yl)amino)-1H-pyra-
zolo[3,4-d]pyrimidin-1-yl)methyl)phenyl)propane-2-
sulfonamide;
N-(3-fluoro-2-((6-((1-methyl-1H-pyrazol-4-yl)amino)-
1H-pyrazolo[3,4-d]pyrimidin-1-yl)methyl)phenyl)
methanesulfonamide;
1-(2-fluorobenzyl)-N-(1-(2-(piperidin-1-ypethyl)-1H-
pyrazol-4-yl)-1H-pyrazolo[3,4-d]pyrimidin-6-amine;
1-(2-fluorobenzyl)-N-(1-(3-(piperidin-1-yl)propyl)-1H-
pyrazol-4-yl)-1H-pyrazolo[3,4-d]pyrimidin-6-amine;
1-(2-fluorobenzyl)-N-(1-(3-morpholinopropyl)-1H-pyra-
zol-4-yl)-1H-pyrazolo[3,4-d]pyrimidin-6-amine;
(3-(6-((1-methyl-1H-pyrazol-4-yl)amino)-1H-pyrazolo
[3,4-d]pyrimidin-1-yl)phenyl)(morpholino)methanone;
N-(2-hydroxyethyl)-3-(6-((1-methyl-1H-pyrazol-4-yl)
amino)-1H-pyrazolo[3,4-d]pyrimidin-1-yl)benzamide;
N-(2-hydroxyethyl)-4-(6-((1-methyl-1H-pyrazol-4-yl)
amino)-1H-pyrazolo[3,4-d]pyrimidin-1-yl)benzamide;
(4-(6-((1-methyl-1H-pyrazol-4-yl)amino)-1H-pyrazolo
[3,4-d]pyrimidin-1-yl)phenyl)(4-methylpiperazin-1-yl)
methanone;
1-(2,5-difluorobenzyl)-N-(1-(2,2-difluoroethyl)-3-me-
thyl-1H-pyrazol-4-yl)-1H-pyrazolo[3,4-d]pyrimidin-6-
amine;

2-((6-((1-(2,2-difluoroethyl)-3-methyl-1H-pyrazol-4-yl) amino)-1H-pyrazolo[3,4-d]pyrimidin-1-yl)methyl)-4-fluorobenzonitrile;

1-(2,5-difluorobenzyl)-N-(1-(2,2-difluoroethyl)-3-methoxy-1H-pyrazol-4-yl)-1H-pyrazolo[3,4-d]pyrimidin-6-amine;

2-((6-((1-(2,2-difluoroethyl)-3-methoxy-1H-pyrazol-4-yl)amino)-1H-pyrazolo[3,4-d]pyrimidin-1-yl)methyl)-4-fluorobenzonitrile;

N-(1-(2,2-difluoroethyl)-1H-pyrazol-4-yl)-1-(3-fluoro-2-methylbenzyl)-1H-pyrazolo[3,4-d]pyrimidin-6-amine;

1-(2,3-difluorobenzyl)-N-(1-(2,2-difluoroethyl)-1H-pyrazol-4-yl)-1H-pyrazolo[3,4-d]pyrimidin-6-amine;

1-(3-chloro-2-fluorobenzyl)-N-(1-(2,2-difluoroethyl)-1H-pyrazol-4-yl)-1H-pyrazolo[3,4-d]pyrimidin-6-amine;

N-(1-(2,2-difluoroethyl)-1H-pyrazol-4-yl)-1-(2,3,6-trifluorobenzyl)-1H-pyrazolo[3,4-d]pyrimidin-6-amine;

N-(1-methyl-1H-pyrazol-4-yl)-1-(2,3,5-trifluorobenzyl)-1H-pyrazolo[3,4-d]pyrimidin-6-amine;

1-(2,6-difluoro-3-methoxybenzyl)-N-(1-methyl-1H-pyrazol-4-yl)-1H-pyrazolo[3,4-d]pyrimidin-6-amine;

1-(2,6-difluorobenzyl)-N-(1-(2,2-difluoroethyl)-1H-pyrazol-4-yl)-1H-pyrazolo[3,4-d]pyrimidin-6-amine;

1-(2-cyclopropylbenzyl)-N-(1-(2,2-difluoroethyl)-1H-pyrazol-4-yl)-1H-pyrazolo[3,4-d]pyrimidin-6-amine;

N-(1-methyl-1H-pyrazol-4-yl)-1-(3-morpholinobenzyl)-1H-pyrazolo[3,4-d]pyrimidin-6-amine;

N-(1-methyl-1H-pyrazol-4-yl)-1-(2,3,5,6-tetrafluorobenzyl)-1H-pyrazolo[3,4-d]pyrimidin-6-amine;

1-(2-fluoro-6-(trifluoromethyl)benzyl)-N-(1-methyl-1H-pyrazol-4-yl)-1H-pyrazolo[3,4-d]pyrimidin-6-amine;

1-(2-fluorobenzyl)-N-(1-(2-(tetrahydro-2H-pyran-4-yl)ethyl)-1H-pyrazol-4-yl)-1H-pyrazolo[3,4-d]pyrimidin-6-amine;

2-(3-((6-((1-methyl-1H-pyrazol-4-yl)amino)-1H-pyrazolo[3,4-d]pyrimidin-1-yl)methyl)phenoxy)ethanol;

N-(1-methyl-1H-pyrazol-4-yl)-1-(3-(2-(piperidin-1-ypethoxy)benzyl)-1H-pyrazolo[3,4-d]pyrimidin-6-amine;

2-(2-((6-((1-methyl-1H-pyrazol-4-yl)amino)-1H-pyrazolo[3,4-d]pyrimidin-1-yl)methyl)phenoxy)ethanol;

1-(3-(3-methoxypropoxy)benzyl)-N-(1-methyl-1H-pyrazol-4-yl)-1H-pyrazolo[3,4-d]pyrimidin-6-amine;

1-((6-fluoropyridin-2-yl)methyl)-N-(1-methyl-1H-pyrazol-4-yl)-1H-pyrazolo[3,4-d]pyrimidin-6-amine;

(S)-1-(3-(2-methoxypropoxy)benzyl)-N-(1-methyl-1H-pyrazol-4-yl)-1H-pyrazolo[3,4-d]pyrimidin-6-amine;

1-(3-(cyclopropylmethoxy)benzyl)-N-(1-methyl-1H-pyrazol-4-yl)-1H-pyrazolo[3,4-d]pyrimidin-6-amine;

1-(2-(cyclopropylmethoxy)benzyl)-N-(1-methyl-1H-pyrazol-4-yl)-1H-pyrazolo[3,4-d]pyrimidin-6-amine;

N-(1-methyl-1H-pyrazol-4-yl)-1-((6-morpholinopyridin-2-yl)methyl)-1H-pyrazolo[3,4-d]pyrimidin-6-amine;

1-(3-((2S,6R)-2,6-dimethylmorpholino)benzyl)-N-(1-methyl-1H-pyrazol-4-yl)-1H-pyrazolo[3,4-d]pyrimidin-6-amine;

N-(1-(2,2-difluoroethyl)-1H-pyrazol-4-yl)-1-(3-(2-methoxyethoxy)benzyl)-1H-pyrazolo[3,4-d]pyrimidin-6-amine;

N-(1-(3-(azetidin-1-yl)propyl)-1H-pyrazol-4-yl)-1-(2-fluorobenzyl)-1H-pyrazolo[3,4-d]pyrimidin-6-amine;

1-(2,3-dichlorobenzyl)-N-(1-methyl-1H-pyrazol-4-yl)-1H-pyrazolo[3,4-d]pyrimidin-6-amine;

2-methyl-3-((6-((1-methyl-1H-pyrazol-4-yl)amino)-1H-pyrazolo[3,4-d]pyrimidin-1-yl)methyl)phenol;

N-(1-methyl-1H-pyrazol-4-yl)-1-(2-morpholinobenzyl)-1H-pyrazolo[3,4-d]pyrimidin-6-amine;

N-(1-methyl-1H-pyrazol-4-yl)-1-(3-((tetrahydrofuran-3-ypoxy)benzyl)-1H-pyrazolo[3,4-d]pyrimidin-6-amine;

1-(2-fluorobenzyl)-N-(1-(2-(piperazin-1-ypethyl)-1H-pyrazol-4-yl)-1H-pyrazolo[3,4-d]pyrimidin-6-amine;

1-((6-(dimethylamino)pyridin-2-yl)methyl)-N-(1-methyl-1H-pyrazol-4-yl)-1H-pyrazolo[3,4-d]pyrimidin-6-amine;

N-(1-(3-(dimethylamino)propyl)-1H-pyrazol-4-yl)-1-(3-(2-methoxyethoxy)benzyl)-1H-pyrazolo[3,4-d]pyrimidin-6-amine;

1-(3-(2-methoxyethoxy)-2-methylbenzyl)-N-(1-methyl-1H-pyrazol-4-yl)-1H-pyrazolo[3,4-d]pyrimidin-6-amine;

N-(1-(3-(dimethylamino)propyl)-1H-pyrazol-4-yl)-1-(3-morpholinobenzyl)-1H-pyrazolo[3,4-d]pyrimidin-6-amine;

(R)-N-(1-methyl-1H-pyrazol-4-yl)-1-((6-((tetrahydrofuran-3-yl)amino)pyridin-2-yl)methyly 1H-pyrazolo[3,4-d]pyrimidin-6-amine;

N-(1-methyl-1H-pyrazol-4-yl)-1-((6-(pyrrolidin-1-yl)pyridin-2-yl)methyl)-1H-pyrazolo[3,4-d]pyrimidin-6-amine;

4-methyl-3-((6-((1-methyl-1H-pyrazol-4-yl)amino)-1H-pyrazolo[3,4-d]pyrimidin-1-yl)methyl)phenol;

2-(4-((1-(3-morpholinobenzyl)-1H-pyrazolo[3,4-d]pyrimidin-6-yl)amino)-1H-pyrazol-1-yl)ethanol;

(3-((6-((1-methyl-1H-pyrazol-4-yl)amino)-1H-pyrazolo[3,4-d]pyrimidin-1-yl)methyl)phenyl)(morpholino)methanone;

1-(2-fluorobenzyl)-N-(1-((1-methylpiperidin-3-yl)methyl)-1H-pyrazol-4-yl)-1H-pyrazolo[3,4-d]pyrimidin-6-amine;

(R)-N-(1-methyl-1H-pyrazol-4-yl)-1-((6-((tetrahydrofuran-2-yl)methoxy)pyridin-2-yl)methyl)-1H-pyrazolo[3,4-d]pyrimidin-6-amine;

1-(2-fluorobenzyl)-N-(1-(3-(4-methylpiperazin-1-yl)propyl)-1H-pyrazol-4-yl)-1H-pyrazolo[3,4-d]pyrimidin-6-amine;

N-(1-methyl-1H-pyrazol-4-yl)-1-(3-(morpholinomethyl)benzyl)-1H-pyrazolo[3,4-d]pyrimidin-6-amine;

2-(4-((1-(2,3,5,6-tetrafluorobenzyl)-1H-pyrazolo[3,4-d]pyrimidin-6-yl)amino)-1H-pyrazol-1-yl)ethanol;

N-(1-methyl-1H-pyrazol-4-yl)-1-(3-(piperidin-1-yl)benzyl)-1H-pyrazolo[3,4-d]pyrimidin-6-amine;

N-(1-methyl-1H-pyrazol-4-yl)-1-(3-(tetrahydro-2H-pyran-4-yl)benzyl)-1H-pyrazolo[3,4-d]pyrimidin-6-amine;

N-(1-methyl-1H-pyrazol-4-yl)-1-(3-(4-methylpiperazin-1-yl)benzyl)-1H-pyrazolo[3,4-d]pyrimidin-6-amine;

N-(2-methoxyethyl)-3-((6-((1-methyl-1H-pyrazol-4-yl)amino)-1H-pyrazolo[3,4-d]pyrimidin-1-yl)methyl)benzamide;

N-(1-methyl-1H-pyrazol-4-yl)-1-(2-methyl-3-morpholinobenzyl)-1H-pyrazolo[3,4-d]pyrimidin-6-amine;

N-methyl-2-(4-((1-(3-morpholinobenzyl)-1H-pyrazolo[3,4-d]pyrimidin-6-yl)amino)-1H-pyrazol-1-yl)acetamide;

ethyl 1-(3-((6-((1-methyl-1H-pyrazol-4-yl)amino)-1H-pyrazolo[3,4-d]pyrimidin-1-yl)methyl)phenyl)piperidine-3-carboxylate;

3-(4-((1-(3-morpholinobenzyl)-1H-pyrazolo[3,4-d]pyrimidin-6-yl)amino)-1H-pyrazol-1-yl)propanamide;

1-(2-fluoro-5-morpholinobenzyl)-N-(1-methyl-1H-pyrazol-4-yl)-1H-pyrazolo[3,4-d]pyrimidin-6-amine;

1-(3-(2-aminopyridin-4-yl)benzyl)-N-(1-methyl-1H-pyrazol-4-yl)-1H-pyrazolo[3,4-d]pyrimidin-6-amine;
N,N-dimethyl-3-(4-((1-(3-morpholinobenzyl)-1H-pyrazolo[3,4-d]pyrimidin-6-yl)amino)-1H-pyrazol-1-yl)propanamide;
(R)-1-(6-((6-(((1-methyl-1H-pyrazol-4-yl)amino)-1H-pyrazolo[3,4-d]pyrimidin-1-yl)methyppyridin-2-yl)pyrrolidin-3-ol;
2-(3-((6-(((1-methyl-1H-pyrazol-4-yl)amino)-1H-pyrazolo[3,4-d]pyrimidin-1-yl)methyl)phenoxy)acetamide;
N-(1-methyl-1H-pyrazol-4-yl)-1-(2,3,6-trifluoro-5-morpholinobenzyl)-1H-pyrazolo[3,4-d]pyrimidin-6-amine;
3-(4-((1-(3-morpholinobenzyl)-1H-pyrazolo[3,4-d]pyrimidin-6-yl)amino)-1H-pyrazol-1-yl)propan-1-ol;
1-(3-(4,4-difluoropiperidin-1-yl)benzyl)-N-(1-methyl-1H-pyrazol-4-yl)-1H-pyrazolo[3,4-d]pyrimidin-6-amine;
3-(4-((1-(3-morpholinobenzyl)-1H-pyrazolo[3,4-d]pyrimidin-6-yl)amino)-1H-pyrazol-1-yl)-1-(piperidin-1-yl)propan-1-one;
1-(2-fluoro-3-morpholinobenzyl)-N-(1-methyl-1H-pyrazol-4-yl)-1H-pyrazolo[3,4-d]pyrimidin-6-amine;
N-(1-methyl-1H-pyrazol-4-yl)-1-(3-(piperazin-1-yl)benzyl)-1H-pyrazolo[3,4-d]pyrimidin-6-amine;
N-(1-(2,2-difluoroethyl)-1H-pyrazol-4-yl)-1-(3-morpholinobenzyl)-1H-pyrazolo[3,4-d]pyrimidin-6-amine;
N-methyl-3-(4-((1-(3-morpholinobenzyl)-1H-pyrazolo[3,4-d]pyrimidin-6-yl)amino)-1H-pyrazol-1-yl)propanamide;
1-(3-(3,6-dihydro-2H-pyran-4-yl)benzyl)-N-(1-methyl-1H-pyrazol-4-yl)-1H-pyrazolo[3,4-d]pyrimidin-6-amine;
6-(6-((1-methyl-1H-pyrazol-4-yl)amino)-1H-pyrazolo[3,4-d]pyrimidin-1-yl)-2H-benzo[b][1,4]oxazin-3(4H)-one;
N-(1-methyl-1H-pyrazol-4-yl)-1-(naphthalen-1-ylmethyl)-1H-pyrazolo[3,4-d]pyrimidin-6-amine;
1-(2-(2-(benzyloxy)ethoxy)benzyl)-N-(1-methyl-1H-pyrazol-4-yl)-1H-pyrazolo[3,4-d]pyrimidin-6-amine;
1-(3-(2-(benzyloxy)ethoxy)benzyl)-N-(1-methyl-1H-pyrazol-4-yl)-1H-pyrazolo[3,4-d]pyrimidin-6-amine;
4-(3-((6-((1-methyl-1H-pyrazol-4-yl)amino)-1H-pyrazolo[3,4-d]pyrimidin-1-yl)methyl)phenyl)thiomorpholine 1,1-dioxide;
N-(1-methyl-1H-pyrazol-4-yl)-1-(2-phenoxybenzyl)-1H-pyrazolo[3,4-d]pyrimidin-6-amine;
1-(2-(3-((6-((1-methyl-1H-pyrazol-4-yl)amino)-1H-pyrazolo[3,4-d]pyrimidin-1-yl)methyl)phenoxy)ethyl)pyrrolidin-2-one;
1-(3-(2-oxa-5-azabicyclo[2.2.2]octan-5-yl)benzyl)-N-(1-methyl-1H-pyrazol-4-yl)-1H-pyrazolo[3,4-d]pyrimidin-6-amine;
4-(3-((6-(((1-methyl-1H-pyrazol-4-yl)amino)-1H-pyrazolo[3,4-d]pyrimidin-1-yl)methyl)phenyl)morpholin-3-one;
1-(benzo[d][1,3]dioxo1-4-ylmethyl)-N-(1-methyl-1H-pyrazol-4-yl)-1H-pyrazolo[3,4-d]pyrimidin-6-amine;
1-((2,3-dihydrobenzo[b][1,4]dioxin-5-yl)methyl)-N-(1-methyl-1H-pyrazol-4-yl)-1H-pyrazolo[3,4-d]pyrimidin-6-amine;
N-(1-methyl-1H-pyrazol-4-yl)-1-(3-(pyridin-4-yl)benzyl)-1H-pyrazolo[3,4-d]pyrimidin-6-amine;
4-(3-((6-((1-(3-(dimethylamino)propyl)-1H-pyrazol-4-yl)amino)-1H-pyrazolo[3,4-d]pyrimidin-1-yl)methyl)phenyl)morpholin-3-one;
4-(3-((6-((1-(2-hydroxyethyl)-1H-pyrazol-4-yl)amino)-1H-pyrazolo[3,4-d]pyrimidin-1-yl)methyl)phenyl)morpholin-3-one;
1-(3-(4-((1-(3-morpholinobenzyl)-1H-pyrazolo[3,4-d]pyrimidin-6-yl)amino)-1H-pyrazol-1-yl)propyl)pyrrolidin-2-one;
N-(1-((3-((dimethylamino)methypoxetan-3-yl)methyl)-1H-pyrazol-4-yl)-1-(3-morpholinobenzyl)-1H-pyrazolo[3,4-d]pyrimidin-6-amine;
4-(3-((6-(((1-methyl-1H-pyrazol-4-yl)amino)-1H-pyrazolo[3,4-d]pyrimidin-1-yl)methyl)phenyl)morpholin-3-ol;
3-((1-(2-fluorobenzyl)-1H-pyrazolo[3,4-d]pyrimidin-6-yl)amino)-1-methyl-1H-pyrazole-5-carboxylic acid;
1-(2-fluorobenzyl)-N-(1-methyl-1H-imidazol-4-yl)-1H-pyrazolo[3,4-d]pyrimidin-6-amine;
2-(3-((1-(2-fluorobenzyl)-1H-pyrazolo[3,4-d]pyrimidin-6-yl)amino)-1H-pyrazol-1-yl)ethanol;
4-((1-(2-fluorobenzyl)-1H-pyrazolo[3,4-d]pyrimidin-6-yl)amino)-N-methyl-1H-pyrrole-2-carboxamide;
2-(4-((1-(2-fluorobenzyl)-1H-pyrazolo[3,4-d]pyrimidin-6-yl)amino)-1H-imidazol-1-yl)ethanol;
1-(2-fluorobenzyl)-N-(1-methyl-1H-pyrrol-3-yl)-1H-pyrazolo[3,4-d]pyrimidin-6-amine;
4-((1-(2-fluorobenzyl)-1H-pyrazolo[3,4-d]pyrimidin-6-yl)amino)-N,1-dimethyl-1H-pyrrole-2-carboxamide;
4-((1-(2-fluorobenzyl)-1H-pyrazolo[3,4-d]pyrimidin-6-yl)amino)-1-methyl-N-(2-morpholinoethyl)-1H-pyrrole-2-carboxamide;
(4-((1-(2-fluorobenzyl)-1H-pyrazolo[3,4-d]pyrimidin-6-yl)amino)-1-methyl-1H-pyrrol-2-y1)(morpholino)methanone;
N-(cyanomethyl)-4-((1-(2-fluorobenzyl)-1H-pyrazolo[3,4-d]pyrimidin-6-yl)amino)-1-methyl-1H-pyrrole-2-carboxamide;
4-((1-(2-fluorobenzyl)-1H-pyrazolo[3,4-d]pyrimidin-6-yl)amino)-N,N,1-trimethyl-1H-pyrrole-2-carboxamide;
2-(3-((1-(2-fluorobenzyl)-1H-pyrazolo[3,4-d]pyrimidin-6-yl)amino)-1H-pyrrol-1-yl)ethanol;
(1-methyl-4-((1-(3-morpholinobenzyl)-1H-pyrazolo[3,4-d]pyrimidin-6-yl)amino)-1H-pyrrol-2-yl)(morpholino)methanone;
N-(1-(3-(dimethylamino)-2-methylpropyl)-1H-pyrazol-4-yl)-1-(3-morpholinobenzyl)-1H-pyrazolo[3,4-d]pyrimidin-6-amine;
1-(dimethylamino)-3-(4-((1-(3-morpholinobenzyl)-1H-pyrazolo[3,4-d]pyrimidin-6-yl)amino)-1H-pyrazol-1-yl)propan-2-ol;
N-(1-(3-aminopropyl)-1H-pyrazol-4-yl)-1-(3-morpholinobenzyl)-1H-pyrazolo[3,4-d]pyrimidin-6-amine;
N-cyclopropyl-3-(4-((1-(3-morpholinobenzyl)-1H-pyrazolo[3,4-d]pyrimidin-6-yl)amino)-1H-pyrazol-1-yl)propanamide;
1-(3-((6-(((1-methyl-1H-pyrazol-4-yl)amino)-1H-pyrazolo[3,4-d]pyrimidin-1-yl)methyl)phenyl)piperazin-2-one;
2-(4-((1-(2,3,6-trifluorobenzyl)-1H-pyrazolo[3,4-d]pyrimidin-6-yl)amino)-1H-pyrazol-1-yl)ethanol;
1-(2,3-difluoro-5-morpholinobenzyl)-N-(1-methyl-1H-pyrazol-4-yl)-1H-pyrazolo[3,4-d]pyrimidin-6-amine;
1-(2,6-difluoro-3-morpholinobenzyl)-N-(1-methyl-1H-pyrazol-4-yl)-1H-pyrazolo[3,4-d]pyrimidin-6-amine;
2-(4-((1-(2-fluoro-3-morpholinobenzyl)-1H-pyrazolo[3,4-d]pyrimidin-6-yl)amino)-1H-pyrazol-1-yl)ethanol;

4-(2-fluoro-3-((6-((1-methyl-1H-pyrazol-4-yl)amino)-1H-pyrazolo[3,4-d]pyrimidin-1-yl)methyl)phenyl)morpholin-3-one;
N-(1-((3-((methylamino)methyl)oxetan-3-yl)methyl)-1H-pyrazol-4-yl)-1-(3-morpholinobenzyl)-1H-pyrazolo[3,4-d]pyrimidin-6-amine;
2-(4-((1-(2-cyclopropylbenzyl)-1H-pyrazolo[3,4-d]pyrimidin-6-yl)amino)-1H-pyrazol-1-yl)ethanol;
2-(4-((1-(2-fluoro-6-(trifluoromethyl)benzyl)-1H-pyrazolo[3,4-d]pyrimidin-6-yl)amino)-1H-pyrazol-1-yl)ethanol;
N-(1-(3-(dimethylamino)propyl)-1H-pyrazol-4-yl)-1-(2,3,6-trifluoro-5-morpholinobenzyl)-1H-pyrazolo[3,4-d]pyrimidin-6-amine;
N-(1-(3-(dimethylamino)propyl)-1H-pyrazol-4-yl)-1-(2-fluoro-3-morpholinobenzyl)-1H-pyrazolo[3,4-d]pyrimidin-6-amine;
2-(4-((1-(2-fluoro-5-morpholinobenzyl)-1H-pyrazolo[3,4-d]pyrimidin-6-yl)amino)-1H-pyrazol-1-yl)ethanol;
2-(4-((1-(2,3,6-trifluoro-5-morpholinobenzyl)-1H-pyrazolo[3,4-d]pyrimidin-6-yl)amino)-1H-pyrazol-1-yl)ethanol;
4-(2-fluoro-3-((6-((1-(2-hydroxyethyl)-1H-pyrazol-4-yl)amino)-1H-pyrazolo[3,4-d]pyrimidin-1-yl)methyl)phenyl)morpholin-3-one;
2-(4-((1-(3-(piperazin-1-yl)benzyl)-1H-pyrazolo[3,4-d]pyrimidin-6-yl)amino)-1H-pyrazol-1-yl)ethanol;
1-(3-morpholinobenzyl)-N-(1-(piperidin-3-ylmethyl)-1H-pyrazol-4-yl)-1H-pyrazolo[3,4-d]pyrimidin-6-amine;
1-(3-fluoro-5-morpholinobenzyl)-N-(1-methyl-1H-pyrazol-4-yl)-1H-pyrazolo[3,4-d]pyrimidin-6-amine;
4-(3-((6-((1-(3-(dimethylamino)propyl)-1H-pyrazol-4-yl)amino)-1H-pyrazolo[3,4-d]pyrimidin-1-yl)methyl)-2-fluorophenyl)morpholin-3-one;
2-(4-((1-(3-fluoro-5-morpholinobenzyl)-1H-pyrazolo[3,4-d]pyrimidin-6-yl)amino)-1H-pyrazol-1-yl)ethanol;
4-(3,4-difluoro-5-((6-((1-methyl-1H-pyrazol-4-yl)amino)-1H-pyrazolo[3,4-d]pyrimidin-1-yl)methyl)phenyl)morpholin-3-one;
1-(2-fluoro-3-((6-((1-methyl-1H-pyrazol-4-yl)amino)-1H-pyrazolo[3,4-d]pyrimidin-1-yl)methyl)phenyl)piperazin-2-one;
1-(2-fluoro-3-((6-((1-(2-hydroxyethyl)-1H-pyrazol-4-yl)amino)-1H-pyrazolo[3,4-d]pyrimidin-1-yl)methyl)phenyl)piperazin-2-one;
2-(4-((1-(2,3-difluoro-5-morpholinobenzyl)-1H-pyrazolo[3,4-d]pyrimidin-6-yl)amino)-1H-pyrazol-1-yl)ethanol;
1-(3-((6-((1-(2-hydroxyethyl)-1H-pyrazol-4-yl)amino)-1H-pyrazolo[3,4-d]pyrimidin-1-yl)methyl)phenyl)piperazin-2-one;
4-(3-fluoro-5-((6-((1-(2-hydroxyethyl)-1H-pyrazol-4-yl)amino)-1H-pyrazolo[3,4-d]pyrimidin-1-yl)methyl)phenyl)morpholin-3-one;
4-(3,4-difluoro-5-((6-((1-(2-hydroxyethyl)-1H-pyrazol-4-yl)amino)-1H-pyrazolo[3,4-d]pyrimidin-1-yl)methyl)phenyl)morpholin-3-one;
1-(3-morpholinobenzyl)-N-(1-(pyrrolidin-3-ylmethyl)-1H-pyrazol-4-yl)-1H-pyrazolo[3,4-d]pyrimidin-6-amine;
4-(2,4,5-trifluoro-3-((6-((1-methyl-1H-pyrazol-4-yl)amino)-1H-pyrazolo[3,4-d]pyrimidin-1-yl)methyl)phenyl)morpholin-3-one;
4-(2,4,5-trifluoro-3-((6-((1-(2-hydroxyethyl)-1H-pyrazol-4-yl)amino)-1H-pyrazolo[3,4-d]pyrimidin-1-yl)methyl)phenyl)morpholin-3-one;
2-(4-((1-(2,3,6-trifluoro-5-(piperazin-1-yl)benzyl)-1H-pyrazolo[3,4-d]pyrimidin-6-yl)amino)-1H-pyrazol-1-yl)ethanol;
1-(3-fluoro-5-((6-((1-(2-hydroxyethyl)-1H-pyrazol-4-yl)amino)-1H-pyrazolo[3,4-d]pyrimidin-1-yl)methyl)phenyl)piperazin-2-one;
1-(3-fluoro-5-((6-((1-methyl-1H-pyrazol-4-yl)amino)-1H-pyrazolo[3,4-d]pyrimidin-1-yl)methyl)phenyl)piperazin-2-one;
1-(3-(3-methoxyazetidin-1-yl)benzyl)-N-(1-methyl-1H-pyrazol-4-yl)-1H-pyrazolo[3,4-d]pyrimidin-6-amine;
N-(1-methyl-1H-pyrazol-4-yl)-1-(2,3,6-trifluoro-5-(piperazin-1-yl)benzyl)-1H-pyrazolo[3,4-d]pyrimidin-6-amine;
1-(2-fluoro-3-(piperazin-1-yl)benzyl)-N-(1-methyl-1H-pyrazol-4-yl)-1H-pyrazolo[3,4-d]pyrimidin-6-amine;
2-(4-((1-(3-fluoro-5-(3-oxomorpholino)benzyl)-1H-pyrazolo[3,4-d]pyrimidin-6-yl)amino)-1H-pyrazol-1-yl)-N-methylacetamide;
2-(4-((1-(2-fluorobenzyl)-1H-pyrazolo[3,4-d]pyrimidin-6-yl)amino)-1H-pyrazol-1-yl)-N-methylacetamide;
2-(4-((1-((6-fluoropyridin-2-yl)methyl)-1H-pyrazolo[3,4-d]pyrimidin-6-yl)amino)-1H-pyrazol-1-yl)-N-methylacetamide;
4-(2,4-difluoro-3-((6-((1-methyl-1H-pyrazol-4-yl)amino)-1H-pyrazolo[3,4-d]pyrimidin-1-yl)methyl)phenyl)morpholin-3-one;
4-(2,4-difluoro-3-((6-((1-(2-hydroxyethyl)-1H-pyrazol-4-yl)amino)-1H-pyrazolo[3,4-d]pyrimidin-1-yl)methyl)phenyl)morpholin-3-one;
4-(3-((6-((1-(3-(dimethylamino)propyl)-1H-pyrazol-4-yl)amino)-1H-pyrazolo[3,4-d]pyrimidin-1-yl)methyl)-2,4,5-trifluorophenyl)morpholin-3-one;
1-(3,4-difluoro-5-((6-((1-methyl-1H-pyrazol-4-yl)amino)-1H-pyrazolo[3,4-d]pyrimidin-1-yl)methyl)phenyl)piperazin-2-one;
1-(3,4-difluoro-5-((6-((1-(2-hydroxyethyl)-1H-pyrazol-4-yl)amino)-1H-pyrazolo[3,4-d]pyrimidin-1-yl)methyl)phenyl)piperazin-2-one;
4-(2,5-difluoro-3-((6-((1-methyl-1H-pyrazol-4-yl)amino)-1H-pyrazolo[3,4-d]pyrimidin-1-yl)methyl)phenyl)morpholin-3-one;
4-(2,5-difluoro-3-((6-((1-(2-hydroxyethyl)-1H-pyrazol-4-yl)amino)-1H-pyrazolo[3,4-d]pyrimidin-1-yl)methyl)phenyl)morpholin-3-one;
4-(3-((6-((1-(3-(dimethylamino)propyl)-1H-pyrazol-4-yl)amino)-1H-pyrazolo[3,4-d]pyrimidin-1-yl)methyl)-2,4-difluorophenyl)morpholin-3-one;
1-(2,4-difluoro-3-((6-((1-methyl-1H-pyrazol-4-yl)amino)-1H-pyrazolo[3,4-d]pyrimidin-1-yl)methyl)phenyl)piperazin-2-one;
1-(2,6-difluoro-3-(piperazin-1-yl)benzyl)-N-(1-methyl-1H-pyrazol-4-yl)-1H-pyrazolo[3,4-d]pyrimidin-6-amine;
1-(2,4-difluoro-3-((6-((1-(2-hydroxyethyl)-1H-pyrazol-4-yl)amino)-1H-pyrazolo[3,4-d]pyrimidin-1-yl)methyl)phenyl)piperazin-2-one;
1-(3-(4-methoxypiperidin-1-yl)benzyl)-N-(1-methyl-1H-pyrazol-4-yl)-1H-pyrazolo[3,4-d]pyrimidin-6-amine;
2-(4-((1-(2,6-difluoro-3-(piperazin-1-yl)benzyl)-1H-pyrazolo[3,4-d]pyrimidin-6-yl)amino)-1H-pyrazol-1-yl)ethanol;
2-(4-((1-(2,3-difluoro-5-(piperazin-1-yl)benzyl)-1H-pyrazolo[3,4-d]pyrimidin-6-yl)amino)-1H-pyrazol-1-yl)ethanol;
1-(2-fluorobenzyl)-N-(1-(pyrrolidin-3-ylmethyl)-1H-pyrazol-4-yl)-1H-pyrazolo[3,4-d]pyrimidin-6-amine;

(3-fluoro-5-((6-((1-methyl-1H-pyrazol-4-yl)amino)-1H-pyrazolo[3,4-d]pyrimidin-1-yl)methyl)phenyl)(morpholino)methanone;

(3-fluoro-5-((6-((1-methyl-1H-pyrazol-4-yl)amino)-1H-pyrazolo[3,4-d]pyrimidin-1-yl)methyl)phenyl)(piperazin-1-yl)methanone;

N-(1H-pyrazol-4-yl)-1-(2,3,6-trifluoro-5-morpholinobenzyl)-1H-pyrazolo[3,4-d]pyrimidin-6-amine;

2-(4-((1-(2,6-difluoro-3-morpholinobenzyl)-1H-pyrazolo[3,4-d]pyrimidin-6-yl)amino)-1H-pyrazol-1-yl)ethanol;

2-(4-((1-(2-fluoro-3-(piperazin-1-yl)benzyl)-1H-pyrazolo[3,4-d]pyrimidin-6-yl)amino)-1H-pyrazol-1-yl)ethanol;

4-(3-((6-((1H-pyrazol-4-yl)amino)-1H-pyrazolo[3,4-d]pyrimidin-1-yl)methyl)-5-fluorophenyl)morpholin-3-one;

(2-Fluoro-3-((6-((1-(2-hydroxyethyl)-1H-pyrazol-4-yl)amino)-1H-pyrazolo[3,4-d]pyrimidin-1-yl)methyl)phenyl)(morpholino)methanone;

2-(4-((1-((6-fluoropyridin-2-yl)methyl)-1H-pyrazolo[3,4-d]pyrimidin-6-yl)amino)-1H-pyrazol-1-yl)ethanol;

1-(2,3-difluoro-5-(piperazin-1-yl)benzyl)-N-(1-methyl-1H-pyrazol-4-yl)-1H-pyrazolo[3,4-d]pyrimidin-6-amine; and (2-fluoro-3-((6-((1-methyl-1H-pyrazol-4-yl)amino)-1H-pyrazolo[3,4-d]pyrimidin-1-yl)methyl)phenyl)(morpholino)methanone.

* * * * *